(12) United States Patent
Muthuppalaniappan et al.

(10) Patent No.: US 8,420,689 B2
(45) Date of Patent: *Apr. 16, 2013

(54) CANNABINOID RECEPTOR LIGANDS, PHARMACEUTICAL COMPOSITIONS CONTAINING THEM, AND PROCESS FOR THEIR PREPARATION

(75) Inventors: Meyyappan Muthuppalaniappan, Navi Mumbai (IN); Gopalan Balasubramanian, Secunderabad (IN); Srinivas Gullapalli, Navi Mumbai (IN); Neelima Khairatkar Joshi, Thane (IN); Shridhar Narayanan, Thane (IN)

(73) Assignee: Glenmark Pharmaceuticals S.A., La Chaux-de-Fonds (CH)

( * ) Notice: Subject to any disclaimer, the term of this patent is extended or adjusted under 35 U.S.C. 154(b) by 127 days.

This patent is subject to a terminal disclaimer.

(21) Appl. No.: 13/006,560

(22) Filed: Jan. 14, 2011

(65) Prior Publication Data

US 2012/0142748 A1 Jun. 7, 2012

Related U.S. Application Data

(62) Division of application No. 11/914,919, filed as application No. PCT/IB2006/001437 on Jun. 1, 2006, now Pat. No. 7,923,465.

(60) Provisional application No. 60/696,433, filed on Jul. 1, 2005, provisional application No. 60/744,071, filed on Mar. 31, 2006.

(30) Foreign Application Priority Data

| Jun. 2, 2005 | (IN) | ............................ 659/MUM/2005 |
| Oct. 10, 2005 | (IN) | .......................... 1370/MUM/2005 |
| Mar. 9, 2006 | (IN) | ............................ 344/MUM/2006 |
| May 3, 2006 | (IN) | ............................ 689/MUM/2006 |

(51) Int. Cl.
*A61K 31/415* (2006.01)
*C07D 487/00* (2006.01)

(52) U.S. Cl.
USPC ........................................ 514/403; 548/359.1

(58) Field of Classification Search .................. 514/403; 548/359.1

See application file for complete search history.

(56) References Cited

U.S. PATENT DOCUMENTS

| 4,973,587 A | 11/1990 | Ward et al. |
| 5,013,837 A | 5/1991 | Ward et al. |
| 5,081,122 A | 1/1992 | Ward |
| 5,112,820 A | 5/1992 | Ward |
| 5,292,736 A | 3/1994 | Kumar et al. |
| 5,532,237 A | 7/1996 | Gallant et al. |
| 6,355,631 B1 | 3/2002 | Achard et al. |
| 6,479,479 B2 | 11/2002 | Achard et al. |
| 7,923,465 B2 * | 4/2011 | Muthuppalaniappan et al. ............................ 514/403 |

FOREIGN PATENT DOCUMENTS

| WO | WO-9729079 | 8/1997 |
| WO | WO-9837061 | 8/1998 |
| WO | WO-9902499 | 1/1999 |
| WO | WO-0010967 A1 | 3/2000 |
| WO | WO-0010968 A2 | 3/2000 |
| WO | WO-0164632 A1 | 9/2001 |
| WO | WO-0164633 A1 | 9/2001 |
| WO | WO-0170700 A1 | 9/2001 |
| WO | WO-02076949 A1 | 10/2002 |
| WO | WO-03026647 A1 | 4/2003 |
| WO | WO-03026648 A1 | 4/2003 |
| WO | WO-03027069 A1 | 4/2003 |
| WO | WO-03027076 A2 | 4/2003 |
| WO | WO-03027114 A1 | 4/2003 |
| WO | WO-03077847 A2 | 9/2003 |
| WO | WO-200413120 A1 | 2/2004 |
| WO | WO-200426301 A1 | 4/2004 |
| WO | WO-2004058145 A2 | 7/2004 |
| WO | WO-2004058744 A1 | 7/2004 |
| WO | WO-200469837 A1 | 8/2004 |
| WO | WO-2004096763 A1 | 11/2004 |

* cited by examiner

*Primary Examiner* — Rei-tsang Shiao

(74) *Attorney, Agent, or Firm* — Blank Rome LLP

(57) ABSTRACT

The present invention relates to novel cannabinoid receptor modulators, in particular cannabinoid 1 (CB1) or cannabinoid 2 (CB2) receptor modulators, and uses thereof for treating diseases, conditions and/or disorders modulated by a cannabinoid receptor.

21 Claims, 3 Drawing Sheets

CANNABINOID RECEPTOR LIGANDS, PHARMACEUTICAL COMPOSITIONS CONTAINING THEM, AND PROCESS FOR THEIR PREPARATION

This application is a divisional of U.S. patent application Ser. No. 11/914,919, filed May 20, 2008, now U.S. Pat. No. 7,923,465 which is the U.S. national phase of International Application No. PCT/IB2006/001437 filed Jun. 1, 2006, which claims the benefit of Indian Patent Application No. 659/MUM/2005 filed on Jun. 2, 2005, U.S. Provisional Application No. 60/696,433, filed Jul. 1, 2005, Indian Patent Application No. 1370/MUM/2005, filed Oct. 10, 2005, Indian Patent Application No 344/MUM/2006, filed Mar. 9, 2006, U.S. Provisional Application No. 60/744,071, filed Mar. 31, 2006 and Indian Patent Application No. 689/MUM/2006, filed May 3, 2006, all of which are hereby incorporated by reference.

FIELD OF THE INVENTION

The present invention relates to novel cannabinoid receptor modulators, in particular cannabinoid 1 (CB1) or cannabinoid 2 (CB2) receptor modulators, and uses thereof for treating diseases, conditions and/or disorders modulated by a cannabinoid receptor (such as pain, neurodegenerative disorders, eating disorders, weight loss or control, and obesity).

BACKGROUND

The endogenous cannabinoid system comprises two main receptors, CB1 and CB2, and a number of ligands including anandamide and virodhamine which demonstrate the greatest activity at the cannabinoid receptor (Jonathan A W & Louis J A, *Obes Man.*, 5-19, 20f05). Anandamide, which is produced postsynaptically, is the main fatty acid involved in the system. It gains access to the extra cellular space and activates CB1 cannabinoid receptors located on presynaptic nerve terminals. This activation causes presynaptic inhibition of γ-aminobutyric acid or glutamate through inhibition of calcium channels, while simultaneously interfering with vesicle release and activating potassium channels.

However, anandamide is prone to rapid enzymatic hydrolysis. This represents a serious drawback in its use as a drug because, inter alia, substances which are susceptible to hydrolytic cleavage may undergo changes in the gastrointestinal tract.

CB1 receptors are predominantly located in the brain and other neurons, while CB2 receptors are predominantly located in immune cells. Stimulation of these receptors is known to affect the central and peripheral action on lipid and glucose metabolism in adipose tissue and most notably, helps to regulate food intake, energy balance and nicotine dependence as well as regulate fear and anxiety.

There is evidence suggesting that CB1 agonists or antagonists, respectively, increase or decrease the motivation to work for palatable ingesta (Gallate J E and McGregor I S, *Psychopharmacology*, 142, 302-308, 1999 and Gallate J E, Saharov T, Mallet P E and McGregor I S, 1999, *Eur. J Pharmacol.* 370, 233-240, 1999). Cannabinoids appear to directly stimulate eating by actions on appetitive processes, making food stimuli more salient and rapidly inducing eating even in satiated animals C M and Kirkham T C, *Physiol. Behan.*, 76, 241-250, 2002).

Current data reveals that cannabinoids mediate suppression of inflammation in vitro and in vivo through stimulation of CB2 receptors (Ehrhart J, et. al. J. *Neuroinflammation*, 2, 29, 2005). The inflammatory mediators such as nitric oxide, cytokines, and chemokines play an important role in microglial cell-associated neuron cell damage. Activated microglial cells have been implicated in a number of neurodegenerative disorders, including Alzheimer's disease, multiple sclerosis, HIV and dementia.

Compounds capable of modulating the cannabinoid (CB) receptor activity can be used in the treatment of CB receptor mediated syndromes, diseases or disorders which include appetite, metabolism, diabetes, obesity, glaucoma associated intra-ocular pressure, mood disorders, seizures, substance abuse, learning disorders, cognition disorders, memory disorders, organ contraction, muscle spasm, respiratory disorders, locomotor activity disorders, movement disorders, immune disorders, inflammation, cell growth disorders, eye-diseases, allergies and allergic reactions, pain, anxiety, psychotic afflictions, pathological states of brain, gastrointestinal disorders, nausea, vomiting, giddiness, urinary and fertility problems, cardiovascular diseases, neuroinflammatory pathologies, diseases of the central nervous system, neurodegenerative syndromes, diseases and disorders, sleep disorders, dermatological disorders, leukocyte activation-associated disorder, autoimmune diseases, nephrological pathologies, delayed or immediate hypersensitivity, infectious parasitic, and viral and bacterial diseases.

At present, various CB modulators have been Characterized as agonists, inverse agonists or antagonists to CB1 and/or CB2 receptors. These modulators include naphthalen-1yl-(4-pentyloxy-naphthalen-1-yl)methanone (believed to be SAB-378), 4-(2,4-dichlorophenylamino)-N-(tetrahydro-pyran-4-ylmethyl)-2-trifluromethyl-benzamide (GW-842166X), N-(1-piperidinyl)-5-(4-chlorophen yl)-1-(2,4-dichlorophenyl)-4-methylpyrazole-3-carbox-amide (SR141716A), 3-(4-chlorophenyl-N'-(4-chlorophenyl)sulfonyl-N-methyl-4-phenyl-4,5-dihydro-1H-pyrazole-1-carboxamide (SLV-319), and (R)-(+)-(2,3-dihydro-5-methyl-3-[4-morpholinylmethyl]-pyrrolo-[1,2,3-de]-1,4-benzoxazin-6-yl)(1-naphthyl)methanone (WTN 55212-2).

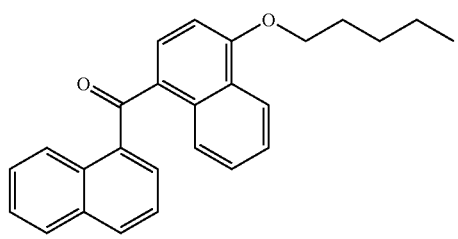

SAB-378 (CB1 Agonist)

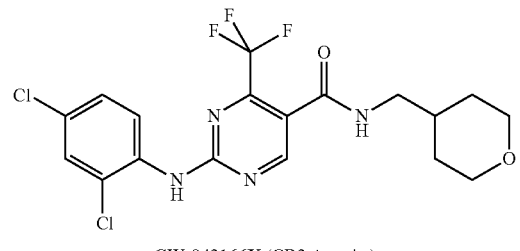

GW-842166X (CB2 Agonist)

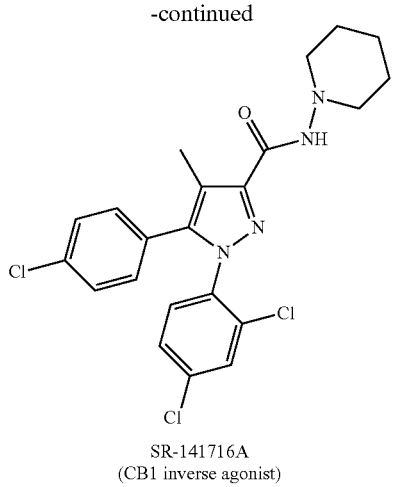

SR-141716A
(CB1 inverse agonist)

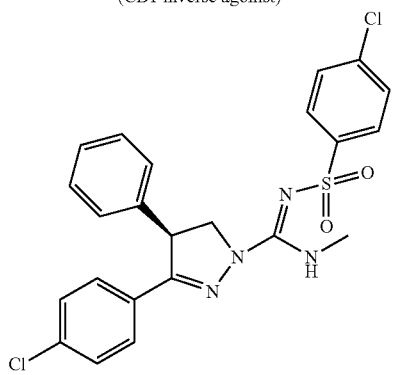

SLV-319
(CB1 Antagonist)

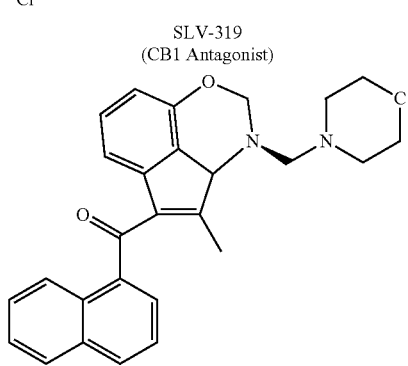

(WIN 55212-2)

These modulators have reached advanced stages of clinical trials for the treatment of pain, neurodegenerative disorders, psychotic disorders, neurological syndromes, diseases or disorders, eating disorders, Alzheimer's disease, alcohol dependency, diabetes, obesity and/or smoking cessation.

U.S. Pat. Nos. 5,624,941, 6,028,084, and 6,509,367, PCT Publication Nos. WO 98/31227, WO 98/41519, WO 98/43636 and WO 98/43635, and European Publication No. EP 0 658 546 disclose certain substituted pyrazoles having activity against the cannabinoid receptors. U.S. Pat. Nos. 6,355,631 and 6,479,479 and PCT Publication Nos. WO 01/64632, 01/64633, and 01/64634 disclose certain azetidine derivatives, which are cannabinoid antagonists.

Other cannabinoid receptor modulating compounds are disclosed in U.S. Pat. Nos. 4,973,587, 5,013,837, 5,081,122, 5,112,820, 5,292,736, and 5,532,237, and PCT Publication Nos. WO 97/29079, WO 98/37061, WO 99/02499, WO 00/10967, WO 00/10968, WO 01/58869, WO 01/70700, WO 02/076949, WO 03/026647, WO 03/026648, WO 03/027069, WO 03/027076, WO 03/027114, WO 03/077847, WO 03/088968, WO 04/13120, WO 04/69837, WO 04/058145, WO 04/26301, WO 04/058744, WO 04/096763 and WO06/030124.

There exists an unmet need for treatment of alcohol abuse. Health risks associated with alcoholism include impaired motor control and decision making, cancer, liver disease, birth defects, heart disease, drug/drug interactions, pancreatitis and interpersonal problems. Studies have suggested that endogenous cannabinoid tone plays a critical role in the control of ethanol intake. The endogenous. CB1 receptor antagonist SR-141716A has been shown to block voluntary ethanol intake in rats and mice. (See, Amone, M, et al., "Selective Inhibition of Sucrose and Ethanol intake by SR141716, an Antagonist of Central Cannabinoid (CB1) Receptors," *Psychopharmacol,* 132, 104-106 (1997)). For a review, see, Hungund, B. L and B. S. Basavarajappa, "Are Anadamide and Cannabinoid Receptors involved in Ethanol Tolerance? A Review of the Evidence," *Alcohol & Alcoholism.* 35(2) 126-133, 2000.

Current treatments for alcohol abuse or dependence generally suffer from non-compliance or potential hepatotoxicity. There is an unmet need for more effective treatments of alcohol abuse/dependence.

There also still exists a need for safer and more effective therapeutic treatments for diseases, conditions and/or disorders modulated by cannabinoid receptors (such as pain, obesity), including those modulated by CB 1 or CB2 receptors.

SUMMARY OF INVENTION

The present invention relates to cannabinoid, receptor modulators of the formula:

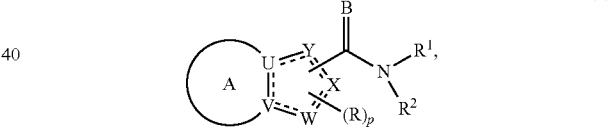

(1)

and analogs thereof, pharmaceutically acceptable salts thereof, pharmaceutically acceptable esters thereof, tautomers thereof, regioisomers thereof, stereoisomers thereof, enantiomers thereof, diastereomers thereof, polymorphs thereof, and pharmaceutically acceptable solvates thereof, wherein each of the dotted lines in formula (1) independently represents an optional double bond;

U and V are independently C or N;

W, X and Y are independently C, N, O, S or —C(O)— with the proviso that at least two of U, V, W, X or Y are independently selected from N, O, —C(O)— or S;

R, $R^1$ and $R^2$ may be same or different and are independently hydrogen, nitro, cyano, formyl, acetyl, halogen, —$OR^3$, —$SR^3$, oxo, thio, substituted or unsubstituted alkyl, substituted or unsubstituted alkenyl, substituted or unsubstituted alkynyl, substituted or unsubstituted cycloalkyl, substituted or unsubstituted cycloalkylalkyl, substituted or unsubstituted cycloalkenyl, substituted or unsubstituted cycloalkenylalkyl, substituted or unsubstituted aryl, substituted or unsubstituted arylalkyl, substituted or unsubstituted heteroaryl, substituted or unsubstituted heteroarylalkyl, substituted or unsubstituted heterocyclic group, substituted or unsubstituted heterocyclylalkyl, —NR³R⁴, —C(=B)—R³, —C(O)O—R³, —C(O)NR³R⁴, —S(O)$_m$—R³, —S(O)$_m$—NR³R⁴, or a protecting group or R¹ and R² may be joined together to form an optionally substituted 3 to 7 membered saturated or unsaturated cyclic ring, which may optionally include at least two heteroatoms selected from O, NR³ or S;

each occurrence of R³ and R⁴ may be same or different and are independently hydrogen, nitro, halo, cyano, —OR$^a$, —SR$^a$, oxo, thio, substituted or unsubstituted alkyl, substituted or unsubstituted alkenyl, substituted or unsubstituted alkynyl, substituted or unsubstituted cycloalkyl, substituted or unsubstituted cycloalkylalkyl, substituted or unsubstituted cycloalkenyl, substituted or unsubstituted cycloalkenylalkyl, substituted or unsubstituted aryl, substituted or unsubstituted arylalkyl, substituted or unsubstituted heteroaryl, substituted or unsubstituted heteroarylalkyl, substituted or unsubstituted heterocyclic group, substituted or unsubstituted heterocyclylalkyl, —C(=B)—R$^a$, —C(O)O—R$^a$, —C(O)NR$^a$R$^b$, —S(O)$_m$—R$^a$, —S(O)$_m$—NR$^a$R$^b$, —NR$^a$R$^b$, or a protecting group or R³ and R⁴, when bound to a common atom, may be joined together to form an optionally substituted 3 to 7 membered saturated or unsaturated cyclic ring, which may optionally include at least two heteroatoms selected from O, NR³ or S;

each occurrence of R$^a$ and R$^b$ may be same or different and are independently hydrogen, halogen, nitro, cyano, formyl, acetyl, oxo, thio, —C(O)—R$^c$, —C(O)O—R$^c$, —C(O)NR$^c$R$^d$, —S(O)$_m$—R$^c$, —S(O)$_m$—NR$^c$R$^d$, —NR$^c$R$^d$, —OR$^c$, —SR$^c$, a protecting group, substituted or unsubstituted alkyl, substituted or unsubstituted alkenyl, substituted or unsubstituted alkynyl substituted or unsubstituted cycloalkyl, substituted or unsubstituted cycloalkylalkyl, substituted or unsubstituted cycloalkenyl, substituted or unsubstituted cycloalkenylalkyl, substituted or unsubstituted aryl, substituted or unsubstituted arylalkyl, substituted or unsubstituted heteroaryl, substituted or unsubstituted heterocyclic group, substituted or unsubstituted heterocyclyl alkyl, or substituted or unsubstituted heteroarylalkyl;

each occurrence of R$^c$ and R$^d$ may be same or different and are independently hydrogen, halogen, nitro, cyano, formyl, acetyl, oxo, thio, a protecting group, substituted or unsubstituted alkyl, substituted or unsubstituted alkenyl, substituted or unsubstituted alkynyl, substituted or unsubstituted cycloalkyl, substituted or unsubstituted cycloalkylalkyl, substituted or unsubstituted cycloalkenyl, substituted or unsubstituted cycloalkenylalkyl, substituted or unsubstituted aryl, substituted or unsubstituted arylalkyl, substituted or unsubstituted heteroaryl, substituted or unsubstituted heterocyclic group, substituted or unsubstituted heterocyclylalkyl, or substituted or unsubstituted heteroaryl alkyl;

each occurrence of B is independently O, S or NR³;
p and m are independently 0, 1 or 2;
A is (a)
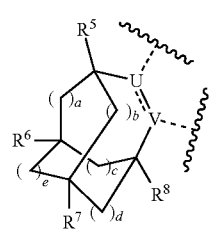

-continued (b)
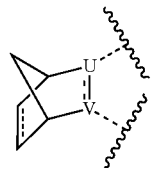

(c)
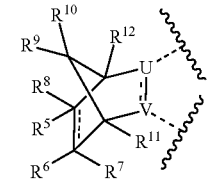

(d)
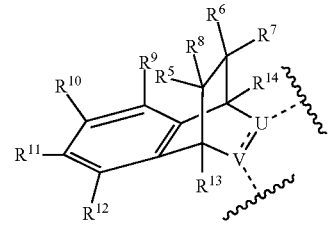

(e)
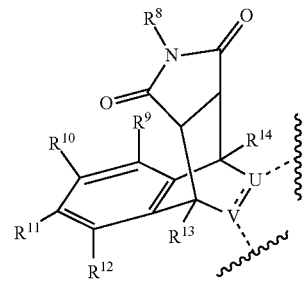

(f)
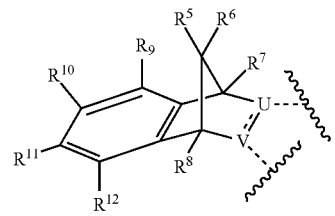

(g)
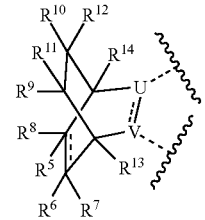

(h)
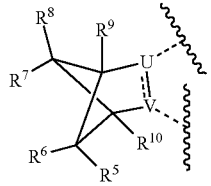

-continued (i) 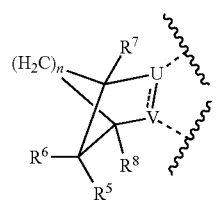

(j) 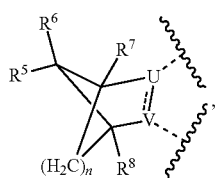

(k) 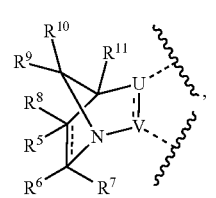

(l) 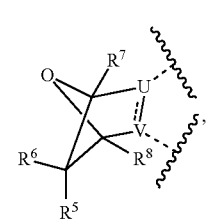

(m) 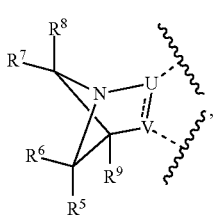

(n) 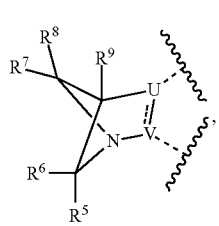

(o) 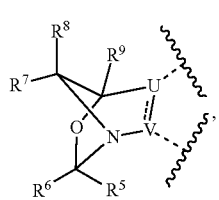

(p) 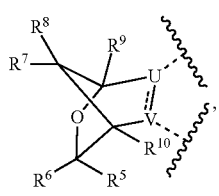

-continued (q) 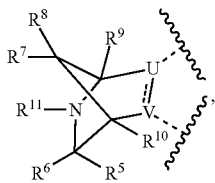

(r) 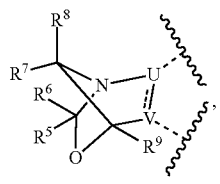

(s) 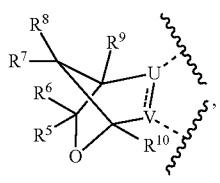

(t) 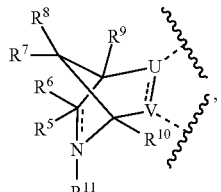

(u) 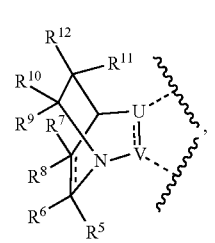

(v) 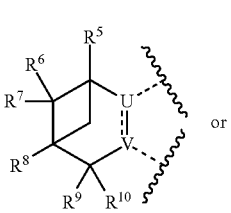

or (w) 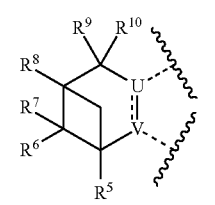

wherein:
each of the dotted lines in A independently represents an optional double bond;
$R^5$, $R^6$, $R^7$, $R^8$, $R^9$, $R^{10}$, $R^{11}$, $R^{12}$, $R^{13}$, and $R^{14}$ are independently hydrogen, nitro, cyano, formyl, acetyl, halogen, —$OR^{15}$, —$SR^{15}$, oxo, thio, substituted or unsubstituted alkyl, substituted or unsubstituted alkenyl, substituted or unsubstituted alkynyl, substituted or unsubstituted cycloalkyl, substituted or unsubstituted cycloalkylalkyl, substituted or unsubstituted cycloalkenyl, substituted or unsubstituted cycloalkenylalkyl, substituted or unsubstituted aryl, substituted or unsubstituted arylalkyl, substituted or unsubstituted heteroaryl, substituted or unsubstituted heteroarylalkyl, substituted or unsubstituted heterocyclic group, substituted or unsubstituted heterocyclylalkyl, —$NR^{15}R^{16}$, —$C(=B)$—$R^{15}$, —$C(O)O$—$R^{15}$, —$C(O)NR^{15}R^{16}$, —$S(O)_m$—$R^{15}$, —$S(O)_m$—$NR^{15}R^{16}$, or a protecting group;

$R^5$ and $R^6$ may be joined together to form an optionally substituted 3 to 11 membered saturated or unsaturated mono or bicyclic ring, which may optionally include at least one heteroatom selected from O, $NR^3$ or S;

$R^9$ and $R^{10}$ may be joined together to form an optionally substituted 3 to 11 membered saturated or unsaturated mono or bicyclic ring, which may optionally include at least one heteroatom selected from O, $NR^3$ or S;

$R^5$ and $R^9$ may be joined together to form an optionally substituted 3, to 11 membered saturated or unsaturated mono or bicyclic ring, which may optionally include at least one heteroatom selected from O, $NR^3$ or S;

$R^7$ and $R^{10}$ may be joined together to form an optionally substituted 3 to 11 membered saturated or unsaturated mono or bicyclic ring, which may optionally include at least one heteroatom selected from O, $NR^3$ or S;

each occurrence of $R^{15}$ and $R^{16}$ may be same or different and are independently hydrogen, nitro, halo, cyano, —$OR^3$, —$SR^3$, oxo, thio, substituted or unsubstituted alkyl, substituted or unsubstituted alkenyl, substituted or unsubstituted alkynyl, substituted or unsubstituted cycloalkyl, substituted or unsubstituted cycloalkylalkyl, substituted or unsubstituted cycloalkenyl, substituted or unsubstituted cycloalkenylalkyl, substituted or unsubstituted aryl, substituted or unsubstituted arylalkyl, substituted or unsubstituted heteroaryl, substituted or unsubstituted heteroarylalkyl, substituted or unsubstituted heterocyclic group, substituted or unsubstituted heterocyclylalkyl, —$C(=B)$—$R^3$, —$C(O)O$—$R^3$, —$C(O)NR^3R^4$, —$S(O)_m$—$R^3$, —$S(O)_m$—$NR^3R^4$, —$NR^3R^4$ or $R^{15}$ and $R^{16}$, when bound to a common atom, may be joined together to form an optionally substituted 3 to 7 membered saturated or unsaturated cyclic ring, which may optionally include at least two heteroatoms selected from O, $NR^3$ or S wherein $R^3$ and $R^4$ are as defined as above;

n is 1, 2, 3, or 4; and a, b, c, d and e are integers independently selected from 0 to 4, with the proviso that the modulator does not have the formula:

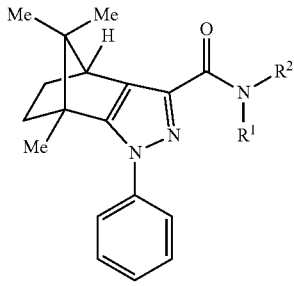

wherein $R^1$ and $R^2$ are as defined above.

Preferred is a compound of general formula (1) wherein U and V are C.

Further preferred is where Y and X are N, and W is C.

Further preferred is where 13 in the —$C(B)NR^1R^2$ group is O.

Further preferred is where R is hydrogen, substituted or unsubstituted alkyl, substituted or unsubstituted aryl.

Further preferred is where R is methyl, phenyl, 2-chlorophenyl, 4-chlorophenyl, 2,4-dichlorophenyl, 2-bromophenyl, 4-bromophenyl, 4-fluorophenyl, 2,4-difluorophenyl, 4-methylphenyl, 4-methoxyphenyl, 2-(4-chlorophenyl)phenyl or 5-chloropyridin-2-yl.

Further preferred is where $R^1$ is hydrogen.

Further preferred is where $R^2$ is substituted or unsubstituted alkyl, substituted or unsubstituted cycloalkyl, substituted or unsubstituted cycloalkylalkyl, substituted or unsubstituted aryl, substituted or unsubstituted arylalkyl, substituted or unsubstituted heterocyclic group, substituted or unsubstituted heteroaryl group, substituted or unsubstituted heteroarylalkyl, or $NR^3R^4$.

Further preferred is where $R^2$ is t-butyl, n-pentyl, cyclopentyl, cyclohexyl, adamantan-1-yl, 2-methyladamantan-2-yl, 3-hydroxyadamantan-1-yl, 1,3,3-trimethylbicyclo[2.2.1]hept-2-yl, 1-phenyl cyclopropyl, cyclohexylmethyl, phenyl, 3-chlorophenyl, 4-chlorophenyl, 3-bromophenyl, 2-methoxyphenyl, 4-tert-butylphenyl, 2,4-difluorophenyl, benzyl, 2-chlorobenzyl, 4-chlorobenzyl, 2,4-dichlorobenzyl, 2-fluorobenzyl, 4-fluorobenzyl, 2,4-difluorobenzyl, 2,6-difluorobenzyl, 2-bromobenzyl, 4-bromobenzyl, 4-trifluoromethylbenzyl, 1-phenylethyl, 1-methyl-1-phenylethyl, 2-phenylethyl, 1-(2-chlorophenyl)ethyl, 2(4-fluorophenyl)ethyl, 1-phenylpropyl, 1-ethyl-1-phenylpropyl, 1-(2-chlorophenyl)1-methylethyl, methylphenylethanoate, 2-hydroxy-1-phenylethyl, piperidinyl, morpholinyl, pyridinyl, 1,2,4-triazol-4-yl, 2-pyridylmethyl, 3-pyridylmethyl, or 4-pyridylmethyl.

Further preferred is where $R^1$ and $R^2$ are joined together to form an optionally substituted 3 to 7 membered saturated or unsaturated cyclic ring, which may optionally include at least two heteroatoms selected from O, $NR^3$ or S.

Further preferred is where $R^1$ and $R^2$ together with nitrogen atom to which are they are bound form piperidin-1-yl or morpholinyl (e.g., morpholin-1-yl).

Further preferred is where $R^2$ is $NR^3R^4$; wherein each occurrence of $R^3$ and $R^4$ may be same or different and are independently hydrogen, substituted or unsubstituted alkyl, substituted or unsubstituted cycloalkyl, substituted or unsubstituted aryl, substituted or unsubstituted heteroaryl or $R^3$ and $R^4$ are joined together to form an optionally substituted 3 to 7 membered saturated or unsaturated cyclic ring, which may optionally include at least two heteroatoms selected from O, $NR^3$ or S.

Further preferred is where $R^3$ is hydrogen, substituted or unsubstituted alkyl, substituted or unsubstituted aryl or substituted or unsubstituted cycloalkyl.

Further preferred is where $R^3$ is methyl, phenyl or cyclohexyl.

Further preferred is where $R^4$ is selected from substituted or unsubstituted aryl, substituted or unsubstituted heteroaryl or substituted or unsubstituted cycloalkyl.

Further preferred is where $R^4$ is phenyl, 2-chlorophenyl, 4-chlorophenyl, 2,4-dichlorophenyl, 3,4-dichlorophenyl, 2-fluorophenyl, 3-fluorophenyl, 4-fluorophenyl, 2,4-difluorophenyl, 3,4-difluorophenyl, 2-bromophenyl, 3-chloropyridin-2-yl, 5-chloropyridin-2-yl, or cyclohexyl.

Further preferred is where $R^2$ is —$NR^3R^4$, wherein $R^3$ and $R^4$ are joined together to form an optionally substituted 3 to 7 membered saturated or unsaturated cyclic ring, which may optionally include at least two heteroatoms selected from O, $NR^3$ or S;

Further preferred is where $R^3$ and $R^4$ are joined together to form piperidin-1yl or morpholin-4-yl.

Further preferred is where A is (a)
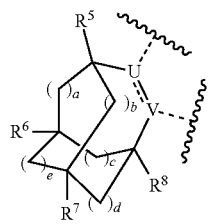

(b)
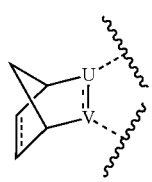

(c)
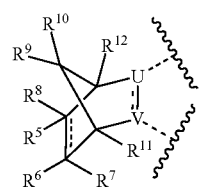

(d)
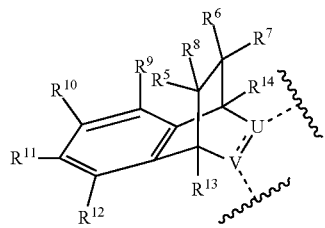

(e)
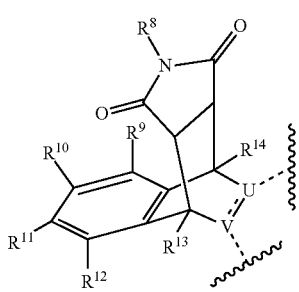

(f)
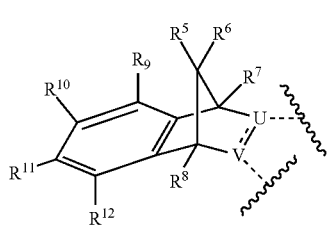

(g)
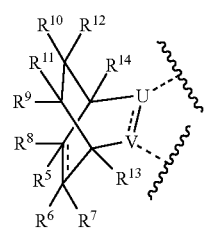

wherein
$R^5$ to $R^{14}$ are independently hydrogen or methyl; and
$R^8$ is substituted or unsubstituted phenyl.
Further preferred is where $R^8$ is 4-chlorophenyl.
Further preferred is where a=b=c=d=e=1.
More preferably, U and V are C, X and Y are N, W is —C(O)NR$^1$R$^2$.
Further preferred is p=1.
According to one embodiment, when A is 1,7,7 trimethyl-bicyclo[2.2.1]heptane and p is 1, then R does not represent unsubstituted phenyl.
According to one preferred embodiment, Y is N, U is C, one of W, V, and X is N and the remaining two are C, B in the group —C(B)NR$^1$R$^2$ is O, and A, R, R$^1$, and R$^2$ are as defined above.
Another embodiment is a cannabinoid receptor modulator of Formula 1A, (1A)
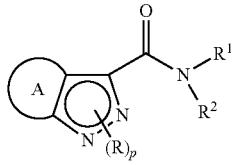

or an analog thereof, pharmaceutically acceptable salt thereof, pharmaceutically acceptable ester thereof, tautomer thereof, regioisomer thereof, stereoisomer thereof, enantiomer thereof, diastereomer thereof, polymorph thereof, or pharmaceutically acceptable solvate thereof,
wherein
R, R$^1$ and R$^2$ may be same or different and are independently hydrogen, substituted or unsubstituted alkyl, substituted or unsubstituted cycloalkyl, substituted or unsubstituted cycloalkylalkyl, substituted or unsubstituted aryl, substituted or unsubstituted arylalkyl, substituted or unsubstituted heterocyclic group, substituted or unsubstituted heteroaryl group or substituted or unsubstituted heteroarylalkyl or R$^1$ and R$^2$ may be joined together to form an optionally substituted 3 to 7 membered saturated or unsaturated cyclic ring, which may optionally include at least two heteroatoms selected from O, NR$^3$ or S. or NR$^3$R$^4$;
each occurrence of R$^3$ and R$^4$ may be same or different and are independently hydrogen, substituted or unsubstituted alkyl, substituted or unsubstituted cycloalkyl, substituted or unsubstituted aryl, substituted or unsubstituted heteroaryl or substituted or unsubstituted heterocyclic group or R$^3$ and R$^4$ may be joined together to form an optionally substituted 3 to 7 membered saturated or unsaturated cyclic ring, which may optionally include at least two heteroatoms selected from O, NR$^3$ or S;
p is 1; and
A is (a)
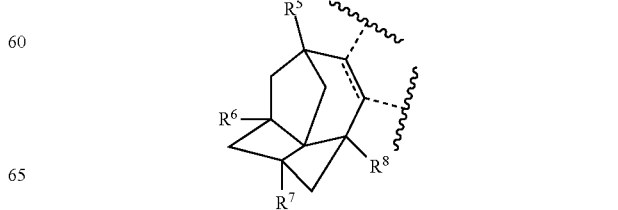

-continued

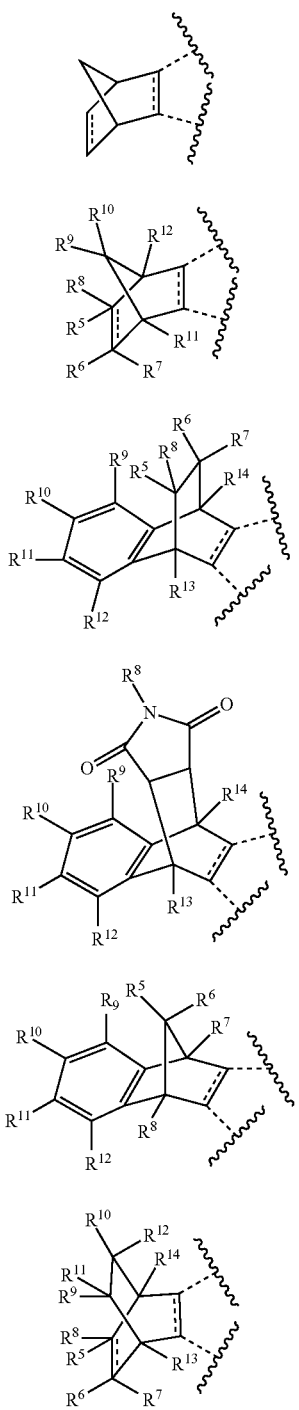

wherein
each of the dotted lines in A independently represents an optional double bond, and
each occurrence of $R^5$, $R^6$, $R^7$, $R^8$, $R^9$, $R^{10}$, $R^{11}$, $R^{12}$, $R^{13}$, and $R^{14}$ is the same or different and selected from hydrogen, substituted or unsubstituted alkyl or substituted or unsubstituted aryl;

with the proviso that the modulator does not have the formula:

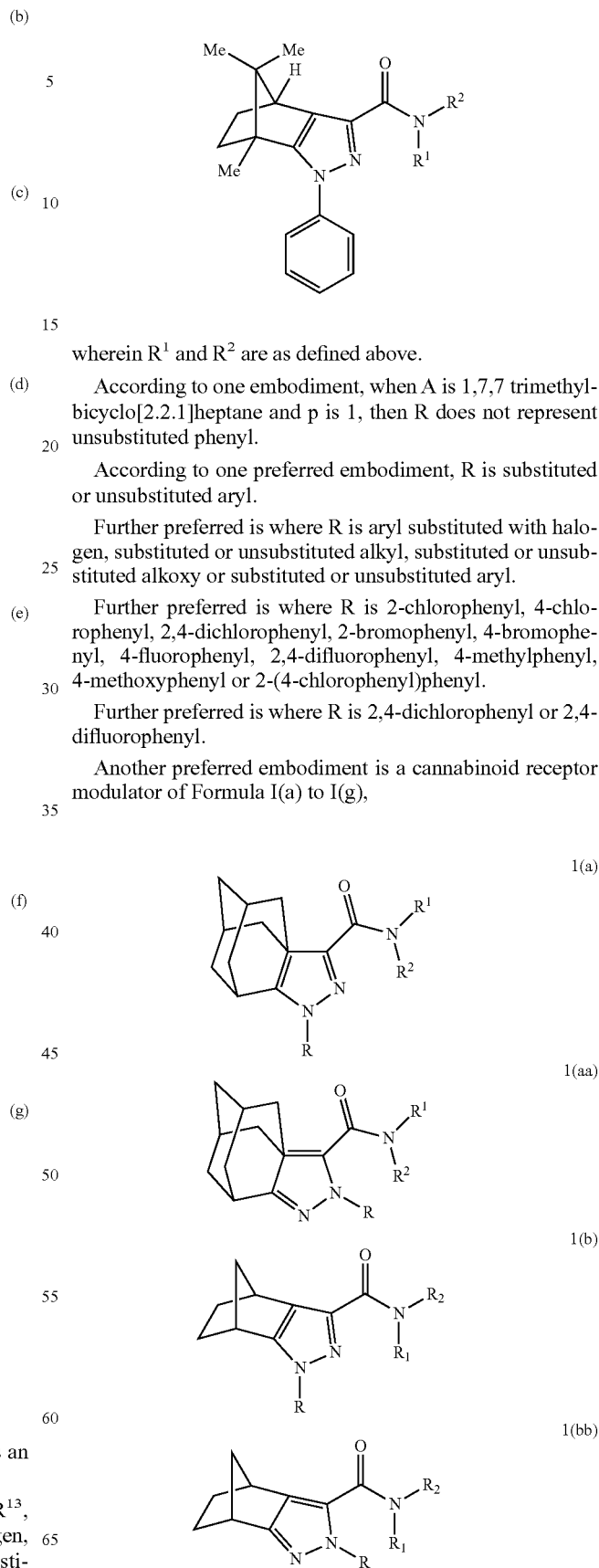

wherein $R^1$ and $R^2$ are as defined above.

According to one embodiment, when A is 1,7,7 trimethyl-bicyclo[2.2.1]heptane and p is 1, then R does not represent unsubstituted phenyl.

According to one preferred embodiment, R is substituted or unsubstituted aryl.

Further preferred is where R is aryl substituted with halogen, substituted or unsubstituted alkyl, substituted or unsubstituted alkoxy or substituted or unsubstituted aryl.

Further preferred is where R is 2-chlorophenyl, 4-chlorophenyl, 2,4-dichlorophenyl, 2-bromophenyl, 4-bromophenyl, 4-fluorophenyl, 2,4-difluorophenyl, 4-methylphenyl, 4-methoxyphenyl or 2-(4-chlorophenyl)phenyl.

Further preferred is where R is 2,4-dichlorophenyl or 2,4-difluorophenyl.

Another preferred embodiment is a cannabinoid receptor modulator of Formula I(a) to I(g), -continued

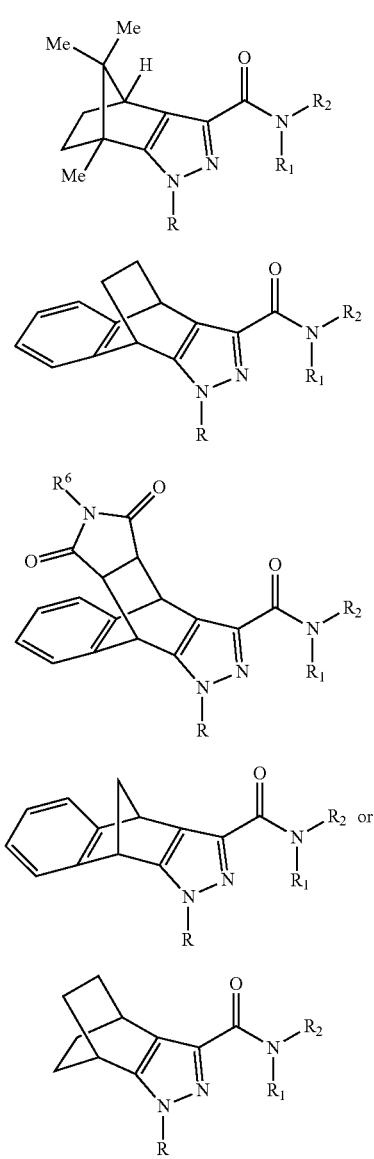

wherein R, $R^1$, $R^2$ and $R^8$ are as defined above and R in formula 1(c) is not unsubstituted phenyl.

According to one preferred embodiment, R is a phenyl group substituted with at least one halogen atom. More preferably, R is a phenyl group substituted with one or two halogen atoms (e.g., 2,4-difluorophenyl or 2,4-dichlorophenyl).

Yet another embodiment is a selective CB2 agonist (i.e., a CB2 agonist that does not substantially inhibit or activate the CB1 receptor) having the formula:

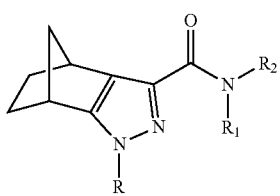

wherein R, $R^1$, and $R^2$ are as defined above. R is preferably a substituted or unsubstituted aryl, more preferably substituted or unsubstituted phenyl, and even more preferably a substituted phenyl. Even more desirably, R is a phenyl group substituted with one or two halogen atoms (e.g., 2,4-difluorophenyl or 2,4-dichlorophenyl). These compounds are particularly useful in the treatment of disorders mediated by agonizing the CB2 receptor, including, but not limited to, ophthalmic diseases, respiratory disorders, immune disorders (such as autoimmune disorders), inflammation, pain (such as neuropathic pain) and neurodegenerative related syndromes. Accordingly, the present invention also includes methods of treating any of these disorders in a subject in need thereof by administering a therapeutically effective amount of one or more compounds of formula 1(b).

Representative compounds of the present invention listed below are illustrative in nature only and do not limit to the scope of the invention.

101. N(7)-Piperidino-5-(2-bromophenyl)-5,6-diazatetracyclo[7.3.1.1$^{3,11}$.0$^{4,8}$]tetradeca-4(8),6-diene-7-arboxamide,
102. N(7)-Benzyl-5-(2-bromophenyl)-5,6-diazatetracyclo[7.3.1.1$^{3,11}$.0$^{4,8}$]tetradeca-4(8),6-diene-7-carboxamide,
103. N(7)-Morpholino-5-(4-chlorophenyl)-5,6-diazatetracyclo[7.3.1.1$^{3,11}$.0$^{4,8}$]tetradeca-4(8),6-diene-7-carboxamide,
104. N(7)-(3-Pyridylmethyl)-5-(4-chlorophenyl)-5,6-diazatetracyclo[7.3.1.1$^{3,11}$.0$^{4,8}$]tetradeca-4(8),6-diene-7-carboxamide,
105. N(7)-(4-Pyridylmethyl)-5-(4-chlorophenyl)-5,6-diazatetracyclo[7.3.1.1$^{3,11}$.0$^{4,8}$]tetradeca-4(8),6-diene-7-carboxamide,
106. N(7)-Cyclohexyl-5-(4-chlorophenyl)-5,6-diazatetracyclo[7.3.1.1$^{3,11}$.0$^{4,8}$]tetradeca-4(8),6-diene-7-carboxamide,
107. N(7)-(N-cyclohexyl-N-methylamino)-5-(4-chlorophenyl)-5,6-diazatetracyclo[7.3.1.1$^{3,11}$.0$^{4,8}$]tetradeca-4(8),6-diene-7-carboxamide,
108. N(7)-Cyclohexylmethyl-5-(4-chlorophenyl)-5,6-diazatetracyclo[7.3.1.1$^{3,11}$.0$^{4,8}$]tetradeca-4(8),6-diene-7-carboxamide,
109. N(7)-(Adamantan-1-yl)-5-(4-chlorophenyl)-5,6-diazatetracyclo[7.3.1.1$^{3,11}$.0$^{4,8}$]tetradeca-4(8)-6-diene-7-carboxamide,
110. N(7)-(1S,2 endo-1,3,3-Trimethyl-bicyclo[2.2.1]hept-2-yl)-5-(4-chlorophenyl)-5,6-diazatetracyclo[7.3.1.1$^{3,11}$.0$^{4,8}$]tetradeca-4(8)-6-diene-7-carboxamide,
111. N(7)-(2-Chlorobenzyl)-5-(4-chlorophenyl)-5,6-diazatetracyclo[7.3.1.1$^{3,11}$.0$^{4,8}$]tetradeca-4(8)-6-diene-7-carboxamide,
112. N(7)-(4-Chlorobenzyl)-5-(4-chlorophenyl)-5,6-diazatetracyclo[7.3.1.1$^{3,11}$.0$^{4,8}$]tetradeca-4(8)-6-diene-7-carboxamide,
113. N(7)-(4-Fluorobenzyl)-5-(4-chlorophenyl)-5,6-diazatetracyclo[7.3.1.1$^{3,11}$.0$^{4,8}$]tetradeca-4(8)-6-diene-7-carboxamide,
114. N(7)-(2,4-Difluorobenzyl)-5-(4-chlorophenyl)-5,6-diazatetracyclo[7.3.1.1$^{3,11}$.0$^{4,8}$]tetradeca-4(8),6-diene-7-carboxamide,
115. N(7)-(2,6-Difluorobenzyl)-5-(4-chlorophenyl)-5,6-diazatetracyclo[7.3.1.1$^{3,11}$.0$^{4,8}$]tetradeca-4(8),6-diene-7-carboxamide,
116. N(7)-(4-Trifluoromethylbenzyl)-5-(4-chlorophenyl)-5,6-diazatetracyclo[7.3.1.1$^{3,11}$.0$^{4,8}$]tetradeca-4(8),6-diene-7-carboxamide,
117. N(7)-(1-Phenylethyl))-5-(4-chlorophenyl)-5,6-diazatetracyclo[7.3.1.1$^{3,11}$.0$^{4,8}$]tetradeca-4(8),6-diene-7-carboxamide, 118. N(7)-(R-1-Phenylethyl))-5-(4-chlorophenyl)-5,6-diazatetracyclo[7.3.1.1$^{3,11}$.0$^{4,8}$]tetradeca-4(8),6-diene-7-carboxamide,
119. N(7)-(1-Methyl-1-phenylethyl))-5-(4-chlorophenyl)-5,6-diazatetracyclo[7.3.1.1$^{3,11}$.0$^{4,8}$]tetradeca-4(8),6-diene-7-carboxamide,
120. N(7)-(2-Pyridylmethyl)-5-(4-chlorophenyl)-5,6-diazatetracyclo[7.3.1.1$^{3,11}$.0$^{4,8}$]tetradeca-4(8),6-diene-7-carboxamide,
121. N(7)-(N'-phenylamino)-5-(4-chlorophenyl)-5,6-diazatetracyclo[7.3.1.1$^{3,11}$.0$^{4,8}$]tetradeca-4(8),6-diene-7-carboxamide,
122. N(7)-(N'-phenylamino)-5-(4-chlorophenyl)-5,6-diazatetracyclo[7.3.1.1$^{3,11}$.0$^{4,8}$]tetradeca-4(8),6-diene-7-carboxamide hydrochloride,
123. N(7)-(2-Chlorophenylamino)-5-(4-chlorophenyl)-5,6-diazatetracyclo[7.3.1.1$^{3,11}$.0$^{4,8}$]tetradeca-4(8),6-diene-7-carboxamide,
124. N(7)-(2-Chlorophenylamino)-5-(4-chlorophenyl)-5,6-diazatetracyclo[7.3.1.1$^{3,11}$.0$^{4,8}$]tetradeca-4(8),6-diene-7-carboxamide, hydrochloride,
125. N(7)-[(4-chlorophenyl)amino)]-5-(4-chlorophenyl)-5,6-diazatetracyclo[7.3.1.1$^{3,11}$.0$^{4,8}$]tetradeca-4(8),6-diene-7-carboxamide,
126. N(7)-(2,4-Dichlorophenylamino)-5-(4-chlorophenyl)-5,6-diazatetracyclo[7.3.1.1$^{3,11}$.0$^{4,8}$]tetradeca-4(8),6-diene-7-carboxamide,
127. N(7)-[(2,4-Dichlorophenyl-N'-methylamino]-5-(4-chlorophenyl)-5,6-diazatetracyclo[7.3.1.1$^{3,11}$.0$^{4,8}$]tetradeca-4(8),6-diene-7-carboxamide,
128. N(7)-[(2,4-Dichlorophenyl-N'-methylamino]-5-(4-chlorophenyl)-5,6-diazatetracyclo[7.3.1.1$^{3,11}$.0$^{4,8}$]tetradeca-4(8),6-diene-7-carboxamide hydrochloride,
129. N(7)-(2,4-Dichlorophenyl-N'-cyclohexylamino)-5-(4-chlorophenyl)-5,6-diazatetracyclo[7.3.1.1$^{3,11}$.0$^{4,8}$]tetradeca-4(8),6-diene-7-carboxamide,
130, N(7)-(4-fluorophenylamino)-5-(4-chlorophenyl)-5,6-diazatetracyclo[7.3.1.1$^{3,11}$.0$^{4,8}$]tetradeca-4(8),6-diene-7-carboxamide,
131. N(7)-(4-Fluorophenylamino)-5-(4-chlorophenyl)-5,6-diazatetracyclo[7.3.1.1$^{3,11}$.0$^{4,8}$]tetradeca-4(8),6-diene-7-carboxamide hydrochloride,
132. N(7)-(2,4-Difluorophenylamino]-5-(4-chlorophenyl)-5,6-diazatetracyclo[7.3.1.1$^{3,11}$.0$^{4,8}$]tetradeca-4(8),6-diene-7-carboxamide,
133. N(7)-(3-fluorophenylamino)-5-(4-chlorophenyl)-5,6-diazatetracyclo[7.3.1.1$^{3,11}$.0$^{4,8}$]tetradeca-4(8),6-diene-7-carboxamide,
134. N(7)-(3-Chloro-2-pyridylamino)-5-(4-chlorophenyl)-5,6-diazatetracyclo[7.3.1.1$^{3,11}$.0$^{4,8}$]tetradeca-4(8),6-diene-7-carboxamide,
135. N(7)-(5-Chloro-2-pyridylamino)-5-(4-chlorophenyl)-5,6-diazatetracyclo[7.3.1.1$^{3,11}$.0$^{4,8}$]tetradeca-4(8),6-diene-7-carboxamide,
136. N(7)-(2-Phenylethyl)-5-(4-chlorophenyl)-5,6-diazatetracyclo[7.3.1.1$^{3,11}$.0$^{4,8}$]tetradeca-4(8),6-diene-7-carboxamide,
137. N(7)-(N',N'-Diphenylamino)-5-(4-chlorophenyl)-5,6-diazatetracyclo[7.3.1.1$^{3,11}$.0$^{4,8}$]tetradeca-4(8),6-diene-7-carboxamide,
138. N(7)-[1-(2-Chlorophenyl)ethyl]-5-(4-chlorophenyl)-5,6-diazatetracyclo[7.3.1.1$^{3,11}$.0$^{4,8}$]tetradeca-4(8),6-diene-7-carboxamide,
139. N(7)-Benzyl-5-(4'-chlorophenyl)-5,6-diazatetracyclo[7.3.1.1$^{3,11}$.0$^{4,8}$]tetradeca-4(8)-6-diene-7-carboxamide,
140. N(7)-Piperidino-5-(4'-chlorophenyl)-5,6-diazatetracyclo[7.3.1.1$^{3,11}$.0$^{4,8}$]tetradeca-4(8)-6-diene-7-carboxamide,
141. 7-(4'-Chlorophenyl)-6,7-diazatetracyclo[7.3.1.1$^{3,11}$.0$^{4,8}$]tetradeca-4(8)-5-dien-5-yl-piperidinomethanone,
142. N(7)-Phenyl-5-(4'-chlorophenyl)-5,6-diazatetracyclo[7.3.1.1$^{3,11}$.0$^{4,8}$]tetradeca-4 (8)-6-diene-7-carboxamide,
143. N(7)-Piperidino-5-(2,4-difluorophenyl)-5,6-diazatetracyclo[7.3.1.1$^{3,11}$.0$^{4,8}$]tetradeca-4(8),6-diene-7-carboxamide,
144. N(7)-(Adamantan-1-yl)-5-(2,4-difluorophenyl)-5,6-diazatetracyclo[7.3.1.1$^{3,11}$.0$^{4,8}$]tetradeca-4(8)-6-diene-7-carboxamide,
145. N(7)-(1S,2endo-1,3,3-Trimethyl-bicyclo[2.2.1]hept-2 (2,4-difluorophenyl)-5,6-diazatetracyclo[7.3.1.1$^{3,11}$.0$^{4,8}$]tetradeca-4(8)-6-diene-7-carboxamide,
146. N(7)-(S-1-phenylethyl))-5-(2,4-difluorophenyl)-5,6-diazatetracyclo[7.3.1.1$^{3,11}$.0$^{4,8}$]tetradeca-4(8)-6-diene-7-carboxamide,
147. N(7)-(R-1-phenylethyl)-5-(2,4-difluorophenyl)-5,6-diazatetracyclo[7.3.1.1$^{3,11}$.0$^{4,8}$]tetradeca-4(8)-6-diene-7-carboxamide,
148. N(7)-(1-Methyl-1-phenylethyl)-5-(2,4-difluorophenyl)-5,6-diazatetracyclo[7.3.1.1$^{3,11}$.0$^{4,8}$]tetradeca-4(8),6-diene-7-carboxamide,
149. N(7)-(2-Chlorobenzyl)-5-(2,4-difluorophenyl)-5,6-diazatetracyclo[7.3.1.1$^{3,11}$.0$^{4,8}$]tetradeca-4 (Y), 6-diene-7-carboxamide,
150. N(7)-(2,4-Dichlorophenylamino)-5-(2,4-difluorophenyl)-5,6-diazatetracyclo[7.3.1.1$^{3,11}$.0$^{4,8}$]tetradeca-4(8),6-diene-7-carboxamide,
151. N(7)-[1-(2-Chlorophenyl)ethyl]-5-(2,4-difluorophenyl)-5,6-diazatetracyclo[7.3.1.1$^{3,11}$.0$^{4,8}$]tetradeca-4 (8),6-diene-7-carboxamide,
152. N(7)-[(5)-1-Phenylpropyl]-5-(2,4-difluorophenyl)-5,6-diazatetracyclo[7.3.1.1$^{3,11}$.0$^{4,8}$]tetradeca-4(8),6-diene-7-carboxamide,
153. N7-[1-(2-Chlorophenyl)-1-methylethyl]-5-(2,4-difluorophenyl)-5,6-diazatetracyclo[7.3.1.1$^{3,11}$.0$^{4,8}$]tetradeca-4 (8),6-diene-7-carboxamide,
154. Methyl(2R)-2-[7-(2,4-difluorophenyl)-6,7-diazatetracyclo[7.3.1.1$^{3,11}$.0$^{4,8}$]tetradeca-4(8),5-dien-5-ylcarboxamido]-2-phenylethanoate,
155. Methyl(2S-2-[7-(2,4-difluorophenyl)-6,7-diazatetracyclo[7.3.1.1$^{3,11}$.0$^{4,8}$]tetradeca-4(8),5-dien-5-ylcarboxamido]-2-phenylethanoate,
156. N7-(3-Hydroxyadamantan-1-yl)-5-(2,4-difluorophenyl)-5,6-diazatetracyclo[7.3.1.1$^{3,11}$.0$^{4,8}$]tetradeca-4(8),6-diene-7-carboxamide,
157. N(7)-(1-Methyl-1-phenylethyl)-5-(4-fluorophenyl)-5,6-diazatetracyclo[7.3.1.1$^{3,11}$.0$^{4,8}$]tetradeca-4(8),6-diene-7-carboxamide,
158. N(7)-(Adamantan-1-yl)-5-(2,4-difluorophenyl)-5,6-diazatetracyclo[7.3.1.1$^{3,11}$.0$^{4,8}$]tetradeca-4(8)-6-diene-7-carboxamide,
158a. N7-(Adamantan-2-yl)-5-(4-fluorophenyl)-5,6-diazatetracyclo[7.3.1.1$^{3,11}$.0$^{4,8}$]tetradeca-4(8),6-diene-7-carboxamide,
159. N7-(1,3,3-Trimethylbicyclo[2.2.1]hept-2-yl)-5-(4-fluorophenyl)-5,6-diazatetracyclo[7.3.1.1$^{3,11}$.0$^{4,8}$]tetradeca-4 (8),6-diene-7-carboxamide,
160. N(7)-Piperidino-5-(4-methylphenyl)-5,6-diazatetracyclo[7.3.1.1$^{3,11}$.0$^{4,8}$]tetradeca-4(8),6-diene-7-carboxamide,
161. N(7)-(2,4-Dichlorophenylamino)-5-(4-methylphenyl)-5,6-diazatetracyclo[7.3.1.1$^{3,11}$.0$^{4,8}$]tetradeca-4(8),6-diene-7-carboxamide, 162. N(7)-(2-Chlorobenzyl)-5-(4-methylphenyl)-5,6-diazatetracyclo[7.3.1.1$^{3,11}$.0$^{4,8}$]tetradeca-4(8),6-diene-7-carboxamide,
163. N(7)-Piperidino-5-(4-methoxyphenyl)-5,6-diazatetracyclo[7.3.1.1$^{3,11}$.0$^{4,8}$]tetradeca-4(8),6-diene-7-carboxamide,
164. N7-(2-Chlorobenzyl)-5-(4-methoxyphenyl)-5,6-diazatetracyclo[7.3.1.1$^{3,11}$.0$^{4,8}$]tetradeca-4(8),6-diene-7-carboxamide,
165. N(7)-(2,4-Dichlorophenylamino)-5-(4-methoxyphenyl)-5,6-diazatetracyclo[7.3.1.1$^{3,11}$.0$^{4,8}$]tetradeca-4(8),6-diene-7-carboxamide,
166. N(7)-Piperidino-5-[(2-chlorophenyl)phenyl]-5,6-diazatetracyclo[7.3.1.1$^{3,11}$.0$^{4,8}$]tetradeca-4(8),6-diene-7-carboxamide,
167. N(7)-[(2,4-Dichlorophenyl)amino]-5-phenyl-5,6-diazatetracyclo[7.3.1.1$^{3,11}$.0$^{4,8}$]tetradeca-4(8),6-diene-7-carboxamide,
168. N(7)-Phenyl-5-phenyl-5,6-diazatetracyclo[7.3.1.1$^{3,11}$.0$^{4,8}$]tetradeca-4(8)-6-diene-7-carboxamide,
169. N(7)-piperidino-5-phenyl-5,6-diazatetracyclo[7.3.1.1$^{3,11}$.0$^{4,8}$]tetradeca-4(8)-6-diene-7-carboxamide,
170. N(7)-Benzyl-5-phenyl-5,6-diazatetracyclo[7.3.1.1$^{3,11}$.0$^{4,8}$]tetradeca-4(8)-6-diene-7-carboxamide,
171. N(7)-phenyl-6,7-diazatetracyclo[7.3.1.1$^{3,11}$.0$^{4,8}$]tetradeca-4(8)-5-dien-5-yl-piperidinomethanone,
172. N(7)-(4-Fluorobenzyl)-5-(2,4-dichlorophenyl)-5,6-diazatetracyclo[7.3.1.1$^{3,11}$.0$^{4,8}$]tetradeca-4(8),6-diene-7-carboxamide,
173. N(7)-Phenylamino-5-(2,4-dichlorophenyl)-5,6-diazatetracyclo[7.3.1.1$^{3,11}$.0$^{4,8}$]tetradeca-4(8),6-diene-7-carboxamide,
174. N(7)-(2-Chlorophenylamino)-5-(2,4-dichlorophenyl)-5,6-diazatetracyclo[7.3.1.1$^{3,11}$.0$^{4,8}$]-4(8),6-diene-7-carboxamide,
175. N(7)-(2,4-Dichlorophenylamino)-5-(2,4-dichlorophenyl)-5,6-diazatetracyclo[7.3.1.1$^{3,11}$.0$^{4,8}$]tetradeca-4(8),6-diene-7-carboxamide,
176. N(7)-(2-Bromophenylamino)-5-(2,4-dichlorophenyl)-5,6-diazatetracyclo[7.3.1.1$^{3,11}$.0$^{4,8}$]tetradeca-4(8),6-diene-7-carboxamide,
177. N(7)-(N',N'-Diphenylamino)-5-(2,4-dichlorophenyl)-5,6-diazatetracyclo[7.3.1.1$^{3,11}$.0$^{4,8}$]tetradeca-4(8),6-diene-7-carboxamide,
178. N(7)-(2-Phenylethyl)-5-(2,4-dichlorophenyl)-5,6-diazatetracyclo[7.3.1.1$^{3,11}$.0$^{4,8}$]tetradeca-4(8),6-diene-7-carboxamide,
179. N(7)-Benzyl-5-(2',4'-dichlorophenyl)-5,6-diazatetracyclo[7.3.1.1$^{3,11}$.0$^{4,8}$]tetradeca-4(8)-6-diene-7-carboxamide,
180. N(7)-piperidino-5-(2',4'-dichlorophenyl)-5,6-diazatetracyclo[7.3.1.1$^{3,11}$.0$^{4,8}$]tetradeca-4(8),6-diene-7-carboxamide,
181. N(7)-(2,4-Dichlorophenylamino)-5-(2-chlorophenyl)-5,6-diazatetracyclo[7.3.1.1$^{3,11}$.0$^{4,8}$]tetradeca-4(8),6-diene-7-carboxamide,
182. N(7)-Benzyl-5-(2'-chlorophenyl)-5,6-diazatetracyclo[7.3.1.1$^{3,11}$.0$^{4,8}$]tetradeca-4(8)-6-diene-7-carboxamide,
183. N(7)-cyclohexyl-5-(2'-chlorophenyl)-5,6-diazatetracyclo[7.3.1.1$^{3,11}$.0$^{4,8}$]tetradeca-4(8)-6-diene-7-carboxamide,
184. N(7)-piperidino-5-(2'-chlorophenyl)-5,6-diazatetracyclo[7.3.1.1$^{3,11}$.0$^{4,8}$]tetradeca-4(8)-6-diene-7-carboxamide,
185. N7-(2-Chlorobenzyl)-5-(5-chloro-2-pyridyl)-5,6-diazatetracyclo[7.3.1.1$^{3,11}$.0$^{4,8}$]tetradeca-4(8),6-diene-7-carboxamide,
186. N(7)-Benzyl-5,6-diazatetracyclo[7.3.1.1$^{3,11}$.0$^{4,8}$]tetradeca-4(8)-6-diene-7-carboxamide,
187. N(7)-piperidino-5,6-diazatetracyclo[7.3.1.1$^{3,11}$.0$^{4,8}$]tetradeca-4(8)-6-diene-7-carboxamide,
188. 6,7-diazatetracyclo[7.3.1.1$^{3,11}$.0$^{4,8}$]tetradeca-4(8)-5-dien-5-yl-piperidinomethanone,
189a N(7)-piperidino-6-methyl-5,6-diazatetracyclo[7.3.1.1$^{3,11}$.0$^{4,8}$]tetradeca-4(8)-6-diene-7-carboxamide,
189b N(7)-piperidino-5-methyl-5,6-diazatetracyclo[7.3.1.1$^{3,11}$.0$^{4,8}$]tetradeca-4(8)-6-diene-7-carboxamide,
190a N(7)-(1-methyl-1-phenylethyl)-6-pentyl-5,6-diazatetracyclo[7.3.1.1$^{3,11}$.0$^{4,8}$]tetradeca-4,7-diene-7-carboxamide,
190b N(7)-(1-methyl-1-phenylethyl)-5-pentyl-5,6-diazatetracyclo[7.3.1.1$^{3,11}$.0$^{4,8}$]tetradeca-4(8)-6-diene-7-carboxamide,
191. N(7)-[(1R)-2-Hydroxy-1-phenylethyl]-5-(2,4-difluorophenyl)-5,6-diazatetracyclo[7.3.1.1$^{3,11}$.0$^{4,8}$]tetradeca-4(8),6-diene-7-carboxamide,
192. N(7)-[(1S-2-Hydroxy-1-phenylethyl]-5-(2,4-difluorophenyl)-5,6-diazatetracyclo[7.3.1.1$^{3,11}$.0$^{4,8}$]tetradeca-4(8),6-diene-7-carboxamide,
201. N(3)-Piperidino-1-phenyl-4,5,6,7-tetrahydro-1H-4,7-methano-indazole-3-carboxamide,
202. N(3)-Cyclohexyl-1-phenyl-4,5,6,7-tetrahydro-1H-4,7-methano-indazole-3-carboxamide,
203. N(3)-Benzyl-1-phenyl-4,5,6,7-tetrahydro-1H-4,7-methano-indazole-3-carboxamide,
204. N(3)-Phenylamino-1-phenyl-4,5,6,7-tetrahydro-1H-4,7-methano-indazole-3-carboxamide,
205. N(3)-Piperidino-1-(2-chlorophenyl)-4,5,6,7-tetrahydro-1H-4,7-methano-indazole-3-carboxamide,
206. N(3)-Cyclohexyl-1-(2-chlorophenyl)-4,5,6,7-tetrahydro-1H-4,7-methano-indazole-3-carboxamide,
207. N(3)-Benzyl-1(2-chlorophenyl)-4,5,6,7-tetrahydro-1H-4,7-methano-indazole-3-carboxamide,
208. N(3)-Phenylamino-1-(2-chlorophenyl)-4,5,6,7-tetrahydro-1H-4,7-methano-indazole-3-carboxamide,
209. N(3)-Piperidino-1-(4-chlorophenyl)-4,5,6,7-tetrahydro-1H-4,7-methano-indazole-3-carboxamide,
210. 1-(4-Chlorophenyl)-4,5,6,7-tetrahydro-1H-4,7-methano-indazol-3-yl piperidino methanone,
211. N(3)-Cyclohexyl-1-(4-chlorophenyl)-4,5,6,7-tetrahydro-1H-4,7-methano-indazole-3-carboxamide,
212. N(3)-Cyclopentyl-1-(4-chlorophenyl)-4,5,6,7-tetrahydro-1H-4,7-methano-indazole-3-carboxamide,
213. N(3)-[(N-Cyclohexyl-N-methyl)amino]-1-(4-chlorophenyl)-4,5,6,7-tetrahydro-1H-4,7-methano-indazole-3-carboxamide,
214. N(3)-Phenyl-1-(4-chlorophenyl)-4,5,6,7-tetrahydro-1H-4,7-methano-indazole-3-carboxamide,
215. N(3)-(3-Chlorophenyl)-1-(4-chlorophenyl)-4,5,6,7-tetrahydro-1H-4,7-methano-indazole-3-carboxamide,
216. N(3)-(4-Chlorophenyl)-1-(4-chlorophenyl)-4,5,6,7-tetrahydro-1H-4,7-methano-indazole-3-carboxamide,
217. N(3)-(3-Bromophenyl)-1-(4-chlorophenyl)-4,5,6,7-tetrahydro-1H-4,7-methano-indazole-3-carboxamide,
218. N(3)-(2-Methoxyphenyl)-1-(4-chlorophenyl)-4,5,6,7-tetrahydro-1H-4,7-methano-indazole-3-carboxamide, 219. N(3)-(4-tert-Butylphenyl)-1-(4-chlorophenyl)-4,5,6,7-tetrahydro-1H-4,7-methano-indazole-3-carboxamide,
220. N(3)-Benzyl-1-(4-chlorophenyl)-4,5,6,7-tetrahydro-1H-4,7-methano-indazole-3-carboxamide,
221. N(3)-(2-Chlorobenzyl)-1-(4-chlorophenyl)-4,5,6,7-tetrahydro-1H-4,7-methano-indazole-3-carboxamide,
222. N(3)-(4-Chlorobenzyl)-1-(4-chlorophenyl)-4,5,6,7-tetrahydro-1H-4,7-methano-indazole-3-carboxamide,
223. N(3)-(2,4-Dichlorobenzyl)-1-(4-chlorophenyl)-4,5,6,7-tetrahydro-1H-4,7-methano-indazole-3-carboxamide,
224. N(3)-(2-Bromobenzyl)-1-(4-chlorophenyl)-4,5,6,7-tetrahydro-1H-4,7-methano-indazole-3-carboxamide,
225. N(3)-(4-Bromobenzyl)-1-(4-chlorophenyl)-4,5,6,7-tetrahydro-1H-4,7-methano-indazole-3-carboxamide,
226. N(3)-(4-Fluorobenzyl)-1-(4-chlorophenyl)-4,5,6,7-tetrahydro-1H-4,7-methano-indazole-3-carboxamide,
227. N(3)-(4-Trifluoromethylbenzyl-1-(4-chlorophenyl)-4,5,6,7-tetrahydro-1H-4,7-methano-indazole-3-carboxamide,
228. N(3)-Phenylamino-1-(4-chlorophenyl)-4,5,6,7-tetrahydro-1H-4,7-methano-indazole-3-carboxamide,
229. N(3)-[(4-Chlorophenyl)amino]-1-(4-chlorophenyl)-4,5,6,7-tetrahydro-1H-4,7-methano-indazole-3-carboxamide,
230. N(3)-[(2,4-Dichlorophenyl)amino]-1-(4-chlorophenyl)-4,5,6,7-tetrahydro-1H-4,7-methano-indazole-3-carboxamide,
231. N(3)-[(3,4-Dichlorophenyl)amino]-1-(4-chlorophenyl)-4,5,6,7-tetrahydro-1H-4,7-methano-indazole-3-carboxamide,
232. N(3)-[2-Fluorophenyl)amino]-1-(4-chlorophenyl)-4,5,6,7-tetrahydro-1H-4,7-methano-indazole-3-carboxamide,
233. N(3)-[(3-Fluorophenyl)amino]-1-(4-chlorophenyl)-4,5,6,7-tetrahydro-1H-4,7-methano-indazole-3-carboxamide,
234. N(3)-[(4-Fluorophenyl)amino]-1-(4-chlorophenyl)-4,5,6,7-tetrahydro-1H-4,7-methano-indazole-3-carboxamide,
235. N(3)-[(2,4-Difluorophenyl)amino]-1-(4-chlorophenyl)-4,5,6,7-tetrahydro-1H-4,7-methano-indazole-3-carboxamide,
236. N(3)-(N',N'-Diphenylamino-1-(4-chlorophenyl)-4,5,6,7-tetrahydro-1H-4,7-methano-indazole-3-carboxamide,
237. N(3)-Cyclohexyl-1-(2,4-dichlorophenyl)-4,5,6,7-tetrahydro-1H-4,7-methano-indazole-3-carboxamide,
238. N(3)-Cyclohexylmethyl-1-(2,4-dichlorophenyl)-4,5,6,7-tetrahydro-1H-4,7-methano-indazole-3-carboxamide,
239. N(3)-(N,N-Dicyclohexylamino)-1-(2,4-dichlorophenyl)-4,5,6,7-tetrahydro-1H-4,7-methano-indazole-3-carboxamide,
240. N(3)-(4H-1,2,4-triazol-4-yl)-1-(2,4-dichlorophenyl)-4,5,6,7-tetrahydro-1H-4,7-methano-indazole-3-carboxamide,
241. N(3)-(1,3,3-Trimethyl bicyclo[2.2.1]hept-2-yl)-1-(2,4-dichlorophenyl)-4,5,6,7-tetrahydro-1H-4,7-methano-indazole-3-carboxamide,
242. N(3)-(Adamantan-1-yl)-1-(2,4-dichlorophenyl)-4,5,6,7-tetrahydro-1H-4,7-methano-indazole-3-carboxamide,
243. N(3)-Phenyl-1-(2,4-dichlorophenyl)-4,5,6,7-tetrahydro-1H-4,7-methano-indazole-3-carboxamide,
244. N(3)-(2,4-Difluorophenyl)-1-(2,4-dichlorophenyl)-4,5,6,7-tetrahydro-1H-4,7-methano-indazole-3-carboxamide,
245. N(3)-(2-Fluorobenzyl)-1-(2,4-dichlorophenyl)-4,5,6,7-tetrahydro-1H-4,7-methano-indazole-3-carboxamide,
246. N(3)-(4-Fluorobenzyl)-1-(2,4-dichlorophenyl)-4,5,6,7-tetrahydro-1H-4,7-methano-indazole-3-carboxamide,
247. N(3)-(2,4-Difluorobenzyl)-1-(2,4-dichlorophenyl)-4,5,6,7-tetrahydro-1H-4,7-methano-indazole-3-carboxamide,
248. N(3)-(2,6-Difluorobenzyl)-1-(2,4-dichlorophenyl)-4,5,6,7-tetrahydro-1H-4,7-methano-indazole-3-carboxamide,
249. N(3)-(2-Chlorobenzyl)-1-(2,4-dichlorophenyl)-4,5,6,7-tetrahydro-1H-4,7-methano-indazole-3-carboxamide,
250. N(3)-(4-Chlorobenzyl)-1-(2,4-dichlorophenyl)-4,5,6,7-tetrahydro-1H-4,7-methano-indazole-3-carboxamide,
251. N(3)-(2,4-Dichlorobenzyl)-1-(2,4-dichlorophenyl)-4,5,6,7-tetrahydro-1H-4,7-methano-indazole-3-carboxamide,
252. N(3)-[S-(1-phenylethyl)]-1-(2,4-dichlorophenyl)-4,5,6,7-tetrahydro-1H-4,7-methano-indazole-3-carboxamide,
253. N(3)-[R-(1-phenylethyl)]-1-(2,4-dichlorophenyl)-4,5,6,7-tetrahydro-1H-4, methano-indazole-3-carboxamide,
254. N(3)-(2-phenylethyl)-1-(2,4-dichlorophenyl)-4,5,6,7-tetrahydro-1H-4,7-methano-indazole-3-carboxamide,
255. N(3)-[2-(2,4-fluorophenyl)ethyl]-1-(2,4-dichlorophenyl)-4,5,6,7-tetrahydro-1H-4,7-methano-indazole-3-carboxamide,
256. N(3)-Phenylamino-1-(2,4-dichlorophenyl)-4,5,6,7-tetrahydro-1H-4,7-methano-indazole-3-carboxamide,
257. N(3)-[(2-Chlorophenyl)-amino]-1-(2,4-dichlorophenyl)-4,5,6,7-tetrahydro-1H-4,7-methano-indazole-3-carboxamide,
258. N(3)-[N-(2-Chlorophenyl)-N-methylamino]-1-(2,4-dichlorophenyl)-4,5,6,7-tetrahydro-1H-4,7-methano-indazole-3-carboxamide,
259. N(3)-[(4-Chlorophenyl)amino]-1-(2,4-dichlorophenyl)-4,5,6,7-tetrahydro-1H-4,7-methano-indazole-3-carboxamide,
260. N(3)-[(2,4-Dichlorophenyl)amino]-1-(2,4-dichlorophenyl)-4,5,6,7-tetrahydro-1H-1-4,7-methano-indazole-3-carboxamide,
261. N(3)-[(2,4-dichlorophenyl)-N-methylamino]-1-(2,4-chlorophenyl)-4,5,6,7-tetrahydro-1H-4,7-methano-indazole-3-carboxamide,
262. N(3)-[(3,4-Dichlorophenyl)amino]-1-(2,4-difluorophenyl)-4,5,6,7-tetrahydro-1H-4,7-methano-indazole-3-carboxamide,
263. N(3)-[(2-Bromophenyl)amino]-1-(2,4-dichlorophenyl)-4,5,6,7-tetrahydro-methano-indazole-3-carboxamide,
264. N(3)-[(2-Fluorophenyl)amino]-1-(2,4-dichlorophenyl)-4,5,6,7-tetrahydro-1H-4,7-methano-indazole-3-carboxamide,
265. N(3)-[(2,4-Difluorophenyl)amino]-(2,4-dichlorophenyl)-4,5,6,7-tetrahydro-1H-4,7-methano-indazole-3-carboxamide,
266. N(3)-[(3-Fluorophenyl)amino]-1-(2,4-dichlorophenyl)-4,5,6,7-tetrahydro-1H-4,7-methano-indazole-3-carboxamide,
267. N(3)-[(3-chloropyridin-2-yl)amino]-1-(2,4-dichlorophenyl)-4,5,6,7-tetrahydro-1H-4,7-methano-indazole-3-carboxamide,
268. N(5)-piperidino-3-(2'-dichlorophenyl)-3,4-diazatricyclo[5.2.1.0$^{2,6}$]deca-2(6),4-diene-5-carboxamide;
269. N(5)-benzyl-3-(2'-dichlorophenyl)-3,4-diazatricyclo[5.2.1.0$^{2,6}$]deca-2(6),4-diene-5-carboxamide,
270. N(3)-Piperidino-1-(2-bromophenyl)-4,5,6,7-tetrahydro-1H-4,7-methano-indazole-3-carboxamide, 271. N(3)-Cyclohexyl-1-(2-bromophenyl)-4,5,6,7-tetrahydro-1H-4,7-methano-indazole-3-carboxamide,
272. N(3)-Benzyl-1-(2-bromophenyl)-4,5,6,7-tetrahydro-1H-4,7-methano-indazole-3-carboxamide,
273. N(3)-Phenylamino-1-(2-bromophenyl)-4,5,6,7-tetrahydro-1H-4,7-methano-indazole-3-carboxamide,
274. N(3)-Piperidino-1-(4-bromophenyl)-4,5,6,7-tetrahydro-1H-4,7-methano-indazole-3-carboxamide,
275. N(3)-Cyclohexyl-1-(4-bromophenyl)-4,5,6,7-tetrahydro-1H-4,7-methano-indazole-3-carboxamide,
276. N(3)-Benzyl-1-(4-bromophenyl)-4,5,6,7-tetrahydro-1H-4,7-methano-indazole-3-carboxamide,
277. N(3)-Phenylamino-1-(4-bromophenyl)-4,5,6,7-tetrahydro-1H-4,7-methano-indazole-3-carboxamide,
278. N(3)-[(2-Fluorophenyl)amino]-1-(4-bromophenyl)-4,5,6,7-tetrahydro-1H-4,7-methano-indazole-3-carboxamide,
279. N(3)-Cyclohexyl-1-(4-fluorophenyl)-4,5,6,7-tetrahydro-1H-4,7-methano-indazole-3-carboxamide,
280. N(3)-Benzyl-1-(4-fluorophenyl)-4,5,6,7-tetrahydro-1H-4,7-methano-indazole-3-carboxyamide,
281. N5-(Adamantan-2-yl)-3-(4-fluorophenyl)-3,4-diaza tricyclo[5.2.1.0$^{2,6}$]deca-2(6),4-diene-5-carboxamide,
282. N5-(1-Methyl-1-phenylethyl)-3-(4-fluorophenyl)-3,4-diazatricyclo[5.2.1.0$^{2,6}$]deca-2(6),4-diene-5-carboxamide,
283. N5-(Adamantan-1-yl)-3-(4-fluorophenyl)-3,4-diazatricyclo[5.2.1.0$^{2,6}$]deca-2(6),4-diene-5-carboxamide,
284. N(3)-Phenylamino-1-(4-fluorophenyl)-4,5,6,7-tetrahydro-1H-4,7-methano-indazole-3-carboxamide,
285. N(3)-Phenylamino-1-(2,4-difluorophenyl)-4,5,6,7-tetrahydro-1H-4,7-methano-indazole-3-carboxamide,
286. N(3)-[(2-Chlorophenyl)amino]-1-(2,4-difluorophenyl)-4,5,6,7-tetrahydro-1H-4,7-methano-indazole-3-carboxamide,
287. N(3)-[(2-bromophenyl)amino]-1-(2,4-difluorophenyl)-4,5,6,7-tetrahydro-1H-4,7-methano-indazole-3-carboxamide,
288. N(3)-[(2-Fluorophenyl)amino]-(2,4-difluorophenyl)-4,5,6,7-tetrahydro-1H-4,7-methano-indazole-3-carboxamide,
289. N(3)-Piperidino-1-(2,4-difluorophenyl)-4,5,6,7-tetrahydro-1H-4,7-methano-indazole-3-carboxamide,
290. N(3)-Cyclohexyl-1-(2,4-difluorophenyl)-4,5,6,7-tetrahydro-1H-4,7-methano-indazole-3-carboxamide,
291. N(3)-(Cyclohexylmethyl)-1-(2,4-difluorophenyl)-4,5,6,7-tetrahydro-1H-4,7-methano-indazole-3-carboxamide,
292. N(3)-[S-(1-Phenylethyl)]-1-(2,4-difluorophenyl)-4,5,6,7-tetrahydro-1H-4,7-methano-indazole-3-carboxamide,
293. N(3)-(R-1-phenylethyl)-1-(2,4-difluorophenyl)-4,5,6,7-tetrahydro-1H-4,7-methano-indazole-3-carboxamide,
294. N(3)-(1-Methyl-1-phenylethyl)-1-(2,4-difluorophenyl)-4,5,6,7-tetrahydro-1H-4,7-methano-indazole-3-carboxamide,
295. N5-[1-(2-Chlorophenyl)-1-methylethyl]-3-(2,4-difluorophenyl)-3,4-diazatricyclo[5.2.1.0$^{2,6}$]deca-2(6),4-diene-5-carboxamide,
296. N(3)-(1,3,3-Trimethylbicyclo[2.2.1]hept-2-yl)-1-(2,4-difluorophenyl)-4,5,6,7-tetrahydro-1H-4,7-methano-indazole-3-carboxamide,
297. N5-(2-Chlorobenzyl)-3-(2,4-difluorophenyl)-3,4-diazatricyclo[5.2.1.0$^{2,6}$]deca-2(6),4-diene-5-carboxamide,
298. N5-(4-Chlorobenzyl)-3-(2,4-difluorophenyl)-3,4-diazatricyclo[5.2.1.0$^{2,6}$]deca-2(6),4-diene-5-carboxamide,
299. N5-(1-Ethyl-1-phenylpropyl)-3-(2,4-difluorophenyl)-3,4-diazatricyclo[5.2.1.0$^{2,6}$]deca-2(6),4-diene-5-carboxamide,
300. N5-[(1S)-1-Phenylpropyl]-3-(2,4-difluorophenyl)-3,4-diazatricyclo[5.2.1.0$^{2,6}$]deca-2(6),4-diene-5-carboxamide,
301. Methyl(2S)-2-[5-(2,4-difluorophenyl)-4,5-diazatricyclo[5.2.1.0$^{2,6}$]deca-2(6),3-dien-3-ylcarboxamido]-2-phenylethanoate,
302. N5-[(1S)-2-Hydroxy-1-phenylethyl]-3-(2,4-difluorophenyl)-3,4-diazatricyclo[5.2.1.0$^{2,6}$]deca-2(6),4-diene-5-carboxamide,
303. N(3)-(tert-Butyl)-1-(2,4-difluorophenyl)-4,5,6,7-tetrahydro-1H-4,7-methano-indazole-3-carboxamide,
304. (4S,7S) or (4S,7R)—N(3)-(tert-Butyl)-1-(2,4-difluorophenyl)-4,5,6,7-tetrahydro-1H-4,7-methano-indazole-3-carboxamide,
305. (4S,7R) or (4R,7S)—N(3)-(tert-Butyl)-1-(2,4-difluorophenyl)-4,5,6,7-tetrahydro-1H-4,7-methano-indazole-3-carboxamide,
306. N5-n-Pentyl-3-(2,4-difluorophenyl)-3,4-diazatricyclo[5.2.1.0$^{2,6}$]deca-2(6),4-diene-5-carboxamide,
307. N5-(2,4-Dichlorobenzyl)-3-(2,4-difluorophenyl)-3,4-diazatricyclo[5.2.1.0$^{2,6}$]deca-2(6),4-diene-5-carboxamide,
308. N5-(1-phenylcyclopropyl)-3-(2,4-difluorophenyl)-3,4-diazatricyclo[5.2.1.0$^{2,6}$]deca-2(6),4-diene-5-carboxamide,
309. N5-(2-Adamantyl)-3-(2,4-difluorophenyl)-3,4-diazatricyclo[5.2.1.0$^{2,6}$]deca-2(6),4-diene-5-carboxamide,
310. N5-(2-Methyl-2-adamantyl)-3-(2,4-difluorophenyl)-3,4-diazatricyclo[5.2.1.0$^{2,6}$]deca-2(6),4-diene-5-carboxamide,
311 N7-(3-Hydroxyadamantan-1-yl)-5-(2,4-difluorophenyl)-5,6-diazatetracyclo[7.3.1.1$^{3,11}$.0$^{4,8}$]tetradeca-4(8),6-diene-7-carboxamide,
312. 4-[5-(2,4-Difluorophenyl)-4,5-diazatricyclo[5.2.1.0$^{2,6}$]deca-2(6),3-dien-3-ylcarboxamido]morpholine,
313. N(3)-(tert-Pentyl)-1-(2,4-difluorophenyl)-4,5,6,7-tetrahydro-1H-4,7-methano-indazole-3-carboxamide,
314. N(3)-Cyclopropanmethyl-1-(2,4-difluorophenyl)-4,5,6,7-tetrahydro-1H-4,7-methano-indazole-3-carboxamide,
315. N(3)-Cyclobutyl-1-(2,4-difluorophenyl)-4,5,6,7-tetrahydro-1H-4,7-methano-indazole-3-carboxamide,
316. N(3)-(Tetrahydro-2H-4-pyranmethyl)-1-(2,4-difluorophenyl)-4,5,6,7-tetrahydro-1H-4,7-methano-indazole-3-carboxamide,
317. N(3)-Cyclopropyl-1-(2,4-difluorophenyl)-4,5,6,7-tetrahydro-1H-4,7-methano-indazole-3-carboxamide,
318. N(3)-(4-methylpiperazino)-1-(2,4-difluorophenyl)-4,5,6,7-tetrahydro-1H-4,7-methano-indazole-3-carboxamide,
319. Methyl(2R)-2-[5-(2,4-difluorophenyl)-4,5-diazatricyclo[5.2.1.0$^{2,6}$]deca-2(6),3-dien-3-ylcarboxamido]-2-phenylethanoate,
320. N(3)-[(1R)-2-Hydroxy-1-phenylethyl]-1-(2,4-difluorophenyl)-4,5,6,7-tetrahydro-1H-4,7-methano-indazole-3-carboxamide,
321. N(3)-(tert-Butyl)-1-(4-chlorophenyl)-4,5,6,7-tetrahydro-1H-4,7-methano-indazole-3-carboxamide, 322. N(3)-(Tetrahydro-2-furanylmethyl)-1-(2,4-difluorophenyl)-4,5,6,7-tetrahydro-1H-4,7-methano-indazole-3-carboxamide,
323. N(3)-(tert-Butyl)-1-(4-fluorophenyl)-4,5,6,7-tetrahydro-1H-4,7-methano-indazole-3-carboxamide,
324. N(3)-(tert-Butyl)-1-(4-bromophenyl)-4,5,6,7-tetrahydro-1H-4,7-methano-indazole-3-carboxamide,
325. N(3)-(tert-Butyl)-1-(3,4-dichlorophenyl)-4,5,6,7-tetrahydro-1H-4,7-methano-indazole-3-carboxamide,
326. Methyl(2S)-2-[5-(2,4-difluorophenyl)-4,5-diazatricyclo[5.2.1.0$^{2,6}$]deca-2(6),3-dien-3-ylcarboxamido]-2-(4-fluorophenyl)ethanoate,
327. N(3)-(tert-Butyl)-1-(2,4-dichlorophenyl)-4,5,6,7-tetrahydro-1H-4,7-methano-indazole-3-carboxamide,
328. N(3)-(4-Hydroxyphenyl)-1-(2,4-difluorophenyl)-4,5,6,7-tetrahydro-1H-4,7-methano-indazole-3-carboxamide,
329. N(3)-(tert-Butyl)-1-(2-ethoxy,4-fluorophenyl)-4,5,6,7-tetrahydro-1H-4,7-methano-indazole-3-carboxamide,
330. N(3)-(2-furylmethyl)-1-(2,4-difluorophenyl)-4,5,6,7-tetrahydro-1H-4,7-methano-indazole-3-carboxamide:
331. N(3)-(2-thiophenemethyl)-1-(2,4-difluorophenyl)-4,5,6,7-tetrahydro-1H-4,7-methano-indazole-3-carboxamide:
332. N(3)-[(1S)-2-Hydroxy-1-(4-fluorophenyl)ethyl]-1-(2,4-difluorophenyl)-4,5,6,7-tetrahydro-1H-4,7-methano-indazole-3-carboxamide:
333. Methyl-(2S)-2-[5-(2,4-difluorophenyl)-4,5-diazatricyclo[5.2.1.0$^{2,6}$]deca-2 (6),3-dien-3-ylcarboxamido]-4-methylpentanoate:
334. N(3)-(Adamantan-1yl)-1-(2,4-difluorophenyl)-4,5,6,7-tetrahydro-1H-4,7-methano-indazole-3-carboxamide:
335a N(3)-(tert-butyl)-1-(4-fluorobenzyl)-4,5,6,7-tetrahydro-1H-4,7-methano-indazole-3-carboxamide:
335b N(3)-(tert-butyl)-2-(4-fluorobenzyl)-4,5,6,7-tetrahydro-1H-4,7-methano-indazole-3-carboxamide:
336a N(3)-(tert-butyl)-1-(4-methylbenzyl)-4,5,6,7-tetrahydro-1H-4,7-methano-indazole-3-carboxamide:
336b N(3)-(tert-butyl)-2-(4-methylbenzyl)-4,5,6,7-tetrahydro-1H-4,7-methano-indazole-3-carboxamide:
337. N(3)-(2-hydroxyethyl)-1-(2,4-difluorophenyl)-4,5,6,7-tetrahydro-1H-4,7-methano-indazole-3-carboxamide,
338. N(3)-(Thienylethyl)-1-(2,4-difluorophenyl)-4,5,6,7-tetrahydro-1H-4,7-methano-indazole-3-carboxamide,
339. N(3)-(Isopropyl)-1-(2,4-difluorophenyl)-4,5,6,7-tetrahydro-1H-4,7-methano-indazole-3-carboxamide,
340. N(3)-[(1S)-2-Methoxy-1-phenylethyl]-1-(2,4-difluorophenyl)-4,5,6,7-tetrahydro-1H-4,7-methano-indazole-3-carboxamide,
401. N(3)-Phenyl-1-(2,4-dichlorophenyl)-7,8,8-trimethyl-4,5,6,7-tetrahydro-1H-4,7-methano-indazole-3-carboxamide,
402. N(3)-[(2-Fluorophenyl)amino]-1-(2,4-Dichlorophenyl)-7,8,8-trimethyl-4,5,6,7-tetrahydro-1H-4,7-methano-indazole-3-carboxamide,
403. N(3)-[(2,4-Difluorophenyl)amino]-(2,4-Dichlorophenyl)-7,8,8-trimethyl-4,5,6,7-tetrahydro-1H-4,7-methano-indazole-3-carboxamide,
404. N(3)-[(3-chloropyridin-2-yl)amino]-1-(2,4-Dichlorophenyl)-7,8,8-trimethyl-4,5,6,7-tetrahydro-1H-4,7-methano-indazole-3-carboxamide,
405. N(3)-(Adamantan-1-yl)-1-(2,4-difluorophenyl)-7,8,8-trimethyl-4,5,6,7-tetrahydro-1H-4,7-methano-indazole-3-carboxamide,
406. N(3)-(1,3,3-Trimethylbicyclo[2.2.1]hept-2-yl)-1-(2,4-difluorophenyl)-7,8,8-trimethyl-4,5,6,7-tetrahydro-1H-4,7-methano-indazole-3-carboxamide,
407. N(3)-(1-Methyl-1-phenylethyl))-1-(2,4-difluorophenyl)-7,8,8-trimethyl-4,5,6,7-tetrahydro-1H-4,7-methano-indazole-3-carboxamide,
408. (4R,7S)—N(3)-tert-Butyl-1-(2,4-difluorophenyl)-7,8,8-trimethyl-4,5,6,7-tetrahydro-1H-methano-indazole-3-carboxamide,
409. Methyl (2R)-2-[1-(2,4-difluorophenyl)-7,8,8-trimethyl-4,5,6,7-tetrahydro-1H-4,7-methano-indazole-3-carboxamido]-2-phenylethanoate,
410. N(3)-[(1R-2-Hydroxy-1-phenylethyl]-1-(2,4-difluorophenyl)-7,8,8-trimethyl-4,5,6,7-tetrahydro-1H-4,7-methano-indazole-3-carboxamide,
411. (4S,7R)—N(3)-tert-Butyl-1-(2,4-difluorophenyl)-7,8,8-trimethyl-4,5,6,7-tetrahydro-1H-methano-indazole-3-carboxamide,
412. N(3)-pentyl-1-(2,4-difluorophenyl)-7,8,8-trimethyl-4,5,6,7-tetrahydro-1H-methano-indazole-3-carboxamide
501. N(12)-Benzyl-10-(2,4-dichlorophenyl)-10,11-diazatetracyclo[6.5.2.0$^{2,7}$.0$^{9,13}$]pentadeca-2,4,6,9(13),11-pentaene-12-carboxamide,
502. N(12)-Piperidino-10-(2,4-dichlorophenyl)-10,11-diazatetracyclo[6.5.2.0$^{2,7}$.0$^{9,13}$]pentadeca-2,4,6,9(13),11-pentaene-12-carboxamide,
503. N(12)-Piperidino-10-(2,4-dichlorophenyl)-10,11-diazatetracyclo[6.5.2.0$^{2,7}$.0$^{9,13}$]pentadeca-2,4,6,9(13),11-pentaene-12-carboxamide, hydrochloride,
504. N(12)-[(N'-Cyclohexyl-N'-methyl)amino]-10-(2,4-dichlorophenyl)-10,11-diazatetracyclo[6.5.2.0$^{2,7}$.0$^{9,13}$]pentadeca-2,6,9(13), 11-pentaene-12-carboxamide,
505. N(12)-{N'-[(2,4-Dichlorophenyl)-N'-methyl]amino}-10-(2,4-dichlorophenyl)-10,11-diazatetracyclo[6.5.2.0$^{2,7}$.0$^{9,13}$]pentadeca-2,4,6,9(13),11-pentaene-12-carboxamide,
506. N(12)-(Adamantan-1yl)-10-(2,4-dichlorophenyl)-10,11-diazatetracyclo[6.5.2.0$^{2,7}$.0$^{9,13}$]pentadeca-2,4,6,9(13),11-pentaene-12-carboxamide,
507. N12-(1,3,3-Trimethylbicyclo[2.2.1]hept-2-yl)-10-(2,4-dichlorophenyl)-10,11-diazatetracyclo[6.5.2.0$^{2,7}$.0$^{9,13}$]pentadeca-2(7),3,5,9(13),11-pentaene-12-carboxamide,
508. N12-(1-Methyl-1-phenylethyl)-10-(2,4,dichlorophenyl)-10,11-diazatetracyclo[6.5.2.0$^{2,7}$.0$^{9,13}$]pentadeca-2,4,6,9(13),11-pentaene-12-carboxamide,
509. N12-(1-Methyl-1-phenylethyl)-10-(2,4-difluorophenyl)-10,11-diazatetracyclo[6.5.2.0$^{2,7}$.0$^{9,13}$]pentadeca-2,4,6,9(13),11-pentaene-12-carboxamide,
601. N(12)-Benzyl-16-(4-chlorophenyl)-10-(2,4-dichlorophenyl)-15,17-dioxo-10,11,16-triazapentacyclo[6.5.2.0$^{2,7}$.0$^{9,13}$.0$^{14,18}$]octadeca-2,4,6,9(13),11-pentaene-12-carboxamide,
602. N(12)-Piperidino-16-(4-chlorophenyl)-10-(2,4-dichlorophenyl)-15,17-dioxo-10,11,16-triazapentacyclo[6.5.2.0$^{2,7}$.0$^{9,13}$.0$^{14,18}$]octadeca-2,4,6,9(13),11-pentaene-12-carboxamide,
701. N12-Benzyl-10-(2,4-difluorophenyl)-10,11-diazatetracyclo[6.5.2.0$^{2,7}$.0$^{9,13}$]tetradeca-2,4,6,9(13),11-pentaene-12-carboxamide,
702. N(12)-tert-Butyl-10-(2,4-difluorophenyl)-10,11-diazatetracyclo[6.5.2.0$^{2,7}$.0$^{9,13}$]tetradeca-2,4,6,9(13),11-pentaene-12-carboxamide,
703. N12-(1-Methyl-1-phenylethyl)-10-(2,4-difluorophenyl)-10,11-diazatetracyclo[6.5.2.0$^{2,7}$.0$^{9,13}$]tetradeca-2,4,6,9(13),11-pentaene-12-carboxamide,
801. N5-(tert-Butyl)-3-(2,4-difluorophenyl)-3,4-diazatricyclo[5.2.1.0$^{2,6}$]undeca-2(6),4-diene-5-carboxamide,
802. N(5)-(tert-Pentyl)-3-(2,4-difluorophenyl)-3,4-diazatricyclo[5.2.1.0$^{2,6}$]undeca-2(6),4-diene-5-carboxamide.

| Example No. | R | R¹ | R² |
|---|---|---|---|
| 101 | 2-bromophenyl | H | piperidin-1-yl |
| 102 | 2-bromophenyl | H | benzyl |
| 103 | 4-chlorophenyl | H | morpholin-4-yl |
| 104 | 4-chlorophenyl | H | pyridin-3-ylmethyl |
| 105 | 4-chlorophenyl | H | pyridin-4-ylmethyl |
| 106 | 4-chlorophenyl | H | cyclohexyl |
| 107 | 4-chlorophenyl | H | N-methyl-N-cyclohexyl |
| 108 | 6-chloropyridin-3-yl | H | cyclohexylmethyl |
| 109 | 4-chlorophenyl | H | adamantan-1-yl |
| 110 | 4-chlorophenyl | H | bornyl |

-continued
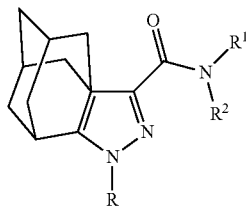
I(a)
| Example No. | R | R¹ | R² |
|---|---|---|---|
| 111 | 4-Cl-C₆H₄- | H | 2-Cl-C₆H₄-CH₂- |
| 112 | 4-Cl-C₆H₄- | H | 5-Cl-pyridin-2-yl-CH₂- |
| 113 | 4-Cl-C₆H₄- | H | 4-F-C₆H₄-CH₂- |
| 114 | 4-Cl-C₆H₄- | H | 2,4-diF-C₆H₃-CH₂- |
| 115 | 4-Cl-C₆H₄- | H | 2,6-diF-C₆H₃-CH₂- |
| 116 | 4-Cl-C₆H₄- | H | 4-CF₃-C₆H₄-CH₂- |
| 117 | 5-Cl-pyridin-2-yl- | H | (S)-CH(CH₃)-C₆H₅ |
| 118 | 4-Cl-C₆H₄- | H | (R)-CH(CH₃)-C₆H₅ |
| 119 | 4-Cl-C₆H₄- | H | C(CH₃)₂-C₆H₅ |
| 120 | 4-Cl-C₆H₄- | H | pyridin-2-yl-CH₂- |

-continued
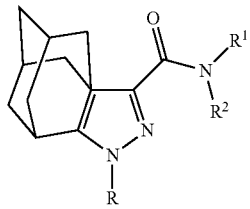
I(a)
| Example No. | R | R¹ | R² |
|---|---|---|---|
| 121 | 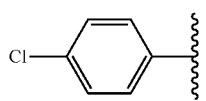 [SMILES: *c1ccc(Cl)cc1] | H | 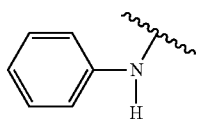 |
| 122* | 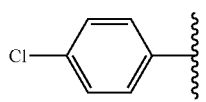 | H | 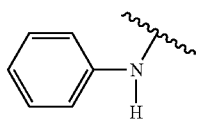 [SMILES: *Nc1ccccc1] |
| 123 | 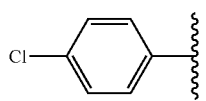 | H | 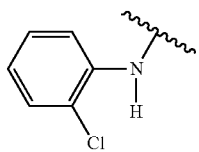 [SMILES: *Nc1ccccc1Cl] |
| 124* | 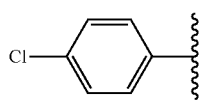 | H | 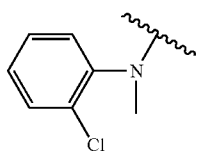 [SMILES: *N(C)c1ccccc1Cl] |
| 125 | 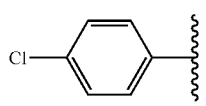 | H | 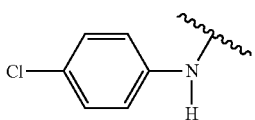 [SMILES: *Nc1ccc(Cl)cc1] |
| 126 | 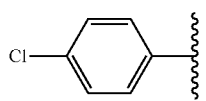 | H | 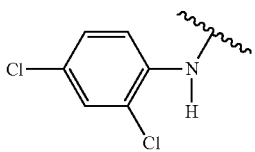 |
| 127 | 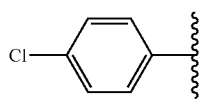 | H | 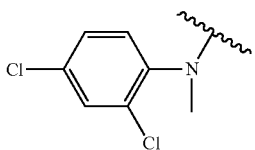 [SMILES: *N(C)c1ccc(Cl)cc1Cl] |
| 128* | 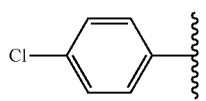 | H | 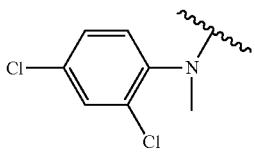 [SMILES: *N(C)c1ccc(Cl)cc1Cl] |

-continued
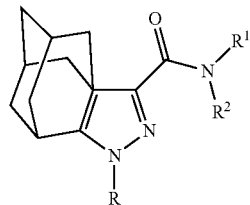
I(a)
| Example No. | R | R¹ | R² |
|---|---|---|---|
| 129 | 4-Cl-C₆H₄- | H | N-(2,4-dichlorophenyl)-cyclohexyl |
| 130 | 4-Cl-C₆H₄- | H | 4-F-C₆H₄-NH- |
| 131* | 4-Cl-C₆H₄- | H | 4-F-C₆H₄-NH- |
| 132 | 4-Cl-C₆H₄- | H | 2,4-diF-C₆H₃-NH- |
| 133 | 4-Cl-C₆H₄- | H | 3-F-C₆H₄-NH- |
| 134 | 6-Cl-pyridin-3-yl | H | 3-Cl-pyridin-2-yl-NH- |
| 135 | 4-Cl-C₆H₄- | H | 5-Cl-pyridin-2-yl-NH- |
| 136 | 4-Cl-C₆H₄- | H | PhCH₂CH₂- |

-continued
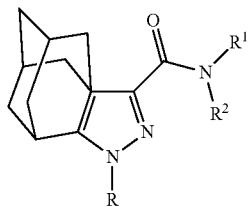
I(a)
| Example No. | R | R¹ | R² |
|---|---|---|---|
| 137 | 4-Cl-phenyl | H | N,N-diphenylamino |
| 138 | 4-Cl-phenyl | H | 1-(2-chlorophenyl)ethyl |
| 139 | 4-Cl-phenyl | H | benzyl |
| 140 | 4-Cl-phenyl | H | piperidin-1-yl |
| 141 | 4-Cl-phenyl | H | piperidin-1-yl |
| 142 | 4-Cl-phenyl | H | phenyl |
| 143 | 2,4-diF-phenyl | H | piperidin-1-yl |
| 144 | 2,4-diF-phenyl | H | adamantan-1-yl |
| 145 | 2,4-diF-phenyl | H | 2-methylbicyclo[2.2.2]octyl |
| 146 | 2,4-diF-phenyl | H | (S)-1-phenylethyl |

-continued
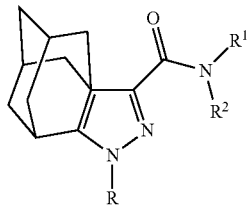
I(a)
| Example No. | R | R¹ | R² |
|---|---|---|---|
| 147 | 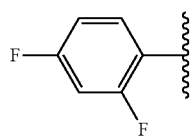 [SMILES: *c1ccc(F)cc1F] | H | 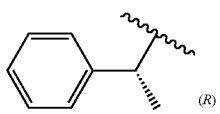 (R) |
| 148 | 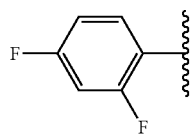 | H | 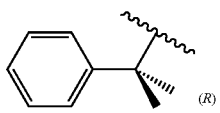 (R) |
| 149 | 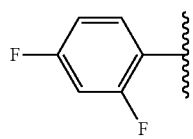 [SMILES: *c1ccc(F)cc1F] | H | 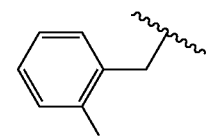 |
| 150 | 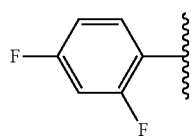 [SMILES: *c1ccc(F)cc1F] | H | 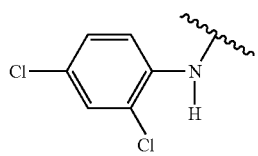 |
| 151 | 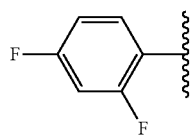 [SMILES: *c1ccc(F)cc1F] | H | 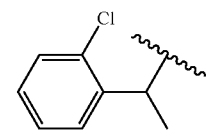 [SMILES: *C(C)c1ccccc1Cl] |
| 152 | 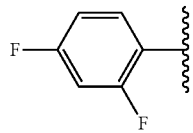 [SMILES: *c1ccc(F)cc1F] | H | 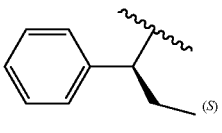 (S) |
| 153 | 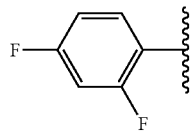 [SMILES: *c1ccc(F)cc1F] | H | 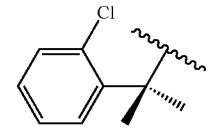 |
| 154 | 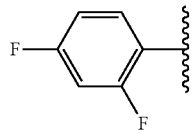 [SMILES: *c1ccc(F)cc1F] | H | 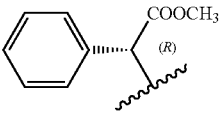 (R) |

-continued
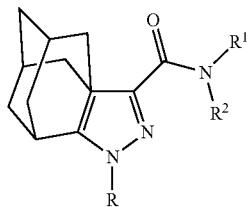
I(a)
| Example No. | R | R¹ | R² |
|---|---|---|---|
| 155 | 2,4-difluorophenyl | H | (S)-CH(Ph)(COOCH₃) |
| 156 | 2,4-difluorophenyl | H | 3-hydroxyadamantan-1-yl |
| 157 | 4-fluorophenyl | H | 2-phenylpropan-2-yl (with methyl stereochemistry) |
| 158 | 4-fluorophenyl | H | adamantan-1-yl |
| 158a | 4-fluorophenyl | H | adamantan-2-yl |
| 159 | 4-fluorophenyl | H | bornyl |
| 160 | 4-methylphenyl | H | piperidin-1-yl |
| 161 | 4-methylphenyl | H | 2,4-dichlorophenylamino |

-continued
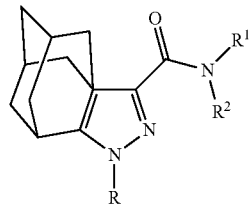
I(a)
| Example No. | R | R¹ | R² |
|---|---|---|---|
| 162 | 4-Me-C₆H₄- | H | 2-Cl-C₆H₄-CH₂- |
| 163 | 4-MeO-C₆H₄- | H | piperidin-1-yl |
| 164 | 4-MeO-C₆H₄- | H | 2-Cl-C₆H₄-CH₂- |
| 165 | 4-MeO-C₆H₄- | H | 2,4-diCl-C₆H₃-NH- |
| 166 | 4'-Cl-biphenyl-2-yl | H | piperidin-1-yl |
| 167 | C₆H₅- | H | 2,4-diCl-C₆H₃-NH- |
| 168 | pyridin-3-yl | H | C₆H₅- |
| 169 | C₆H₅- | H | piperidin-1-yl |
| 170 | C₆H₅- | H | C₆H₅-CH₂- |
| 171 | C₆H₅- | H | piperidin-1-yl |

-continued
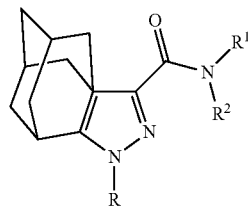
I(a)
| Example No. | R | R¹ | R² |
|---|---|---|---|
| 172 | 2,4-diCl-phenyl | H | 4-F-benzyl |
| 173 | 2,4-diCl-phenyl | H | phenyl-NH- |
| 174 | 2,4-diCl-phenyl | H | 2-Cl-phenyl-NH- |
| 175 | 2,4-diCl-phenyl | H | 2,4-diCl-phenyl-NH- |
| 176 | 2,4-diCl-phenyl | H | 2-Br-phenyl-NH- |
| 177 | 2,4-diCl-phenyl | H | N,N-diphenyl |
| 178 | 2,4-diCl-phenyl | H | 2-phenylethyl |
| 179 | 2,4-diCl-phenyl | H | benzyl |

-continued
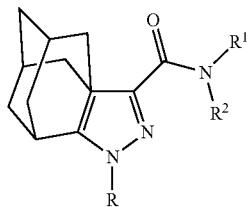
I(a)
| Example No. | R | R¹ | R² |
|---|---|---|---|
| 180 | 2,4-dichlorophenyl | H | piperidin-1-yl |
| 181 | 2-chlorophenyl | H | (2,4-dichlorophenyl)NH– |
| 182 | 2-chlorophenyl | H | benzyl |
| 183 | 2-chlorophenyl | H | cyclohexyl |
| 184 | 2-chlorophenyl | H | piperidin-1-yl |
| 185 | 5-chloropyridin-2-yl | H | 2-chlorobenzyl |
| 186 | H | H | benzyl |
| 187 | H | H | piperidin-1-yl |
| 188 | H | H | piperidin-1-yl |

-continued
I(a)
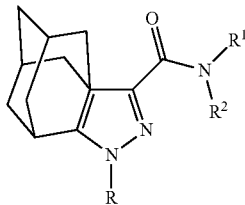
| Example No. | R | R¹ | R² |
|---|---|---|---|
| 189b | CH₃I | H | piperidin-1-yl |
| 190b | hexyl | H | 2-phenylpropan-2-yl (cumyl) |
| 191 | 2,4-difluorophenyl | H | (R)-2-phenyl-2-hydroxymethyl (β-hydroxy, phenyl) |
| 192 | 2,4-difluorophenyl | H | (S)-2-phenyl-2-hydroxymethyl |
I(aa)
| Example no | R | R₁ | R₂ |
|---|---|---|---|
| 189a | CH₃ | H | piperidin-1-yl |
| 190a | hexyl | H | 2-phenylpropan-2-yl (cumyl) |
*Indicates HCl salt
TABLE (Ib)
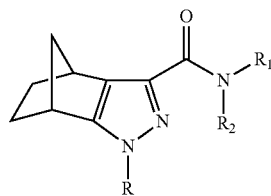
| Example No. | R | R₁ | R₂ |
|---|---|---|---|
| 201 | phenyl | H | piperidin-1-yl |
| 202 | phenyl | H | cyclohexyl |
| 203 | phenyl | H | benzyl |

TABLE (Ib)-continued

| Example No. | R | R₁ | R₂ |
|---|---|---|---|
| 204 | phenyl | H | 2-NH-phenyl |
| 205 | 2-chlorophenyl | H | piperidin-1-yl |
| 206 | 2-chlorophenyl | H | cyclohexyl |
| 207 | 2-chlorophenyl | H | benzyl |
| 208 | 2-chlorophenyl | H | 2-NH-phenyl |
| 209 | 4-chlorophenyl | H | piperidin-1-yl |
| 210 | 4-chlorophenyl | H | piperidin-1-yl |
| 211 | 4-chlorophenyl | H | cyclohexyl |
| 212 | 4-chlorophenyl | H | cyclopentyl |
| 213 | 2,4-dichlorophenyl | H | N(Me)cyclohexyl |
| 214 | 4-chlorophenyl | H | phenyl |
| 215 | 4-chlorophenyl | H | 3-chlorophenyl |
| 216 | 4-chlorophenyl | H | 4-chlorophenyl |
| 217 | 4-chlorophenyl | H | 3-bromophenyl |
| 218 | 4-chlorophenyl | H | 2-methoxyphenyl |
| 219 | 4-chlorophenyl | H | 4-tert-butylphenyl |
| 220 | 4-chlorophenyl | H | α-methylbenzyl |
| 221 | 4-chlorophenyl | H | 2-chlorobenzyl |
| 222 | 4-chlorophenyl | H | α-methyl-4-chlorobenzyl |
| 223 | 4-chlorophenyl | H | 2,4-dichlorobenzyl |

TABLE (Ib)-continued

| Example No. | R | R₁ | R₂ |
|---|---|---|---|
| 224 | 4-Cl-C₆H₄- | H | 2-Br-benzyl |
| 225 | 4-Cl-C₆H₄- | H | 4-Br-benzyl |
| 226 | 4-Cl-C₆H₄- | H | 4-F-benzyl |
| 227 | 4-Cl-C₆H₄- | H | 4-CF₃-benzyl |
| 228 | 4-Cl-C₆H₄- | H | phenyl-NH- |
| 229 | 4-Cl-C₆H₄- | H | 4-Cl-phenyl-NH- |
| 230 | 4-Cl-C₆H₄- | H | 2,5-diCl-phenyl-NH- |
| 231 | 4-Cl-C₆H₄- | H | 3,4-diCl-phenyl-NH- |
| 232 | 4-Cl-C₆H₄- | H | 2-F-phenyl-NH- |
| 233 | 4-Cl-C₆H₄- | H | 3-F-phenyl-NH- |
| 234 | 4-Cl-C₆H₄- | H | 4-F-phenyl-NH- |
| 235 | 4-Cl-C₆H₄- | H | 2,4-diF-phenyl-NH- |
| 236 | 4-Cl-C₆H₄- | H | N,N-diphenyl |
| 237 | 2,4-diCl-C₆H₃- | H | cyclohexyl |
| 238 | 2,4-diCl-C₆H₃- | H | cyclohexylmethyl |
| 239 | 2,4-diCl-C₆H₃- | H | N,N-dicyclohexyl |
| 240 | 2,4-diCl-C₆H₃- | H | 1,2,4-triazol-1-yl |
| 241 | 2,4-diCl-C₆H₃- | H | bornyl (1S, endo) |
| 242 | 2,4-diCl-C₆H₃- | H | 1-adamantyl |

TABLE (Ib)-continued

| Example No. | R | R₁ | R₂ |
|---|---|---|---|
| 243 | 2,4-diCl-phenyl | H | phenyl-CH₂- |
| 244 | 2,4-diCl-phenyl | H | 2,4-diF-phenyl-CH₂- |
| 245 | 2,4-diCl-phenyl | H | 2-F-phenyl-CH(CH₃)- |
| 246 | 2,4-diCl-phenyl | H | 4-F-phenyl-CH₂- |
| 247 | 2,4-diCl-phenyl | H | 2,3-diF-phenyl-CH₂- |
| 248 | 2,4-diCl-phenyl | H | 2,6-diF-phenyl-CH(CH₃)- |
| 249 | 2,4-diCl-phenyl | H | 2-Cl-phenyl-CH(CH₃)- |
| 250 | 2,4-diCl-phenyl | H | 4-Cl-phenyl-CH₂- |
| 251 | 2,4-diCl-phenyl | H | 2,4-diCl-phenyl-CH₂- |
| 252 | 2,4-diCl-phenyl | H | (S)-1-phenylethyl |
| 253 | 2,4-diCl-phenyl | H | (R)-1-phenylethyl |
| 254 | 2,4-diCl-phenyl | H | phenyl-CH₂CH₂- |
| 255 | 2,4-diCl-phenyl | H | 4-F-phenyl-CH₂CH₂- |
| 256 | 2,4-diCl-phenyl | H | phenyl-NH- |
| 257 | 2,4-diCl-phenyl | H | 2-Cl-phenyl-NH- |
| 258 | 2,4-diCl-phenyl | H | 2-Cl-phenyl-N(Me)- |
| 259 | 2,4-diCl-phenyl | H | 4-Cl-phenyl-NH- |
| 260 | 2,4-diCl-phenyl | H | 2,4-diCl-phenyl-NH- |
| 261 | 2,4-diCl-phenyl | H | 2,4-diCl-phenyl-N(Me)- |

TABLE (Ib)-continued

| Example No. | R | R₁ | R₂ |
|---|---|---|---|
| 262 | 2,4-diCl-phenyl | H | 3,4-diCl-phenyl-NH |
| 263 | 2,4-diCl-phenyl | H | 2-Br-phenyl-NH |
| 264 | 2,4-diCl-phenyl | H | 2-F-phenyl-NH |
| 265 | 2,4-diCl-phenyl | H | 2,4-diF-phenyl-NH |
| 266 | 2,4-diCl-phenyl | H | 3-F-phenyl-NH |
| 267 | 2,4-diCl-phenyl | H | 3-Cl-pyridin-2-yl-NH |
| 268 | 2,4-diCl-phenyl | H | piperidin-1-yl |
| 269 | 2,4-diCl-phenyl | H | benzyl |
| 270 | 2-Br-phenyl | H | piperidin-1-yl |
| 271 | 2-Br-phenyl | H | cyclohexyl |
| 272 | 2-Br-phenyl | H | benzyl |
| 273 | 2-Br-phenyl | H | phenyl-NH |
| 274 | 4-Br-phenyl | H | piperidin-1-yl |
| 275 | 4-Br-phenyl | H | cyclohexyl |
| 276 | 4-Br-phenyl | H | benzyl |
| 277 | 4-Br-phenyl | H | phenyl-NH |
| 278 | 4-Br-phenyl | H | 2-F-phenyl-NH |
| 279 | 4-F-phenyl | H | cyclohexyl |
| 280 | 4-F-phenyl | H | benzyl |

TABLE (Ib)-continued

| Example No. | R | R₁ | R₂ |
|---|---|---|---|
| 281 | 4-F-phenyl | H | adamantan-2-yl |
| 282 | 4-F-phenyl | H | 2-phenylpropan-2-yl |
| 283 | 4-F-phenyl | H | adamantan-1-yl |
| 284 | 4-F-phenyl | H | phenyl-NH- |
| 285 | 2,4-diF-phenyl | H | phenyl-NH- |
| 286 | 2,4-diF-phenyl | H | 2-Cl-phenyl-NH- |
| 287 | 2,4-diF-phenyl | H | 2-Br-phenyl-NH- |
| 288 | 2,4-diF-phenyl | H | 2-F-phenyl-NH- |
| 289 | 2,4-diF-phenyl | H | piperidin-1-yl |
| 290 | 2,4-diF-phenyl | H | cyclohexyl |
| 291 | 2,4-diF-phenyl | H | cyclohexylmethyl |
| 292 | 2,4-diF-phenyl | H | (S)-1-phenylethyl |
| 293 | 2,4-diF-phenyl | H | (R)-1-phenylethyl |
| 294 | 2,4-diF-phenyl | H | 2-phenylpropan-2-yl |
| 295 | 2,4-diF-phenyl | H | 1-(2-Cl-phenyl)ethyl |
| 296 | 2,4-diF-phenyl | H | bornyl |
| 297 | 2,4-diF-phenyl | H | 1-(2-Cl-phenyl)ethyl |
| 298 | 2,4-diF-phenyl | H | 4-Cl-benzyl |

TABLE (Ib)-continued

| Example No. | R | R₁ | R₂ |
|---|---|---|---|
| 299 | 2,4-difluorophenyl | H | 3-phenylpentan-3-yl |
| 300 | 2,4-difluorophenyl | H | 1-phenylpropyl |
| 301 | 2,4-difluorophenyl | H | α-(methoxycarbonyl)benzyl |
| 302 | 2,4-difluorophenyl | H | 2-phenyl-3-hydroxypropyl |
| 303 | 2,4-difluorophenyl | H | tert-butyl |
| 304 | 2,4-difluorophenyl | H | tert-butyl (4R,7S) or (4S,7R) |
| 305 | 2,4-difluorophenyl | H | tert-butyl (4S,7R) or (4R,7S) |
| 306 | 2,4-difluorophenyl | H | hexyl |
| 307 | 2,4-difluorophenyl | H | 2,4-dichlorobenzyl |
| 308 | 2,4-difluorophenyl | H | 1-phenylcyclopropyl |
| 309 | 2,4-difluorophenyl | H | 2-adamantyl |
| 310 | 2,4-difluorophenyl | H | 2-methyl-2-adamantyl |
| 311 | 2,4-difluorophenyl | H | 3-hydroxy-1-adamantyl |
| 312 | 2,4-difluorophenyl | H | morpholino |
| 313 | 2,4-difluorophenyl | H | 2,2-dimethylbutyl |
| 314 | 2,4-difluorophenyl | H | cyclopropylmethyl |
| 315 | 2,4-difluorophenyl | H | cyclobutyl |
| 316 | 2,4-difluorophenyl | H | (tetrahydro-2H-pyran-4-yl)methyl |

TABLE (Ib)-continued

| Example No. | R | R₁ | R₂ |
|---|---|---|---|
| 317 | 2,4-difluorophenyl | H | cyclopropyl |
| 318 | 2,4-difluorophenyl | H | 4-methylpiperazin-1-yl |
| 319 | 2,4-difluorophenyl | H | -CH(Ph)COOCH₃ |
| 320 | 2,4-difluorophenyl | H | -CH(Ph)CH₂OH |
| 321 | 4-chlorophenyl | H | tert-butyl |
| 322 | 2,4-difluorophenyl | H | tetrahydrofuran-2-ylmethyl |
| 323 | 4-fluorophenyl | H | tert-butyl |
| 324 | 4-bromophenyl | H | tert-butyl |
| 325 | 3,4-dichlorophenyl | H | tert-butyl |
| 326 | 2,4-difluorophenyl | H | -CH(4-F-C₆H₄)COOCH₃ |

TABLE (Ib)-continued

| Example No. | R | R₁ | R₂ |
|---|---|---|---|
| 327 | 2,4-dichlorophenyl | H | tert-butyl |
| 328 | 2,4-difluorophenyl | H | 4-hydroxyphenyl |
| 329 | 4-fluoro-2-ethoxyphenyl | H | tert-butyl |
| 330 | 2,4-difluorophenyl | H | furan-2-ylmethyl |
| 331 | 2,4-difluorophenyl | H | thiophen-2-ylmethyl |
| 332 | 2,4-difluorophenyl | H | (S)-2-(4-fluorophenyl)-2-hydroxymethyl |
| 333 | 2,4-difluorophenyl | H | (S)-CH(iBu)CO₂CH₃ |
| 334 | 2,4-difluorophenyl | H | 1-adamantyl |
| 335a | 4-fluorobenzyl | H | tert-butyl |
| 336a | 4-methylbenzyl | H | tert-butyl |

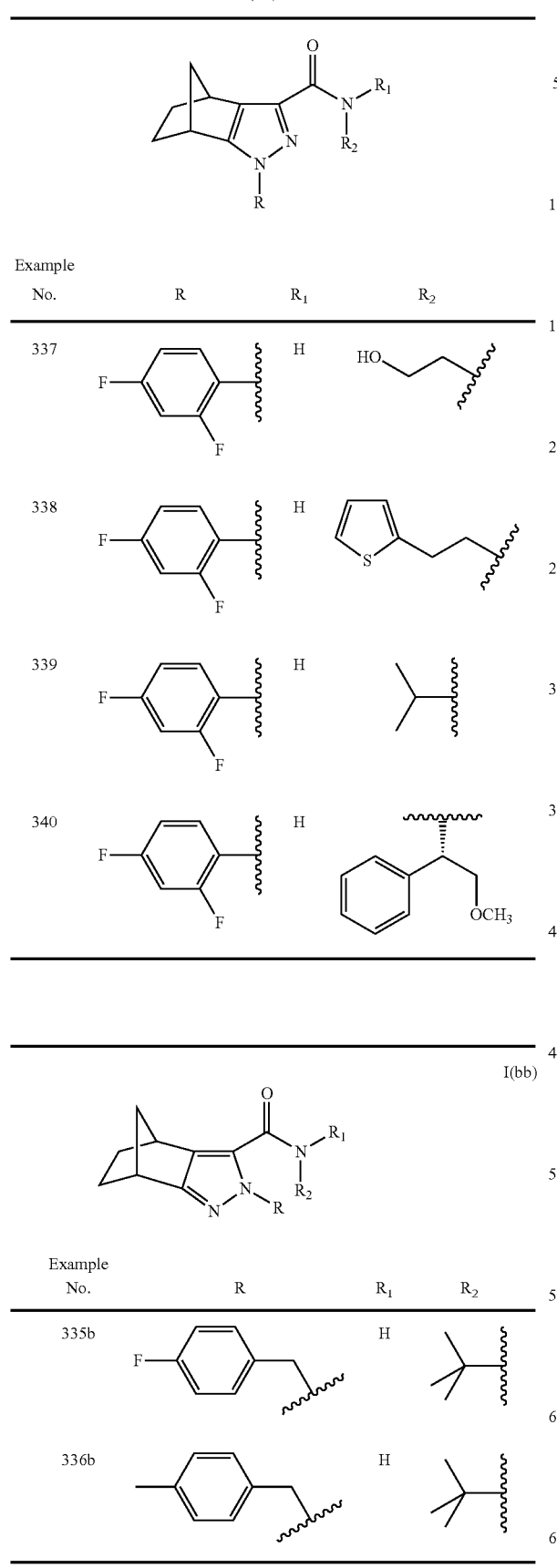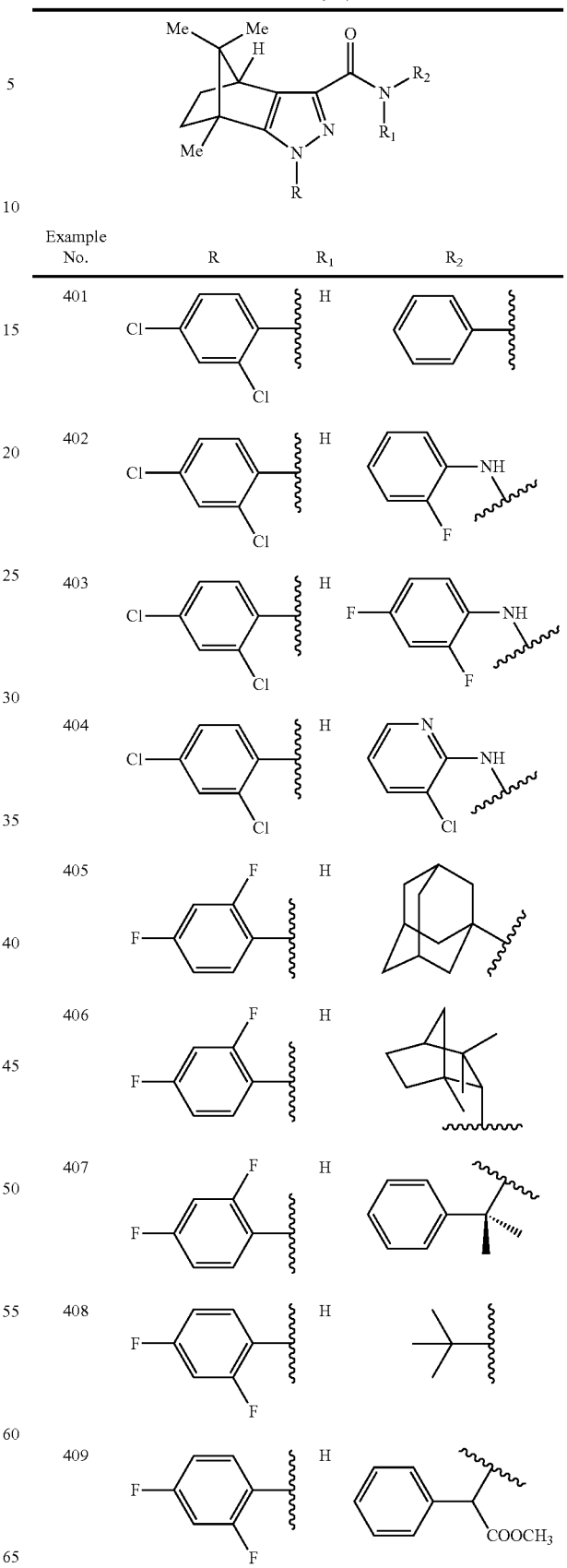

TABLE (1c)-continued
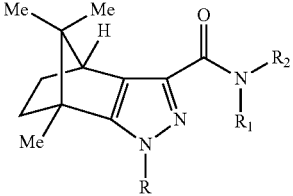
| Example No. | R | R₁ | R₂ |
|---|---|---|---|
| 410 | 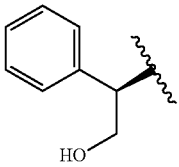 | H | 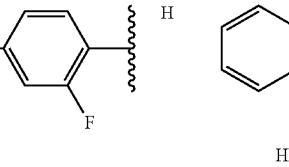 |
| 411 | 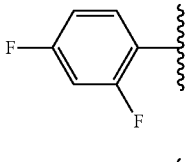 | H |  |
| 412 | 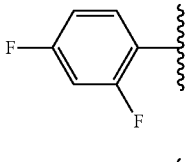 | H | 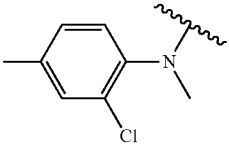 |
TABLE (1d)
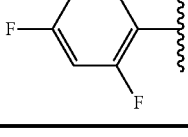
| Example No. | R | R₁ | R₂ |
|---|---|---|---|
| 501 | 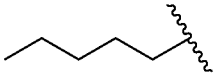 [SMILES: *CCCCC] | H | 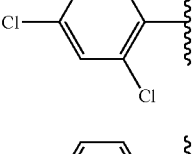 |
| 502 | 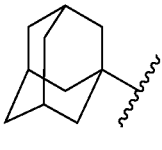 [SMILES: *C12CC3CC(CC(C3)C1)C2] | H | 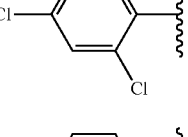 |
| 503* | 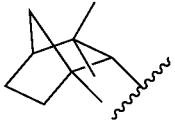 [SMILES: *C1C2(C)CCC(C2)C1(C)C] | H | 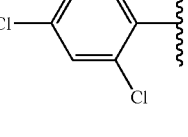 |
| 504 | 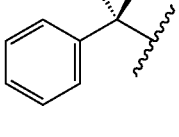 | H | 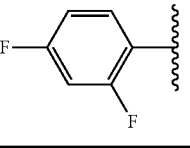 |
TABLE (1d)-continued
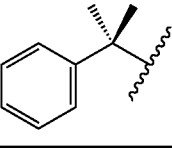
| Example No. | R | R₁ | R₂ |
|---|---|---|---|
| 505 |  | H |  |
| 506 | 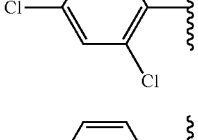 | H | 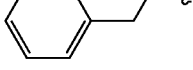 |
| 507 | 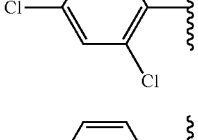 | H | 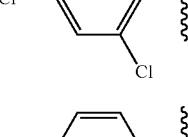 |
| 508 | 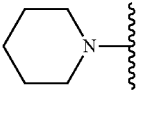 | H | 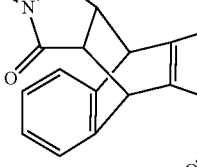 |
| 509 | 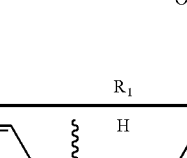 | H | 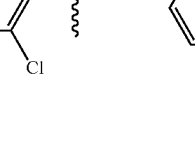 |
TABLE (1e)
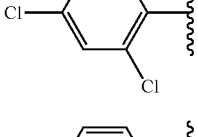
| Example No. | R | R₁ | R₂ |
|---|---|---|---|
| 601 | 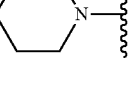 | H | 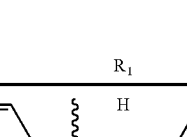 |

TABLE (1e)-continued

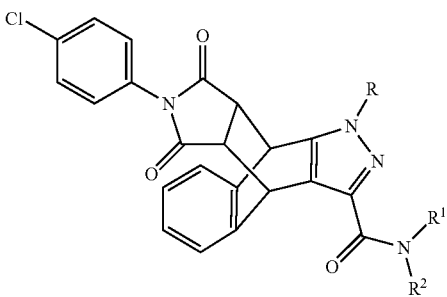

| Example No. | R | R₁ | R₂ |
|---|---|---|---|
| 602 | 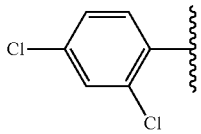 [SMILES: *c1ccc(Cl)cc1Cl] | H | 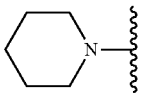 |

TABLE I(f)

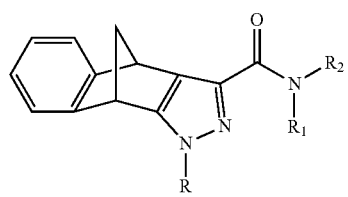

| Example No. | R | R¹ | R² |
|---|---|---|---|
| 701 | 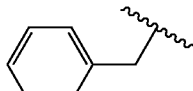 | H | 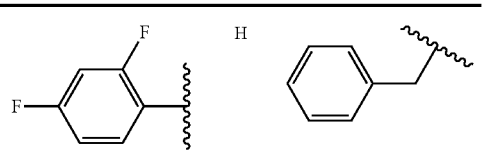 |
| 702 |  | H | 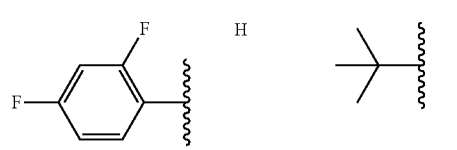 |
| 703 | 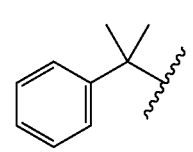 [SMILES: *C(C)(C)c1ccccc1] | H | 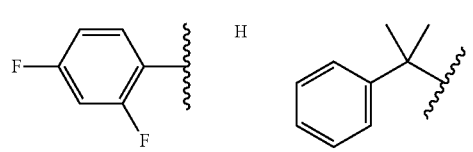 |

TABLE (1g)

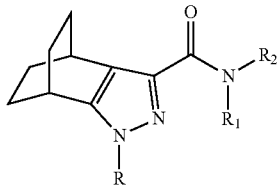

| Example No. | R | R¹ | R² |
|---|---|---|---|
| 801 | 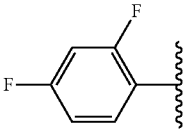 [SMILES: *c1ccc(F)cc1F] | H | 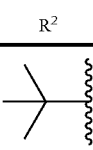 |
| 802 | 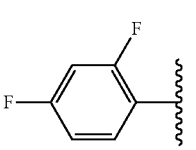 | H | 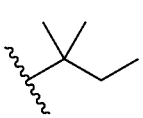 [SMILES: *C(C)(C)CC] |

Another embodiment of the invention is a pharmaceutical composition comprising at least one compound of the present invention and a pharmaceutically acceptable excipient (such as a pharmaceutically acceptable carrier or diluent). Preferably, the pharmaceutical composition comprises a therapeutically effective amount of the compound(s) of the present invention.

Yet another embodiment is a method for preventing, ameliorating or treating a cannabinoid receptor mediated disease, disorder or syndrome (such as a disease, disorder or syndrome mediated by interaction with the CB1 or CB2 receptor) in a subject in need thereof comprising administering to the subject a therapeutically effective amount of a compound of the present invention.

Such conditions include, but are not limited to, appetite disorders, metabolism disorders, catabolism disorders, diabetes, obesity, ophthalmic diseases, social related disorders, mood disorders, seizures, substance abuse, learning disorders, cognition disorders, memory disorders, organ contraction, muscle spasm, respiratory disorders, disorders and diseases, locomotor activity disorders, movement disorders, immune disorders (such as autoimmune disorders), inflammation, cell growth, pain and neurodegenerative related syndromes.

A preferred condition is pain, ophthalmic diseases, respiratory disorders, immune disorders (such as autoimmune disorders), inflammation, cell growth, and neurodegenerative related syndromes.

Yet another embodiment is a method for preventing, ameliorating or treating an appetite disorder, social related disorder, autoimmune or inflammation, pain or neurodegenerative related syndrome, disorder or disease, or substance abuse, in a subject in need thereof by administering to the subject a therapeutically effective amount of a compound of the present invention.

Yet another embodiment is a method for preventing, ameliorating or treating an appetite related disease, disorder or syndrome, such as obesity, an overweight condition, anorexia, bulimia, cachexia, dysregulated appetite, an obesity related syndrome, disorder, disease or symptom (including, but not limited to, obesity as a result of genetics, diet, food intake volume, metabolic syndrome, disorder or disease, hypothalmic disorder or disease, age, abnormal adipose mass distribution, abnormal adipose compartment distribution, a compulsive eating disorder, or a motivational disorder which includes the desire to consume sugars, carbohydrates, alcohols or drugs or any ingredient with hedonic value, and/or reduced activity) in a subject in need thereof by administering to the subject a therapeutically effective amount of a compound of the present invention.

Yet another embodiment is a method for preventing, ameliorating or treating a social related disease, disorder or syndrome, including, but not limited to, depression and its types, bipolar depression, unipolar depression, single or recurrent major depressive episodes with or without psychotic features, catatonic features, melancholic features, atypical features or postpartum onset, seasonal affective disorder, dysthymic disorders with early or late onset and with or without atypical features, neurotic depression and social phobia, depression accompanying dementia, anxiety, psychosis, social affective disorders, and/or cognitive disorders, in a subject in need thereof by administering to the subject a therapeutically effective amount of a compound of the present invention.

Yet another embodiment is a method for preventing, ameliorating or treating an autoimmune or inflammation related disease, disorder or syndrome, including, but not limited to, psoriasis, lupus erythematosus, diseases of the connective tissue, Sjögren's syndrome, ankylosing spondylarthritis; rheumatoid arthritis, reactional arthritis, undifferentiated spondylarthritis, Behcet's disease, autoimmune hemolytic anaemias, multiple sclerosis, amyotrophic lateral sclerosis, amyloses, graft rejection or diseases affecting the plasma cell line, allergic diseases (such as delayed or immediate hypersensitivity, allergic rhinitis, contact dermatitis or allergic conjunctivitis infectious parasitic), viral or bacterial diseases (such as AIDS and meningitis), inflammatory diseases (such as diseases of the joints including, but not limited to, arthritis, rheumatoid arthritis, osteoarthritis, spondylitis, gout, vasculitis, Crohn's disease, inflammatory bowel disease (IBD) and irritable bowel syndrome (IBS)) and osteoporosis in a subject in need thereof by administering to the subject a therapeutically effective amount of a compound of the present invention.

Yet another embodiment is a method for preventing, ameliorating or treating pain or a neurodegenerative related syndrome, disorder or disease, including, but not limited to, central and peripheral pathway mediated pain, bone and joint pain, migraine headache associated pain, cancer pain, dental pain, menstrual cramps, labor pain, chronic pain of the inflammatory type, pain associated with allergies, rheumatoid arthritis, dermatitis or immunodeficiency, chronic neuropathic pain (including pain associated with diabetic neuropathy, sciatica, non specific lower back pain, fibromyalgia, and HIV-related neuropathy), post herpetic neuralgia, trigeminal neuralgia, pain resulting from physical trauma, amputation, cancer, toxins or chronic inflammatory conditions, Hodgkin's disease, myasthenia gravis, nephrotic syndrome, scleroderma and thyroiditis, in a subject in need thereof by administering to the subject a therapeutically effective amount of a compound of the present invention.

Yet another embodiment is a method for preventing, ameliorating or treating a substance abuse related syndrome, disorder or disease including, but not limited to, drug abuse and drug withdrawal in which, for example, the substance of abuse or dependence is alcohol, amphetamines, amphetamine like substances, caffeine, cannabis, cocaine, hallucinogens, inhalants, opioids, nicotine (and/or tobacco products), heroin abuse, barbiturates, phencyclidine (or phencyclidine-like compounds), sedative-hypnotics, benzodiazepines, or combinations of substances of abuse, in a subject in need thereof by administering to the subject a therapeutically effective amount of a compound of the present invention.

Yet another embodiment is a method for reducing tobacco craving in a subject in need thereof by administering to the subject a therapeutically effective amount of a compound of the present invention.

Yet another embodiment is a method for treating nicotine dependency, addiction, withdrawal or aiding in the cessation or lessening of tobacco use in a subject in need thereof by administering to the subject a therapeutically effective amount of a compound of the present invention.

Yet another embodiment is a method of preparing a compound of formula (1), where Y is N, U is C, one of W, V, and X is N and the remaining two are C, B is O, and A, R, $R^1$, $R^2$ and p are as defined above. The method includes the step of coupling an amine of the formula $HNR^1R^2$ with a compound of the formula:

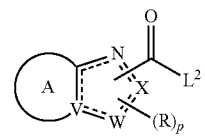

wherein $L^2$ is a leaving group, to form the compound of formula (1).

Yet another embodiment is a method of preparing a compound of formula (1), where W and Y are N, U, V, and X are C, B is O, and A, R, $R^1$, $R^2$ and p are as defined above. The method includes the steps of:

(a) oxidizing a compound of formula K:

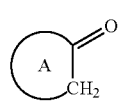

to yield a compound of formula B:

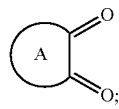

(b) subjecting the compound of formula B to reductive amination to form the vicinal diamine of formula C:

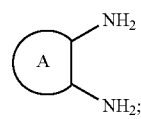

(c) monoacylating the vicinal diamine of formula C to form a mono N-acyl diamine of formula D:

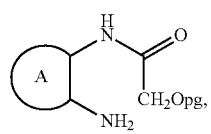

D wherein pg is a protecting group;

(d) subjecting the compound of formula D to cyclization to form a compound of formula E:

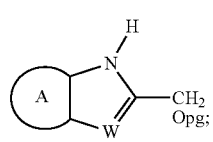

E (e) dehydrogenating the compound of formula E to form a compound of formula F:

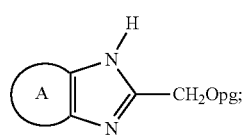

F (f) derivatizing the compound of form F to form compound G1, compound G2, or a mixture thereof:

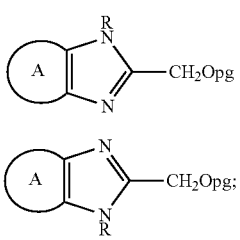

G1

G2

(g) hydrolyzing compound. G1, compound G2, or both to form compound H1, compound H2, or both:

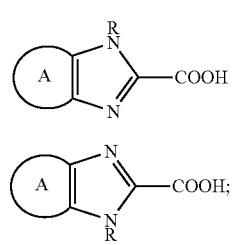

H1

H2 and (h) coupling an amine of the formula $HNR^1R^2$ with compound H1, compound H2, or both to form the compound of formula (1).

Yet another embodiment is a method of preparing a compound of formula (1), where X and Y are N, U, V, and W are C, B is O, and A, R, $R^1$, $R^2$ and p are as defined above. The method includes the steps of:

(a) deprotonating a compound of formula K:

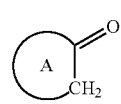

K followed by acylation to yield a compound of formula L:

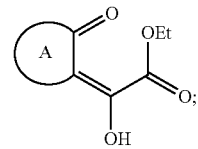

L (b) reacting the compound of formula L with a hydrazine having the formula $RNHNH_2$ to form compound M, compound N, or both:

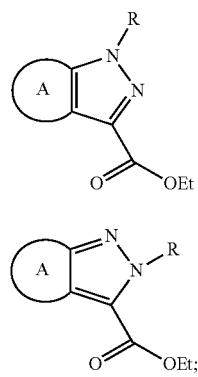

M

N and (c) hydrolyzing and coupling compound M, compound N, or both with an amine of the formula $HNR^1R^2$ to form the compound of formula (1).

Yet another embodiment is a method of preparing a compound of formula (1), where V and Y are N, U, W, and X are C, B is O, p is 0 or 1, and A, R, $R^1$ and $R^2$ are as defined above. The method includes the steps of:

(a) converting a compound of formula O:

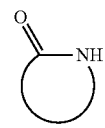

O to a compound of formula P:

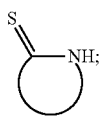

(b) coupling compound P with an amine of the formula Q:

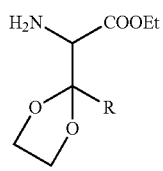

to form a compound of formula R:

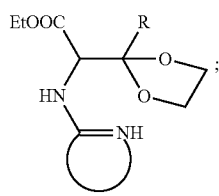

(c) deprotecting the compound of formula R followed by condensation to form a compound of formula S:

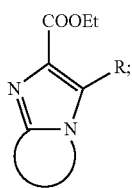

and (d) hydrolyzing and coupling the compound of formula S with an amine of the formula $HNR^1R^2$ to form the compound of formula (1).

DETAILED DESCRIPTION OF THE INVENTION

Definitions

Figure 1:
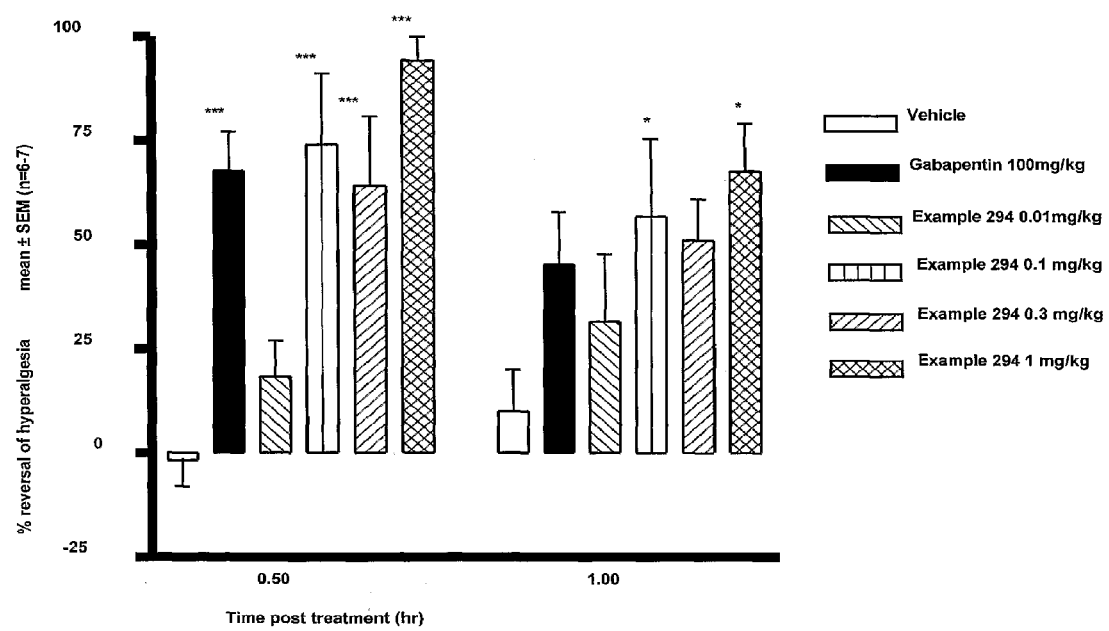
FIG. 1 is a bar graph of the mean percent reversal of neuropathic hyperalgesia(±SEM) as measured by the Seltzer model (protocol V) 0.5 and 1 hour after dosing with vehicle, 100 mg/kg gabapentin, or 0.01, 0.1, 0.3, or 1 mg/kg of the compound of Example 294.

The term "aryl" refers to aromatic radicals having 6 to 14 carbon atoms such as phenyl, naphthyl, tetrahydronapthyl, indanyl, and biphenyl.

The term "arylalkyl" refers to an aryl group as defined above directly bonded to an alkyl group as defined above. e.g., $-CH_2C_6H_5$ and $-C_2H_5C_6H_5$.

The term "heterocyclic ring" refers to a stable 3- to 15-membered ring radical which consists of carbon atoms and from one to five heteroatoms selected from nitrogen, phosphorus, oxygen and sulfur. For purposes of this invention, the heterocyclic ring radical may be a monocyclic, bicyclic or tricyclic ring system, which may include fused, bridged or spino ring systems, and the nitrogen, phosphorus, carbon, oxygen or sulfur atoms in the heterocyclic ring radical may be optionally oxidized to various oxidation states. In addition, the nitrogen atom may be optionally quaternized; and the ring radical may be partially or fully saturated (i.e., heterocyclic or heteroaryl). Examples of such heterocyclic ring radicals include, but are not limited to, azetidinyl, acridinyl, benzodioxolyl, benzodioxanyl, benzofurnyl, carbazolyl, cinnolinyl, dioxolanyl, indolizinyl, naphthyridinyl, perhydroazepinyl, phenazinyl, phenothiazinyl, phenoxazinyl, phthalazinyl, pyridyl, pteridinyl, purinyl, quinazolinyl, quinoxalinyl, quinolinyl, isoquinolinyl, tetrazoyl, imidazolyl, tetrahydroisouinolyl, piperidinyl, piperazinyl, 2-oxopiperazinyl, 2-oxopiperidinyl, 2-oxopyrrolidinyl, 2-oxoazepinyl, azepinyl, pyrrolyl, 4-piperidonyl, pyrrolidinyl, pyrazinyl, pyrimidinyl, pyridazinyl, oxazolyl, oxazolinyl, oxasolidinyl, triazolyl, indanyl, isoxazolyl, isoxasolidinyl, morpholinyl, thiazolyl, thiazolinyl, thiazolidinyl, isothiazolyl, quinuclidinyl, isothiazolidinyl, indolyl, isoindolyl, indolinyl, isoindolinyl, octahydroindolyl, octahydroisoindolyl, quinolyl, isoquinolyl, decahydroisoquinolyl, benzimidazolyl, thiadiazolyl, benzopyranyl, benzothiazolyl, benzooxazolyl, furyl, tetrahydrofurtyl, tetrahydropyranyl, thienyl, benzothienyl, thiamorpholinyl, thiamorpholinyl sulfoxide, thiamorpholinyl sulfone, dioxaphospholanyl, oxadiazolyl, chromanyl, and isochromanyl. The heterocyclic ring radical may be attached to the main structure at any heteroatom or carbon atom that results in the creation of a stable structure.

The term "heteroaryl" refers to an aromatic heterocyclic ring radical. The heteroaryl ring radical may be attached to the main structure at any heteroatom or carbon atom that results in the creation of a stable structure.

The term "heteroarylalkyl" refers to a heteroaryl ring radical directly bonded to an alkyl group. The heteroarylalkyl radical may be attached to the main structure at any carbon atom from the alkyl group that results in the creation of a stable structure.

The term "heterocyclyl" refers to a heterocyclic ring radical as defined above. The heterocyclyl ring radical may be attached to the main structure at any heteroatom or carbon atom that results in the creation of a stable structure.

The term "heterocyclylalkyl" refers to a heterocyclic ring radical directly bonded to an alkyl group. The heterocyclylalkyl radical may be attached to the main structure at any carbon atom in the alkyl group that results in the creation of a stable structure.

The term "alkyl" refers to a straight or branched hydrocarbon chain radical consisting solely of carbon and hydrogen atoms, containing no unsaturation, having from one to eight carbon atoms, and which is attached to the rest of the molecule by a single bond, e.g., methyl, ethyl, n-propyl, 1-methylethyl (isopropyl), n-butyl, n-pentyl, and 1,1-dimethylethyl (t-butyl).

The term "alkenyl" refers to an aliphatic hydrocarbon group containing a carbon-carbon double bond and which may be a straight or branched chain having 2 to about 10 carbon atoms, e.g., ethenyl, 1-propenyl, 2-propenyl(allyl), iso-propenyl, 2-methyl-1-propenyl, 1-butenyl, and 2-butenyl.

The term "alkynyl" refers to a straight or branched chain hydrocarbyl radical having at least one carbon-carbon triple bond, and having 2 to about 12 carbon atoms (with radicals having 2 to about 10 carbon atoms being preferred), e.g., ethynyl, propynyl, and butynyl.

The term "alkoxy" denotes an alkyl group attached via an oxygen linkage to the rest of the molecule. Representative examples of such groups are —$OCH_3$ and —$OC_2H_5$.

The term "cycloalkyl" denotes a non-aromatic mono or multicyclic ring system of 3 to about 12 carbon atoms, such as cyclopropyl, cyclobutyl, cyclopentyl, and cyclohexyl. Examples of multicyclic cycloalkyl groups include, but are not limited to, perhydronaphthyl, adamantyl and norbornyl groups, bridged cyclic groups or spirobicyclic groups, e.g., sprio(4,4)non-2-yl.

The term "cycloalkylalkyl" refers to a cyclic ring-containing radical, having 3 to about 8 carbon atoms, directly attached to an alkyl group. The cycloalkylalkyl group may be attached to the main structure at any carbon atom in the alkyl group that results in the creation of a stable structure. Non-limiting examples of such groups include cyclopropylmethyl, cyclobutylethyl, and cyclopentylethyl.

The term "cycloalkylaryl" refers to a cyclic ring-containing radical, having 3 to about 8 carbon atoms, directly attached to an aryl group Non-limiting examples of such groups include phenylcyclopropyl, phenylcyclobutyl and phenylcyclopentyl.

The term "cycloalkenyl" refers to a cyclic ring-containing radical having 3 to about 8 carbon atoms with at least one carbon-carbon double bond, such as cyclopropenyl, cyclobutenyl, and cyclopentenyl.

Unless otherwise specified, the term "substituted" as used herein refers to substitution with any one or any combination of the following substituents: hydroxy, halogen, carboxyl, cyano, nitro, oxo (=O), thio (=S), substituted or unsubstituted alkyl, substituted or unsubstituted alkoxy, substituted or unsubstituted alkenyl, substituted or unsubstituted alkynyl, substituted or unsubstituted aryl, substituted or unsubstituted arylalkyl, substituted or unsubstituted cycloalkyl, substituted or unsubstituted cycloalkenyl, substituted or unsubstituted amino, substituted or unsubstituted aryl, substituted or unsubstituted heteroaryl, substituted or unsubstituted heterocyclylalkyl ring, substituted or unsubstituted heteroarylalkyl, substituted or unsubstituted heterocyclic ring, substituted or unsubstituted guanidine, —$COOR_x$, —$C(O)R_x$, —$C(S)R^x$, —$C(O)NR_xR_y$, —$C(O)ONR_xR_y$, —$NR_xCONR_yR_z$, —$N(R_x)$ $SOR_y$, —$N(R_x)S\ O_2R_y$, —$(=N—N(R_x)R_y)$, —$NR_xC(O)$ $OR_y$, —$NR_xR_y$, —$NR_xC(O)R_y$, —$NR_xC(S)R_y$, —$NR_x(S)$ $NR_yR_z$, —$SONR_xR_y$, —$SO_2NR_xR_y$, —$OR_x$, —$OR_xC(O)$ $NR_yR_z$, —$OR_xC(O)OR_y$, —$OC(O)R_x$, —$OC(O)NR_xR_y$, —$R_xNR_yC(O)R_z$, —$R_xOR_y$, —$R_xC(O)OR_y$, —$R_xC(O)$ $NR_yR_z$, —$R_xC(O)R_y$, —$R_xOC(O)R_y$, —$SR_x$, —$SOR_x$, —$SO_2R_x$, and —$ONO_2$, wherein $R_x$, $R_y$ and $R_z$ are independently selected from hydrogen, substituted or unsubstituted alkyl, substituted or unsubstituted alkoxy, substituted or unsubstituted alkenyl, substituted or unsubstituted alkynyl, substituted or unsubstituted aryl, substituted or unsubstituted arylalkyl, substituted or unsubstituted cycloalkyl, substituted or unsubstituted cycloalkenyl, substituted or unsubstituted amino, substituted or unsubstituted aryl, substituted or unsubstituted heteroaryl, substituted heterocyclylalkyl ring, substituted or unsubstituted heteroarylalkyl, or substituted or unsubstituted heterocyclic ring. According to one embodiment, the substituents in the aforementioned "substituted" groups cannot be further substituted. For example, when the substituent on "substituted alkyl" is "substituted aryl" the substituent on "substituted aryl" cannot be "substituted alkenyl".

The term "protecting group" or "PG" refers to a substituent that is employed to block or protect a particular functionality. Other functional groups on the compound may remain reactive. For example, an "amino-protecting group" is a substituent attached to an amino group that blocks or protects the amino functionality in the compound. Suitable amino-protecting groups include, but are not limited to, acetyl, trifluoroacetyl, t-butoxycarbonyl (BOC), benzyloxycarbonyl (CBz) and 9-fluorenylmethylenoxycarbonyl (Fmoc). Similarly, a "hydroxy-protecting group" refers to a substituent of a hydroxy group that blocks or protects the hydroxy functionality. Suitable hydroxy-protecting groups include, but are not limited to, acetyl and silyl. A "carboxy-protecting group" refers to a substituent of the carboxy group that blocks or protects the carboxy functionality. Suitable carboxy-protecting groups include, but are not limited to, —$CH_2CH_2SO_2Ph$, cyanoethyl, 2-(trimethylsilyl)ethyl, 2-(trimethylsilyl) ethoxymethyl, 2-(p-toluenesulfonyl)ethyl, 2-(p-nitrophenylsulfenyl)ethyl, 2-(diphenylphosphino)-ethyl, and nitroethyl. For a general description of protecting groups and their use, see T. W. Greene, Protective Groups in Organic Synthesis, John Wiley & Sons, New York, 1991.

The term "cannabinoid receptor" refers to any one of the known or heretofore unknown subtypes of the class of cannabinoid receptors, including CB1 and/or CB2 receptors, that may be bound by a cannabinoid modulator compound of the present invention.

The term "modulator" further refers to the use of a compound of the invention as a CB (e.g., CB1 and/or CB2) receptor agonist, partial agonist, antagonist or inverse-agonist.

The term "treating" or "treatment" of a state, disorder or condition includes:

(1) preventing or delaying the appearance of clinical symptoms of the state, disorder or condition developing in a subject that may be afflicted with or predisposed to the state, disorder or condition but does not yet experience or display clinical or subclinical symptoms of the state, disorder or condition;

(2) inhibiting the state, disorder or condition, i.e., arresting or reducing the development of the disease or at least one clinical or subclinical symptom thereof; or (3) relieving the disease, i.e., causing regression of the state, disorder or condition or at least one of its clinical or subclinical symptoms.

The benefit to a subject to be treated is either statistically significant or at least perceptible to the subject or to the physician.

The term "subject" includes mammals (especially humans) and other animals, such as domestic animals (e.g., household pets including cats and dogs) and non-domestic animals (such as wildlife).

A "therapeutically effective amount" means the amount of a compound that, when administered to a subject for treating a state, disorder or condition, is sufficient to effect such treatment. The "therapeutically effective amount" will vary depending on the compound, the disease and its severity and the age, weight, physical condition and responsiveness of the subject to be treated.

Pharmaceutically acceptable salts forming part of this invention include salts derived from inorganic bases (such as Li, Na, K, Ca, Mg, Fe, Cu, Zn, and Mn), salts of organic bases (such as N,N'-diacetylethylenediamine, glucamine, triethylamine, choline, hydroxide, dicyclohexylamine, metformin, benzylamine, trialkylamine, and thiamine), salts of chiral bases (such as alkylphenylamine, glycinol, and phenyl glycinol), salts of natural amino acids (such as glycine, alanine, valine, leucine, isoleucine, norleucine, tyrosine, cystine, cysteine, methionine, proline, hydroxy proline, histidine, ornithine, lysine, arginine, and serine), salts of non-natural amino acids (such as D-isomers or substituted amino acids), salts of guanidine, salts of substituted guanidine (Wherein the substituents are selected from nitro, amino, alkyl, alkenyl, or alkynyl), ammonium salts, substituted ammonium salts, and aluminum salts. Other pharmaceutically acceptable salts include acid addition salts (where appropriate) such as sulphates, nitrates, phosphates, perchlorates, borates, hydrohalides, acetates (such as trifluoroacetate), tartrates, maleates, citrates, fumarates, succinates, palmoates, methanesulphonates, benzoates, salicylates, benzenesulfonates, ascorbates, glycerophosphates, and ketoglutarates. Yet other pharmaceutically acceptable salts include, but are not limited to, quaternary ammonium salts of the compounds of invention with alkyl halides or alkyl sulphates (such as MeI or $(Me)_2SO_4$).

Pharmaceutically acceptable solvates includes hydrates and other solvents of crystallization (such as alcohols). The compounds of the present invention may form solvates with standard low molecular weight solvents by methods known in the art.

Pharmaceutical Compositions

The pharmaceutical composition of the present invention comprises at least one compound of the present invention and a pharmaceutically acceptable excipient (such as a pharmaceutically acceptable carrier or diluent). Preferably, the pharmaceutical composition comprises a therapeutically effective amount of the compound(s) of the present invention. The compound of the present invention may be associated with a pharmaceutically acceptable excipient (such as a carrier or a diluent) or be diluted by a carrier, or enclosed within a carrier which can be in the form of a capsule, sachet, paper or other container.

Examples of suitable carriers include, but are not limited to, water, salt solutions, alcohols, polyethylene glycols, polyhydroxyethoxylated castor oil, peanut oil, olive oil, gelatin, lactose, terra alba, sucrose, dextrin, magnesium carbonate, sugar, cyclodextrin, amylose, magnesium stearate, talc, gelatin, agar, pectin, acacia, stearic acid or lower alkyl ethers of cellulose, silicic acid, fatty acids, fatty acid amines, fatty acid monoglycerides and diglycerides, pentaerythritol fatty acid esters, polyoxyethylene, hydroxymethyl cellulose and polyvinylpyrrolidone.

The carrier or diluent may include a sustained release material, such as glyceryl monostearate or glyceryl distearate, alone or mixed with a wax.

The pharmaceutical composition may also include one or more pharmaceutically acceptable auxiliary agents, wetting agents, emulsifying agents, suspending agents, preserving agents, salts for influencing oxmetic pressure, buffers, sweetening agents, flavoring agents, colorants, or any combination of the foregoing. The pharmaceutical composition of the invention may be formulated so as to provide quick, sustained, or delayed release of the active ingredient after administration to the subject by employing methods known in the art.

The pharmaceutical compositions of the present invention may be prepared by conventional techniques, e.g., as described in *Remington: The Science and Practice of Pharmacy*, 20th Ed., 2003 (Lippincott Williams & Wilkins). For example, the active compound can be Mixed with a carrier, or diluted by a carrier, or enclosed within a carrier, which may be in the form of an ampoule, capsule, sachet, paper, or other container. When the carrier serves as a diluent, it may be a solid, semi-solid, or liquid material that acts as a vehicle, excipient, or medium for the active compound. The active compound can be adsorbed on a granular solid container, for example, in a sachet.

The pharmaceutical compositions may be in conventional forms, for example, capsules, tablets, aerosols, solutions, suspensions or products for topical application.

The route of administration may be any route which effectively transports the active compound of the invention to the appropriate or desired site of action. Suitable routes of administration include, but are not limited to, oral, nasal, pulmonary, buccal, subdermal, intradermal, transdermal, parenteral, rectal, depot, subcutaneous, intravenous, intraurethral, intramuscular, intranasal, ophthalmic (such as with an ophthalmic solution) or topical (such as with a topical ointment). The oral route is preferred.

Solid oral formulations include, but are not limited to, tablets, capsules (soft or hard gelatin), dragees (containing the active ingredient in powder or pellet form), troches and lozenges. Tablets, dragees, or capsules having talc and/or a carbohydrate carrier or binder or the like are particularly suitable for oral application. Preferable carriers for tablets, dragees, or capsules include lactose, cornstarch, and/or potato starch. A syrup or elixir can be used in cases where a sweetened vehicle can be employed.

A typical tablet that may be prepared by conventional tabletting techniques may contain: (1) Core: Active compound (as free compound or salt thereof), 250 mg colloidal silicon dioxide (Aerosil®), 1.5 mg microcrystalline cellulose (Avicel®), 70 mg modified cellulose gum (Ac-Di-Sol®), and 7.5 mg magnesium stearate; (2) Coating: HPMC, approx. 0.9 mg Mywacett 9-40 T and approx. 0.9 mg acylated monoglyceride Liquid formulations include, but are not limited to, syrups, emulsions, soft gelatin and sterile injectable liquids, such as aqueous or non-aqueous liquid suspensions or solutions.

For parenteral application, particularly suitable are injectable solutions or suspensions, preferably aqueous solutions with the active compound dissolved in polyhydroxylated castor oil.

Methods of Treatment

The present invention provides compounds and pharmaceutical formulations thereof that are useful in the treatment, amelioration, and/or prevention of diseases, conditions and/or disorders modulated by a cannabinoid (CB) receptor, especially those modulated by the CB1 or CB2 receptor including those discussed below.

The present invention further provides a method of treating a disease, condition and/or disorder modulated by a cannabinoid receptor (CB), and in particular the CB1 or CB2 receptor, in a subject in need thereof by administering to the subject a therapeutically effective amount of a compound or a pharmaceutical composition of the present invention.

Diseases, conditions, and/or disorders that are modulated by a CB receptor, include, but are not limited to, appetite disorders, metabolism disorders, catabolism disorders, diabetes, obesity, social related disorders, mood disorders, seizures, substance abuse, learning disorders, cognition disorders, memory disorders, organ contraction, muscle spasm, respiratory disorders, locomotor activity disorders, movement disorders, immune disorders (such as autoimmune disorders), inflammation, cell growth, pain (such as neuropathic pain) and neurodegenerative related syndromes, disorders and diseases.

Appetite related syndromes, disorders or diseases include, but are not limited to, obesity, overweight conditions, anorexia, bulimia, cachexia, dysregulated appetite and the like. Obesity related syndromes, disorders or diseases include, but are not limited to, obesity as a result of genetics, diet, food intake volume, metabolic syndrome, disorder or disease, hypothalmic disorder or disease, age, abnormal adipose mass distribution, abnormal adipose compartment distribution, compulsive eating disorders, motivational disorders which include the desire to consume sugars, carbohydrates, alcohols or drugs or any ingredient with hedonic value and the like. Symptoms associated with obesity related syndromes, disorders, and diseases include, but are not limited to, reduced activity.

Metabolism related syndromes, disorders or diseases include, but are not limited to, metabolic syndrome, dyslipidemia, elevated blood pressure, insulin sensitivity or resistance, hyperinsulinemia, hypercholesterolemia, hyperlipidemias, atherosclerosis, hypertriglyceridemias, arteriosclerosis, other cardiovascular diseases, osteoarthritis, dermatological diseases, sleep disorders (disturbances of circadian rhythm, dyssomnia, insomnia, sleep apnea and narcolepsy), cholelithiasis, hepatomegaly, steatosis, abnormal alanine aminotransferase levels, polycystic ovarian disease, inflammation, and the like.

Diabetes related syndromes, disorders or diseases include, but are not limited to, glucose dysregulation, insulin resistance, glucose intolerance, hyperinsulinemia, dyslipidemia, hypertension, obesity, hyperglycemia and the like.

Catabolism related syndromes, disorders or diseases include, but are not limited to, catabolism in connection with pulmonary dysfunction and ventilator dependency; cardiac dysfunction, e.g., associated with valvular disease, myocardial infarction, cardiac hypertrophy or congestive heart failure.

Ophthalmic diseases include, but are not limited to, glaucoma, glaucoma-associated intraocular pressure retinitis, retinopathies, uveitis, acute injury to the eye tissue (e.g. conjunctivitis).

Social or mood related syndromes, disorders or diseases include, but are not limited to, depression (including, but not limited to, bipolar depression, unipolar depression, single or recurrent major depressive episodes with or without psychotic features, catatonic features, melancholic features, atypical features or postpartum onset, seasonal affective disorder, dysthymic disorders with early or late onset and with or without atypical features, neurotic depression and social phobia, depression accompanying dementia, anxiety, psychosis, social affective disorders, cognitive disorders and the like).

Substance abuse related syndromes, disorders or diseases include, but are not limited to, drug abuse and drug withdrawal. Abused substances include, but are not limited to, alcohol, amphetamines (or amphetamine like substances), caffeine, cannabis, cocaine, hallucinogens, inhalants, opioids, nicotine (and/or tobacco products), heroin abuse, barbiturates, phencyclidine (or phencyclidine-like compounds), sedative-hypnotics, benzodiazepines, or combinations of any of the foregoing. The compounds and pharmaceutical compositions can also be used to treat withdrawal symptoms and substance-induced anxiety or mood disorder.

The present invention further provides a method of treating nicotine dependency, addiction, withdrawal or aiding in the cessation or lessening of tobacco in a subject in need thereof by administering to the subject a therapeutically effective amount of a compound or a pharmaceutical composition of the present invention.

Learning, cognition or memory related syndromes, disorders or diseases which can be treated with the compounds of the present invention include, but are not limited to, memory loss or impairment as a result of age, disease, side effects of medications (adverse events) or the like. Memory impairment is a primary symptom of dementia and can also be a symptom associated with such diseases as Alzheimer's disease, schizophrenia, Parkinson's disease, Huntington's disease, Pick's disease, Creutzfeld-Jakob disease, HIV, cardiovascular disease, and head trauma as well as age-related cognitive decline. Generally, dementias are diseases that include memory loss and additional intellectual impairment separate from memory. The compounds and pharmaceutical compositions of the present invention are also useful in treating cognitive impairments related to attentional deficits, such as attention deficit disorder.

Muscle spasm syndromes, disorders or diseases include, but are not limited to, multiple sclerosis, cerebral palsy and the like.

Locomotor activity and movement syndromes, disorders or diseases include, but are not limited to, stroke, Parkinson's disease, multiple sclerosis, epilepsy and the like.

Respiratory related syndromes, disorders or diseases include, but are not limited to, diseases of the respiratory tract, chronic obstructive pulmonary disorder, emphysema, asthma, bronchitis and the like.

Kidney dysfunction nephritis which can be treated with the modulators of the present invention include, but is not limited to, mesangial proliferative glomerulonephritis, nephritic syndrome, liver dysfunction (hepatitis, cirrhosis).

Autoimmune or inflammation related syndromes, disorders or diseases include, but are not limited to, psoriasis, lupus erythematosus, diseases of the connective tissue, Sjögren's syndrome, ankylosing spondylarthritis, rheumatoid arthritis, reactional arthritis, undifferentiated spondylarthritis, Behcet's disease, autoimmune hemolytic anaemias, multiple sclerosis, amyotrophic lateral sclerosis, amyloses, graft rejection or diseases affecting the plasma cell line; allergic diseases: delayed or immediate hypersensitivity, allergic rhinitis, contact dermatitis or allergic conjunctivitis infectious parasitic, viral or bacterial diseases (such as AIDS and meningitis), inflammatory diseases (such as diseases of the joints including, but not limited to, arthritis, rheumatoid arthritis, osteoarthritis, spondylitis, gout, vasculitis, Crohn's disease, inflammatory bowel disease (IBD) and irritable bowel syndrome (IBS)) and osteoporosis.

Cell growth related syndromes, disorders or diseases include, but are not limited to, dysregulated mammalian cell proliferation, breast cancer cell proliferation, prostrate cancer cell proliferation and the like.

Pain related syndromes, disorders or diseases include, but are not limited to, central and peripheral pathway mediated pain, bone and joint pain, migraine headache associated pain, cancer pain, dental pain, menstrual cramps, labor pain, chronic pain of the inflammatory type, allergies, rheumatoid arthritis, dermatitis, immunodeficiency, chronic neuropathic pain, (e.g. pain associated with diabetic neuropathy, sciatica, non specific lower back pain, fibromyalgia; HIV-related neuropathy; post herpetic neuralgia, trigeminal neuralgia, and pain resulting from physical trauma, amputation, cancer, toxins or chronic inflammatory conditions), hodgkin's disease, myasthenia gravis, nephrotic syndrome, scleroderma, thyroiditis and the like.

Neurodegenerative related syndromes, disorders or diseases include, but are not limited to, Parkinson's disease, multiple sclerosis, epilepsy, ischemia or secondary biochemical injury collateral to traumatic head or brain injury, brain inflammation, eye injury or stroke and the like.

The compounds of this invention may also be used in conjunction with other pharmaceutical agents for the treatment of the diseases, conditions and/or disorders described herein. Therefore, methods of treatment that include administering compounds of the present invention in combination with other pharmaceutical agents are also provided. Suitable pharmaceutical agents that may be used in combination with the compounds of the present invention include, but are not limited to, anti-obesity agents such as apolipoprotein-B secretion/microsomal triglyceride transfer protein (apo-B/MTP) inhibitors, 11β-hydroxy steroid dehydrogenase-1 (11β-HSD type 1) inhibitors, peptide $YY_{3-36}$ or analogs thereof, MCR-4 agonists, cholecystokinin-A (CCK-A) agonists, monoamine reuptake inhibitors (such as sibutramine), sympathomimetic agents, $\beta_3$ adrenergic receptor agonists, dopamine receptor agonists (such as bromocriptine), melanocyte-stimulating hormone receptor analogs, $5HT_{2c}$ receptor agonists, melanin concentrating hormone antagonists, leptin (the OB protein), leptin analogs, leptin receptor agonists, galanin antagonists, lipase inhibitors (such as tetrahydrolipstatin, i.e. orlistat), anorectic agents (such as a bombesin agonist), neuropeptide-Y receptor antagonists, thyromimetic agents, dehydroepiandrosterone or an analog thereof, glucocorticoid receptor agonists or antagonists, orexin receptor antagonists, glucagon-like peptide-1 (GLP-1) receptor agonists, Protein Tyrosine Phosphatase (PTP-1B) inhibitors, dipeptidyl peptidase IV (DPP-IV) inhibitors, ciliary neurotrophic factors (such as Axokine™ available from Regeneron Pharmaceuticals, Inc., Tarrytown, N.Y. and Procter & Gamble Company, Cincinnati, Ohio), human agouti-related protein (AGRP) inhibitors, ghrelin receptor antagonists, histamine 3 receptor antagonists or inverse agonists, and neuromedin U receptor agonists. Other anti-obesity agents, including the preferred agents set forth herein below, are well known, or will be readily apparent in light of the instant disclosure, to one of ordinary skill in the art.

Especially preferred are anti-obesity agents such as orlistat, sibutramine, bromocriptine, ephedrine, leptin, peptide $YY_{3-36}$ or an analog thereof (including the complete peptide YY), and pseudoephedrine. Preferably, compounds of the present invention and combination therapies are administered in conjunction with exercise and a sensible diet.

Anti-obesity agents for use in the combinations, pharmaceutical compositions, and methods of the invention can be prepared using methods known to one of ordinary skill in the art, for example, sibutramine can be prepared as described in U.S. Pat. No. 4,929,629; bromocriptine can be prepared as described in U.S. Pat. Nos. 3,752,814 and 3,752,888; orlistat can be prepared as described in U.S. Pat. Nos. 5,274,143, 5,420,305, 5,540,917, and 5,643,874; and $PYY_{3-36}$ (including analogs) can be prepared as described in U.S. Patent Publication No. 2002/0141985 and International Publication No. WO 03/027637. All of the above recited references are incorporated herein by reference.

Other suitable pharmaceutical agents that may be administered in combination with the compounds of the present invention include agents designed to treat tobacco abuse (e.g., nicotine receptor partial agonists, bupropion hypochloride (also known under the tradename Zyban™) and nicotine replacement therapies), agents to treat erectile dysfunction (e.g., dopaminergic agents, such as apomorphine), ADD/ADHD agents (e.g., Ritalin™ (methylphenidate hydrochloride), Strattera™ (atomoxetine hydrochloride), Concerta™ (methylphenidate hydrochloride) and Adderall™ (amphetamine aspartate; amphetamine sulfate; dextroamphetamine saccharate; and dextroamphetamine sulfate)), and agents to treat alcoholism, such as opioid antagonists (e.g., naltrexone (also known under the tradename ReVia™) and nalmefene), disulfiram (also known under the tradename Antabuse™), and acamprosate (also known under the tradename Campral™)). In addition, agents for reducing alcohol withdrawal symptoms may also be co-administered, such as benzodiazepines, beta-blockers, clonidine, carbamazepine, pregabalin, and gabapentin (Neurontin™). Treatment for alcoholism is preferably administered in combination with behavioral therapy including such components as motivational enhancement therapy, cognitive behavioral therapy, and referral to self-help groups, including Alcohol Anonymous (AA).

Other pharmaceutical agents that may be useful include antihypertensive agents; antidepressants (e.g., fluoxetine hydrochloride (Prozac™)); cognitive improvement agents (e.g., donepezil hydrochloride (Aircept™) and other acetylcholinesterase inhibitors); neuroprotective agents (e.g., memantine); antipsychotic medications (e.g., ziprasidone (Geodon™), risperidone (Risperdal™), and olanzapine (Zyprexa™)); insulin and insulin analogs (e.g., LysPro insulin); GLP-1 (7-37) (insulinotropin) and GLP-1 (7-36)-$NH_2$; sulfonylureas and analogs thereof: chlorpropamide, glibenclamide, tolbutamide, tolazamide, acetohexamide, Glypizide®, glimepiride, repaglinide, meglitinide; biguanides: metformin, phenformin, buformin; α2-antagonists and imidazolines: midaglizole, isaglidole, deriglidole, idazoxan, efaroxan, fluparoxan; other insulin secretagogues: linogliride, A-4166; glitazones: ciglitazone, Actos™ (pioglitazone), englitazone, troglitazone, darglitazone, Avandia® (BRL49653); fatty acid oxidation inhibitors: clomoxir, etomoxir; α-glucosidase inhibitors: acarbose, miglitol, emiglitate, voglibose, MDL-25,637, camiglibose, MDL-73,945; β-agonists: BRL 35135, BRL 37344, RO 16-8714, ICI D7114, CL 316,243; phosphodiesterase inhibitors: L-386, 398; lipid-lowering agents: benfluorex: fenfluramine; vanadate and vanadium complexes (e.g., Naglivan®) and peroxovanadium complexes; amylin antagonists; glucagon antagonists; gluconeogenesis inhibitors; somatostatin analogs; antilipolytic agents: nicotinic acid, acipimox, WAG 994, pramlintide (Symlin™), AC 2993, nateglinide, aldose reductase inhibitors (e.g., zopolrestat), glycogen phosphorylase inhibitors, sorbitol dehydrogenase inhibitors, sodium-hydrogen exchanger type 1 (NHE-1) inhibitors and/or cholesterol biosynthesis inhibitors or cholesterol absorption inhibitors, especially a HMG-CoA reductase inhibitor, or a HMG-CoA synthase inhibitor, or a HMG-COA reductase or synthase gene expression inhibitor, a CETP inhibitor, a bile acid sequesterant, a fibrate, an ACAT inhibitor, a squalene synthetase inhibitor, an anti-oxidant or niacin. The compounds of the present invention may also be administered in combination with a naturally occurring compound that acts to lower plasma cholesterol levels. Such naturally occurring compounds are commonly called nutraceuticals and include, for example, garlic extract, Hoodia plant extracts, and niacin.

The compounds of the present invention (including the pharmaceutical compositions and processes used therein) may be used alone or in combination with other pharmaceutical agents in the manufacture of a medicament for the therapeutic applications described herein.

General Method of Preparation

The compound of general formula (1) can be synthesized by the schemes illustrated below.

The compounds of formula (1), wherein W and Y are N; U, V and X are C; B is O; p is 0 or 1; and R, $R^1$ and $R^2$ are as described in the general description, can be synthesized as shown in scheme 1.

e.g., benzyl or methoxymethyl (MOM))) to obtain a mono N-acyl diamine of general formula D. The compound of general formula D can be subjected to intramolecular cyclisation to give compound E. Compound E can be dehydrogenated (e.g., using an oxidizing agent (such as ceric ammonium nitrate or 2,3-dichloro-5,6-dicyano-1,4-benzoquinone (DDQ))) to yield the compound of general formula F. Compound F is converted to compounds G1 and/or G2. For example, derivatisation of compound F by acylaytion, alkylation or arylation would provide compounds of general formula G1 and/or G2 which may be separated. The compound of general formula G1 and/or G2 thus obtained can be hydrolysed to form compound(s) 11.1 and/or 112. Com-

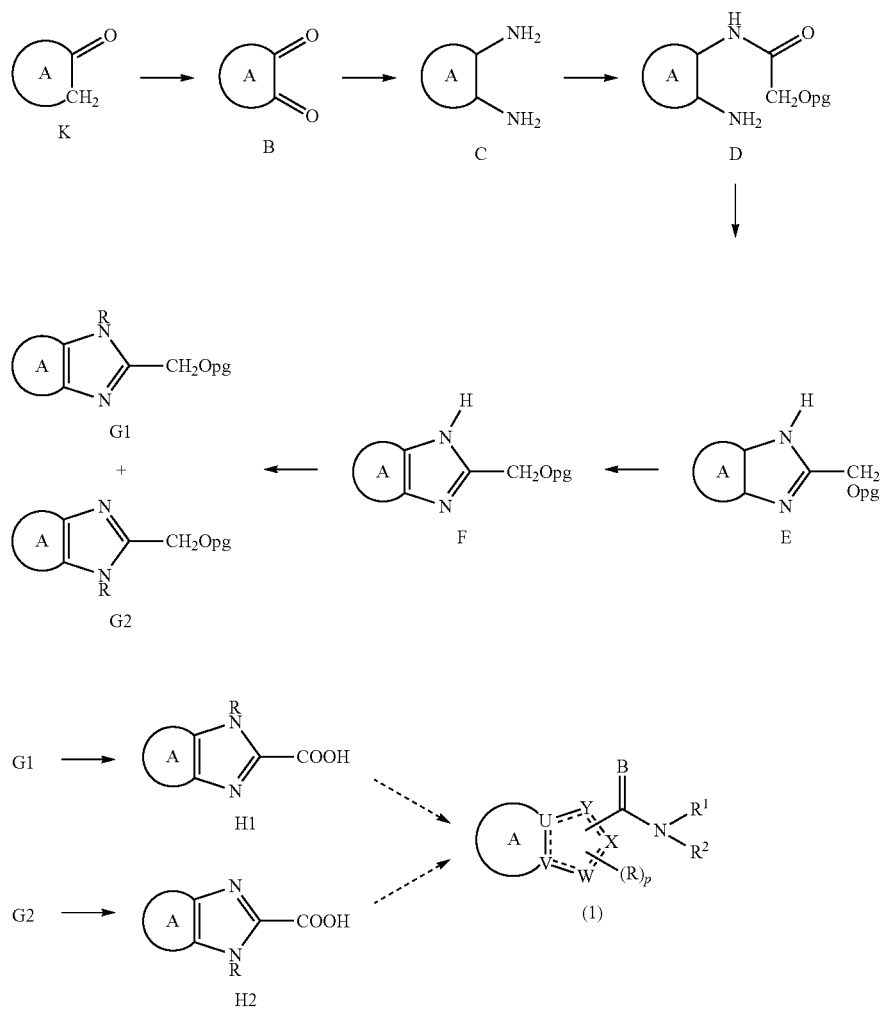

In the above scheme, the compound of general formula K may be oxidised (for example, with $SeO_2$ (selenium dioxide)) to give a compound of general formula B, which may then be subjected to reductive amination (e.g., under standard conditions (e.g., hydrogenation in the presence of $NH_4OAc$, Pd/C)) to obtain the vicinal diamine of general formula C. Compound C may be monoacylated (e.g., with an acid chloride of the formula $pgOCH_2COCl$ or an anhydride of the formula $(pgOCH_{12})CO$ (wherein pg is an alcohol protecting group, pounds H1 and/or H2 can be coupled with an amine (e.g., $HNR^1R^2$) to form a compound of formula (1). Suitable amines include, but are not limited to, N,N'-dicyclohexylcarbodiimide (DCC), 1-(3-dimethylaminopropyl)-3-ethyl carbodiimide hydrochloride (EDC) and benzotriazol-1-yloxy-tris(dimethylamino)-phosphonium hexafluorophosphate (BOP) reagent.

In another embodiment, the compounds of the formula (1) wherein X and Y are N; U, V and W are C; B is O; p is 0 or 1; R, $R^1$ and $R^2$ are as described in the general description, can be synthesized as shown in scheme 2.

Scheme 2

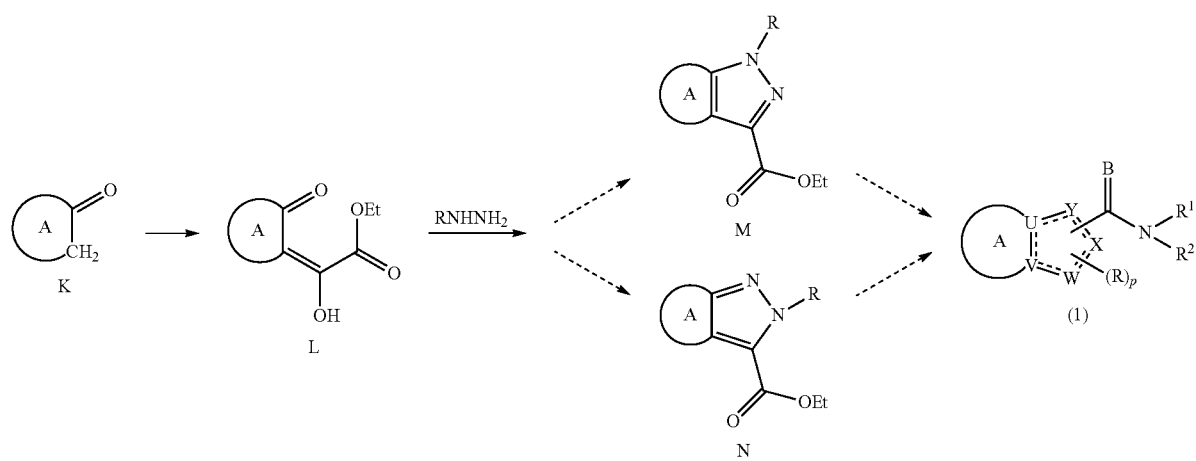

In the above scheme, the compound of general formula K can be deprotonated, e.g., using a base (such as LiHMDS or LDA), followed by acylation, e.g., using diethyl oxalate, to obtain compound of general formula L. The compound of general formula L can be then treated with a substituted hydrazine (such as RNHNH$_2$) to obtain the compound(s) of general formula M and/or N. The compound(s) of general formula M and/or N thus obtained can be hydrolysed and coupled with an amine (e.g., HNR$^1$R$^2$) to form a compound of formula (1). Suitable amines include, but are not limited to, N,N'-dicyclohexylcarbodiimide (DCC), 1-(3-dimethylaminopropyl)-3-ethyl carbodiimide hydrochloride (EDC) and benzotriazol-1-yloxytris(dimethylamino)-phosphonium hexafluorophosphate (BOP) reagent.

In yet another embodiment, the compounds of the formula (1) wherein V and Y are nitrogen; U, W and X are carbon; B is oxygen; p is 0 or 1 and R, R$^1$ and R$^2$ are as described in the general description, can be synthesized as shown in scheme 3.

Scheme 3

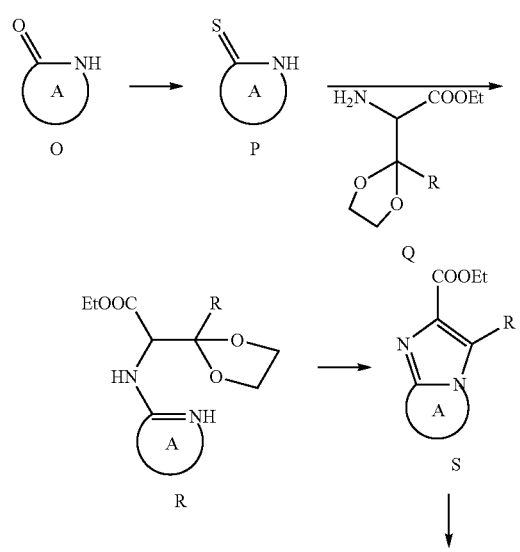

-continued

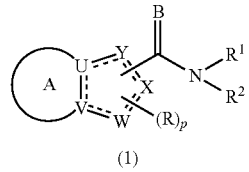

In the above scheme, the compound of general formula O is converted to a compound of general formula P. Compound P is then coupled with an amine of the general formula Q, for example, thermally or catalysed by reagents such as Hg(OAc)$_2$, to form a compound of the general formula R. Compound R is deprotected and condensed to form a compound of the general formula S. The deprotection and subsequent intramolecular condensation of compound. R is preferably performed in the presence of an acid (such as p.TsOH, MsOH, TfOH or CF$_3$COOH). The compound of general formula S can be hydrolysed and coupled with an amine (e.g., HNR$^1$R$^2$) to form a compound of formula (1). Suitable amines include, but are not limited to, N,N'-dicyclohexylcarbodiimide (DCC), 1-(3-dimethylaminopropyl)-3-ethyl carbodiimide hydrochloride (EDC) and benzotriazol-1-yloxytris(dimethylamine)-phosphonium hexafluorophosphate (HOP) reagent.

It is to be understood that the present invention encompasses all isomers of compounds of formula (I) and their pharmaceutically acceptable derivatives, including all geometric, tautomeric 10 and optical forms, and mixtures thereof (e.g. racemic mixtures). Where additional chiral centres are present in compounds of formula (I), the present invention includes within its scope all possible diastereoisomers, including mixtures thereof. The different isomeric forms may be separated or resolved one from the other by conventional methods, or any given isomer may be obtained by conventional synthetic methods or by stereospecific or asymmetric syntheses. The subject invention also includes isotopically-labeled compounds, which are identical to those recited in formulas I and following, but for the fact that one or more atoms are replaced by an atom having an atomic mass or mass number different from the atomic mass or mass number usually found in nature. Examples of isotopes that can be incorporated into compounds of the invention include isotopes of hydrogen, carbon, nitrogen, oxygen, phosphorous, fluorine, iodine, 20 and chlorine such as $^3H$, $^{11}C$, $^{14}C$, $^{18}F$, $^{123}I$ and $^{125}I$.

Compounds of the present invention and pharmaceutically acceptable salts of the compounds that contain the aforementioned isotopes and/or other isotopes of other atoms are within the scope of the present invention. Isotopically-labeled compounds of the present invention, for example those into which radioactive isotopes such as $^3H$, $^{14}C$ are incorporated, are useful in drug and/or substrate tissue distribution assays. Tritiated, i.e., $^3H$, and carbon-14, i.e., 14C, isotopes are particularly preferred for their ease of preparation and detectability. $^{11}C$ and $^8F$ isotopes are particularly useful in PET (positron emission tomography), and $^{125}I$ isotopes are particularly useful in SPECT (single photon emission computerized tomography), all useful in brain imaging. Further, substitution with heavier isotopes such as deuterium, i.e, 2H, can afford 30 certain therapeutic advantages resulting from greater metabolic stability, for example increased in vivo half-life or reduced dosage requirements and, hence, may be preferred in some circumstances. Isotopically labeled compounds of formula I and following of this invention can generally be prepared by carrying out the procedures disclosed in the Schemes and/or in the Examples below, by substituting a readily available isotopically labeled reagent for a non-isotopically labeled reagent.

The compounds of formula (I) may be prepared in crystalline or non-crystalline form, and, if crystalline, may optionally be hydrated or solvated. This invention includes within its scope stoichiometric hydrates or solvates as well as compounds containing variable amounts of water and/or solvent.

Embodiments of the present invention are illustrated by the following examples. It is to be understood, however, that the embodiments of the invention are not limited to the specific details of these examples, as other variations thereof will be known, or apparent in light of the instant disclosure, to one of ordinary skill in the art.

EXPERIMENTAL SECTION

Abbreviations and notations: The following abbreviations and notations have been used in the following text. M.P.: melting point. BOP reagent: (Benzotriazol-1-yloxy)tris(dimethylamino)phosphonium hexafluorophosphate. FC: Flash Chromatography. J: Coupling constants expressed in units of Hz. THF: tetrahydrofuran. Et$_3$N: triethyl amine. BuLi: butyl lithium. LiHMDS: lithium hexamethyl disilazide Intermediate 1

5-(2-bromophenyl)-5,6-diazatetracyclo[7.3.1.1$^{3,11}$.0$^{4,8}$]tetradeca-4(8),6-diene-7-carboxylic acid Step 1: Ethyl 2-oxo-(5-oxotricyclo[4.3.1.1.$^{3,8}$]undec-4-yl) acetate A 1.6M soln. of n-BuLi in hexane was added to a solution of hexamethyldisilazane (1.27 ml, 5.4 mmol) in diethyl ether (10.0 ml) at −78° C. and stirred at that temperature for 15 min. To this mixture was added a solution of homoadamantanone [900 mg, 5.4 mmol, prepared according to: Black, R. M. and Gill, G. B., J. Chem. Soc. (C), 1970, 671] in diethyl ether (27.0 ml) and stirring at −78° C. was continued for further 45 min. Diethyl oxalate (0.98 ml, 6.5 mmol) was added and the mixture was allowed to slowly warm up to 25° C. After stirring overnight, water (25 ml) was added to the solution and the layers separated. The aqueous layer was washed twice with diethyl ether (20 ml), acidified with 1N HCl and extracted into diethyl ether (3×20 ml), the organic layer was dried over Na$_2$SO$_4$, filtered and evaporated. Flash chromatography (petroleum ether/ethyl acetate 97:3) gave the title compound as a yellow oil (589 mg, 36%). $^1$H-NMR (δ ppm, CDCl$_3$, 300 MHz): 15.75 (s, 1H); 4.33 (q, J=7.2, 2H); 2.80 (br. t, J=6, 1H); 2.75-2.70 (m, 1H); 2.13-85 (m, 8H); 1.81-1.69 (m, 4H); 1.36 (m, t, J=7.2, 3H). IR (cm$^{-1}$ neat): 3423 (br.), 2982 (w), 2919 (s), 2851 (m), 1741 (s), 1599 (s, br.).

Step 2: Ethyl 5-(2-bromophenyl)-5,6-diazatetracyclo[7.3.1.1$^{3,11}$.0$^{4,8}$]tetradeca-4(8),6-diene-7-carboxylate A solution of intermediate 1 (2.0 g, 7.56 mmol), 2-bromophenylhydrazine hydrochloride (1.86 g, 8.32 mmol) and ethanol (30 ml) was refluxed for 1 h. After cooling, the precipitated solid was collected by filtration and dried to give the title product in pure form (2.04 g, 65%). $^1$H-NMR (δ ppm, CDCl$_3$, 300 MHz): 7.67 (dd, J=7.8, 1.2, 1H); 7.42-7.26 (m, 3H); 4.40 (q, J=7.2, 2H); 3.79 (br. t, J=5.4, 1H); 2.54 (br. t, J=7.2, 1H); 2.18 (br. s, 2H); 2.14-1.92 (m, 4H); 1.92-1.60 (m, 6H); 1.39 (t, J=7.2, 3H).

Step 3: 5-(2-bromophenyl)-5,6-diazatetracyclo[7.3.1.1$^{3,11}$.0$^{4,8}$]tetradeca-4(8),6-diene-7-carboxylic acid A solution of Ethyl 5-(2-bromophenyl)-5,6-diazatetracyclo[7.3.1.1$^{3,11}$.0$^{4,8}$]tetradeca-4(8),6-diene-7-carboxylate in ethanol:water (20:1) was refluxed with KOH (270 mg, 4.82 mmol) for 2 h. After removal of ethanol, the residue was dissolved in water and acidified to pH 4.0 with aqueous 1N HCl. The precipitate was filtered and dried to give pure intermediate 1 (715 mg, 77%) was obtained. $^1$H-NMR (δ ppm, CDCl$_3$, 300, MHz): 7.71 (dd, J=7.8, 1.5, 1H); 7.50-7.32 (m, 3H); 3.79 (br. t, J=5.1, 1H); 2.56 (br. t, J=5.0, 1H); 2.19 (s, 2H); 2.12-1.90 (m, 4H); 1.90-1.66 (m, 6H).

The intermediates 2 to 11 were prepared according to the process as described in step 2 & 3 of intermediate 1, using Ethyl 2-oxo-(5-oxotricycle[4.3.1.1.$^{3,8}$]undec-4-yl)acetate, appropriate (un)substituted phenyl or pyridyl hydrazine and alkali Intermediate 2

5-(4-chlorophenyl)-5,6-diazatetracyclo[7.3.1.1$^{3,11}$.0$^{4,8}$]tetradeca-4(8),6-diene-7-carboxylic acid Step 1: Ethyl 5-(4chlorophenyl)-5,6-diazatetracyclo[7.3.1.1$^{3,11}$.0$^{4,8}$]tetradeca-4(8),6-diene-7-carboxylate Yield: 54%, $^1$H-NMR (δ ppm, CDCl$_3$, 300 MHz): 7.43, 7.30 (AB, J=10, 4H); 4.40 (q, J=7.5, 2H); 3.79 (t, J=5.1, 1H); 3.0 (t, J=5.4, 1H); 2.21 (br. s, 2H); 2.06-1.77 (m, 1.0H); 1.40 (t, J=7.5, 3H).

Step 2: 5-(4-chlorophenyl)-5,6-diazatetracyclo[7.3.1.1$^{3,11}$.0$^{4,8}$]tetradeca-4(8),6-diene-7-carboxylic acid Yield: 89%. $^1$H-NMR (δ ppm, DMSO-d$_6$): 7.59 (d, J=8.7, 2H); 7.39 (d, J=8.7, 2H); 3.76 (br. s, 1H); 2.97 (br. s, 1H); 2.14 (br. s, 2H); 1.67-1.98 (m, 10H).

Intermediate 3

5-(2,4-Difluorophenyl)-5,6-diazatetracyclo[7.3.1.1$^{3,11}$.0$^{4,8}$]tetradeca-4(8),6-diene-7-carboxylic acid Step 1: Ethyl 5-(2,4-Difluorophenyl)-5,6-diazatetracyclo[7.3.1.1$^{3,11}$.0$^{4,8}$]tetradeca-4(8),6-diene-7-carboxylate Yield: 96%. $^1$H-NMR (δ ppm, CDCl$_3$, 300 MHz): 7.50-7.40 (m, 1H); 7.02-6.90 (m, 2H); 4.38 (q, J=7.2, 2H); 3.76 (br. s, 1H); 2.66 (br. s, 1H); 2.17 (br. s, 2H); 2.05-1.70 (m, 10H), 1.37 (t, J=7.2, 3H).

Step 2: 5-(2,4-Difluorophenyl)-5,6-diazatetracyclo[7.3.1.1$^{3,11}$.0$^{4,8}$]tetradeca-4(8),6-diene-7-carboxylic acid Yield: 95%. $^{1}$H-NMR (δ ppm, CDCl$_3$, 300 MHz): 12.80 (br. s, 1H); 7.70-7.55 (m, 2H); 7.30 (br. t, J=7.5, 1H); 3.66 (br. s, 1H); 2.63 (br. s, 1H); 2.13 (s, 2H); 2.00-1.71 (m, 10H).

Intermediate 4

5-(4-Fluorophenyl)-5,6-diazatetracyclo[7.3.1.1$^{3,11}$.0$^{4,8}$]tetradeca-4(8),6-diene-7-carboxylic acid Step 1: Ethyl 5-(4-Fluorophenyl)-5,6-diazatetracyclo[7.3.1.1$^{3,11}$.0$^{4,8}$]tetradeca-4(8),6-diene-7-carboxylate Yield: 55%. $^{1}$H-NMR (δ ppm, CDCl$_3$, 300 MHz): 7.38-7.31 (m, 2H); 7.18-7.11 (m, 2H); 4.39 (q, J=7.5, 2H); 3.78 (br. s, 1H); 2.95 (br. s, 1H); 2.20 (br. s, 2H); 2.06-1.76 (m, 10H); 1.39 (t, J=7.2, 3H).

Step 2: 5-(4-Fluorophenyl)-5,6-diazatetracyclo[7.3.1.1$^{3,11}$.0$^{4,8}$]tetradeca-4(8),6-diene-7-carboxylic acid Yield: 81%. $^{1}$H-NMR (δ ppm, DMSO-d$_6$, 300 MHz): 12.60 (br. s, 1H); 7.47-7.35 (m, 4H); 3.67 (br. s, 1H); 2.91 (br. s, 1H); 2.14 (br. s, 2H); 1.98-1.71 (m, 10H).

Intermediate 5

5-(4-methylphenyl)-5,6-diazatetracyclo[7.3.1.1$^{3,11}$.0$^{4,8}$]tetradeca-4(8),6-diene-7-carboxylic acid Step 1: Ethyl 5-(4-methylphenyl)-5,6-diazatetracyclo[7.3.1.1$^{3,11}$.0$^{4,8}$]tetradeca-4(8),6-diene-7-carboxylate Yield: 91%. $^{1}$H-NMR (δ ppm, CDCl$_3$, 300 MHz): 7.23 (s, 4H); 4.39 (q, J=7.2, 2H); 3.79 (br. t, J=5.7, 1H); 3.00 (br. s, (H); 2.41 (s, 3H); 2.19 (br. s, 2H); 2.07-1.95 (m, 2H); 1.95-1.73 (m, 8H); 1.40 (t, J=7.2, 3H).

Step 2: 5-(4-methylphenyl)-5,6-diazatetracyclo[7.3.1.1$^{3,11}$.0$^{4,8}$]tetradeca-4(8),6-diene-7-carboxylic acid Yield: 99%. $^{1}$H-NMR (δ ppm, DMSO-d$_6$, 300 MHz): 12.60 (br. s, 1H); 7.34 (d, J=8.1, 2H); 7.26 (d, J=8.1, 2H); 3.68 (br. s, 1H); 2.94 (br. s, 1H); 2.37 (s, 3H); 2.12 (br. s, 2H); 2.05-1.62 (m, 10H).

Intermediate 6

5-(4-Methoxyphenyl)-5,6-diazatetracyclo[7.3.1.1$^{3,11}$.0$^{4,8}$]tetradeca-4(8),6-diene-7-carboxylic acid Step 1: Ethyl 5-(4-Methoxyphenyl)-5,6-diazatetracyclo[7.3.1.1$^{3,11}$.0$^{4,8}$]tetradeca-4(8),6-diene-7-carboxylase Yield: 78%. $^{1}$H-NMR (δ ppm, CDCl$_3$, 300 MHz): 7.29 (d, J=9.0); 6.96 (d, J=9.0, 2H); 4.39 (q, J=7.2, 2H); 3.79 (br. t, J=5.0, 1H); 2.96 (br. s, 1H); 2.19 (br. s, 2H); 2.08-1.96 (m, 2H); 1.96-1.74 (m, 8H); 1.39 (t, J=7.2, 3H).

Step 2: 5-(4-Methoxyphenyl)-5,6-diazatetracyclo[7.3.1.1$^{3,11}$.0$^{4,8}$]tetradeca-4(8),6-diene-7-carboxylic acid Yield: 95%. $^{1}$H-NMR (δ ppm, CDCl$_3$, 300 MHz): 7.28 (d, J=9.0, 2H); 6.98 (d, J=9.0, 2H); 3.86 (s, 3H); 3.78 (t, J=5.4, 1H); 2.99 (br. s, 1H); 2.21 (br. s, 2H); 2.10-1.70 (m, 10H).

Intermediate 7

5-phenyl-5,6-diazatetracyclo[7.3.1.1$^{3,11}$.0$^{4,8}$]tetradeca-4(8),6-diene-7-carboxylic acid Step 1: Ethyl 5-phenyl-5,6-diazatetracyclo[7.3.1.1$^{3,11}$.0$^{4,8}$]tetradeca-4(8),6-diene-7-carboxylate Yield: 63%. $^{1}$H-NMR (δ ppm, CDCl$_3$, 300 MHz): 7.50-7.32 (m, 5H); 4.40 (q, J=7.5, 2H); 3.80 (t, J=5.4, 1H); 3.02 (br. t, J=4.8, 1H); 2.22 (br. s, 2H); 2.07-1.95 (m, 2H); 1.95-1.76 (m, 8H); 1.40 (t, J=7.5, 3H).

Step 2: 5-phenyl-5,6-diazatetracyclo[7.3.1.1$^{3,11}$.0$^{4,8}$]tetradeca-4(8),6-diene-7-carboxylic acid Yield: 91%. $^{1}$H-NMR (δ ppm, CDCl$_3$, 300 MHz): 7.58-7.42 (m, 3H); 7.37 (dd, J=7.8, 1.2, 2H); 3.80 (t, J=5.4, 1H); 3.06 (br. s, 1H); 2.22 (br. s, 2H); 2.10-1.75 (m, 10H).

Intermediate 8

5(2,4-dichlorophenyl)-5,6-diazatetracyclo[7.3.1.1$^{3,11}$.0$^{4,8}$]tetradeca-4(8),6-diene-7-carboxylic acid Step 1: Ethyl 5-(2,4-dichlorophenyl)-5,6-diazatetracyclo[7.3.1.1$^{3,11}$.0$^{4,8}$]tetradeca-4(8),6-diene-7-carboxylate Yield: 71%. $^{1}$H-NMR (δ ppm, CDCl$_3$, 300 MHz): 7.52 (s, 1H); 7.34 (s, 2H); 4.39 (q, J=6.9, 2H); 3.79 (br. t, J=5.4, 1H); 2.55 (br. t, J=4.6, 1H); 2.19 (br. s, 2H); 2.10-1.60 (m, 10H); 1.39 (t, J=6.9, 3H).

Step 2: 5-(2,4-dichlorophenyl)-5,6-diazatetracyclo[7.3.1.1$^{3,11}$.0$^{4,8}$]tetradeca-4(8),6-diene-7-carboxylic acid Yield: 95%. $^{1}$H-NMR (δ ppm, CDCl$_3$, 300 MHz): 7.57 (d, J=1.8, 1H); 7.38 (dd, J=8.4, 1.8, 1H); 7.32 (d, J=8.4, 1H); 3.78 (br. t, J=5.4, 1H); 2.57 (br, t, J=4.6, 1H); 2.20 (br. s, 2H); 2.10-2.65 (m, 10H).

Intermediate 9

5-(2-chlorophenyl)-5,6-diazatetracyclo[7.3.1.1$^{3,11}$.0$^{4,8}$]tetradeca-4(8),6-diene-7-carboxylic acid Step 1: Ethyl 5-(2-chlorophenyl)-5,6-diazatetracyclo[7.3.1.1$^{3,11}$.0$^{4,8}$]tetradeca-4(8),6-diene-7-carboxylate Yield: 56% $^{1}$H-NMR (δ ppm, CDCl$_3$, 300 MHz): 7.53-7.48 (m, 1H); 7.45-7.32 (m, 3H); 4.40 (q, J=7.5, 2H); 3.80 (t, J=5.7, 1H); 2.57 (br. t, J=5.4, 1H); 2.17 (m, 2H); 2.08-1.65 (m, 10H); 1.39 (t, J=7.5, 3H).

Step 2: 5-(2-chlorophenyl)-5,6-diazatetracyclo[7.3.1.1$^{3,11}$.0$^{4,8}$]tetradeca-4(8),6-diene-7-carboxylic acid Yield: 96%. $^{1}$H-NMR (δ ppm, DMSO-d$_6$, 300 MHz): 12.66 (br. s, 1H); 7.72 (d, J=8.1, 1H); 7.70-7.51 (m, 3H); 3.68 (t, J=5.1, 1H); 2.46 (br. s, 1H); 2.13 (br. s, 2H); 2.03-1.64 (m, 10H).

Intermediate 10

5-(5-chloropyridyl)-5,6-diazatetracyclo[7.3.1.1$^{3,11}$.0$^{4,8}$]tetradeca-4(8),6-diene-7-carboxylic acid Step 1: Ethyl 5-(5-chloropyridyl)-5,6-diazatetracyclo[7.3.1.1$^{3,11}$.0$^{4,8}$]tetradeca-4(8),6-diene-7-carboxylate Yield: 28%. $^{1}$H-NMR (δ ppm, DMSO-d$_6$, 300 MHz): 8.46-8.44 (d, J=2.7, 1H); 8.08 (dd, J=8.7, 2.7, 1H); 7.74 (d, J=8.7, 1H); 4.21 (q, J=6.9, 2H); 3.13-3.06 (m, 2H); 2.12-1.62 (m, 12H); 1.12 (t, J=7.2, 3H).

Step 2: 5-(5-chloropyridyl)-5,6-diazatetracyclo[7.3.1.1$^{3,11}$.0$^{4,8}$]tetradeca-4(8),6-diene-7-carboxylic acid Yield: 78%. $^{1}$H-NMR (δ ppm, DMSO-d$_6$, 300 MHz): 13.25 (br. s, 1H); 8.44 (d, J=2.5, 1H); 8.06 (dd, J=8.0, 2.5, 1H); 7.70 (d, J=8.1, 1H); 3.22 (br. s, 1H); 3.05 (br. s, 1H); 2.12-1.64 (m, 12H).

Intermediate 11

5,6-diazatetracyclo[7.3.1.1$^{3,11}$.0$^{4,8}$]tetradeca-4(8),6-diene-7-carboxylic acid Step 1: Ethyl 5,6-diazatetracyclo[7.3.1.1$^{3,11}$.0$^{4,8}$]tetradeca-4(8),6-diene-7-carboxylate Yield: 97%. $^1$H-NMR (δ ppm, CDCl$_3$): 4.36 (q, J=7.2, 2H); 3.61 (br. t, J=5.4, 1H); 3.10 (br. s, 1H), 2.16 (br. s, 2H); 2.08-1.95 (m, 4H); 1.85-1.70 (m, 6H); 1.38 (t, J=7.2, 2H).

Step 2: 5,6-diazatetracyclo[7.3.1.1$^{3,11}$.0$^{4,8}$]tetradeca-4(8),6-diene-7-carboxylic acid Yield: 79%. $^1$H-NMR (δ ppm, DMSO-d$_6$): 12.78 (br. s, 1H); 3.54 (br. s, 1H); 2.97 (br. s, 1H); 2.09 (br. s, 2H); 1.97-1.85 (m, 4H); 1.77 (br. s, 2H); 1.68 (t, J=12.0, 4H).

Intermediates 12a and Intermediate 12b

Ethyl 6-methyl-5,6-diazatetracyclo[7.3.1.1$^{3,11}$.0$^{4,8}$]tetradeca-4(8),6-diene-7-carboxylate (intermediate 12a) and Ethyl 5-methyl-5,6-diazatetracyclo[7.3.1.1$^{3,11}$.0$^{4,8}$]tetradeca-4(8),6-diene-7-carboxylate (Intermediate 12 b)

A solution of 5,6-diazatetracyclo[7.3.1.1$^{3,11}$.0$^{4,8}$]tetradeca-4(8),6-diene-7-carboxylic acid (100 mg, 0.38 mmol) in DMF (2 ml) was treated with NaH (50% dispersion in mineral oil, 20 mg, 0.4 mmol) and stirred at room temperature for 45 minutes and then iodomethane (60 mg, 0.026 mmol) was added to the mixture. Stirring was continued for a further 1.5 h. The mixture was poured into water, extracted into ethyl acetate and dried over anhydrous sodium sulfate. Evaporation and separation by flash chromatography gave Intermediate 12a and Intermediate 12b.

Intermediate 12a: Yield: 36%. $^1$H-NMR (δ ppm, CDCl$_3$): 4.37 (q, J=7.2, 2H); 3.82 (s, 3H); 3.71 (t, J=5.4, 1H); 3.00 (br. t, J=4.8, 1H); 2.18 (br. s, 2H); 2.10-1.80 (m, 4H); 1.80 (br. t, J=12.3, 6H); 1.39 (t, J=7.2, 3H). $^{13}$C-NMR (δ ppm, CDCl$_3$): 161.02, 158.50, 132.17, 127.49, 60.58, 39.36, 36.29, 35.35, 34.69, 32.41, 28.63, 27.15, 14.2.1.

Intermediate 12b: Yield: 36%. $^1$H-NMR (δ ppm, CDCl$_3$): 4.34 (q, J=7.2, 2H); 4.02 (s, 3H); 3.54 (t, J=5.7, 1H); 3.03 (t, J=5.1, 1H); 2.14 (br. s, 2H); 2.07-1.93 (m, 4H); 1.84-1.67 (m, 6H); 1.37 (t, J=7.2, 3H). $^{13}$C-NMR (δ ppm, CDCl$_3$): 163.32, 150.32, 136.54, 130.80, 60.32, 36.78, 36.14, 34.65, 33.65, 29.57, 28.68, 26.46, 14.40.

Intermediates 13a and Intermediate 13b

6-Pentyl-5,6-diazatetracyclo[7.3.1.1$^{3,11}$.0$^{4,8}$]tetradeca-4,7-diene-7-carboxylic acid (Intermediate 13a) and 5-Pentyl-5,6-diazatetracyclo[7.3.1.1$^{3,11}$.0$^{4,8}$]tetradeca-4(8)-6-diene-7-carboxylic acid (Intermediate 13b)

Step 1: Ethyl 6-pentyl-5,6-diazatetracyclo[7.3.1.1$^{3,11}$.0$^{4,8}$]tetradeca-4,7-diene-7-carbaoxylate (Intermediate 13aa) and Ethyl 5-pentyl-5,6-diazatetracyclo[7.3.1.1$^{3,11}$.0$^{4,8}$]tetradeca-4(8)-6-diene-7-carboxylate (Intermediate 13bb)

Intermediate 13aa and 13bb were prepared by a procedure similar to that described for intermediate 12a and 12b, using intermediate 11 (1.00 g, 3.84 mmol), DMF (3 ml) and 1-bromo-n-pentane ((53 μl, 4.20 mmol).

Intermediates 13aa: $^1$H-NMR (δ ppm, CDCl$_3$, 300 MHz): 4.39-4.28 (m, 4H); 3.53 (t, J=5.4, 1H); 3.04 (t, J=5.4, 1H); 2.13 (br. s, 2H); 2.04-1.94 (m, 4H); 1.84-1.66 (m, 8H); 1.37 (t, J=6.9, 3H); 1.30-1.24 (m, 4H); 0.88 (t, J=6.9, 3H).

Intermediates 13bb: $^1$H-NMR (δ ppm, CDCl$_3$, 300 MHz): 4.37 (q, J=6.9, 2H); 4.07 (t, J=7.5, 2H); 3.71 (br. s, 1H); 2.98 (br. s, 1H); 2.18 (br. s, 2H); 2.02-1.92 (m, 4H); 1.85-1.71 (m, 8H); 1.38 (t, J=6.9, 3H); 1.40-1.24 (m, 4H); 0.89 (t, J=7.2, 3H).

Step 2: 6-Pentyl-5,6-diazatetracyclo[7.3.1.1$^{3,11}$.0$^{4,8}$]tetradeca-4,7-diene-7-carboxylic acid (Intermediate 13a) and 5-Pentyl-5,6-diazatetracyclo[7.3.1.1$^{3,11}$.0$^{4,8}$]tetradeca-4(8)-6-diene-7-carboxylic acid (Intermediate 13b)

Intermediate 13aa (400 mg, 1.21 mmol) & Intermediate 13bb (400 mg, 1.21 mmol), KOH (136 mg, 2.42 mmol), ethanol (10 ml) and H$_2$O (0.5 ml) yielded intermediate 13a (270 mg, 73%). $^1$H-NMR (δ ppm, CDCl$_3$, 300 MHz): 4.39 (t, J=7.8, 2H); 3.64 (br. s, 1H); 3.07 (br. s, 1H); 2.14 (br. s, 2H); 2.04-1.94 (m, 4H); 1.79-1.72 (m, 8H); 1.35-1.28 (m, 4H); 0.89 (t, J=7.5, 3H) and intermediate 13b (290 mg, 79%). $^1$H-NMR (δ ppm. CDCl$_3$, 300 MHz): 4.06 (t, J=7.2, 2H); 3.70 (br. s, 1H); 2.98 (br. s, 1H); 2.18 (br. s, 2H); 2.02-1.93 (m, 4H); 1.84-1.68 (m, 8H); 1.40-1.24 (m, 4H); 0.89 (t, J=7.2, 3H) respectively.

The intermediates 14 to 21 were prepared according to the process as described in step 2 & step 3 of intermediate 1, using Ethyl 2-oxo-2(3-oxobicyclo[2.2.1]hept-2-yl)acetate, appropriate (un)substituted phenyl hydrazine and alkali.

Intermediate 14

1-Phenyl-4,5,6,7-tetrahydro-1H-4,7-methano-indazole-3-carboxylic acid

Step 1: Ethyl 2-oxo-2(3-oxobicyclo[2.2.1]hept-2-yl)acetate

The title product was prepared by a procedure similar to that described in step 1 of intermediate 1, from hexamethyldisilazane (4.2 ml, 20.0 mmol), ether (91 ml), nBuLi (2.3M in hexane, 11.63 ml, 27.3 mmol), norcamphor (2.0 g, 18.2 mmol) and diethyl oxalate (2.96 ml, 21.82 mmol) the title product was obtained.

Yield: 56%. $^1$H-NMR (δ ppm, CDCl$_3$,300 MHz): 11.41 (br. s, 1H); 4.35 (q, J=7.2, 2H); 3.81 (br. s, 1H); 2.81 (br. s, 1H); 2.05-1.85 (m, 3H); 1.80 (br. d, J=10.5, 1H); 1.59 (br. t, J=7.2, 2H); 1.41 (t, J=7.2, 3H).

Step 2: Ethyl 1-phenyl-4,5,6,7-tetrahydro-1H-4,7-methano-indazole-3-carboxylate

Yield: 52%. $^1$H-NMR (δ ppm, CDCl$_3$, 300 MHz): 7.73 (d, J=8.7, 2H); 7.47 (t, J=7.2, 2H); 7.33 (t, J=7.2, 1H); 4.42 (q, J=7.2, 2H); 3.72 (br. s, 1H); 3.68 (br. s, 1H); 2.13 (br. d, J=8.7, 1H); 2.05-1.95 (m, 2H); 1.72 (d, J=8.7, 1H); 1.42 (t, J=7.2, 3H); 1.30-1.18 (m, 2H).

Step 3: 1-Phenyl-4,5,6,7-tetrahydro-1H-4,7-methano-indazole-3-carboxylic acid

Yield: 79%. $^1$H-NMR (δ ppm, CDCl$_3$, 300 MHz): 7.73 (d, J=7.8, 2H); 7.50 (t, J=7.8, 2H); 7.36 (t, J=7.5, 1H); 3.75 (s, 1H); 3.72 (s, 1H); 2.17 (br. d, J=9.0, 1H); 2.10-1.93 (m, 2H); 1.74 (d, J=8.7, 1H); 1.38-1.08 (m, 2H).

Intermediate 15

1-(2-Chlorophenyl)-4,5,6,7-tetrahydro-1H-4,7-methano-indazole-3-carboxylic acid

Step 1: Ethyl 1-(2-chlorophenyl)-4,5,6,7-tetrahydro-1H-4,7-methano-indazole-3-carboxylate Yield: 87%. $^1$H-NMR (δ ppm, CDCl$_3$, 300 MHz): 7.72-7.60 (m, 2H); 7.41-7.33 (m, 2H); 4.42 (q, J=7.2, 2H); 3.69 (s, 1H); 3.40 (s, 1H); 2.14 (br. d, J=9.0, 1H); 2.05-1.82 (m, 2H); 1.72 (d, J=9.3, 1H); 1.30 (t, J=7.2, 3H); 1.35-1.12 (m, 2H).

Step 2: 1-(2-Chlorophenyl)-4,5,6,7-tetrahydro-1H-4,7-methano-indazole-3-carboxylic acid Yield: 93%. $^1$H-NMR (δ ppm, CDCl$_3$, 300 MHz): 7.59-7.50 (m, 2H); 7.45-7.33 (m, 2H); (dt, J=8.7, 1.8, 2H); 3.72 (s, 1H); 3.42 (s, 1H); 2.17 (br. d, J=8.7, 1H); 2.10-1.85 (m, 2H); 1.74 (d, J=8.7, 1H); 1.38-1.18 (m, 2H).

Intermediate 16

1-(4-Chlorophenyl)-4,5,6,7-tetrahydro-1H-4,7-methano-indazole-3-carboxylic acid

Step 1: Ethyl 1-(4-chlorophenyl)-4,5,6,7-tetrahydro-1H-4,7-methano-indazole-3-carboxylate Yield: 72%. $^1$H-NMR (δ ppm, CDCl$_3$, 300 MHz): 7.60 (d, J=8.7, 2H); 7.43 (d, J=8.7, 2H); 4.42 (q, J=7.2, 2H); 3.69 (br. s, 1H); 3.66 (br. s, 1H); 2.14 (br. d, J=8.7, 1H); 2.10-1.95 (m, 2H); 1.72 (br. d, J=8.7, 1H); 1.42 (t, J=7.2, 3H), 1.30-1.15 (m, 2H).
IR (KBr, cm$^{-1}$): 2977 (m), 2871 (m), 1716 (s), 1502 (s), 1373 (s), 1230 (s), 1092 (s), 831 (m).

Step 2: 1-(4-Chlorophenyl)-4,5,6,7-tetrahydro-1H-4,7-methano-indazole-3-carboxylic acid Yield: 74.5%. $^1$H-NMR (δ ppm, CDCl$_3$, 300 MHz): 7.70 (d, J=6.7, 2H); 7.50 (d, J=6.7, 2H); 3.70 (s, 2H); 2.16 (br. d, J=8.7, 1H); 2.10-1.94 (m, 2H); 1.74 (br. d, J=8.7, 1H); 1.2 (m, 2H). IR (KBr, cm$^{-1}$): 3460 (vs); 2943 (m), 2873 (m), 1705 (vs), 1684 (vs), 1500 (vs), 1357 (s?), 1252 (vs), 1093 (vs), 835 (s).

Intermediate 17

1-(2,4-Dichlorophenyl)-4,5,6,7-tetrahydro-1H-4,7-methano-indazole-3-carboxylic acid Step 1: Ethyl 1-(2,4-dichlorophenyl)-4,5,6,7-tetrahydro-1H-4,7-methano-indazole-3-carboxylate Yield: 51%. $^1$H-NMR (δ ppm, CDCl$_3$, 300 MHz): 7.53 (d, J=2.4, 1H); 7.49 (d, J=8.4, 1H); 7.36 (dd, J=8.4, 2.4, 1H); 4.41 (q, J=7.2, 2H); 3.69 (br. s, 1H); 3.38 (br. s, 1H); 2.14 (br. d, J=9.0, 1H); 2.07-1.82 (m, 2H); 1.70 (br. d, J=9.0, 1H); 1.41 (t, J=7.2, 3H); 1.29-1.13 (m, 2H).

Step 2: 1-(2,4-Dichlorophenyl)-4,5,6,7-tetrahydro-1H-4,7-methano-indazole-3-carboxylic acid Yield: 87%. $^1$H-NMR (δ ppm, CDCl$_3$, 300 MHz): 7.56 (d, J=2.1, 1H); 7.48 (d, J=8.4, 1H); 7.38 (dd, J=8.4, 2.1, 1H); 3.71 (br. s, 1H); 3.41 (br s, 1H); 2.16 (br. d, J=8.7, 1H); 2.07-1.82 (m, 2H); 1.72 (br. d, J=8.7, 1H); 1.31-1.14 (m, 2H).

Intermediate 18

1-(2-Bromophenyl)-4,5,6,7-tetrahydro-1H-4,7-methano-indazole-3-carboxylic acid

Step 1: Ethyl 1-(2-bromophenyl)-4,5,6,7-tetrahydro-1H-4,7-methano-indazole-3-carboxylate Yield: 79%. $^1$H-NMR (δ ppm, CDCl$_3$, 300 MHz): 7.69 (dd, J=7.8, 1.5, 1H); 7.50 (dd, J=7.8, 2.1, 1H); 7.44 (td, J=7.8, 1.5, 1H); 7.32 (td, J=7.8, 2.1, 1H); 4.41 (q, J=7.2, 2H); 3.69 (br. s, 1H); 3.39 (br. s, 1H); 2.18 (br. d, J=9.0, 1H); 2.05-1.81 (m, 2H); 1.70 (d, J=8.7, 1H); 1.41 (t, J=7.2, 3H); 1.30-1.12 (m, 2H).

Step 2: 1-(2-Bromophenyl)-4,5,6,7-tetrahydro-1H-4,7-methano-indazole-3-carboxylic acid Yield: 92%. $^1$H-NMR (δ ppm, CDCl$_3$, 300 MHz): 7.71 (dd, J=8.4, 1.5, 1H); 7.53-7.40 (m, 2H); 7.34 (td, J=7.8, 2.1, 1H); 3.73 (br. s, 1H); 3.41 (br. s, 1H); 2.19 (br. d, J=8.7, 1H); 2.04-1.82 (m, 2H); 1.73 (d, J=7.2, 1.5, 1H); 1.32-1.15 (m, 2H).

Intermediate 19

1-(1-Bromophenyl)-4,5,6,7-tetrahydro-1H-4,7-methano-indazole-3-carboxylic acid

Step 1: Ethyl 1-(4-bromophenyl)-4,5,6,7-tetrahydro-1H-4,7-methano-indazole-3-carboxylate Yield: 81%. $^1$H-NMR (δ ppm, CDCl$_3$, 300 MHz): 7.65-7.50 (m, 4H); 4.42 (q, J=7.2, 2H); 3.69 (s, 2H); 3.67 (s, 2H); 2.13 (br. d, J=8.7, 1H); 2.06-1.95 (m, 2H); 1.74 (d, J=8.7, 1H); 1.42 (t, J=7.2, 3H); 1.28-1.15 (m, 2H).

Step 2: 1-(4-Bromophenyl)-4,5,6,7-tetrahydro-1H-4,7-methano-indazole-3-carboxylic acid Yield: 83%. $^1$H-NMR (δ ppm, CDCl$_3$, 300 MHz): 7.62 (s, 4H); 3.71 (s, 2H); 2.17 (hr. d, J=9.0, 1H); 2.06-2.01 (m, 2H); 1.75 (d, J=9.0, 1H); 1.30-1.17 (m, 2H).

Intermediate 20

1-(4-Fluorophenyl)-4,5,6,7-tetrahydro-1H-4,7-methano-indazole-3-carboxylic acid

Step 1: Ethyl 1-(4-fluorophenyl)-4,5,6,7-tetrahydro-1H-4,7-methano-indazole-3-carboxylate Yield: 86%. $^1$H-NMR (δ ppm, CDCl$_3$, 300 MHz): 7.69 (dd, J=9.0, 4.8, 2H); 7.15 (t, J=9.0, 2H); 4.42 (q, J=7.2, 2H); 3.67 (br. s, 2H); 3.40 (br. s, 1H); 2.16 (br. d, J=8.7, 1H); 2.03-1.85 (m, 2H); 1.72 (br. d, J=9.0, 1H); 1.43 (t, J=7.2, 3H); 1.32-1.17 (m, 2H).

Step 2: 1-(4-Fluorophenyl)-4,5,6,7-tetrahydro-1H-4,7-methano-indazole-3-carboxylic acid Yield: 60%. $^1$H-NMR (δ ppm, CDCl$_3$, 300 MHz): 7.70 (dd, J=8.7, 4.8, 2H); 7.18 (t, J=8.7, 2H); 3.70 (s, 2H); 2.17 (br. d, J=3.7, 1H); 2.10-1.90 (m, 2H); 1.74 (d, J=8.7, 1H); 1.35-1.18 (m, 2H).

Intermediate 21

1-(2,4-Difluorophenyl)-4,5,6,7-tetrahydro-1H-4,7-methano-indazole-3-carboxylic acid Step 1: Ethyl 1-(2,4-difluorophenyl)-4,5,6,7-tetrahydro-1H-4,7-methano-indazole-3-carboxylate Yield: 81%. $^1$H-NMR (δ ppm, CDCl$_3$, 300 MHz): 7.80-7.68 (m, 1H); 7.05-6.95 (m, 2H); 4.42 (q, J=7.2, 2H); 3.67 (br. s, 1H); 3.47 (br. s, 1H); 2.12-2.08 (br. d, J=8.7, 1H); 2.03-1.90 (m, 2H); 1.72-1.65 (br. d, J=8.7, 1H); 1.41 (t, J=7.2, 3H); 1.30-1.17 (m, 2H).

Step 2: 1-(2,4-Difluorophenyl)-4,5,6,7-tetrahydro-1H-4,7-methano-indazole-3-carboxylic acid Yield: 78%. M.P.: 153-156° C. $^1$H-NMR (δ ppm, CDCl$_3$, 300 MHz): 7.80-7.70 (m, 1H); 7.10-6.97 (m, 2H); 3.70 (br. s, 1H); 3.50 (br. s, 1H); 2.12 (d, J=7.2, 1H); 2.08-1.86 (m, 2H); 1.72 (d, J=8.7, 1H); 1.35-1.17 (m, 2H).

Optical Resolution of 1-(2,4-difluorophenyl)-4,5,6,7-tetrahydro-1H-4,7-methano-indazole-3-carboxylic acid: Intermediate 21

Intermediate 21a

A slurry of intermediate 21 (racemic, 15.0 g, 51.72 mmol) in acetonitrile (LR grade) (150 ml) was treated with (S)-(−)-

α-methylbenzylamine (3.66 ml, 28.44 mmol), stirred at RT for 5-10 min and the mixture was heated at reflux for 15 min. Methanol (24 ml) was added slowly till a clear solution resulted and heating was continued for further 30 min. after which the mixture was allowed to cool slowly to RT. The separated crystals were collected by filteration and washed with acetonitrile/MeOH 9:1 (~15 ml). The acid was recovered from the diastereomeric salt by dissolving in $CH_2Cl_2$ and extraction with aq. 1N HCl. Reiteration of the same procedure several times gave a mixture (100 mg) enriched in the late eluting enantiomer [Intermediate 21a, $R_t$=38.20 min. on a CHIRALCEL AS-H column (dimensions: 250×4.6 mm, particle size: 5μ) using a 90:10:0.1 mixture of n-hexane:isopropanol:trifluoroacetic acid as the eluent at 1 ml/min. flow rate]. M.P.: 114-115° C.; e.e=92%.

Intermediate 21b

The mother liquor obtained in the first step of the process described above was evaporated, distributed between $CH_2Cl_2$ and aq. 1N HCl and the layers were separated. Drying ($Na_2SO_4$) and evaporation of the organic layer gave a mixture of the two enantiomeric acids (9 g) enriched in the fast eluting enantiomer ($R_t$=34.65 min. under the same conditions described above; e.e=34%). The mixture was enriched in this enantiomer to an e.e of 91% (Intermediate 21b, yield=72 mg) by replacing (S)-(−)-α-methylbenzylamine with (R)-(+)-α-methylbenzylamine in the process described above for the late eluting enantiomer. M.P.: 110-112° C.

The intermediates 22 and 23 were prepared according to the process as described in step 2 & step 3 of intermediate 1, using Ethyl 2-(3-hydroxy-4,7,7-trimethyl bicyclo[2.2.1]hept-2-en-2-yl)-2-oxoacetate, appropriate (un)substituted phenyl hydrazine and alkali.

Intermediate 22

1-(2,4-Dichlorophenyl)-7,8,8-trimethyl-4,5,6,7-tetrahydro-1H-4,7-methano-indazole-3-carboxylic acid Step 1: Ethyl 2-(3-hydroxy-4,7,7-trimethyl bicyclo[2.2.1]hept-2-en-2-yl)-2-oxoacetate A solution of DL-camphor (5 g, 33 mmol) in toluene (25 ml) was added to a slurry of sodium hydride (60% dispersion, 1.34 g, 56 mmol) and diethyl oxalate (6.69 g, 49 mmol) in toluene (30 ml) at 60"C and the mixture stirred at the same temperature for 1 hour. The reaction mixture was quenched into ice, acidified with 1N HCl, extracted with ethyl acetate and the organic layers dried over $Na_2SO_4$ and the solvent was removed under vacuum to give the title product (7.3 g, 88%) which was used without further purification for the next step.

Yield: 88%. $^1$H-NMR (δ ppm, $CDCl_3$, 300 MHz): 11.39 (br. s, 1H); 4.35 (q, J=7.2, 2H); 3.29 (d, J=4.2, 1H); 2.30-2.04 (m, 1H); 1.70-1.40 (m, 1H); 1.46 (hr. d, J=8.7, 2H); 1.38 (t, J=7.2, 3H); 1.01, 0.97, 0.83 (3s, 9H).

Step 2: Ethyl 1-(2,4-dichlorophenyl)-7,8,8-trimethyl-4,5,6,7-tetrahydro-1H-4,7-methano-indazole-3-carboxylate Yield: 42%. $^1$H-NMR (δ ppm, $CDCl_3$, 300 MHz): 7.53 (s, 1H); 7.36 (s, 2H); 4.40 (q, J=7.2, 2H); 3.16 (d, J=3.6, 1H); 2.13 (m, 1H); 1.40 (t, J=7.2, 3H); 1.26 (m, 2H); 0.88 (s, 6H); 0.83 (s, 3H).

Step 3: 1-(2,4-Dichlorophenyl)-7,8,8-trimethyl-4,5,6,7-tetrahydro-1H-4,7-methano-indazole-3-carboxylic acid Yield: 72%. $^1$H-NMR (δ ppm, DMSO-$d_6$, 300 MHz): 12.80 (br. s, 1H); 7.95 (d, J=2.1, 1H); 7.67 (d, J=8.7, 1H); 7.63 (dd, J=8.7, 2.1, 1H); 3.01 (d, J=3.6, 1H); 2.13-2.06 (m, 1H); 1.79 (br. t, J=8.7, 1H); 1.32 (hr. t, J=9.3, 1H); 1.16-1.00 (m, 1H); 0.88 (s, 3H); 0.84 (s, 3H); 0.77 (s, 3H).

Intermediate 23

3-(2,4-difluorophenyl)-1,10,10-trimethyl-3,4-diazatricyclo[5.2.1.0$^{2,6}$]deca-2(6),4-diene-5-carboxylic acid Step 1: Ethyl 3-(2,4-difluorophenyl)-1,10,10-trimethyl-3,4-diazatricyclo[5.2.1.0$^{2,6}$]deca-2(6),4-diene-5-carboxylate Yield: 42%. $^1$H-NMR (δ ppm, $CDCl_3$, 300 MHz): 7.58-7.48 (m, 1H); 7.03-6.80 (m, 2H); 4.40 (q, J=7.2, 2H); 3.15 (d, J=4.2, 1H); 2.20-2.08 (m, 1H); 1.88-1.76 (m, 1H); 1.40 (t, J=7.2, 3H); 1.40-1.08 (m, 2H); 0.99, 0.92, 0.79 (3s, 9H).

Step 2: 3-(2,4-difluorophenyl)-1,10,10-trimethyl-3,4-diazatricyclo[5.2.1.0$^{2,6}$]deca-2(6),4-diene-5-carboxylic acid Yield: 72%. $^1$H-NMR (δ ppm, DMSO-$d_6$, 300 MHz): 12.80 (br. s, 1H); 7.80-7.57 (m, 2H); 7.29 (br. t, J=8.4, 1H); 3.0.1 (d, J=3.6, 1H); 2.08-2.02 (m, 1H); 1.79 (br. t, J=9.6, 1H); 1.32 (br. t, J=9.0, 1H); 1.06 (br. t, J=9.0, 1H); 0.91, 0.88, 0.73 (3s, 9H).

The intermediate 24 and 25 were prepared according to the process as described in step 2& step 3 of intermediate 1, using Ethyl 2-oxo-2-(10-oxotricyclo[6.2.2.0$^{2,7}$]dodeca-2,4,6-trien-9-yl)acetate, appropriate (un)substituted phenyl hydrazine and alkali.

Intermediate 24

10-(2,4-dichlorophenyl)-10,11-diazatetracyclo[6.5.2.0$^{2,7}$.0$^{9,13}$]pentadeca-2,4,6,9(13),11-pentaene-12-carboxylic acid Step 1: Ethyl 2-oxo-2-(10-oxotricyclo[6.2.2.0$^{2,7}$]dodeca-2,4,6-trien-9-yl)acetate The title product was prepared by a procedure similar to that described for step 1 of intermediate 1. From tricyclo[6.2.2.0$^{2,7}$]dodeca-2,4,6-trien-9-one [prepared by one of the methods available in the art of organic synthesis, e.g., as described in Hales et. al. *Tetrahedron*, 1995, 51, 7777-7790] (2.5 g, 14.53 mmol), hexamethyldisilazane (4.9 ml, 23.2 mmol), 2.34M n-BuLi (10 ml, 23.4 mmol) and diethyl oxalate (3.18 ml, 21.18 mmol) the desired product was obtained (2.3 g, 63%).

Yield: 63%. $^1$H-NMR (δ ppm, $CDCl_3$, 400 MHz): 12.9 (s, 1H); 7.20-7.15 (m, 4H); 4.91 (s, 1H); 4.31 (q, J=7.2, 2H); 3.79 (s, 1H); 2.00-1.90 (m, 2H); 1.73-1.60 (m, 2H); 1.34 (t, J=7.2, 3H).

Step 2: Ethyl 10-(2,4-dichlorophenyl)-10,11-diazatetracyclo[6.5.2.0$^{2,7}$.0$^{9,13}$]-pentadeca-2,9,6,9(13), 11-pentaene-12-carboxylate Yield: 91%. $^1$H-NMR (δ ppm, $CDCl_3$, 400 MHz): 7.58 (d, J=2.2, 1H); 7.45 (d, J=8.5, 1H); 7.38 (dd, J=8.5, 2.0, 1H); 7.33 (br. d, J=7.0, 1H); 7.16 (br. d, J=7.08, 1H); 7.13 (td, J=7.6, 1.5, 1H); 7.08 (td, J=7.5, 1.5, 1H); 4.91 (s, 1H); 4.45 (q, J=7.2, 2H); 4.29 (s, 1H); 1.81-1.72 (m, 4H); 1.43 (t, J=7.2, 3H).

Step 3: 10-(2,4-dichlorophenyl)-10,11-diazatetracyclo[6.5.2.0$^{2,7}$.0$^{9,13}$]pentadeca-2,4,6,9(13),11-pentaene-12-carboxylic acid $^1$H-NMR (δ ppm, $CDCl_3$, 400 MHz): 7.60 (d, J=2.1, 1H); 7.45 (d, J=8.5, 1H); 7.41 (dd, J=8.5, 2.1, 1H); 7.35 (br. d, J=6.8, 1H); 7.17 (br. d, J=7.2, 1H); 7.14 (td, J=7.5, 1.3, 1H); 7.09 (td, J=7.5, 1.3, 1H); 4.94 (s, 1H); 4.32 (s, 1H); 1.82-1.73 (m, 4H).

Intermediate 25

10-(2,4-difluorophenyl)-10,11-diazatetracyclo[6.5.2.0$^{2,7}$.0$^{9,13}$]pentadeca-2,4,6,9(13),11-pentaene-12-carboxylic acid Step 1: Ethyl 10-(2,4-difluorophenyl)-10,11-diazatetracyclo[6.5.2.0$^{2,7}$.0$^{9,13}$]pentadeca-2,4,6,9(13),11-pentaene-12-carboxylate Yield: 71%. $^1$H-NMR (δ ppm, CDCl$_3$, 300 MHz): 7.67-7.57 (m, 1H); 7.34 (d, J=6.9, 1H); 7.20-7.01 (m, 5H); 4.90 (s, 1H); 4.44 (q, J=6.9, 2H); 4.39 (br. s, 1H); 1.79 (s, 4H); 1.45 (t, J=6.9, 3H).

Step 2: 10-(2,4-difluorophenyl)-10,11-diazatetracyclo[6.5.2.0$^{2,7}$.0$^{9,13}$]pentadeca-2,4,6,9(13),11-pentaene-12-carboxylic acid Yield: 86%. $^1$H-NMR (δ ppm, CDCl$_3$, 300 MHz): 7.68-7.58 (m, 1H); 7.35 (d, J=7.2, 1H); 7.2.1-7.04 (m, 5H); 4.94 (s, 1H); 4.41 (br. s, 1H); 1.81 (br. s, 41-1)

The intermediate 26 was prepared according to the process as described in step 2 & step 3 of intermediate 1, using Ethyl 9endo,13endo-2-[11-(4-chlorophenyl)-10,12,15-trioxo-11-azatetracyclo[6.5.2.0$^{2,7}$.0$^{9,13}$]pentadeca-2,4,6-trien-14-yl]-2-oxoacetate appropriate (un)substituted phenyl hydrazine and alkali.

Intermediate 26

13Endo,14endo-16-(4-chlorophenyl)-15,17-dioxo-10-(2,4-dichlorophenyl)-10,11,16-triazapentacyclo[6.5.5.0$^{2,7}$. 0$^{9,13}$. 0$^{14,18}$]octadeca-2,4,6,9(13),11-pentaene-12-carboxylic acid Step 1: 9-Endo,13-endo-11-(4-chlorophenyl)-11-azatetracyclo[6.5.2.0$^{2,7}$.0$^{9,13}$]pentadeca-2,4,6-triene-10,12,14-trione A solution of 11-oxatetracyclo[6.5.2.0$^{2,7}$.0$^{9,13}$]pentadeca-2,4,6-triene-10,12,14-trione [prepared as described by Takeda et. al. *Tetrahedron* 1970, 26, 1435-1451] (1.0 g, 4.11 mmols), 4-chloroaniline (1.2 g, 9.05 mmols) in xylene was refluxed for 6 h. Water was added to the reaction mixture and extracted with AcOEt. Organic layers dried over Na$_2$SO$_4$ and the solvent evaporated. The residue, after PC (AcOEt-petroleum ether 4:96→16:84) gave the title product (930 mg, 65%).

Yield: 65%. $^1$H-NMR (δ ppm, CDCl$_3$, 300 MHz): 7.40-7.222 (m, 6H); 6.47 (d, J=8.7, 2H); 4.18 (dd, J=3.3, 1H); 4.07-4.02 (m, 1H); 3.59 (dd, J=8.7, 3.3, 1H); 3.49 (dd, J=8.4, 3.3, 1H); 2.56 (dd, J=20.4, 2.1, 1H); 2.43 (dd, J=20.4, 3.3, 1H).

Step 2: Ethyl 9endo,13endo-2-[11-(4-chlorophenyl)-10,12,15-trioxo-11-azatetracyclo[6.5.2.0$^{2,7}$. 0$^{9,13}$]pentadeca-2,4,6-trien-14-yl]-2-oxoacetate The title product was prepared by a procedure similar to that described for step 1 of intermediate 1. From 9-Endo,13-endo-11-(4-chlorophenyl)-11-azatetracyclo[6.5.2.0$^{2,7}$.0$^{9,13}$]pentadeca-2,4,6-triene-10,12,14-trione (800 mg, 2.28 mmol), hexamethyldisilazane (0.68 ml, 3.2 mmol), n-BuLi (15% in hexane, 1.31 ml, 3.1 mmol) and diethyl oxalate (0.62 ml, 4.6 mmol) title product (530 mg, 52%) was obtained in pure form after FC.

Yield: 52%. $^1$H-NMR (δ ppm, CDCl$_3$, 300 MHz): 13.0 (br. s, 1H); 7.36-7.20 (m, 6H); 6.47 (d, J=7.2, 2H); 5.54 (br. s, 1H); 4.49-4.38 (m, 3H); 3.54 (br. s, 2H); 1.45 (t, J=7.2, 3H).

Step 3: Ethyl 13endo,14endo-16-(4-chlorophenyl)-15,17-dioxo-10-(2,4-dichlorophenyl)-10,11,16-triazapentacyclo[6.5.5.0$^{2,7}$. 0$^{9,13}$.0$^{14,18}$]octadeca-2,4,6,9(13),11-pentaene-12-carboxylate Yield: 66%. $^1$H-NMR (δ ppm, CDCl$_3$, 300 MHz): 7.63 (d, J=2.4, 1H); 7.51 (d, J=8.4, 1H); 7.47-7.35 (m, 3H); 7.30-7.15 (m, 4H); 6.44 (d, J=9.0, 2H); 5.44 (d, J=3.0, 1H); 4.83 (d, J=2.7, 1H); 4.49 (q, J=7.2, 2H); 3.56 (dd, J=8.7, 3.3, 1H); 3.48 (br. d, 8.7, 1H); 1.46 (t, J=7.2, 3H).

Step 4: 13Endo,14endo-16-(4-chlorophenyl)-15,17-dioxo-10-(2,4-dichlorophenyl)-10,11,16-triazapentacyclo[6.5.5.0$^{2,7}$.0$^{9,13}$.0$^{14,18}$]octadeca-2,4,6,9(13),11-pentaene-12-carboxylic acid Yield: 76%. $^1$H-NMR (δ ppm, CDCl$_3$, 300 MHz): 7.66 (d, J=2.4, 1H); 7.54-7.40 (m, 3H); 7.28-7.19 (m, 5H); 6.45 (d, J=8.7, 2H); 5.50 (d, J=3.0, 1H); 4.87 (d, T=3.0, 1H); 3.59 (dd, J=8.7, 3.0, 1H); 3.50 (br. d, J=8.7, 1H).

Intermediate 27

10-(2,4-Difluorophenyl)-10,11-diazatetracyclo[6.5.1.0$^{2,7}$.0$^{9,13}$]tetradeca-2,4,6,9(13),11-pentaene-12-carboxylic acid Step 1: Ethyl 2-oxo-2-(10-oxotricyclo[6.2.1.0$^{2,7}$]undeca-2(7),3,5-trien-9-yl)acetate The title product was prepared by a procedure similar to that described for step 1 of intermediate 22. From Benzonorbornanone (2.4 g, 15.1.8 mmol), sodium hydride (60% dispersion, 619 mg, 25 mmol) and diethyl oxalate (3.09 ml, 22.7 mmol) title product (2.6 g, 52%) was obtained. $^1$H-NMR (δ ppm, CDCl$_3$, 300 MHz): 10.63 (br. s, 1H); 7.75-7.20 (m, 5H); 4.81 (d, J=1.5, 1H); 4.35 (q, J=7.2, 2H); 3.75 (d, J=1.5, 1H); 2.57 (dt, J=9.3, 1.8, 1H); 2.42 (d, J=8.7, 1.5, 1H); 1.43 (t, J=7.2, 3H).

Step 2: Ethyl 10-(2,4-difluorophenyl)-10,11-diazatetracyclo[6.5.1.0$^{2,7}$.0$^{9,13}$]tetradeca-2,4,6,9(13),11-pentaene-12-carboxylate The title product was prepared by a procedure similar to that described for step 3 of intermediate 20. From Ethyl (2Z)-hydroxy(10-oxotricyclo[6.2.1.0$^{2,7}$]undeca-2,4,6-trien-9-ylidene)acetate (1.0 g, 3.87 mmol), 2,4-difluorophenylhydrazine hydrochloride (838 mg, 4.64 mmol) ethanol (13.0 ml) and acetic acid (15.0 ml) title product (1.21 g, 85%) was obtained. $^1$H-NMR (δ ppm, CDCl$_3$, 300 MHz): 7.79-7.69 (m, 1H); 7.35-7.26 (m, 2H); 7.05-6.94 (m, 4H), 4.52 (br. s, 1H); 4.41 (q, J=7.5, 2H); 4.32 (br. s, 1H); 3.00 (br. d, J=8.1, 1H); 2.85 (dt, J=8.1, 1.5, 1H); 1.41 (t, J=7.5, 3H).

Step 3: 10-(2,4-Difluorophenyl)-10,11-diazatetracyclo[6.5.1.0$^{2,7}$.0$^{9,13}$]tetradeca-2,4,6,9(13),11-pentaene-12-carboxylic acid The title product was prepared by a procedure similar to that described for intermediate. From Ethyl 10-(2,4-difluorophenyl)-10,11-diazatetracyclo[6.5.1.0$^{2,7}$.0$^{9,13}$]tetradeca-2,4,6,9(13),11-pentaene-12-carboxylate KOH (367 mg, 6.5 mmol), ethanol (10.4 ml) and H$_2$O (0.5 ml) title product (810 mg, 73%) was obtained. $^1$H-NMR (δ ppm, DMSO-d$_6$, 300 MHz): 12.95 (m, 1H); 7.78-7.57 (m, 2H); 7.32-7.25 (m, 3H); 6.98-6.89 (m, 2H); 4.43 (s, 2H); 2.89 (d, J=8.1, 1H); 2.71 (d, J=8.1, 1H).

The intermediate 28 to 30 were prepared according to the process as described in step 2 & step 3 of intermediate 1, using Ethyl 2-hydroxy-2-(3-oxabicyclo[2.2.2]octa-2-yliden)acetate appropriate (un)substituted phenyl hydrazine and alkali.

Intermediate 28

3-(2,4-difluorophenyl)-3,4-diazatricyclo[5.2.2.0$^{2,6}$]undeca-2(6),4-diene-5-carboxylic acid Step 1: Ethyl 2-hydroxy-2-(3-oxabicyclo[2.2.2]octa-2-yliden)acetate A solution of bicyclo[2.2.2]octan-2-one (2.4 g, 19.35 mmol) in toluene (20 ml) was added to a slurry of sodium hydride (60% dispersion, 603 mg, 25.16 mmol) and diethyl oxalate (3.15 ml, 23.22 mmol) in toluene (10 mmol) at 60° C. and the mixture stirred at the same temperature for 1 hour. The reaction mixture was quenched into ice, acidified with 1N HCl, extracted with ethyl acetate and the organic layers dried over Na$_2$SO$_4$ and the solvent was removed under vacuum to give Intermediate 28 (1.2 g, 27%) which was used without further purification for the next step. $^1$H-NMR (δ ppm, CDCl$_3$, 300 MHz): 13.80 (br. s, 1H); 4.36 (q, J=6.9, 2H); 3.57 (br. s, 1H); 2.52 (br. s, 1H); 1.82-1.60 (m, 8H); 1.38 (t, J=6.9, 3H).

Step 2: Ethyl-3-(2,4-difluorophenyl)-3,4-diazatricyclo[5.2.2.0$^{2,6}$]undeca-2(6),4-diene-5-carboxylate Yield: 48%. $^1$H-NMR (δ ppm, CDCl$_3$, 300 MHz): 7.70-7.60 (m, 1H); 7.06-6.94 (m, 2H); 4.43 (q, J=7.2, 2H); 3.70 (br. s, 1H); 3.15 (br. s, 1H); 1.78 (d, 7.8, 4H); 1.45-1.36 (m, 7H).

Step 3: 3-(2,4-difluorophenyl)-3,4-diazatricyclo[5.2.2.0$^{2,6}$]undeca-2(6),4-diene-5-carboxylic acid Yield: 90%. $^1$H-NMR (δ ppm, CDCl$_3$, 300 MHz): $^1$H-NMR (δ ppm, CDCl$_3$, 300 MHz): 7.72-7.60 (m, 1H); 7.09-6.98 (m, 2H); 3.73 (br. s, 1H); 3.18 (br. s, 1H); 1.80 (d, J=6.6, 4H); 1.40 (d, J=7.8, 4H).

Intermediate 29

3-(3,4-dichlorophenyl)-3,4-diazatricyclo[5.2.1.0$^{2,6}$]deca-2(6),4-diene-5-carboxylic acid Step 1: Ethyl 3-(3,4-dichlorophenyl)-3,4-diazatricyclo[5.2.1.0$^{2,6}$]deca-2(6),4-diene-5-carboxylate Yield: 69%. $^1$H-NMR (δ ppm, CDCl$_3$, 300 MHz): 7.90 (d, J=2.1, 1H); 7.59 (dd, J=7.5, 2.1, 1H); 7.52 (d, J=8.7, 1H); 4.42 (q, J=7.5, 2H); 3.71 (br. s, 1H); 3.66 (br. s, 1H); 2.14 (d, J=8.7, 1H); 2.00 (d, J=8.4, 2H); 1.73 (d, J=9.3, 1H); 1.42 (t, J=7.5, 3H); 1.20 (d, J=6.9, 2H).

Step 2: 3-(3,4-dichlorophenyl)-3,4-diazatricyclo[5.2.1.0$^{2,6}$]deca-2(6),4-diene-5-carboxylic acid Yield: 90%. $^1$H-NMR (δ ppm, CDCl$_3$, 300 MHz): 7.92-7.87 (m, 1H); 7.62-7.52 (m, 2H); 3.73 (br. s, 1H); 3.71 (br. s, 1H); 2.16 (d, J=6.6, 1H); 2.03 (d, J=6.3, 2H); 1.76 (d, J=8.7, 1H); 1.23 (d, J=6.0, 2H).

Intermediate 30

3-(2-ethoxy-4-fluorophenyl)-3,4-diazatricyclo[5.2.1.0$^{2,6}$]deca-2(6),4-diene-5-carboxylic acid Step 1: Ethyl 3-(2-ethoxy-4-fluorophenyl)-3,4-diazatricyclo[5.2.1.0$^{2,6}$]deca-2(6),4-diene-5-carboxylate $^1$H-NMR (δ ppm, CDCl$_3$, 300 MHz): 7.53 (q, J=6.3, 1H); 6.78-6.66 (m, 2H); 4.40 (q, J=6.9, 2H); 4.10-4.00 (m, 2H); 3.65 (br. s, 1H); 3.35 (br. s, 1H); 2.08 (d, J=8.1, 1H); 2.00-1.80 (m, 2H); 1.66 (d, J=9.0, 1H); 1.44-1.32 (m, 6H); 1.24 (d, J=6.0, 2H).

Step 2: 3-(2-ethoxy-9-fluorophenyl)-3,4-diazatricyclo[5.2.1.0$^{2,6}$]deca-2(6),4-diene-5-carboxylic acid Yield: 0.91%. $^1$H-NMR (δ ppm, DMSO-d$_6$, 300 MHz): 12.62 (br. s, 1H); 7.48 (t, J=7.8, 1H); 7.18 (d, J=8.4, 1H); 6.94-6.86 (m, 1H); 4.17 (d, J=6.6, 2H); 3.49 (br. s, 1H); 3.34 (br. s, 1H); 2.00-1.88 (m, 3H); 1.63 (d, J=7.8, 1H); 1.30 (t, J=6.6, 1H); 1.09 (t, J=10.5. 2H).

The intermediates 31a & 31b, 32a & 32b were prepared according to the process as described for intermediate 12a & 12 b followed by hydrolysis as described for intermediate 13a & 13b, using Ethyl 2-oxo-2(3-oxobicyclo[2.2.1]hept-2-yl)acetate hydrazine hydrate, 4-methyl benzyl bromide and 4-fluoro benzyl bromide respectively.

Intermediate 31a

Step 1: Ethyl 4,5,6,7-tetrahydro-1H-4,7-methano-indazole-3-carboxylate

Yield: 1.30 g, 66%. $^1$H-NMR (δ ppm, CDCl$_3$): 4.36 (q, J=6.9, 2H); 3.58 (br. s, 1H); 3.45 (br. s, 1H), 2.02-1.92 (m, 3H); 1.71 (d, J=9.0, 1H); 1.38 (t, J=6.9, 3H); 1.30-1.20 (m, 2H).

Step 2: Ethyl 1-(4-methylbenzyl)-4,5,6,7-tetrahydro-1H-4,7-methano-indazole-3-carboxylate: (Intermediate 31aa) and

Ethyl 2-(4-methylbenzyl)-4,5,6,7-tetrahydro-2H-4,7-methano-indazole-3-carboxylate (Intermediate 31 bb)

Intermediate 31aa; $^1$H-NMR (δ ppm, CDCl$_3$, 300 MHz): 7.15 (s, 4H); 5.28 (d, J=4.8, 2H); 4.38 (q, 7.2, 2H); 3.54 (br. s, 1H); 2.97 (br. s, 1H); 2.34 (s, 3H); 1.98-1.78 (m, 3H); 1.52 (d, J=8.7, 1H); 1.39 (t, J=6.9, 3H); 1.12-0.98 (m, 1H); 0.82-0.68 (m, 1H).

Intermediate 31bb: $^1$H-NMR (δ ppm, CDCl$_3$, 300 MHz): 7.20-7.05 (m, 4H); 5.72 (d, J=15.6, 1H); 5.49 (d, 14.7, 1H); 4.38-4.25 (m, 2H); 3.52 (br. s, 1H); 3.41 (br. s, 1H); 2.29 (s, 3H); 2.22 (br. s, 1H); 1.99-1.80 (m, 2H); 1.66 (d, J=7.2, 1H); 1.35 (t, J=6.9, 3H); 1.26-1.19 (m, 2H)

Step 3a: 3-(4-methylbenzyl)-3,4-diazatricyclo[5.2.1.0$^{2,6}$]deca-2(6),4-diene-5-carboxylic acid Intermediate 31a (294 mg, 82%). $^1$H-NMR (δ ppm, CDCl$_3$, 300 MHz): 7.15 (s, 4H); 5.27 (d, J=3.6, 2H); 3.57 (br. s, 1H); 3.03 (br. s, 1H); 2.34 (s, 3H); 1.96-1.81 (m, 2H); 1.74-1.65 (m, 1H); 1.55 (d, J=9.0, 1H); 1.12-1.02 (m, 1H); 0.83-0.74 (m, 1H).

Step 3b: 2-(4-Methylbenzyl)-4,5,6,7-tetrahydro-2H-4,7-methano-indazole-3-carboxylic Acid Intermediate 31b: (68 mg, 85%). $^1$H-NMR (δ ppm, CDCl$_3$, 300 MHz): 7.10 (d, J=3.3, 4H); 5.72 (d, 15.0, 1H); 5.49 (d, J=14.4, 1H); 3.58 (br. s, 1H); 3.42 (br. s, 1H); 2.29 (s, 3H); 1.99-1.88 (m, 3H); 1.67 (d, J=8.7, 1H); 1.23 (d, J=10.5, 2H).

Intermediate 32a and 32b

Step 1: Ethyl 1-(4-fluorobenzyl)-4,5,6,7-tetrahydro-1H-4,7-methano-indazole-3-carboxylate (Intermediate 32aa) and

Ethyl 2-(1-fluorobenzyl)-4,5,6,7-tetrahydro-2H-4,7-methano-indazole-3-carboxylate (Intermediate 32bb)

Intermediates 32aa: $^1$H-NMR (δ ppm, CDCl$_3$, 300 MHz): 7.28-7.20 (m, 2H); 7.03 (t, J=8.7, 2H); 5.29 (d, J=3.3, 2H); 4.38 (q, 6.9, 2H); 3.55 (br. s, 1H); 3.02 (br. s, 1H); 1.98-1.79 (m, 2H); 1.70-1.62 (m, 1H); 1.55 (d, J=9.0, 1H); 1.39 (t, j=6.9, 3H); 1.14-0.98 (m, 1H); 0.82-0.68 (m, 1H).

Intermediates 32bb: $^1$H-NMR (δ ppm, CDCl$_3$, 300 MHz): 7.24-7.17 (m, 2H); 6.95 (t, J=8.4, 2H); 5.72 (d, J=15.6, 1H); 5.48 (d, 15.0, 1H); 4.29 (q, J=7.2, 2H); 3.51 (br. s, 1H); 3.40

(br. s, 1H); 1.94 (d, J=6.0, 3H); 1.66 (d, J=9.0, 1H); 1.35 (t, J=7.2, 3H),1.28-1.18 (m, 2H).

Step 2a: 1-(4-Fluorobenzyl)-4,5,6,7-tetrahydro-1H-4,7-methano-indazole-3-carboxylic acid Intermediate 32a: (294 mg, 72%). $^1$H-NMR (δ ppm, DMSO-d$_6$, 300 MHz): 12.42 (br. s, 1H); 7.36-7.25 (m, 2H); 7.20 (t, J=9.0, 2H); 5.31 (br. s, 2H); 3.39 (br. s, 1H); 3.32 (br. s, 1H); 1.90-1.70 (m, 3H); 1.55 (d, J=8.7, 1H); 0.99-0.80 (m, 1H); 0.79-0.62 (m, 1H).

Step 2b: 2-(4-Fluorobenzyl)-4,5,6,7-tetrahydro-2H-4,7-methano-indazole-3-carboxylic acid Intermediate 32b: (55 mg, 60%). $^1$H-NMR (δ ppm, CDCl$_3$, 300 MHz): 7.25-7.17 (m, 2H); 6.96 (t, J=8.7, 2H); 5.72 (d, J=14.4, 1H); 5.50 (d, 15.3, 1H); 3.59 (br. s, 1H); 3.43 (br. s, 1H); 1.84 (d, J=6.9, 3H); 1.69 (d, J=8.4, 1H); 1.23 (d, J=10.2, 2H).

Example 101

N(7)-Piperidino-5-(2-bromophenyl)-5,6-diazatetracyclo[7.3.1.1$^{3,11}$.0$^{4,8}$]tetradeca-4(8),6-diene-7-arboxamide A solution of intermediate 1 (300 mg, 0.78 mmol) in DMF (3 ml), was treated with BOP reagent (319 mg, 0.72 mmol) and Et$_3$N (0.10 ml, 0.99 mmol) at room temperature for 15 minutes after which period, N-aminopiperidine (80 µl, 0.90 mmol) was added to the mixture and stirred at room temperature for 1 h. The mixture was poured into water and the precipitate formed was collected, by filtration, dried and purified by flash chromatography to get pure title compound (270 mg, 74%). M.P.: 244° C. $^1$H-NMR (δ ppm, CDCl$_3$, 300 MHz): 7.72 (d, J=7.6, 1H); 7.65 (br. s, 1H); 7.50-7.30 (m, 3H, 3.97 (br. s, 1H); 2.85 (br. s, 4H); 2.51 (br. s, 1H); 2.16 (br. s, 2H); 2.10-1.50 (m, 14H); 1.40 (br. s, 2H). IR (cm$^{-1}$, KBr): 3311 (w), 2913 (s), 2844 (m), 2793 (m), 1687 (s), 1570 (w), 1522 (s), 1489 (m), 1479 (m), 1440 (m), 1352 (m), 1227 (m), 1214 (m). MS (m/z) 469.4 ([M+H]$^+$).

Example 102

N(7)-Benzyl-5-(2-bromophenyl)-5,6-diazatetracyclo[7.3.1.1$^{3,11}$.0$^{4,8}$]tetradeca-4(8),6-diene-7-carboxamide The title compound was synthesized by a procedure similar to that described for example 101 Intermediate 1 (300 mg, 0.78 mmol), DMF (3 ml), Et$_3$N (0.10 ml, 0.99 mmol), BOP reagent (319 mg, 0.72 mmol) and benzylamine (80 µl, 0.72 mmol) gave the title compound (280 mg, 76%). M.P.: 201° C. $^1$H-NMR (δ ppm, CDCl$_3$, 300 MHz): 7.70 (d, J=7.5, 1H); 7.44 (dd, J=7.5, 1.5, 1H); 7.41-7.20 (m, 8H); 4.63 (dd, J=14.4, 6.0, 1H); 4.50 (dd, J=16.5, 5.4, 1H); 4.00 (br. t, J=5.1, 1H); 2.52 (hr. t, J=5.1, 1H); 2.13 (br. s, 2H); 2.13-1.92 (m, 4H); 1.92-1.65 (m, 6H). IR (cm$^{-1}$, KBr): 3428 (m), 2908 (s), 2845 (m), 1672 (s), 1.566 (m), 1522 (s), 1498 (s), 1472 (s), 1351 (m), 1087 (m), 1024 (m), 1010 (m), 778 (m), 763 (m), 726 (m), 698 (m). MS (m/z): 476.4 ([M+H]$^+$).

Example 103

N(7)-Morpholino-5-(4-chlorophenyl)-5,6-diazatetracyclo[7.3.1.1$^{3,11}$.0$^{4,8}$]tetradeca-4(8),6-diene-7-carboxamide The title compound was synthesized by a procedure similar to that described for example 101. Intermediate 2 (100 mg, 0.29 mmol), DMF (1.0 ml), Et$_3$N (40 µl, 0.29 mmol), BOP reagent (129 mg, 0.29 mmol) and N-aminomorpholine (28 µl, 0.29 mmol) yielded the title compound (97 mg, 78%). M.P.: 220° C. $^1$H-NMR (δ ppm, CDCl$_3$, 300 MHz): 7.75 (br. s, 1H); 7.47 (d, J=8.1, 2H); 7.29 (d, J=8.1, 2H); 3.96 (br. s, 1H); 3.85 (t, J=4.5, 4H); 2.99 (br. s, 1H); 2.95 (t, J=4.5, 5H); 2.20 (br. s, 2H); 2.10-1.76 (m, 10H). IR (KBr, cm$^{-1}$): 2915 (s), 2848 (m), 1674 (s), 1532 (m), 1498 (s), 1304 (m), 1267 (m), 1219 (m), 1112 (s), 1091 (s), 895 (m), 838 (s). MS (m/z): 427.3 ([M+H]$^+$).

Example 104

N(7)-(3-Pyridylmethyl)-5-(4-chlorophenyl)-5,6-diazatetracyclo[7.3.1.1$^{3,11}$.0$^{4,8}$]tetradeca-4(8),6-diene-7-carboxamide The title compound was synthesized by a procedure similar to that described for example 101. Intermediate 2 (100 mg, 0.29 mmol), DMF (1.0 ml), Et$_3$N (48 µl, 0.34 mmol), BOP reagent (128 mg, 0.29 mmol) and 3-aminomethylpyridine (30 µl, 0.29 mmol) furnished the title compound (98 mg, 78%). M.P.: 180° C. $^1$H-NMR (δ ppm, DMSO-d$_6$, 300 MHz): 8.76 (t, J=6.0, 1H); 8.52 (br. s, 1H); 8.43 (dd, J=4.8, 1.5, 1H); 7.70 (d, J=8.1, 1H); 7.62 (d, J=8.4, 2H); 7.46 (d, J=8.4, 2H); 7.34 (dd, J=8.1, 4.8, 1H); 4.39 (d, J=6.0, 2H); 3.80 (br. s, 1H); 2.95 (br. s, 1H); 2.14 (br. s, 2H), 2.00-1.69 (m, 10H). MS (m/z): 433.2 ([M+H]$^+$).

Example 105

N(7)-(4-Pyridylmethyl)-5-(4-chlorophenyl)-5,6-diazatetracyclo[7.3.1.1$^{3,11}$.0$^{4,8}$]tetradeca-4(8),6-diene-7-carboxamide The title compound was synthesized by a procedure similar to that described for example 101. Intermediate 2 (100 mg, 0.29 mmol), DMF (1.0 ml), Et$_3$N (48 µl, 0.34 mmol), BOP reagent (0.128 mg, 0.29 mmol) and 4-aminomethylpyridine ((30 µl, 0.29 mmol) furnished the title compound (119 mg, 94%). M.P.: 167-168° C. $^1$H-NMR (δ ppm, DMSO-d$_6$, 300 MHz): 8.79 (t, J=6.3, 1H); 8.48 (d, J=4.5, 2H); 7.65 (dd, J=7.5, 1.5, 2H); 7.48 (dd, J=7.5, 1.5, 2H); 7.27 (d, J=4.5, 2H); 4.39 (d, J=5.7, 2H); 3.80 (br. s, 1H); 2.97 (br. s, 1H); 2.14 (br. s, 2H), 2.00-1.68 (m, 10H). IR (cm$^{-1}$, KBr): 3212 (m), 2913 (s), 2850 (m), 1656 (s), 1529 (m), 1498 (s), 1419 (m), 1363 (m), 1232 (m), 1160 (m), 1084 (m), 842 (m). MS (m/z): 433.1 ([M+H]$^+$).

Example 106

N(7)-Cyclohexyl-5-(4-chlorophenyl)-5,6-diazatetracyclo[7.3.1.1$^{3,1}$.0$^{4,8}$]tetradeca-4(8),6-diene-7-carboxamide The title compound was synthesized by a procedure similar to that described for example 101. Intermediate 2 (100 mg, 0.29 mmol), DMF (1.0 ml), Et$_3$N (40 µl, 0.29 mmol), BOP reagent (129 mg, 0.29 mmol) and cyclohexylamine (40 µl, 0.29 mmol) gave the title compound (110 mg, 89%). M.P.: 162° C. $^1$H-NMR (δ ppm, CDCl$_3$, 300 MHz): 7.47 (d, J=8.7, 2H); 730 (d, J=8.7, 2H); 6.85 (d, J=8.7, 1H); 4.01 (br. t, J=5.5, 1H); 4.00-3.80 (m, 1H); 2.99 (br. t, J=5.6, 1H); 2.20 (br. s, 2H); 2.08-1.68 (m, 12H); 1.48-1.10 (m, 8H). IR (cm$^{-1}$, KBr): 3336 (m), 2928 (s), 2909 (s), 2846 (m), 1649 (s), 1537 (s), 1498 (s), 1366 (m), 1231 (m), 1164 (m), 1088 (m), 838 (m). MS (m/z): 424.1 ([M+H]$^+$).

Example 107

N(7)-(N-cyclohexyl-N-methylamino)-5-(4-chlorophenyl)-5,6-diazatetracyclo[7.3.1.1$^{3,11}$.0$^{4,8}$]tetradeca-4(8),6-diene-7-carboxamide The title compound was synthesized by a procedure similar to that described for example 101. Intermediate 2 (250 mg, 0.72 mmol), DMF (3 ml), Et$_3$N (0.22.0 ml, 1.60 mmol), BOP reagent (322 mg, 0.72 mmol) and 3-N-cyclohexyl-N-methyl hydrazine (140 mg, 1.10 mmol) yielded the title compound (215 mg, 65%). M.P.: 219° C. $^1$H-NMR (δ ppm, CDCl$_3$, 300 MHz): 7.64 (br. s, 1H); 7.46 (d, J=9.0, 2H), 7.31 (d, J=9.0, 2.1, 2H), 3.97 (br. s, 1H); 2.98 (br. s, 1H), 2.69 (s, 3H), 2.62 (br. s, 1H); 2.19 (br. s, 2H); 2.05-1.70 (m, 14H); 1.40-1.00 (m, 6H). IR (cm$^{-1}$, KBr): MS (m/z): 453.20 ([M+H]$^+$).

Example 108

N(7)-Cyclohexylmethyl-5-(4-chlorophenyl)-5,6-diazatetracyclo[7.3.1.1$^{3,11}$.0$^{4,8}$]tetradeca-4(8),6-diene-7-carboxamide The title compound was synthesized by a procedure similar to that described for example 101. Intermediate 2 (100 mg, 0.29 mmol), Et$_3$N (40 μl, 0.29 mmol), BOP reagent (129 mg, 0.29 mmol) and cyclohexanemethylamine (38 μl, 0.23 mmol) gave the title compound (93 mg, 73%). M.P.: 117° C. $^1$H-NMR (δ ppm, CDCl$_3$, 300 MHz): 7.46 (d, J=8.1, 2H); 7.29 (d, J=8.1, 2H); 7.03 (br. s, 1H); 4.01 (br. s, 1H), 3.22 (t, J=6.6, 2H); 3.00 (br. s, 1H); 2.20 (br. s, 2H); 2.10-1.50 (m, 15H); 1.40-1.10 (m, 4H), 1.10-0.85 (m, 2H). IR (cm$^{-1}$, KBr): 3441 (m), 2924 (s), 2849 (m), 1670 (s), 1528 (m), 1499 (s), 1477 (m), 1364 (m), 1214 (m), 1232 (m), 1162 (w), 1087 (m), 838 (m). MS (m/z): 438.2 ([M+H]$^+$).

Example 109

N(7)-(Adamantan-1-yl)-5-(4-chlorophenyl)-5,6-diazatetracyclo[7.3.1.1$^{3,11}$.0$^{4,8}$]tetradeca-4(8)-6-diene-7-carboxamide The title compound was synthesized by a procedure similar to that described for example 101. Intermediate 2 (120 mg, 0.35 mmol), DMF (1.0 ml), Et$_3$N (58 μl, 0.42 mmol), BOP reagent (154 mg, 0.35 mmol) and 1-adamantylamine (52 mg, 0.35 mmol) furnished the title compound (117 mg, 70%). M.P.: 249-252° C. $^1$H-NMR (δ ppm, CDCl$_3$, 300 MHz): 7.47 (d, J=8.7, 2H); 7.29 (d, J=8.7, 2H); 6.73 (br. s, 1H); 4.00 (br. s, 1H); 2.98 (br. s, 1H); 2.23-1.54 (m, 27H). IR (cm$^{-1}$, KBr): 3389 (s), 2904 (s), 2849 (m), 1674 (s), 1561 (w), 1527 (s), 1499 (s), 1479 (m), 1455 (m), 1364 (m), 1356 (m), 1232 (m), 1219 (m), 1170 (w), 1090 (m), 1014 (w), 837 (m). MS (m/z): 476.2 ([M+H]$^+$).

Example 110

N(7)-(1S,2endo-1,3,3-Trimethyl-bicyclo[2.2.1]hept-2-yl)-5-(4-chlorophenyl)-5,6-diazatetracyclo[7.3.1.1$^{3,11}$.0$^{4,8}$]tetradeca-4(8)-6-diene-7-carboxamide The title compound was synthesized by a procedure similar to that described for example 101. Intermediate 2 (120 mg, 0.35 mmol), DMF (1.0 ml), Et$_3$N (58 μl, 0.42 mmol), BOP reagent (154 mg, 0.35 mmol) and 1,3,3-Trimethyl-bicyclo[2.2.1]hept-2-yl amine (53 mg, 0.80 mmol) furnished the title compound (135 mg, 80%). M.P.: 229° C. $^1$H-NMR (δ ppm, CDCl$_3$, 300 MHz): 8.91 (s, 1H); 7.47 (d, J=8.7, 2H); 7.39 (d, J=8.1, 2H); 7.34-7.20 (m, 3H); 6.99 (t, J=8.8, 1H); 3.86 (br. t, J=4.8, 1H); 3.35 (s, 3H); 3.00 (br. s, 1H); 2.17 (br. s, 2H); 2.00-1.70 (m, 10H). IR (cm$^{-1}$, KBr): 3396 (s), 2909 (s), 2845 (m), 1685 (s), 1587 (m), 1563 (m), 1498 (s), 1475 (m), 1464 (s), 1438 (s), 1366 (m), 1223 (m), 1152 (m), 1092 (s), 1083 (m), 1014 (m), 837 (s). MS (m/z): 478.3 ([M+H]$^+$).

Example 111

N(7)-(2-Chlorobenzyl)-5-(4-chlorophenyl)-5,6-diazatetracyclo[7.3.1.1$^{3,11}$.0$^{4,8}$]tetradeca-4(8),6-diene-7-carboxamide The title compound was synthesized by a procedure similar to that described for example 101. Intermediate 2 (100 mg, 0.29 mmol), DMF (1.0 ml), Et$_3$N (40 μl, 0.29 mmol), BOP reagent (129 mg, 0.29 mmol) and 2-chlorobenzylamine (35 μl, 0.29 mmol) yielded the title compound (102 mg, 75%). M.P.: 162-164° C. $^1$H-NMR (δ ppm, CDCl$_3$, 300 MHz): 7.50-7.18 (m, 9H); 4.67 (d, J=6.3, 2H); 3.99 (br. t, J=4.3, 1H); 3.00 (br. t, J=4.8, 1H); 2.20 (br. s, 2H); 2.00-1.70 (m, 10H). IR (KBr, cm$^{-1}$): 3422 (m), 2916 (s), 2845 (m), 1670 (s), 1564 (m), 1531 (s), 1497 (s), 1478 (s), 1442 (m), 1360 (m), 1249 (m), 1232 (m), 1163 (m), 1085 (s), 1047 (m), 1012 (m), 976 (m), 835 (m). MS (m/z): 466.0 ([M+H]$^+$).

Example 112

N(7)-(4-Chlorobenzyl)-5-(4-chlorophenyl)-5,6-diazatetracyclo[7.3.1.1$^{3,11}$.0$^{4,8}$]tetradeca-4(8)-6-diene-7-carboxamide The title compound was synthesized by a procedure similar to that described for example 101. Intermediate 2 (100 mg, 0.29 mmol), Et$_3$N (40 μl, 0.29 mmol), BOP reagent (129 mg, 0.29 mmol) and 4-chlorobenzylamine (36 μl, 0.29 mmol) gave the title compound (115 mg, 85%). M.P.: 198° C. $^1$H-NMR (δ ppm, CDCl$_3$, 300 MHz): 7.45 (d, J=8.7, 2H); 7.40-7.20 (m, 7H), 4.54 (d, J=6.3, 2H), 4.00 (br. s, 1H); 3.00 (br. s, IR); 2.21 (br. s, 2H); 2.10-1.95 (m, 2H); 1.95-1.70 (m, 8H). IR (cm$^{-1}$, KBr): 331.7 (m), 2914 (s), 2847 (m), 1657 (s), 1538 (s), 1498 (s), 1365 (m), 1247 (m), 1087 (m), 1015 (m); 839 (m). MS (m/z): 466.3 ([M+H]$^+$).

Example 113

N(7)-(4-Fluorobenzyl)-5-(4-chlorophenyl)-5,6-diazatetracyclo[7.3.1.1$^{3,11}$.0$^{4,8}$]tetradeca-4(8)-6-diene-7-carboxamide The title compound was synthesized by a procedure similar to that described for example 101. Intermediate 2 (100 mg, 0.29 mmol), DMF (1.0 ml), Et$_3$N (40 μl, 0.29 mmol), BOP reagent (129 mg, 0.29 mmol) and 4-fluorobenzylamine (33 μl, 29 mmol) gave the title compound (96 mg, 73%). M.P.: 201° C. $^1$H-NMR (δ ppm, CDCl$_3$, 300 MHz): 7.44 (d, J=8.4, 2H); 7.30-7.25 (m, 5H); 7.00 (t, J=8.4, 2H); 4.54 (d, J=6.0, 2H), 4.01 (br. s, 1H); 3.00 (br. s, 1H); 2.20 (br. s, 2H); 2.05-1.95 (m, 2H); 1.95-1.80 (m, 8H). IR (cm$^{-1}$, KBr): 3345 (m), 2921 (s), 2900 (m), 2850 (m), 1648 (s), 1542 (s), 1508 (s), 1364 (m), 1354(m), 1258 (m), 1233 (m), 1217 (s), 1155 (m), 1087 (m), 834 (s). MS (m/z): 450.0 ([M+H]$^+$).

Example 114

N(7)-(2,4-Difluorobenzyl)-5-(4-chlorophenyl)-5,6-diazatetracyclo[7.3.1.1$^{3,11}$.0$^{4,8}$]tetradeca-4(8),6-diene-7-carboxamide

The title compound was synthesized by a procedure similar to that described for example, 101. Intermediate 2 (150 mg, 0.43 mmol), DMF (2.0 ml), Et$_3$N (60 µl, 0.43 mmol), BOP reagent (193 mg, 0.43 mmol) and 2,4-difluorobenzylamine (52 µl, 0.43 mmol) yielded the title compound (195 mg, 96%). M.P.: 185° C. $^1$H-NMR (δ ppm, CDCl$_3$, 300 MHz): 7.49-7.27 (m, 6H); 6.90-6.75 (m, 2H); 4.57 (d, J=6.3, 2H); 3.98 (t, J=5.7, 1H); 2.99 (br. t, 5.4, 1H), 2.20 (br. s, 2H), 2.05-1.80 (m, 10H). IR (cm$^{-1}$, KBr): 3428 (s), 2920 (m), 2898 (m), 1673 (s), 1535 (s), 1500 (s), 1430 (s), 1229 (m), 1161 (m), 1064 (m), 986 (m), 835(m), 960 (m), 861 (m). MS (In/z): 468.10 ([M+H]$^+$).

Example 115

N(7)-(2,6-Difluorobenzyl)-5-(4-chlorophenyl)-5,6-diazatetracyclo[7.3.1.1$^{3,11}$.0$^{4,8}$]tetradeca-4(8),6-diene-7-carboxamide

The title compound was synthesized by a procedure similar to that described for example 101. Intermediate 2 (150 mg, 0.43 mmol), DMF (2.0 ml), Et$_3$N (60 µl, 0.43 mmol), BOP reagent (193 mg, 0.43 mmol) and 2,6-difluorobenzylamine (52 µl, 0.43 mmol) yielded the title compound (178 mg, 87%). M.P.: 166-167° C. $^1$H-NMR (δ ppm, CDCl$_3$, 300 MHz): 7.44 (d, J=8.7, 2H); 7.30-7.20 (m, 3H); 6.88 (t, J=7.8, 2H); 4.68 (d, J=5.7, 2H), 4.00 (br. t, J=5.4, 1H); 2.98 (br. s, 1H), 2.19 (br. s, 2H), 2.05-1.60 (m, 10H). IR (cm$^{-1}$, KBr): 3427 (m), 2930 (m), 2905 (m), 1681 (s), 1594 (m), 1563 (m), 1530 (s), 1499 (s), 1471 (s), 1364 (m), 1260 (m), 1161 (m), 1087 (s), 994 (s), 839 (m). MS (m/z): 468.10 ([M+H]$^{+s}$).

Example 116

N(7)-(4-Trifluoromethylbenzyl)-5-(4-chlorophenyl)-5,6-diazatetracyclo[7.3.1.1$^{3,11}$.0$^{4,8}$]tetradeca-4(8),6-diene-7-carboxamide

The title compound was synthesized by a procedure similar to that described for example 101. Intermediate 2 (100 mg, 0.29 mmol), Et$_3$N (40 µl, 0.29 mmol), BOP reagent (129 mg, 0.29 mmol) and 4-(trifluoromethyl)benzylamine (42 µl, 0.27 mmol) furnished the title compound (115 mg, 79%). M.P.: 228° C. $^1$H-NMR (δ ppm, CDCl$_3$, 300 MHz): 7.57 (d, J=8.6, 2H); 7.46-7.39 (m, 4H); 7.37 (hr. t, J=5.4, 1H); 7.28 (d, J=8.7, 2H); 4.63 (d, J=6.0, 2H), 3.99 (br. t, J=4.2, 1H); 3.00 (br. s, 1H), 2.21 (br. s, 2H); 2.05-1.96 (m, 2H); 1.96-1.84 (m, 8H). IR (cm$^{-1}$, KBr): 3350 (m), 2916 (s), 2850 (m), 1.647 (s), 1618 (m), 1541 (s), 1498 (s), 1325 (s), 1256 (m), 1232 (m), 1159 (s), 1124 (s), 1112 (s), 1086 (s), 1065 (s), 1015 (m), 978 (m), 850 (m), 834 (m).

Example 117

N(7)-(1-Phenylethyl)-5-(4-chlorophenyl)-5,6-diazatetracyclo[7.3.1.1$^{3,11}$.0$^{4,8}$]tetradeca-4(8),6-diene-7-carboxamide

The title compound was synthesized by a procedure similar to that described for example 101. Intermediate 2 (150 mg, 0.43 mmol), AMP (2.0 ml), Et$_3$N (60 µl, 0.43 mmol), BOP reagent (193 mg, 0.43 mmol) and S-(−)-Phenylethylamine (58 µl, 0.43 mmol) furnished the title compound (130 mg, 67%). M.P.: 85-86° C. $^1$H-NMR (δ ppm, CDCl$_3$, 300 MHz): 7.50-7.40 (m, 5H); 736-7.20 (m, 4H); 5.27 (quintet, 7.2, 1H), 4.00 (t, J=5.6, 1H); 2.98 (t, J=5.6, 1H), 2.19 (br. s, 2H), 2.10-1.75 (m, 10H), 1.57 (d, J=6.9, 3H). IR (cm$^{-1}$, KBr): 3410 (m), 2913 (s), 2845 (m), 1667 (s), 1526 (s), 1498 (s), 1478 (s), 1363 (m), 1219 (m), 1160 (m), 1084 (s), 1014 (m), 835 (m), 699 (m). MS (m/z): 446.10 ([M+H]$^+$).

Example 118

N(7)-(R-1-Phenylethyl))-5-(4-chlorophenyl)-5,6-diazatetracyclo[7.3.1.1$^{3,11}$.0$^{4,8}$]tetradeca-4(8),6-diene-7-carboxamide

The title compound was synthesized by a procedure similar to that described for example 101. Intermediate 2 (100 mg, 0.29 mmol), DMF (1.0 ml), Et$_3$N (46 µl, 0.32 mmol), BOP reagent (136 mg, 0.32 mmol) and R-1-phenylethylamine (39 mg, 0.32 mmol) furnished the title compound (90 mg, 69%). M.P.: 65-70° C. $^1$H-NMR (δ ppm, CDCl$_3$, 300 MHz): 7.50-7.18 (m, 10H); 5.35-5.18 (m, 1H); 4.00 (br. s, 1H); 2.98 (br. s, 1H); 2.19 (br. s, 2H) 2.10-1.71 (m, 10H); 1.57 (d, J=6.9, 3M). IR (cm$^{-21}$, KBr): 3408 (s), 3062 (w), 3029 (w), 2914 (s), 2845 (s), 1667 (s), 1596 (w), 1585 (w), 1526 (s), 1498 (s), 1478 (s), 1441 (s), 1406 (m), 1363 (m), 1353 (w), 1271 (m), 1232 (s), 1218 (m), 1159 (m), 1083 (s), 1033 (m), 1013 (m), 933 (w), 835 (m). MS (m/z): 446.3 ([M+H]$^+$).

Example 119

N(7)-(1-Methyl-1-phenylethyl))-5-(4-chlorophenyl)-5,6-diazatetracyclo[7.3.1.1$^{3,11}$.0$^{4,8}$]tetradeca-4(8),6-diene-7-carboxamide

The title compound was synthesized by a procedure similar to that described for example 101. Intermediate 2 (100 mg, 0.29 mmol), DMF (1.0 ml), Et$_3$N (46 µl, 32 mmol), BOP reagent (136 mg, 0.32 mmol) and α,α-dimethylbenzylamine (48 mg, 0.36 mmol) furnished the title compound (90 mg, 67%). M.P.: 181° C. $^1$H-NMR (δ ppm, CDCl$_3$, 300 MHz): 7.47 (hr. d, J=8.7, 4H); 7.36-7.28 (m, 5H); 7.22 (br. t, J=7.2, 1H); 3.92 (br. s, 1H); 3.35 (s, 3H); 2.99 (br. s, 1H); 2.18 (br. s, 2H); 2.00-1.74 (m, 10H); 1.79 (s, 6H). IR (cm$^{-1}$, KBr): 3407 (m), 3090 (w), 3060 (w), 3024 (w), 2965 (w), 2898 (s), 2845 (m), 1675 (s), 1563 (w), 1497 (s), 1479 (s), 1438 (m), 1407 (w), 1379 (w), 1362 (m), 1340 (w), 1254 (w), 1231 (w), 1219 (w), 1194 (w), 1159 (w), 1085 (m), 1031 (w), 1015 (w), 834 (m). MS (m/z): 460.1 (25, [M+H]$^+$); 342.3 (100).

Example 120

N(7)-(2-Pyridylmethyl)-5-(4-chlorophenyl)-5,6-diazatetracyclo[7.3.1.1$^{3,11}$.0$^{4,8}$]tetradeca-4(8),6-diene-7-carboxamide

The title compound was synthesized by a procedure similar to that described for example 101. Intermediate 2 (100 mg, 0.29 mmol), DMF (1.0 ml), Et$_3$N (48 µl, 0.34 mmol), BOP reagent (128 mg, 0.29 mmol) and 2-aminomethylpyridine ((30 µl, 0.29 mmol) gave the title compound (98 mg, 78%). M.P.: 187° C. $^1$H-NMR (δ ppm, DMSO-d$_6$, 300 MHz): 8.66 (t, J=6.0, 1H); 8.49 (br. d, J=5.1, 1H); 7.76 (td, 7.6, 1.8, 1H); 7.64 (d, 9.0, 2H); 7.51 (d, J=9.0, 2H); 7.31 (d, J=7.6, 1H); 7.26 (m, 1H); 4.50 (d, J=6.0, 2H); 3.82 (br. s, 1H); 2.98 (br. s, 1H); 2.15 (br. s, 2H), 2.00-1.70 (m, 10H). IR (cm$^{-1}$, KBr): 2918

(m), 2847 (m), 1781 (s), 1496 (s), 1443 (m), 1366 (m), 1230 (m), 1113 (m), 1089 (m), 1059 (m), 835 (m). MS (m/z): 433.2 ([M+H]$^+$).

Example 121

N(7)-(N'-phenylamino)-5-(4-chlorophenyl)-5,6-diazatetracyclo[7.3.1.1$^{3,11}$.0$^{4,8}$]tetradeca-4(8),6-diene-7-carboxamide The title compound was synthesized by a procedure similar to that described for example 101. Intermediate 2 (200 mg, 0.29 mmol), Et$_3$N (80 µl, 0.58 mmol), BOP reagent (258 mg, 0.58 mmol) and phenylhydrazine (60 µl, 0.58 mmol) gave the title compound (185 mg, 73%). M.P.: 103-105° C. $^1$H-NMR (δ ppm, CDCl$_3$, 300 MHz): 8.59 (s, 1H); 7.48 (d, J=8.7, 2H); 7.33 (d, J=8:7, 2H); 7.22 (t, J=7.5, 2H); 6.94 (d, J=8.7, 2H); 6.88 (t, J=7.5, 1H); 3.89 (br. t, J=4.7, 1H); 3.03 (br. s, J=3.5, 1H); 2.20 (br. s, 2H); 2.00-1.75 (m, 10H). IR (cm$^{-1}$, KBr): 3279 (m), 2912 (s), 2845 (m), 1678 (s), 1603 (m), 1497 (s), 1467 (m), 1353 (m), 1232 (m), 1090 (m), 1012 (m), 835 (m). MS (m/z): 433.1 ([M+H]$^+$).

Example 122

N(7)-(N'-phenylamino)-5-(4-chlorophenyl)-5,6-diazatetracyclo[7.3.1.1$^{3,11}$.0$^{4,8}$]tetradeca-4(8),6-diene-7-carboxamide hydrochloride A solution of example 121 (100 mg, 0.23 mmol) in dry ether (2.0 ml) was treated with a saturated solution of HCl in ether (2.0 ml) at RT and stirred at RT for 1 hour and the precipitated solid was filtered to yield the title compound (90 mg, 73%). M.P.: 135-136° C. $^1$H-NMR (δ ppm, DMSO-d$_6$, 300 MHz): 9.95 (s, 1H); 7.65 (d, J=9.0, 2H); 7.52 (d, J=9.0, 2H); 7.13 (t, J=7.8, 2H); 6.74 (d, J=7.5, 2H); 6.69 (t, J=7.5, 1H); 3.67 (br. s, 1H); 3.02 (br. s, 1H); 2.15 (br. s, 2H); 2.00-1.71 (m, 101-1). IR (cm$^{-1}$, KBr): 3419 (br. s), 3020 (m), 1642(s), 1498 (m), 1216 (m), 1092 (w), 1014(w), 836 (m). MS (m/z): 433.3 ([M+H]$^+$).

Example 123

N(7)-(2-Chlorophenylamino)-5-(4-chlorophenyl)-5,6-diazatetracyclo[7.3.1.1$^{3,11}$.0$^{4,8}$]tetradeca-4(8),6-diene-7-carboxamide The title compound was synthesized by a procedure similar to that described for example 101. Intermediate 2 (200 mg, 0.58 mmol), Et$_3$N (90 µl, 1, 0.64 mmol), BOP reagent (258 mg, 0.58 mmol) and 2-chlorophenylhydrazine hydrochloride (104 mg, 0.58 mmol) furnished the title compound (168 mg, 62%). M.P.: 155° C. $^1$H-NMR (δ ppm, CDCl$_3$, 300 MHz): 8.60 (s, 1H); 7.49 (d, J=8.7, 2H); 7.38-7.20 (m, 3H); 7.11 (t, J=7.2, 1H); 7.04 (dd, J=7.5, 1.5, 1H); 6.82 (t, J=7.6, 1H); 6.56 (br. s, 1H); 3.90 (br. s, 1H); 3.03 (br. s, 1H); 2.20 (br. s, 2H); 2.01-1.70 (m, 10H). IR (cm$^{-1}$, KBr): 3376 (m), 3310 (m), 2909 (m), 1683 (s), 1597 (m), 1563 (w), 1498 (s), 1470 (s), 1423 (w), 1364 (m), 1212 (m), 1088 (m), 1026 (m), 835 (m). MS (m/z): 467.9 ([M+H]$^+$).

Example 124

N(7)-(2-Chlorophenylamino)-5-(4-chlorophenyl)-5,6-diazatetracyclo[7.3.1.1$^{3,11}$.0$^{4,8}$]tetradeca-4(8),6-diene-7-carboxamide hydrochloride The title compound was synthesized by a procedure similar to that described for example 101. Intermediate 2 (250 mg, 0.73 mmol), DMF (3 ml), Et$_3$N (0.12.0 ml, 0.86 mmol), BOP reagent (322 mg, 0.73 mmol) and N-(2-chlorophenyl)-N-methylhydrazine hydrochloride (220 mg, 0.80 mmol) furnished the title compound (210 mg, 60%). M.P.: 229° C. $^1$H-NMR (δ ppm, CDCl$_3$, 300 MHz): 8.91 (s, 1H); 7.47 (d, J=8.7, 2H); 7.39 (d, J=8.1, 2H); 7.34-7.20 (m, 3H); 6.99 (t, J=8.8, 1H); 3.86 (br. t, J=4.8, 1H); 3.35 (s, 3H); 3.00 (br. s, 1H); 2.17 (br. s, 2H); 2.00-1.70 (m, 10H). IR (cm$^{-1}$, KBr): 3396 (s), 2909 (s), 2845 (m), 1685 (s), 1587 (m), 1563 (m), 1498 (s), 1475 (s), 1464 (s), 1438 (s), 1366 (m), 1223 (m), 1152 (m), 1092 (s), 1083 (m), 1014 (m), 837 (s).

Example 125

N(7)-[(4-chlorophenyl)amino]-5-(4-chlorophenyl)-5,6-diazatetracyclo[7.3.1.1$^{3,11}$.0$^{4,8}$]tetradeca-4(8),6-diene-7-carboxamide The title compound was synthesized by a procedure similar to that described for example 101. Intermediate 2 (100 mg, 0.29 mmol), Et$_3$N (0.27 ml, 1.94 mmol), BOP reagent (129 mg, 0.29 mmol) and 4-chlorophenylhydrazine hydrochloride (52 mg, 0.29 mmol) furnished the title compound. (105 mg, 77%). M.P.: 208-210° C. $^1$H-NMR (δ ppm, CDCl$_3$, 300 MHz): 8.58 (s, 1H); 7.49 (d, J=8.4, 2H); 7.33 (d, J=8.4, 2H); 7.18 (d, J=8.7, 2H); 6.88 (d, J=8.7, 2H); 6.00 (br. s, 1H); 3.87 (br. s, 1H); 3.03 (br. s, 1H); 2.20 (s, 2H); 2.00-1.70 (m, 10H). IR (cm$^{-1}$, KBr): 3282 (m), 2912 (s), 2845 (m), 1670 (s), 1596 (m), 1498 (s), 1470 (s), 1253 (m), 1231 (m), 1091 (s), 1013 (m), 834 (m). MS (m/z): 467.2 ([M+H]$^+$).

Example 126

N(7)-(2,4-Dichlorophenylamino)-5-(4-chlorophenyl)-5,6-diazatetracyclo[7.3.1.1$^{3,11}$.0$^{4,8}$]tetradeca-4(8),6-diene-7-carboxamide The title compound was synthesized by a procedure similar to that described for example 101. Intermediate 2 (200 mg, 0.58 mmol), Et$_3$N (90 µl, 0.65 mmol), BOP reagent (258 mg, 0.58 mmol) and 2,4-dichlorophenylhydrazine hydrochloride (125 mg, 0.59 mmol) furnished the title compound (226 mg, 77%). M.P.: 214-215° C. $^1$H-NMR (δ ppm, CDCl$_3$, 300 MHz): 8.60 (s, 1H); 7.49 (d. J=8.7, 2H); 7.40-7.22 (m, 3H); 7.11 (dd, J=8.7, 2.4, 1H); 6.97 (d, J=8.7, 1H); 6.49 (br. s, 1H); 3.87 (br. t, J=4.61, 1H); 3.03 (br. s, 1H); 2.20 (br. s, 2H); 2.04-1.70 (m, 10H). IR (cm$^{-1}$, KBr): 3300 (m), 2907 (m), 2845 (m), 1681 (s), 1498 (s), 1471 (s), 1232 (m), 1089 (m), 863 (m), 837(m).

Example 127

N(7)-[(2,4-Dichlorophenyl-N'-methylamino]-5-(4-chlorophenyl)-5,6-diazatetracyclo[7.3.1.1$^{3,11}$.0$^{4,8}$] tetradeca-4(8),6-diene-7-carboxamide The title compound was synthesized by a procedure similar to that described for example 101. Intermediate 2 (300 mg, 0.88 mmol), DMF (3.0 ml), Et$_3$N (0.15 ml, 1.05 mmol), BOP reagent. (387 mg, 0.88 mmol) and N-(2,4-dichlorophenyl)-N-methylhydrazine (296 mg, 0.97 mmol) gave the title compound (220 mg, 49%). M.P.: 192° C. $^1$H-NMR (δ ppm, CDCl$_3$, 400 MHz): 8.90 (s, 1H); 7.44 (dt, J=8.8, 2.0, 2H); 7.29-7.26 (m, 4H); 7.17 (dd, J=8.4, 2.4, 1H); 3.80 (br. s, 1H); 3.30 (s, 3H); 2.97 (br. s, 1H); 2.15 (s, 2H); 1.86-1.75 (m, 10H). IR (cm$^{-1}$, KBr): 3396 (s), 2909 (s), 2845 (m), 1685 (s), 1587 (m), 1563 (m), 1498 (s), 1475 (s), 1464 (s), 1.438 (s), 1366

(m), 1223 (m), 1152 (m), 1092 (s), 1083 (m), 1014 (m), 837 (s). MS (m/z): 514.9 ([M+H]$^+$).

Example 128

N(7)-[(2,4-Dichlorophenyl-N'-methylamino]-5-(4-chlorophenyl)-5,6-diazatetracyclo[7.3.1.1$^{3,11}$.0$^{4,8}$]tetradeca-4(8),6-diene-7-carboxamide hydrochloride A solution of example 127 (100 mg, 0.19 mmol) in ether (2.0 ml) was treated with ether saturated with HCl (2.0 ml) and maintained at RT for 1 hour and the precipitated solid was filtered to yield the title compound (102 mg, 95%). M.P.: 203° C. $^1$H-NMR (δ ppm, CDCl$_3$, 400 MHz): 9.86 (s, 1H); 7.53 (d, J=7.2, 2H); 7.42-7.36 (m, 3H); 7.33 (d, J=1.7, 1H); 7.20 (dd, J=8.8, 1.7, 1H); 3.29 (s, 3H); 2.99 (br. s, 1H); 2.21 (s, 2H); 1.88 (m, 4H); 1.88-1.80 (m, IR (cm$^{-1}$, KBr): 3386 m), 3197 (m), 2916 (s), 2901 (s), 2845 (m), 1687 (s), 1474 (s), 1439 (s), 1260 (m), 1323 (m), 1241 (m), 1124 (m), 1106 (m), 1089 (s), 1012 (m), 938 (m), 845 (m), 8.29 (m). MS (m/z): 515.0 ([M−HCl+H]$^+$).

Example 129

N(7)-(2,4-Dichlorophenyl-N'-cyclohexylamino)-5-(4-chlorophenyl)-5,6-diazatetracyclo[7.3.1.1$^{3,11}$.0$^{4,8}$]tetradeca-4(8),6-diene-7-carboxamide The title compound was synthesized by a procedure similar to that described for example 101. Intermediate 2 (200 mg, 0.58 mmol), Et$_3$N (0.26 ml, 1.87 mmol), BOP reagent (258 mg, 0.58 mmol) and N-cyclohexyl-N-(2,4-dichlorophenyl)hydrazine hydrochloride (427 mg, 1.28 mmol) gave the title compound (162 mg, 48%). M.P.: 95-96° C. $^1$H-NMR (δ ppm, CDCl$_3$, 300 MHz): 8.72 (s, 1H); 7.47 (d, J=8.4, 2H); 7.42 (d, J=8.7, 1H); 7.40-7.20 (m, 3H); 7.17 (dd, J=8.7, 2.4, 1H), 3.86 (br. t, J=5.2, 1H); 3.75 (br. s, 1H); 2.99 (br. s, 1H); 2.17 (s, 2H); 2.00-1.70 (m, 14H), 1.43-1.10 (m, 6H). IR (cm$^{-1}$, KBr): 3400 (m), 2919 (s), 2850 (s), 1683 (s), 1564 (w), 1498 (s), 1474 (s), 1363 (m), 1233 (m), 1218 (m), 1100 (m), 1062 (m), 833 (m), 753 (w). MS (m/z): 583.1 ([M+H]$^+$).

Example 130

N(7)-(4-Fluorophenylamino)-5-(4-chlorophenyl)-5,6-diazatetracyclo[7.3.1.1$^{3,11}$.0$^{4,8}$]tetradeca-4(8),6-diene-7-carboxamide The title compound was synthesized by a procedure similar to that described for example 101. Intermediate 2 (200 mg, 0.58 mmol), Et$_3$N (0.16 ml, 1.15 mmol), BOP reagent (258 mg, 0.58 mmol) and 4-fluorophenylhydrazine hydrochloride (95 mg, 0.58 mmol) gave the title compound (218 mg, 83%). M.P.: 125-127° C. $^1$H-NMR (δ ppm, CDCl$_3$, 300 MHz): 8.59 (s, 1H); 7.48 (d, J=8.6, 2H); 7.32 (d, J=8.6, 2H); 7.00-6.80 (m, 4H); 3.88 (br. s, 1H); 3.03 (br. s, 1H); 2.20 (br. s, 2H); 2.05-1.70 (m, 10H). IR (cm$^{-1}$, KBr): 3263 (m), 2912 (s), 2847 (m), 1671 (s), 1508 (s), 1498 (s), 1475 (m), 1234 (m), 1219 (m), 1088 (m), 884 (w), 831(m). MS (m/z): 451.0 ([M+H]$^+$).

Example 131

N(7)-(4-Fluorophenylamino)-5-(4-chlorophenyl)-5,6-diazatetracyclo[7.3.1.1$^{3,11}$.0$^{4,8}$]tetradeca-4(8),6-diene-7-carboxamide hydrochloride.

A solution of example 130 (100 mg, 0.22 mmol) in ether (2.0 ml) was treated with a saturated solution of HCl in ether (2.0 ml) at RT and stirred at RT for 1 hour and the precipitated solid was filtered and washed with ether to yield the title compound (106 mg, 98%). M.P.: 175° C. $^1$H-NMR (δ ppm, DMSO-d$_6$, 300 MHz): 9.99 (s, 1H); 7.64 (d, J=8.5, 2H); 7.50 (d, J=8.5, 2H); 6.98 (t, J=8.7, 2H); 6.74 (dd, J=8.7, 4.8, 2H); 3.67 (br. s, 1H); 3.01 (br. s, 1H); 2.15 (s, 2H); 2.00-1.70 (m, 10H). IR (cm$^{-1}$, KBr): 3247 (br. m), 2916 (m), 2844 (m), 1694 (s), 1507 (s), 1498 (s), 1234 (s), 1089 (m), 1014 (m), 990 (w), 836 (m). MS (m/z): 45.1.0 ([M+H]$^+$).

Example 132

N(7)-(2,4-Difluorophenylamino]-5-(4-chlorophenyl)-5,6-diazatetracyclo[7.3.1.1$^{3,11}$.0$^{4,8}$]tetradeca-4(8),6-diene-7-carboxamide The title compound was synthesized by a procedure similar to that described for example 101. Intermediate 2 (200 mg, 0.58 mmol), Et$_3$N (22 μl, 1.58 mmol), BOP reagent (258 mg, 0.58 mmol) and 2,4-difluorophenylhydrazine hydrochloride (105 mg, 0.58 mmol) gave the title compound (225 mg, 82%). M.P.: 195-196° C. $^1$H-NMR (δ ppm, CDCl$_3$, 300 MHz): 8.56 (s, 1H); 7.49 (d, J=9.0, 2H); 7.32 (d, J=9.0, 2H); 7.01 (m, 1H); 6.86-6.74 (m, 2H); 6.24 (br. s, 1H), 3.87 (br. t, J=4.6, 1H); 3.03 (br. s, 1H); 2.20 (br. s, 2H); 2.02-1.78 (m, 10H). IR (cm$^{-1}$, KBr): 3276 (w), 2912 (m), 2846 (m), 1683 (s), 1499 (s), 1467 (m), 1137 (m), 1114 (m), 848 (m), 836 (m). MS (m/z): 469.1 ([M+H]$^+$).

Example 133

N(7)-(3-fluorophenylamino)-5-(4-chlorophenyl)-5,6-diazatetracyclo[7.3.1.1$^{3,11}$.0$^{4,8}$]tetradeca-4(8),6-diene-7-carboxamide The title compound was synthesized by a procedure similar to that described for example 101. Intermediate 2 (250 mg, 0.72 mmol), DMF (3 ml), Et$_3$N (0.22.0 ml, 1.60 mmol), BOP reagent (322 mg, 0.72 mmol) and 3-fluorophenylhydrazine hydrochloride (119 μl, 0.72 mmol) yielded the title compound (165 mg, 50%). M.P.: 203° C. $^1$H-NMR (δ ppm, CDCl$_3$, 300 MHz): 8.58 (s, 1H); 7.51 (d, J=9.0, 2H); 7.33 (d, J=9.0, 2H), 7.16 (q, J=6.6, 1H); 6.72-6.53 (m, 3H); 3.88 (br. s, 1H); 3.03 (br. s. 1H); 2.21 (br. s, 2H); 2.05-1.80 (m, 10H). IR (cm$^{-1}$, KBr): 3259 (m), 2913 (s), 1617 (s), 1601 (m), 1498 (s), 1442 (m), 1269 (m), 1234 (m), 1140 (m), 1089 (s), 1012 (m), 832 (m), 760 (m), 679 (m). MS (m/z): 451.10 ([M+H]$^+$).

Example 134

N(7)-(3-Chloro-2-pyridylamino)-5-(4-chlorophenyl)-5,6-diazatetracyclo[7.3.1.1$^{3,11}$.0$^{4,8}$]tetradeca-4(8),6-diene-7-carboxamide The title compound was synthesized by a procedure similar to that described for example 101. Intermediate 2 (150 mg, 0.44 mmol), DMF (1.5 ml), Et$_3$N (68 μl, 48 mmol), BOP reagent (203 mg, 0.46 mmol) and 3-chloro-2-hydrazinopyridine (69 mg, 0.48 mmol) furnished the title compound (170 mg, 83%). M.P.: 200-203° C. $^1$H-NMR (δ ppm, DMSO-d$_6$, 300 MHz): 9.85 (s, 1H); 8.46 (s, 1H); 8.0 (dd, J=4.5, 1.5, 1H); 7.69 (dd, J=7.5, 1.5, 1H); 7.66 (d, J=8.7, 2H); 7.51 (d, J=9.0, 2H); 6.75 (dd, J=7.8, 4.8, 1H); 3.73 (br. s, 1H); 3.02 (br. s, 1H); 2.15 (s, 2H); 2.00-1.70 (m, 10H). IR (cm$^{-1}$, KBr): 3382 (m), 2902 (m), 2846 (m), 1683 (m), 1664 (m); 1589 (s), 1498 (s), 1455 (s), 1401 (m), 1229 (m), 1117 (m), 1089 (m), 1030 (m), 833 (m). MS (m/z): 468.10 ([M+H]$^+$).

Example 135

N(7)-(5-Chloro-2-pyridylamino)-5-(4-chlorophenyl)-5,6-diazatetracyclo[7.3.1.1$^{3,11}$.0$^{4,8}$]tetradeca-4(8),6-diene-7-carboxamide The title compound was synthesized by a procedure similar to that described for example 101. Intermediate 2 (150 mg, 0.44 mmol), DMF (1.5 ml), Et$_3$N (68 µl, 0.48 mmol), BOP reagent (203 mg, 0.46 mmol) and 5-chloro-2-hydrazinopyridine (70 mg, 0.49 mmol) furnished the title compound (170 mg, 83%). M.P.: 130-135° C. $^1$H-NMR (δ ppm, DMSO-d$_6$, 300 MHz): 10.02 (s, 1H); 8.62 (s, 1H); 8.06 (d, J=2.4, 1H); 7.66 (d, J=8.5, 2H); 7.60 (dd, J=8.7, 2.5, 1H); 7.51 (d, J=8.5, 2H); 6.60 (d, J=8.7, 1H); 3.69 (br. s, 1H); 3.01 (br. s, 1H); 2.15 (br. s, 2H); 2.00-1.70 (m, 10H). IR (cm$^{-1}$, KBr): 3285 (m), 2909 (s), 2847 (m), 1671 (s), 1595 (m), 1498 (s), 1477 (s), 1364 (m), 1255 (m), 1233 (m), 1089 (m), 1012 (m), 832 (m). MS (m/z): 468.10 ([M+H]$^+$).

Example 136

N(7)-(2-Phenylethyl)-5-(4-chlorophenyl)-5,6-diazatetracyclo[7.3.1.1$^{3,11}$.0$^{4,8}$]tetradeca-4(8)-6-diene-7-carboxamide The title compound was synthesized by a procedure similar to that described for example 101. Intermediate 2 (100 mg, 0.29 mmol), Et$_3$N (40 µl, 0.29 mmol), BOP reagent (129 mg, 0.29 mmol) and phenethylamine (36 µl, 0.29 mmol) furnished the title compound (105 mg, 81%). M.P.: 148° C. $^1$H-NMR (δ ppm, CDCl$_3$, 300 MHz): 7.46 (d, J=8.7, 2H); 7.35-7.18 (m, 7H); 7.07 (br. t, J=7.5, 1H); 3.99 (br. t, J=4.7, 1H); 3.63 (q, J=7.5, 2H); 3.00 (br. t, J=4.7, 1H); 2.90 (t, J=7.5, 2H); 2.20 (br. s, 2H); 2.05-1.95 (m, 2H); 1.94-1.75 (m, 8H). IR (cm$^{-1}$, KBr) 3398 (m), 2913 (s), 2843 (m), 1673 (s), 1538 (s), 1498 (s), 1483 (s), 1382 (m), 1231 (m), 1086 (m), 998 (m), 839 (m). MS (m/z): 446.1 ([M+H]$^+$).

Example 137

N(7)-(N',N'-Diphenylamino)-5-(4-chlorophenyl)-5,6-diazatetracyclo[7.3.1.1$^{3,11}$.0$^{4,8}$]tetradeca-4(8),6-diene-7-carboxamide The title compound was synthesized by a procedure similar to that described for example 101. Intermediate 2 (300 mg, 0.88 mmol), DMF (3 ml), Et$_3$N (0.27 ml, 1.94 mmol), BOP reagent (387 mg, 0.88 mmol) and N,N-diphenylhydrazine hydrochloride (192 mg, 0.87 mmol) gave the title compound (370 mg, 83%). M.P.: 214° C. $^1$H-NMR (δ ppm, CDCl$_3$, 300 MHz): 9.04 (s, 1H); 7.47 (d, J=8.4, 2H); 7.33 (d, J=8.4, 2H); 7.28-7.20 (m, 8H); 7.00 (t, J=8.4, 2H); 3.94 (br. s, 1H); 3.03 (br. s, 1H); 2.20 (s, 2H); 2.05-1.80 (m, 101-1). IR (cm$^{-1}$, KBr): 3384 (m), 2912 (m), 2900 (m), 1702 (s), 1591 (m), 1497 (s), 1466 (m), 1277 (w), 1235 (w), 1092 (m), 1012 (w). MS (m/z): 509.4 ([M+H]$^+$).

Example 138

N7-[1-(2-Chlorophenyl)ethyl]-5-(4-chlorophenyl)-5,6-diazatetracyclo[7.3.1.1$^{3,11}$.0$^{4,8}$]tetradeca-4(8),6-diene-7-carboxamide The title compound was synthesized by a procedure similar to that described for example 101. Intermediate 2 (100 mg, 0.29 mmol), DMF (1.0 ml), Et$_3$N (48 µl, 0.34 mmol), BOP reagent (141 mg, 0.31 mmol) and (±)-1-(2-chlorophenyl)ethylamine (48 µl, 0.29 mmol) furnished the title compound (104 mg, 77° A)). M.P.: 198° C. $^1$H-NMR (δ ppm, CDCl$_3$, 300 MHz): 7.48-7.18 (m, 8H); 5.27 (quintet, J=7.2, 1H); 3.99 (br. s, 1H); 2.98 (br. s, 1H); 2.18 (br. s, 2H); 2.06-1.74 (m, 10H); 1.56 (d, J=7.2, 3H). IR (cm$^{-1}$, KBr): 3400 (m), 2915 (s), 2880 (s), 1666 (s), 1498 (s), 1528 (s), 1480 (s), 1362 (m), 1229 (m), 1085 (m), 1012(w), 834 (m), 696 (m).

Example 139

N(7)-Benzyl-5-(4'-chlorophenyl)-5,6-diazatetracyclo[7.3.1.1$^{3,11}$.0$^{4,8}$]tetradeca-4(8)-6-diene-7-carboxamide The title compound was synthesized as per the procedure described for example 10:1 using intermediate 2 (100 mg, 0.29 mmol), DMF (1 ml), triethylamine (0.04 ml, 0.29 mmol), BOP reagent (128 mg, 0.29 mmol) and benzylamine (0.031 ml, 0.291 mmol) to give the title compound (72 mg, 57%). M.P.: 164-166° C. $^1$H-NMR (δ ppm, CDCl$_3$): 7.45 (d, J=8.4, 2H); 7.39-7.21 (m, 7H); 4.58 (d, J=6.0, 2H); 4.02 (t, J=5.4, 1H); 3.00 (br. t, J=4.7, 1H); 2.20 (br. d, 2H); 2.04-1.77 (m, 10H). IR (cm$^{-1}$, KBr): 3471(m), 3403 (m), 2919 (s), 2884 (n1), 1672 (s), 1534 (m), 1499 (s).

Example 140

N(7)-Piperidino-5-(4-chlorophenyl)-5,6-diazatetracyclo[7.3.1.1$^{3,11}$.0$^{4,8}$]tetradeca-4(8)-6-diene-7-carboxamide The title compound was synthesized as per the procedure described for example 101 using intermediate 2 (100 mg, 0.291 mmol), triethylamine (0.04 ml, 0.29 mmol), BOP reagent (128 mg, 0.29 mmol) and 1-aminopiperidine (0.031 ml, 0.291 mmol) to give the title compound (85 mg, 68%). M.P.: 185-188° C. $^1$H-NMR (δ ppm, CDCl$_3$): 7.67 (br. s, 1H); 7.46 (d, J=8.7, 2H); 7.29 (d, J=8.7, 2H); 3.99 (br. t, J=5.4, 1H); 2.99 (br. t, 1H); 2.85 (br. s, 4H); 2.19 (br. s, 2H); 2.06-1.69 (m, 14H); 1.44-1.38 (m, 2H). IR (cm$^{-1}$, KBr): 3436 (m), 3320 (m); 2921 (s), 2853 (m), 1694 (m), 1668 (s), 1499 (m).

Example 141

7-(4'-Chlorophenyl)-6,7-diazatetracyclo[7.3.1.1$^{3,11}$.0$^{4,8}$]tetradeca-4(8)-5-dien-5-yl-piperidinoethanone The title compound was synthesized as per the procedure described for example 101 using intermediate 2 (100 mg, 0.291 mmol), triethylamine (0.04 ml, 0.29 mmol), BOP reagent (128 mg, 0.29 mmol) and piperidine (0.028 ml, 0.291 mmol) to give the title compound (85 mg, 71%). M.P.: 151-153° C. $^1$H-NMR (δ ppm, CDCl$_3$): 7.43 (d, J=9.0); 7.31 (d, J=9.0); 3.70 (br. s, 2H); 3.55 (t, J=5.1, 2H); 3.00-3.10 (m, 2H); 2.21 (br. s, 2H); 2.05-1.78 (m, 10H); 1.75-1.50 (m, 18H). IR (cm$^{-1}$, KBr): 2913 (m), 1634 (s), 1498 (m).

Example 142

N(7)-Phenyl-5-(4'-chlorophenyl)-5,6-diazatetracyclo[7.3.1.1$^{3,11}$.0$^{4,8}$]tetradeca-4(8)-6-diene-7-carboxamide The title compound was synthesized as per the procedure described for example 101 using intermediate 2 (100 mg, 0.291 mmol), triethylamine (0.04 ml, 0.29 mmol), BOP reagent (128 mg, 0.29 mmol) and aniline (0.026 ml, 0.29 mmol) to give the title compound (95 mg, 77%). M.P.: 188-190° C. $^1$H-NMR (δ ppm, CDCl$_3$): 8.78 (br. s, 1H); 7.67 (d, J=8.4, 2H); 7.50 (d, J=8.7, 2H); 7.30-7.37 (m, 4H); 7.12 (t, J=8.4, 1H); 4.05 (t, J=5.4, 1H); 3.02 (t, J=4.8, 1H); 2.22 (br. s, 2H); 2.10-1.75 (m, 101-1). IR (cm$^{-1}$, KBr): 3365 (m), 2915 (m), 2844 (m), 1682 (s), 1532 (s), 1498 (s).

Example 143

N(7)-Piperidino-5-(2,4-difluorophenyl)-5,6-diazatetracyclo[7.3.1.1$^{3,11}$.0$^{4,8}$]tetradeca-4(8),6-diene-7-carboxamide The title compound was synthesized by a procedure similar to that described for example 101. Intermediate 3 (100 mg, 0.30 mmol), DMF (1.0 ml), Et$_3$N (42 μl, 0.31 mmol), BOP reagent (135 mg, 0.31 mmol) and N-aminopiperidine ((33 μl, 0.31 mmol) gave the title compound (96 mg, 73%). M.P.: 215° C. $^1$H-NMR (δ ppm, CDCl$_3$, 300 MHz): 7.61 (br. s, 1H); 7.49-7.40 (m, 1H); 7.05-6.95 (m, 2H); 3.96 (br. s, 1H); 2.86 (br. s, 4H); 2.65 (br. s, 1H); 2.18 (br. s, 2H), 2.04-1.90 (m, 2H); 1.85-1.62 (m, 12H); 1.42 (br. s, 2H). IR (cm$^{-1}$, KBr): MS (m/z): 427.20 ([M+H]$^+$).

Example 144

N(7)-(Adamantan-1-yl)-5-(2,4-difluorophenyl)-5,6-diazatetracyclo[7.3.1.1$^{3,11}$.0$^{4,8}$]tetradeca-4(8)-6-diene-7-carboxamide The title, compound was synthesized by a procedure similar to that described for example 101. Intermediate 3 (150 mg, 0.44 mmol), DMF (1.0 ml), Et$_3$N (72 μl, 0.52 mmol), BOP reagent (192 mg, 0.44 mind) and 1-adamantylamine (65 mg, 0.44 mmol) furnished the title compound (156 mg, 75%). M.P.: 221-224° C. $^1$H-NMR (δ ppm, CDCl$_3$, 300 MHz): 7.50-7.38 (m, 1H); 7.06-6.93 (m, 2H); 6.68 (br. s, 1H); 3.97 (br. s, 1H); 3.35 (br. s, 3H); 2.22-1.54 (m, 27H). IR (cm$^{-1}$, KBr): 3394 (m), 2915 (s), 2850 (s), 1669 (s), 1611 (m), 1566 (m), 1520 (s), 1483 (m), 1440 (m), 1359 (m), 1353 (m), 1273 (m), 1225 (m), 1220 (m), 1140 (m), 1092 (m), 1082 (m), 966 (m), 850 (m). MS (m/z): 478.2 ([M+H]$^+$).

Example 145

N(7)-(1S,2endo-1,3,3-Trimethyl-bicyclo[2.2.1]hept-2-yl)-5-(2,4-difluorophenyl)-5,6-diazatetracyclo [7.3.1.1$^{3,11}$.0$^{4,8}$]tetradeca-4(8)-6-diene-7-carboxamide The title compound was synthesized by a procedure similar to that described for example 101. Intermediate 3 (150 mg, 0.44 mmol), DMF (1.0 ml), Et$_3$N (72 μl, 0.52 mmol), BOP reagent (192 mg, 0.44 mmol) and 2-amino-1,3,3-Trimethyl-bicyclo[2.2.1]heptane (66 mg, 0.44 mmol) furnished the title compound (176 mg, 84%). M.P.: 235-23° C. $^1$H-NMR (δ ppm, CDCl$_3$, 300 MHz): 7.51-7.42 (m, 1H); 7.07-6.95 (m, 3H); 3.98 (br. s, 1H); 3.72 (d, J=6.0, 1H); 2.67 (br. s, 1H); 2.18 (br. s, 2H); 2.06-1.54 (m, 13H); 1.54-1.28 (m, 2H); 1.28-1.14 (m, 2H); 1.16, 1.10, 0.85 (3s, 9H). IR (cm$^{-1}$, KBr): 3419 (s), 2927 (s), 2905 (s), 2870 (m), 1669 (s), 1567 (m), 1515 (s), 1480 (m), 1442 (m), 1366 (m), 1.275 (m), 1226 (m), 1226 (m), 1097 (m), 1080 (m), 967 (m), 858 (m), 845 (m). MS (m/z): 480.3 ([M+H]$^+$).

Example 146

N(7)-(S-1-phenylethyl))-5-(2,4-difluorophenyl)-5,6-diazatetracyclo[7.3.1.1$^{3,11}$.0$^{4,8}$]tetradeca-4(8),6-diene-7-carboxamide The title compound was synthesized by a procedure similar to that described for example 101. Intermediate 3 (150 mg, 0.46 mmol), DMF (1.5 ml), Et$_3$N(75 μl, 0.51 mmol), BOP reagent (214 mg, 0.53 mmol) and S-1-phenylethylamine (65 μl, 0.50 mmol) furnished the title compound (120 mg, 58%). M.P.: 123-128° C. 7.50-7.13 (m, 7H); 7.06-6.94 (m, 2H); 5.27 (quintet, J=7.2, 1H); 3.97 (br. s, 1H); 2.65 (br. s, 1H); 2.17 (br. s, 2H); 2.06-1.74 (m, 10H); 1.56 (d, J=7.2, 3H). IR (cm$^{-1}$, KBr): 3404 (m), 2911 (s), 2846 (m), 1668 (s), 1519 (s), 1480 (m), 1439 (m), 1367 (w), 1352 (w), 1275 (m), 1227 (m), 1145 (m), 1081 (m), 966 (w), 854 (m). MS (m/z): 448.2 ([M+H]$^+$).

Example 147

N(7)-(R-1-phenylethyl)-5-(2,4-difluorophenyl)-5,6-diazatetracyclo[7.3.1.1$^{3,11}$.0$^{4,8}$]tetradeca-4(8),6-diene-7-carboxamide The title compound was synthesized by a procedure similar to that described for example 101. Intermediate 3 (150 mg, 0.46 mmol), DMF (1.5 ml), Et$_3$N(75 μl, 0.51 mmol), BOP reagent (214 mg, 0.53 mmol) and R-1-phenylethylamine (65 μl, 0.50 mmol) furnished the title compound (125 mg, 61%). M.P.: 123-128° C. $^1$H-NMR (δ ppm, CDCl$_3$, 300 MHz): 7.50-7.12 (m, 7H); 7.06-6.94 (m, 2H); 5.27 (quintet, J=7.5, 1H); 3.97 (br. s, 1H); 2.65 (br. s, 1H); 2.17 (br. s, 2H); 2.07-1.70 (m, 10H); 1.56 (d, J=7.5, 3H). JR (cm$^{-1}$, KBr): 3404 (m), 2911 (s), 2846 (m), 1669 (s), 1519 (s), 1480 (m), 1439 (m), 1367 (w), 1352 (w), 1275 (m), 1227 (m), 1145 (m), 1081 (w), 966 (m), 853 (m). MS (m/z): 448.2 ([M+H]$^+$).

Example 148

N(7)-(1-Methyl-1-phenylethyl)-5-(2,4-difluorophenyl)-5,6-diazatetracyclo[7.3.1.1$^{3,11}$.0$^{4,8}$]tetradeca-4(8),6-diene-7-carboxamide The title compound was synthesized by a procedure similar to that described for example 101. Intermediate 3 (150 mg, 0.46 mmol), DMF (1.5 ml), Et$_3$N(75 μl, 0.51 mmol), BOP reagent (214 mg, 0.53 mmol) and α,α-dimethylbenzylamine (68 mg, 0.51 mmol) furnished the title compound (70 mg, 33%). M.P.: 150-152° C. $^1$H-NMR (δ ppm, CDCl$_3$, 300 MHz): 7.60-7.41 (m, 3H); 7.33 (t, J=7.2, 2H); 7.22 (t, J=7.2, 1H); 7.05-6:95 (m, 2H); 3.89 (br. s, 1H); 2.65 (br. s, 1H); 2.16 (br. s, 2H); 2.00-1.54 (m, 10H); 1.78 (s, 6H). IR (cm$^{-1}$, KBr): 3419 (m), 2906 (m), 1678 (s), 1519 (s), 1276 (m), 1261 (m), 1134 (m), 968 (m), 848 (m). MS (m/z): 462.2 (100, [M+H]$^+$), 344.1 (90).

Example 149

N(7)-(2-Chlorobenzyl)-5-(2,4-difluorophenyl)-5,6-diazatetracyclo[7.3.1.1$^{3,11}$.0$^{4,8}$]tetradeca-4(8),6-diene-7-carboxamide The title compound was synthesized by a procedure similar to that described for example 101. Intermediate 3 (100 mg, 0.29 mmol), DMF (1.0 ml), Et$_3$N (48 μl, 0.34 mmol), BOP reagent (128 mg, 0.29 mmol) and 2-chlorobenzylamine ((55 μl, 0.46 mmol) gave the title compound (152 mg, 71%). M.P.:

136° C. ¹H-NMR (δ ppm, CDCl₃, 300 MHz): 7.51-7.39 (m, 3H); 7.35 (dd, J=7.5, 2.4, 1H); 7.24-7.18 (m, 2H); 7.05-6.95 (m, 2H); 4.67 (d, J=6.0, 2H); 3.98 (t, J=5.4, 1H); 2.67 (br. s, 1H); 2.19 (br. s, 2H), 2.10-1.95 (m, 2H); 1.95-1.65 (m, 10H). IR (cm⁻¹, KBr): 3329 (m), 2918 (s), 2849 (m), 1648 (s), 1537 (m), 1515 (m), 1442 (m), 1220 (m), 1083 (m), 1051 (m), 750 (m). MS (m/z): 468.0 ([M+H]⁺).

Example 150

N(7)-(2,4-Dichlorophenylamino)-5-(2,4-difluorophenyl)-5,6-diazatetracyclo[7.3.1.1³,¹¹.0⁴,⁸]tetradeca-4(8),6-diene-7-carboxamide The title compound was synthesized by a procedure similar to that described for example 101. Intermediate 3 (150 mg, 0.46 DMF (2.0 ml), Et₃N (63 µl, 0.46 mmol), BOP reagent (203 mg, 0.46 mmol) and 2,4-dichlorophenylhydrazine hydrochloride (98 mg, 0.46 mmol) furnished the title compound (107 mg, 47%). M.P.: 162° C. ¹H-NMR (δ ppm, CDCl₃, 300 MHz): 8.70 (br. s, 1H); 7.48 (m, 1H); 7.30 (d, J=1.2, 1H); 7.16-6.96 (m, H); 3.87 (br. s, 1H); 2.71 (br. s, 1H); 2.19 (br. s, 2H), 2.05-1.70 (m, 10H). IR (cm⁻¹, KBr): 3394 (br. s, s), 2916 (s), 1683 (s), 1519 (m), 1274 (m), 1216 (m), 1145 (s), 1118 (s), 1099 (m), 967 (m), 850 (m), 817 (m). MS (m/z): 503.0 ([M+H]⁺).

Example 151

N(7)[1-(2-Chlorophenyl)ethyl]-5-(2,4-difluorophenyl)-5,6-diazatetracyclo[7.3.1.1³,¹¹.0⁴,⁸]tetradeca-4(8),6-diene-7-carboxamide The title compound was synthesized by a procedure similar to that described for example 101. Intermediate 3 (100 mg, 0.29 mmol), DMF (1.0 ml), Et₃N (48 µl, 0.34 mmol), BOP reagent (141 mg, 0.31 mmol) and (±)-1-(2-chlorophenyl)ethylamine (48 µl, 0.29 mmol) furnished the title compound (60 mg, 41%). M.P.: 143-146° C. ¹H-NMR (δ ppm, CDCl₃, 300 MHz): 7.46-7.14 (m, 5H); 7.04-6.94 (m, 2H); 5.26 (quintet, J=7.2, 1H); 3.97 (br. s, 1H); 2.65 (br. s, 1H); 2.17 (br. s, 2H); 2.04-1.70 (m, 10H); 1.56 (d, J=7.2, 3H). IR (cm⁻¹, KBr): 3419 (m), 2915 (s), 2847 (m), 1666 (s), 1612 (m), 1519 (s), 1481 (m), 1442 (m), 1368(w), 1353(w), 1273 (m), 1219(m), 1144 (m), 1082 (m), 967 (m), 852 (m).

Example 152

N(7)-[(S)-1-Phenylpropyl]-5-(2,4-difluorophenyl)-5,6-diazatetracyclo[7.3.1.1³,¹¹.0⁴,⁸]tetradeca-4(8),6-diene-7-carboxamide The title compound was synthesized by a procedure similar to that described for example 101. Intermediate 3 (100 mg, 0.29 mmol), DMF (1.0 ml), Et₃N (48 µl, 0.34 mmol), BOP reagent (141 mg, 0.31 mmol) and (s)-1-phenylpropylamine (41 µl, 0.29 mmol) furnished the title compound (84 mg, 63%). M.P.: 127-129° C. ¹H-NMR (δ ppm, CDCl₃, 300 MHz): 7.50-7.10 (m, 1H); 7.34-7.15 (m, 6H); 7.05-6.90 (m, 2H); 4.99 (q, J=7.5, 1H); 3.96 (t. J=6.2, 1H); 2.64 (br. s, 1H); 2.16 (br. s, 2H); 2.04-1.70 (m, 12H); 0.94 (t, J=7.2, 3H). IR (cm⁻¹, KBr): 3410 (m), 3325 (m), 2916 (m), 2848 (m), 1666 (s), 1612 (m), 1519 (s), 1481 (m), 1442 (m), 1367 (w), 1353 (w), 1273 (m), 1226 (m), 1217 (m), 1144 (m), 1083 (m),1030 (w), 966 (w), 966 (m), 852 (w), 756 (s), 700 (m). MS (m/z): 462.1 ([M+H]⁺).

Example 153

N7-[1-(2-Chlorophenyl)-1-methylethyl]-5-(2,4-difluorophenyl)-5,6-diazatetracyclo[7.3.1.1³,¹¹.0⁴,⁸]tetradeca-4(8),6-diene-7-carboxamide The title compound was synthesized by a procedure similar to that described for example 101. Intermediate 3 (100 mg, 0.29 mmol), DMF (1.0 ml), Et₃N (45 µl, 0.31 mmol), BOP reagent (141 mg, 0.31 mmol) and 2-(2-chlorophenyl)-prop-2-ylamine (73 mg, 0.43 mmol) furnished the title compound (95 mg, 66%). M.P.: 145-147° C. ¹H-NMR (δ ppm, CDCl₃, 300 MHz): 7.57 (dd, J=7.5, 1.2, 1H); 7.52-7.39 (m, 2H); 7.32 (dd, J=7.8, 1.5, 1H); 7.26-7.20 (m, 1H); 7.16 (td, J=7.8, 1.5, 1H), 7.08-6.94 (m, 2H); 3.82 (br. t. J=6.2, 1H); 2.64 (br. s, 1H); 2.14 (br. s, 2H); 1.95-1.74 (m, 10H); 1.38 (s, 6H). IR (cm⁻¹, KBr): 3419 (m), 2919 (m), 2892 (m), 2841 (m), 1674 (s), 1515 (s), 1441 (m), 1384 (w), 1362 (w), 1274 (m), 1249 (m), 1226 (m), 1139 (m), 1083 (m), 1039 (m), 967 (m), 843 (m), 727 (n). MS (m/z): 496.2 ([M×H]⁺).

Example 154

Methyl(2R)-2-[7-(2,4-difluorophenyl)-6,7-diazatetracyclo[7.3.1.1³,¹¹.0⁴,⁸]tetradeca-4(8),5-dien-5-ylcarboxamido]-2-phenylethanoate The title compound was synthesized by a procedure similar to that described for example 101. Intermediate 3 (200 mg, 0.58 mmol), DMF (2.0 ml), Et₃N (193 µl, 1.39 mmol), BOP reagent (282 mg, 0.64 mmol) and (R)-(+)-2-phenylglycine methyl ester hydrochloride (117 mg, 0.58 mmol) furnished the title compound (140 mg, 57%). M.P.: 138-141° C. ¹H-NMR (δ ppm, CDCl₃, 300 MHz): 7.78 (d, J=7.2, 1H); 7.49-7.30 (m, 6H); 7.10-6.90 (m, 2H); 5.72 (d, J=7.5, 1H); 3.91 (t. J=6.1, 1H); 3.74 (s, 3H); 2.66 (br. s, 1H); 2.16 (br. s, 2H); 2.00-1.70 (m, 10H). IR (cm⁻¹, KBr): 3411 (m), 2915 (s), 2848 (m), 1744 (s), 1671 (s), 1613 (m), 1570 (m), 1519 (m), 1478 (m), 1478 (m), 1441 (m), 1352 (w), 1367 (w), 1352 (w), 1322 (m), 1273 (m),1209 (m), 1081 (m), 967 (w), 851 (w), 754 (m), 698 (m). MS (m/z): 492.1 ([M+H]⁺).

Example 155

Methyl(2S)-2-[7-(2,4-difluorophenyl)-6,7-diazatetracyclo[7.3.1.1³,¹¹.0⁴,⁸]tetradeca-461),5-dien-5-ylcarboxamido]-2-phenylethanoate The title compound was synthesized by a procedure similar to that described for example 101. Intermediate 3 (500 mg, 1.45 mmol), DMF (4.0 ml), Et₃N (480 µl, 3.48 mmol), BOP reagent (706 mg, 1.59 mmol) and (S)-(+)-2-phenylglycine methyl ester hydrochloride (293 mg, 1.45 mmol) furnished the title compound (525 mg, 73%). M.P.: 132-135° C. ¹H-NMR (δ ppm, CDCl₃, 300 MHz): 7.78 (d, J=6.9, 1H); 7.52-7.25 (m, 6H); 7.05-6.90 (m, 2H); 5.71 (d, J=7.2, 1H); 3.90 (t. J=6.2, 1H); 3.74 (s, 3H); 2.66 (br. s, 1H); 2.16 (br. s, 2H); 2.04-1.70 (m, 10H). IR (cm⁻¹, KBr): 3432 (m), 3413 (m), 2919 (s), 2849 (m), 1755 (s), 1740 (s), 1672 (s), 1614 (m), 1570 (m), 1522 (s), 1479 (m), 1439 (m), 1223 (m), 1308 (m), 1326 (m), 1274 (m), 1259 (m), 1207 (m), 1161 (m), 1143 (m), 1082 (m), 1029 (w), 967 (m), 845 (m), 697. MS (m/z): 492.1 ([M+H]⁺).

Example 156

N7-(3-Hydroxyadamantan-1-yl)-5-(2,4-difluorophenyl)-5,6-diazatetracyclo[7.3.1.1³,¹¹.0⁴,⁸]tetradeca-4(8),6-diene-7-carboxamide The title compound was synthesized by a procedure similar to that described for example 101. Intermediate 3 (200 mg, 0.58 mmol), DMF (2.0 ml), Et₃N (88 µl, 0.63 mmol), BOP reagent (282 mg, 0.63 mmol) and 3-amino-1-adamantanol (97 mg, 0.58 mmol) furnished the title compound (143 mg, 51%). M.P.: 240-243° C. ¹H-NMR (δ ppm, CDCl₃, 300 MHz): 7.48-7.33 (m, 1H); 7.05-6.94 (m, 2H); 6.74 (br. s, 1H); 3.94 (br. s, 1H); 2.64 (br. s, 1H); 2.28 (br. s, 2H); 2.17 (br. s, 2H); 2.11 (br. s, 2H); 2.04-1.56 (m, 21H). IR (cm⁻¹, KBr): 3385 (m), 2911 (s), 2849 (m), 1657 (s), 1610 (w), 1560 (w), 1520 (m), 1482 (m), 1441 (w), 1441 (w), 1362 (w), 1352 (w), 1273 (w), 1253 (w), 1227 (m), 1150 (m), 1132 (m), 1101 (w), 1084 (w), 1048 (w), 1025 (w), 966 (m), 872 (m). MS (m/z): 494.0 ([M+H]⁺).

Example 157

N(7)-(1-Methyl-1-phenylethyl)-5-(4-fluorophenyl)-5,6-diazatetracyclo[7.3.1.1³,¹¹.0⁴,⁸]tetradeca-4(8),6-diene-7-carboxamide The title compound was synthesized by a procedure similar to that described for example 101. Intermediate 4 (100 mg, 0.30 mmol), DMF (1.5 ml), Et₃N (50 µl, 0.36 mmol), BOP reagent (148 mg, 0.33 mmol) and α,α-dimethylbenzylamine (49 mg, 0.36 mmol) furnished the title compound (92 mg, 68%). M.P.: 180-182° C. ¹H-NMR (δ ppm, CDCl₃, 300 MHz): 7.47 (d, J=7.8, 2H); 7.38-7.14 (m, 8H); 3.91 (br. s, 1H); 2.95 (br. s, 1H); 2.17 (br. s, 2H); 1.97-1.76 (m, 16H). IR (cm⁻¹, KBr): 3412 (m), 3064 (w), 2981 (w), 2916 (s), 2846 (m), 1672 (s), 1565 (w), 1512 (s), 1482 (m), 1439 (m), 1382 (w), 1363 (w), 1257 (m), 1215 (s), 1155 (m), 1084 (m), 844 (m). MS (m/z): 443.9 (100%), 444.9 ([M+H]⁺).

Example 158

N(7)-(Adamantan-1-yl)-5-(4-fluorophenyl)-5,6-diazatetracyclo[7.3.1.1³,¹¹.0⁴,⁸]tetradeca-4(8)-6-diene-7-carboxamide The title compound was synthesized by a procedure similar to that described for example 101. Intermediate 4 (150 mg, 0.46 mmol), DMF (1.5 ml), Et₃N(76 µl, 0.55 mmol), BOP reagent (223 mg, 0.50 mmol) and 1-adamantylamine (69 mg, 0.46 mmol) furnished the title compound (150 mg, 71%). M.P.: 214-216° C. ¹H-NMR (δ ppm, CDCl₃, 300 MHz): 7.36-7.26 (m, 2H); 7.20-7.12 (m, 2H); 6.73 (br. s, 1H); 3.99 (br. s, 1H); 2.94 (br. s, 1H); 2.19-1.55 (m, 27H). IR (cm⁻¹, KBr): 3392 (m), 2905 (s), 2847 (m), 1671 (s), 1560 (w), 1529 (m), 1512 (s), 1481 (m), 1454 (w), 1441 (w), 1357 (m), 1219 (m), 1092 (m), 841 (m). MS (m/z): 460.3 ([M+H]⁺).

Example 158a

N7-(Adamantan-2-yl)-5-(4-fluorophenyl)-5,6-diazatetracyclo[7.3.1.1³,¹¹.0⁴,⁸]tetradeca-4(8),6-diene-7-carboxamide The title compound was synthesized by a procedure similar to that described for example 101. Intermediate 4 (100 mg, 0.36 mmol), DMF (1.0 ml), Et₃N (124 µl, 0.88 mmol), BOP reagent (170 mg, 0.38 mmol) and 2-adamantylamine hydrochloride (103 mg, 0.55 mmol) furnished the title compound (120 mg, 80%). M.P.: 196-1.98° C. ¹H-NMR (δ ppm, CDCl₃, 300 MHz): 7.69-7.63 (m, 2H); 7.17 (t, J=8.1, 2H); 4.23 (d, J=8.4, 1H); 3.75 (br. s, 1H); 3.65 (br. s, 1H); 2.14-1.87 (m, 14H), 1.78-1.54 (m, 4H), 1.26-1.21 (m, 2H). IR (cm⁻¹, KBr): 3414 (s), 2979 (w), 2901 (s), 285.1 (s), 1663 (s), 1542 (s), 1517 (s), 1488 (s), 1454 (m), 1445 (m), 1347 (w), 1255 (w), 1224 (m), 1213 (s), 1159 (m), 1126 (m),1091 (m), 953 (w), 833 (m). MS (m/z): 406.2 ([M+H]⁺).

Example 159

N7-(1,3,3-Trimethylbicyclo[2.2.1]hept-2-yl)-5-(4-fluorophenyl)-5,6-diazatetracyclo[7.3.1.1³,¹¹.0⁴,⁸]tetradeca-4(8),6-diene-7-carboxamide The title compound was synthesized by a procedure similar to that described for example 101. Intermediate 4 (100 mg, 0.30 mmol), DMF (1.5 ml), Et₃N (103 □l, 0.73 mmol), BOP reagent (142 mg, 0.32 mmol) and 1S,2endo-amino-1,3,3-trimethyl-bicyclo[2.2.1]heptane (86 mg, 0.46 mmol) furnished the title compound (101 mg, 71%). M.P.: 139-141° C. ¹H-NMR, δ ppm, CDCl₃, 300 MHz): 7.38-7.31 (m, 2H); 7.21-7.04 (m, 3H); 4.00 (br. s, 1H); 3.73 (d, J=9.6, 1H); 2.98 (br. s, 1H), 2.19 (br. s, 1H), 2.05-1.66 (m, 14H), 1.51-1.39 (m, 2H), 1.25-1.08 (m, 1H), 1.21, 1.01, 0.85 (3s, 9H). IR (cm⁻¹, KBr): 3418 (s), 2927 (s), 2904 (s), 2870 (m), 1670 (s), 1607 (w), 1560 (m), 1510 (s), 1525 (s), 1479 (m), 1440 (m), 1375 (w), 1355 (w), 1365 (w), 1220 (m), 1159 (m),1151 (m), 1089 (m), 1029 (m), 838 (m). MS (m/z): 462.3 ([M+H]⁺).

Example 160

N(7)-Piperidino-5-(4-methylphenyl)-5,6-diazatetracyclo[7.3.1.1³,¹¹.0⁴,⁸]tetradeca-4(8),6-diene-7-carboxamide The title compound was synthesized by a procedure similar to that described for example 101. Intermediate 5 (100 mg, 0.31 mmol), DMF (1.0 ml), Et₃N (46 µl, 0.33 mmol), BOP reagent (137 mg, 0.31 mmol) and 1-aminopiperidine (35 µl, 0.33 mmol) yielded the title compound (70 mg, 56%). M.P.: 228-232° C. ¹H-NMR (δ ppm, CDCl₃, 300 MHz): 7.70 (br. s, 1H); 7.28 (d, J=9.0, 2H); 7.23 (d, J=9.0, 2H); 3.99 (br. t, J=4.83, 1H); 2.99 (br. s, 1H); 2.85 (br. s, 4H); 2.42 (s, 3H); 2.18 (br. s, 2H); 2.04-1.95 (m, 2H); 1.95-1.65 (m, 12H); 1.41 (br. s, 2H). IR (cm⁻¹, KBr): 3306 (m), 2949 (s), 2937 (s), 2911 (s), 2849 (s), 2790 (m), 1690 (s), 1563 (w), 1518 (s), 1488 (m), 1462 (m), 1349 (m), 1216 (m), 1127 (m), 1108 (m), 987 (m), 830 (m). MS (m/z): 405.20 ([M+H]⁺).

Example 161

N(7)-(2,4-Dichlorophenylamino)-5-(4-methylphenyl)-5,6-diazatetracyclo[7.3.1.1³,¹¹.0⁴,⁸]tetradeca-4(8),6-diene-7-carboxamide The title compound was synthesized by a procedure similar to that described for example 101. Intermediate 5 (100 mg, 0.31 mmol), DMF (1.0 ml), Et₃N (46 µl, 0.33 mmol), BOP reagent (137 mg, 0.31 mmol) and 2,4-dichlorophenylhydrazine hydrochloride (70 mg, 0.32 mmol) gave the title compound (110 mg, 73%). M.P.: 208-215° C. ¹H-NMR (δ ppm, CDCl₃, 300 MHz): 9.42 (br. s, 1H); 7.38-7.20 (m, 7H); 7.14-7.00 (m, 1H); 3.96 (br. s, 1H); 3.04 (br. s, 1H); 2.45 (s, 3H); 2.40-1.80 (m, 12H). IR (cm⁻¹, KBr): 3314 (m), 3247 (m), 2914 (s), 2846 (m), 1674 (s), 1661 (s), 1515 (s), 1477 (s), 1478 (s), 1390 (m), 1363 (m), 1254 (m), 1235 (m), 1216 (m), 1089 (m), 1079 (m), 862 (m), 825 (s). MS (m/z): 481.10 ([M+H]⁺).

Example 162

N(7)-(2-Chlorobenzyl)-5-(4-methylphenyl)-5,6-diazatetracyclo[7.3.1.1$^{3,11}$.0$^{4,8}$]tetradeca-4(8),6-diene-7-carboxamide The title compound was synthesized by a procedure similar to that described for example 101. Intermediate 5 (100 mg, 0.31 mmol), DMF (1.0 ml), Et$_3$N (46 µl, 0.33 mmol), BOP reagent (1.37 mg, 0.31 mmol) and 2-chlorobenzylamine (40 µl, 0.36 mmol) furnished the title compound (80 mg, 58%). M.P.: 127-130° C. $^1$H-NMR (δ ppm, CDCl$_3$, 300 MHz): 7.70 (br. s, 1H); 7.48 (br. d, J=6.9, 1H); 7.38-7.16 (m, 7H); 4.68 (d, J=6.0, 2H); 4.02 (br. t, J=4.6, 1H); 3.00 (br. s, 1H); 2.42 (s, 3H); 2.20 (br. s, 2H); 2.10-1.70 (m, 10H). IR (cm$^{-1}$, KBr): 3410 (m), 2915 (s), 2904 (s), 2842 (m), 1663 (s), 1526 (s), 15.17 (s), 1478 (s), 1465 (s), 1439 (s), 1365 (m), 1352 (m), 1.232 (m), 1215 (m), 1085 (m), 829 (m), 756 (m). MS (m/z): 446.10 ([M+H]$^+$).

Example 163

N(7)-Piperidino-5-(4-methoxyphenyl)-5,6-diazatetracyclo[7.3.1.1$^{3,11}$.0$^{4,8}$]tetradeca-4(8),6-diene-7-carboxamide The title compound was synthesized by a procedure similar to that described for example 101. Intermediate 6 (100 mg, 0.27 mmol), DMF (2.0 ml), Et$_3$N (44 µl, 0.32 mmol), BOP reagent (129 mg, 0.32 mmol) and 1-aminopiperidine (29 µl, 0.29 mmol) gave the title compound (65 mg, 58%). M.P.: 156° C. (fuses). $^1$H-NMR (δ ppm, CDCl$_3$, 300 MHz): 7.22 (d, J=6.9, 3H); 6.98 (d, J=6.9, 2H); 3.86 (br. s, 3H); 3.74 (br. s, 1H); 3.01 (br. s, 1H), 2.38-1.70 (m, 20H). IR (cm$^{-1}$, KBr): 3284 (m), 2917 (s), 2849 (s), 1655 (s), 1609 (m), 1519 (s), 1471 (s), 1440 (s), 1353 (m), 1298 (m), 1256 (s), 1231 (s), 1147 (m), 1071 (m), 1010 (m), 891 (m), 814 (s). MS (m/z): 421.20 ([M+H]$^+$).

Example 164

N7-(2-Chlorobenzyl)-5-(4-methoxyphenyl)-5,6-diazatetracyclo[7.3.1.1$^{3,11}$.0$^{4,8}$]tetradeca-4(8),6-diene-7-carboxamide The title compound was synthesized by a procedure similar to that described for example 101. Intermediate 6 (100 mg, 0.27 mmol), DMF (1.0 ml), Et$_3$N (44 µl, 0.32 mmol), BOP reagent (129 mg, 0.32 mmol) and 2-chlorobenzylamine (32 µl, 0.27 mmol) yielded the title compound (85 mg, 69%). M.P.: 178° C. $^1$H-NMR (δ ppm, CDCl$_3$, 300 MHz): 7.50-7.45 (m, 2H); 7.37-7.10 (m, 5H); 6.98 (br. d, J=7.5, 2H); 4.67 (br. s, 2H); 4.00 (br. s, 1H); 3.86 (br. s, 3H); 2.96 (br. s, 1H); 2.19 (br. s, 2H), 2.10-1.40 (m, 10H). IR (cm$^{-1}$, KBr): 3395 (s), 2904 (m), 2848 (m), 1667 (s), 1531 (s), 1515 (s), 1444 (s), 1353 (s), 1242 (s), 1230 (s), 1222 (s), 1231 (s), 1162 (m), 985 (m), 839 (m). MS (m/z): 462.10 ([M+H]$^+$).

Example 165

N(7)-(2,4-Dichlorophenylamino)-5-(4-methoxyphenyl)-5,6-diazatetracyclo[7.3.1.1$^{3,11}$.0$^{4,8}$]tetradeca-4(3),6-diene-7-carboxamide The title compound was synthesized by a procedure similar to that described for example 101. Intermediate 6 (100 mg, 0.36 mmol), DMF (1.0 ml), Et$_3$N (44 µl, 0.32 mmol), BOP reagent (125 mg, 0.28 mmol) and 2,4-dichlorophenylhydrazine hydrochloride (57 mg, 0.27 mmol) furnished the title compound (78 mg, 56%). M.P.: 199° C. $^1$H-NMR (δ ppm, CDCl$_3$, 300 MHz): 8.75 (br. s, 1H); 7.36-7.27 (m, 3H); 7.10 (dd, J=9.0, 1.8, 1H); 7.06-6.94 (d, J=9.0, 1H); 6.97 (br. s, 1H); 6.50 (br. s, 1H); 3.87 (br. s, 4H); 3.00 (br. s, 1H); 2.19 (br. s, 2H), 2.02-1.80 (m, 10H). IR (cm$^{-1}$, KBr): 3359 (s), 3020 (w), 2912 (s), 2844 (m), 1678 (s), 1517 (s), 1473 (s), 1247 (s), 1229 (s), 1075 (M), 1020 (m), 837 (s). MS (m/z): 497.10 ([M+H]$^+$).

Example 166

N(7)-Piperidino-5-[(2-chlorophenyl)phenyl]-5,6-diazatetracyclo[7.3.1.1$^{3,11}$.0$^{4,8}$]tetradeca-4(8),6-diene-7-carboxamide A soln. of example 101 (170 mg, 0.36 mmol) in dioxane (4.0 ml) was treated with 4-chlorophenyl boronic acid (62 mg, 0.33 mmol), Pd(PPh$_3$)$_2$Cl$_2$ (6 mg, 0.009 mml) and sodium carbonate (115 mg, 1.08 mmol) and refluxed for 7 h. The solvent was evaporated and residue dissolved in AcOEt and washed with water. The organic layer was dried over Na$_2$SO$_4$, filtered and the solvent was removed. The residue was subjected to FC to give ca. 70% (as analysed by HPLC) pure product which was further purified by preparative TLC to afford the title compound (70 mg, 39%). HPLC-purity: 99.8%. M.P.: 206° C. $^1$H-NMR (δ ppm, CDCl$_3$, 300 MHz): 7.59-7.38 (m, 4H); 7.27 (d, 8.4, 2H); 6.99 (d, 8.4, 2H); 3.84 (br. s, 1H); 3.35 (s, 3H); 2.89 (br. s, 4H); 2.35 (br. s, 1H); 2.00-1.70 (m, 18H). MS (m/z): 501.2 ([M+H]$^+$).

Example 167

N(7)-[(2,4-Dichlorophenyl)amino]-5-phenyl-5,6-diazatetracyclo[7.3.1.1$^{3,11}$.0$^{4,8}$]tetradeca-4(8),6-diene-7-carboxamide The title compound was synthesized by a procedure similar to that described for example 101 using intermediate 7 (100 mg, 0.33 mmol), DMF (1.0 ml), Et$_3$N (50 µl, 0.36 mmol), BOP reagent (151 mg, 0.34 mmol) and 2,4-dichlorophenylhydrazine hydrochloride (77 mg, 0.36 mmol) to give the title compound (110 mg, 71%). M.P.: 166-170° C. $^1$H-NMR (δ ppm, CDCl$_3$, 300 MHz): 8.60 (s, 1H); 7.56-7.42 (m, 3H); 7.39 (dd, J=7.5, 2.1, 2H); 7.29 (d, d=2.2, 2H); 7.12 (dd, J=9.0, 2.2, 1H); 6.80 (d, J=9.0, 1H); 6.55 (br. s, 1H); 3.90 (t, J=6.0, 1H); 3.15 (br. s, 1H); 2.20 (s, 2H); 2.04-1.74 (m, 10H). IR (cm$^{-1}$, KBr): 3371 (s), 3307 (m), 2910 (s), 2848 (m), 1683 (s), 1596 (m), 1564 (m), 1501 (m), 1463 (s), 1450 (s), 1393 (m), 1361 (m), 1231 (m), 1214 (m), 1075 (m), 1018 (m), 872 (m). MS (adz): 467.1 ([M±H]$^+$).

Example 168

N(7)-Phenyl-5-phenyl-5,6-diazatetracyclo[7.3.1.1$^{3,11}$.0$^{4,8}$]tetradeca-4(8)-6-diene-7-carboxamide The title compound was synthesized as per the procedure described for example 101 using intermediate 7 (100 mg, 0.32 mmol), DMF (2 ml), triethylamine (0.05 ml, 0.35 mmol), BOP reagent (151 mg, 0.34 mmol) and aniline (33 µl, 0.35 mmol) to give the title compound (70 mg, 56%). M.P.: 178-181° C. $^1$H-NMR (δ ppm, CDCl$_3$): 8.82 (br. s, 1H); 7.67 (d, J=7.8, 2H); 7.56-7.29 (m, 7H); 7.09 (t, J=7.5); 4.06 (br. t, J=5, 1H); 3.07 (br. t, J=4.3, 1H); 2.22 (br. s, 2H); 2.09-1.98 (m, 2H); 1.98-1.76 (m, 8H). (cm$^{-1}$, KBr): 3449 (br., m), 3384(m), 2922 (m), 2904 (m), 2844 (m), 1689 (s), 1601 (m), 1591 (m), 1528 (s), 1502 (s).

Example 169

N(7)-piperidino-5-phenyl-5,6-diazatetracyclo [7.3.1.1$^{3,11}$.0$^{4,8}$]tetradeca-4(8)-6-diene-7-carboxamide The title compound was synthesized as per the procedure described for example 101 using intermediate 7 (155 mg, 0.5 mmol), DMF (2 ml), triethylamine (77 µl, 0.55 mmol), BOP reagent (235 mg, 0.53 mmol) and 1-aminopiperidine (60 µl, 0.55 mmol) to give the title compound (120 mg, 61%). $^1$H-NMR (δ ppm, CDCl$_3$): 7.69 (br. s, 1H); 7.53-7.32 (m, 5H); 4.00 (br. t, J=5.5, 1H); 3.02 (br. t, J=4.6, 1H); 2.84 (br. t, J=4.8, 4H); 2.19 (br. s, 2H); 2.05-1.68 (m, 14H); 1.44-1.36 (m, 2H). IR (cm$^{-1}$, KBr): 3345 (m), 3306(m), 2941 (s), 2920 (s), 2906 (s), 1687 (s), 1525 (m), 1500 (m).

Example 170

N(7)-Benzyl-5-phenyl-5,6-diazatetracyclo [7.3.1.1$^{3,11}$.0$^{4,8}$]tetradeca-4(8)-6-diene-7-carboxamide The title compound was synthesized as per the procedure described for example 101 using intermediate 7 (100 mg, 0.32 mmol), DMF (2 ml), triethylamine (0.05 ml, 0.35 mmol), BOP reagent (151 mg, 0.34 mmol) and benzylamine (39 µl, 0.35 mmol) to give the title compound (70 mg, 55%). M.P.: 137-139° C. $^1$H-NMR (δ ppm, CDCl$_3$): 7.51-7.21 (m, 11. H); 4.58 (d, J=5.7, 2H); 4.03 (br. t, JK=5, 1H); 3.03 (br. t, J=4.3, 1H); 2.20 (br. s, 2H); 2.08-1.98 (m, 2H); 1.98-1.76 (m, 8H). IR (cm$^{-1}$, KBr): 3405 (m), 3361(m), 2916 (s), 2900 (s), 2844 (m), 1659 (s), 1541 (s), 1504 (m).

Example 171

N(7)-phenyl-6,7-diazatetracyclo[7.3.1.1$^{3,11}$.0$^{4,8}$] tetradeca-4(8)-5-dien-5-yl-piperidino methanone The title compound was synthesized as per the procedure described for example 101 using intermediate 7 (100 mg, 0.32 mmol), DMF (2 ml), triethylamine (0.05 ml, 0.35 mmol), BOP reagent (151 mg, 0.34 mmol) and piperidine (36 µl, 0.35 mmol) to give the title compound (50 mg, 50%). M.P.: 123-125° C. $^1$H-NMR (δ ppm, CDCl$_3$): 7.49-7.35 (m, 5H); 3.71 (br. s, 2H); 3.57 (t, J=5.4, 2H); 3.11 (br. s, 1H); 3.05 (br. s, 1H); 2.21 (br. s, 2H); 2.04-1.74 (m, 10H); 1.70-1.51 (m, 8H). IR (cm$^{-1}$, KBr): 2916 (s), 2845 (m), 1630 (s), 1597 (m), 1500 (m).

Example 172

N(7)-(4-Fluorobenzyl)-5-(2,4-dichlorophenyl)-5,6-diazatetracyclo[7.3.1.1$^{3,11}$.0$^{4,8}$]tetradeca-4(8),6-diene-7-carboxamide The title compound was synthesized by a procedure similar to that described for example 101. Intermediate 8 (100 mg, 0.28 mmol), DMF (1.0 ml), Et$_3$N (41 µl, 0.29 mmol), BOP reagent (123 mg, 0.28 mmol) and 4-fluorobenzylamine (37 mg, 33 µl, 0.29 mmol) gave the title compound (95 mg, 74%). M.P.: 68-70° C. $^1$H-NMR (δ ppm, CDCl$_3$, 300 MHz): 7.54 (d, J=2.4, 1H); 7.38-7.15 (m, 5H); 7.00 (t, J=8.4, 2H); 4.53 (dd, J=14.1, 5.7, 2H)); 3.98 (br. s, 1H); 2.53 (br. s, 1H); 2.18 (br. s, 2H); 2.00-1.61 (m, 101-1). IR (cm$^{-1}$, KBr): 3415 (m), 3307 (m), 2913 (s), 2846 (m), 1667 (s), 1537 (s), 1509 (s), 1498 (s), 1441 (m), 1352 (m), 1220 (s), 1.1.56 (m), 1088 (m), 1071 (m), 824 (s). MS (m/z): 484.1 ([M+H]$^+$).

Example 173

N(7)-Phenylamino-5-(2,4-dichlorophenyl)-5,6-diazatetracyclo[7.3.1.1$^{3,11}$.0$^{4,8}$]tetradeca-4(8),6-diene-7-carboxamide The title compound was synthesized by a procedure similar to that described for example 101. Intermediate 8 (100 mg, 0.28 mmol), DMF (1.0 ml), Et$_3$N (41 µl, 0.29 mmol), BOP reagent (123 mg, 0.29 mmol) and phenylhydrazine (29 µl, 0.29 mmol) gave the title compound (80 mg, 65%). M.P.: 162-163° C. $^1$H-NMR (δ ppm, CDCl$_3$, 300 MHz): 8.53 (s, 1H); 7.59 (d, J=2.4, 1H); 7.42 (dd, J=8.4, 2.1, 1H); 7.35 (d, J=8.4, 1H); 7.22 (t, J=8.4, 2H); 6.95 (d, J=−8.4, 2H); 6.89 (t, J=7.2, 1H); 3.87 (br. s, 1H); 2.57 (br. s, 1H); 2.18 (br. s, 2H); 2.00-1.67 (m, 10H). IR (cm$^{-1}$, KBr): 3292 (m), 2911 (s), 2845 (m), 1670 (s), 1603 (m), 1566 (m), 1525 (m), 1.496 (s), 1477 (m), 1441 (m), 1351 (m), 1232 (m), 1219 (m), 1133 (m), 1121 (m), 1104 (m), 1086 (m), 887(m) 825 (m). MS (m/z) 467.8 ([M+H]$^+$).

Example 174

N(7)-(2-Chlorophenylamino)-5-(2,4-dichlorophenyl)-5,6-diazatetracyclo[7.3.1.1$^{3,11}$.0$^{4,8}$]tetradeca-4 (8),6-diene-7-carboxamide The title compound was synthesized by a procedure similar to that described for example 101. Intermediate 8 (100 mg, 0.27 mmol), DMF (1.0 ml), Et$_3$N (94 µl, 0.66 mmol), BOP reagent (129 mg, 0.29 mmol) and 2-chlorophenylhydrazine hydrochloride (52 mg, 0.29 mmol) gave the title compound (88 mg, 66%). M.P.: 110° C. $^1$H-NMR (δ ppm, CDCl$_3$, 300 MHz): 8.54 (s, 1H); 7.59 (d, J=2.1, 1H); 7.42 (dd, J=8.4, 2.4, 1H); 7.34 (d, J=8.4, 1H); 7.28 (dd, J=8.1, 1.6, 1H); 7.15 (td, J=8.1, 1.6, 1H); 7.04 (dd, J=8.1, 1.5, 1H); 6.82 (td, J=8.1, 1.5, 1H); 6.55 (br. s, 1H); 3.87 (br. t, J=5.1, 1H); 2.58 (br. t, J=5.1, 1H); 2.18 (br. s, 2H); 2.05-1.63 (m, 8H); 1.35-1.20 (m, 2H). IR (cm$^{-1}$, KBr): 3217 (m), 2916 (s), 2847 (m), 1678 (s), 1668 (s), 1595 (m), 1498 (s), 1475 (s), 1441 (s), 1361 (m), 1232 (m), 1218 (m), 1133 (m), 1106 (m), 1084 (m), 1063 (m), 937 (w), 826 (m). MS (m/z) 501.0 ([M+H]$^+$).

Example 175

N(7)-(2,4-Dichlorophenylamino)-5-(2,4-dichlorophenyl)-5,6-diazatetracyclo[7.3.1.1$^{3,11}$.0$^{4,8}$]tetradeca-4(8),6-diene-7-carboxamide The title compound was synthesized by a procedure similar to that described for example 101. Intermediate 8 (100 mg, 0.27 mmol), DMF (1.0 ml), Et$_3$N (82 µl, 0.59 mmol), BOP reagent (123 mg, 0.28 mmol) and 2,4-dichlorophenylhydrazine hydrochloride (62 mg, 0.29 mmol) gave the title compound (95 mg, 67%). M.P.: 153-156° C. $^1$H-NMR (δ ppm, CDCl$_3$, 300 MHz): 8.52 (br. s, 1H); 7.59 (d, J=1.8, 1H); 7.42 (dd, J=8.1, 1.8, 1H); 7.36-7.24 (m, 2H); 7.12 (d, J=8.7, 2.4, 1H); 6.97 (d, J=8.7, 1H); 6.48 (br. s, 1H); 3.85 (br. s, 1H); 2.57 (br. s, 1H); 2.18 (br. s, 2H); 2.00-1.60 (m, 10H). IR (cm$^{-1}$, KBr): 3307 (m), 2920 (s), 2905 (s); 2848 (m), 1682 (s), 1495 (s), 1469 (s), 1388 (m), 1353 (m), 890 (m), 864 (m). MS (m/z): 535.1 ([M+H]$^+$).

Example 176

N(7)-(2-Bromophenylamino)-5-(2,4-dichlorophenyl)-5,6-diazatetracyclo[7.3.1.1$^{3,11}$.0$^{4,8}$]tetradeca-4 (8),6-diene-7-carboxamide The title compound was synthesized by a procedure similar to that described for example 101. Intermediate 8 (100 mg, 0.27 mmol), DMF (1.0 ml), Et$_3$N (82 µl, 0.59 mmol), BOP reagent (123 mg, 0.28 mmol) and 2-bromophenylhydrazine hydrochloride (62 mg, 0.29 mmol) yielded the title compound (70 mg, 48%). M.P.: 196-199° C. $^1$H-NMR (δ ppm, CDCl$_3$, 300 MHz): 8.56 (br. s, 1H); 7.59 (d, J=1.8, 1H); 7.45 (br. t, J=8.1, 2H); 7.41 (d, J=8.1, 1H); 7.19 (t, J=7.8, 1H); 7.02 (d, J=7.8, 1H); 6.75 (t, J=7.8, 1H); 6.52 (br. s, 1H); 3.87 (br. s, 1H); 2.57 (br. s, 1H); 2.18 (br. s, 2H); 2.00-1.60 (m, 8H); 1.30-1.26 (m, 2H). IR (cm$^{-1}$, KBr): 3216 (m), 2915 (s), 2847 (m), 1685 (s), 1595 (m), 1566 (m), 1497 (s), 1441(m), 1387 (m), 1352 (m), 1263 (m), 1232 (m), 1218 (m), 1129 (m), 1105 (m), 1085 (m), 1062 (m), 1019 (m), 936 (w), 889 (w), 866 (w), 825 (m). MS (m/z): 545.1 ([M+H]).

Example 177

N(7)-(N'N'-Diphenylamino)-5-(2,4-dichlorophenyl)-5,6-diazatetracyclo[7.3.1.1$^{3,11}$.0$^{4,8}$]tetradeca-4(8),6-diene-7-carboxamide The title compound was synthesized by a procedure similar to that described for example 101. Intermediate 8 (100 mg, 0.27 mmol), DMF (1.0 ml), Et$_3$N(74 µl, 0.53 mmol), BOP reagent (123 mg, 0.28 mmol) and N,N-diphenylhydrazine hydrochloride (141 mg, 0.64 mmol) gave the title compound (85 mg, 59%). M.P.: 176-180° C. $^1$H-NMR (δ ppm, CDCl$_3$, 300 MHz): 8.96 (s, 1H); 7.57 (d, J=2.1, 1H); 7.40 (dd, J=8.4, 2.1, 1H); 7.35-7.21 (m, 9H); 7.01 (br. t, J=8.4, 2H); 3.91 (br. s, 1H), 2.57 (br. s, 1H); 2.18 (br. s, 2H); 2.00-1.73 (m, 10H). IR (cm$^{-1}$, KBr): 3392 (m), 2915 (m), 2881 (m), 2845 (m), 1686 (s), 1590 (m), 1493 (s), 1462 (m), 1386 (m), 1354 (m), 1340(m), 1311 (m), 1292 (m), 1273(m), 1204 (m), 1150 (m), 1102 (m), 1088 (m), 1076 (w), 1028 (w), 866 (w), 822 (w). MS (m/z): 543.3 ([M+H]$^+$).

Example 178

N(7)-(2-Phenylethyl)-5-(2,4-dichlorophenyl)-5,6-diazatetracyclo[7.3.1.1$^{3,11}$.0$^{4,8}$]tetradeca-4(8),6-diene-7-carboxamide The title compound was synthesized by a procedure similar to that described for example 101. Intermediate 8 (100 mg, 0.28 mmol), DMF (1.0 ml), Et$_3$N (41 µl, 0.29 mmol), BOP reagent (123 mg, 0.29 mmol) and phenethylamine (37 µl, 0.29 mmol) gave the title compound (90 mg, 71%). M.P.: 63-66° C. $^1$H-NMR (δ ppm, CDCl$_3$, 300 MHz): 7.56 (d, J=2.1, 1H); 7.38 (dd, J=8.4, 2.1, 1H); 7.40-7.18 (m, 6H); 7.02 (t, J=7.2, 1H); 3.97 (br. s, 1H); 3.61 (q, J=7.2, 2H); 2.90 (t, J=8.1, 2H); 2.54 (br. s, 1H); 2.18 (br. s, 2H); 2.00-1.65 (m, 10H). IR (cm$^{-1}$, KBr): 3413 (m), 2912 (s), 2845 (m), 1667 (s), 1535 (s), 1497 (s), 1478 (s), 1352 (m), 1233 (m), 1219 (m), 1162 (m), 1.103 (m), 1088 (m), 996 (m), 866 (w), 699 (m). MS (m/z): 480.1 ([M+H]$^+$).

Example 179

N(7)-Benzyl-5-(2',4'-dichlorophenyl)-5,6-diazatetracyclo[7.3.1.1$^{3,11}$.0$^{4,8}$]tetradeca-4(8)-6-diene-7-carboxamide A solution of intermediate 8 (100 mg, 0.27 mmol) in DMF (2 ml) was treated with BOP reagent (123 mg, 0.28 mmol) and triethylamine (41 µl, 0.29 mmol) at room temperature for 15 minutes after which period, benzylamine (32 µl, 0.29 mmol) was added to the mixture and stirred at room temperature for 1 h. The mixture was poured into water and the precipitate formed was collected by filtration, dried and purified by flash chromatography to get pure title compound (90 mg, 73%). M.P.: 65-66° C. $^1$H-NMR (δ ppm, CDCl$_3$): 7.54 (d, J=2.4, 1H); 7.40-7.18 (m, 5H); 4.62 (dd, J=14.7, 6.0, 1H); 4.52 (dd, J=14.7, 6.0, 1H); 4.0 (t, J=5.4, 1H); 2.53 (br. s, 1H); 2.18 (br. s, 2H); 1.05-2.10 (m, 10H). IR (cm$^{-1}$, KBr): 3413 (m), 2914 (s), 2846 (m), 1664 (s), 1534 (s).

Example 180

N(7)-piperidino-5-(2',4'-dichlorophenyl)-5,6-diazatetracyclo[7.3.1.1$^{3,11}$.0$^{4,8}$]tetradeca-4(8),6-diene-7-carboxamide The title compound was synthesized as per the procedure described for example 101 using intermediate 8 (160 mg, 0.42 mmol), DMF (2 ml), triethylamine (0.06 ml, 0.41 mmol), BOP reagent (187 mg, 0.42 mmol) and 1-aminopiperidine (0.05 ml, 0.46 mmol) to give the title compound (106 mg, 52%). M.P.: 101-104° C. $^1$H-NMR (δ ppm, CDCl$_3$): 7.58 (br. s, 1H); 7.56 (d, J=2.1, 1H); 7.38 (dd, J=8.7, 2.4, 1H); 7.31 (d, J=8.7, 1H); 3.96 (br. t, J=5.4, 1H); 2.84 (br. s, 4H); 2.53 (br. s, 1H); 2.17 (br. s, 2H); 1.05-2.10 (m, 14H); 1.72-1.9 (m, 2H). IR (cm$^{-1}$, KBr): 3413 (m), 2914 (s), 2846 (m), 1664 (s), 1534 (s).

Example 181

N(7)-(2,4-Dichlorophenylamino)-5-(2-chlorophenyl)-5,6-diazatetracyclo[7.3.1.1$^{3,11}$.0$^{4,8}$]tetradeca-4 (8),6-diene-7-carboxamide The title compound was synthesized by a procedure similar to that described for example 101. Intermediate 9 (100 mg, 0.29 mmol), DMF (1.0 ml), Et$_3$N (45 µl, 0.32 mmol), BOP reagent (136 mg, 0.31 mmol) and 2,4-dichlorophenylhydrazine hydrochloride (69 mg, 0.32 mmol) gave the title compound (95 mg, 65%). M.P.: 233-240° C. $^1$H-NMR (δ ppm, CDCl$_3$, 300 MHz): 8.60 (s, 1H); 7.57 (dd, J=7.6, 1.6, 2H); 7.48 (td, J=8.8, 2.4, 1H); 7.47-7.37 (m, 2H); 7.29 (d, J=2.4, 1H); 7.11 (dd, J=8.8, 2.4, 1H); 6.98 (d, J=8.8, 1H); 3.87 (br. t, J=5.6, 1H); 2.60 (br. t, J=5.6, 1H); 2.20 (br. s, 2H); 2.10-1.60 (m, 10H). IR (cm$^{-1}$, KBr): 3386 (m), 3343 (m), 2907 (m), 2870 (m), 2847 (m), 1694 (s), 1497 (m), 1469 (m), 1349 (m), 1277 (m), 1259 (m), 1232 (m), 1216 (m), 1087 (m), 1058 (m), 1014 (m), 359 (n). MS (m/z): 501.1 ([M+H]$^+$).

Example 182

N(7)-Benzyl-5-(2-chlorophenyl)-5,6-diazatetracyclo [7.3.1.1$^{3,11}$.0$^{4,8}$]tetradeca-4(8)-6-diene-7-carboxamide The title compound was synthesized as per the procedure described for example 101 using intermediate 9 (100 mg, 0.29 mmol), DMF (2 ml), triethylamine (46 µl, 0.32 mmol), BOP reagent (136 mg, 0.32 mmol) and benzylamine (36 µl, 0.32 mmol) to give the title compound (83 mg, 65%). M.P.: 159-161° C. $^1$H-NMR (δ ppm, CDCl$_3$): 7.52 (d, J=7.5, 1H); 7.47-7.24 (m, 8H); 4.62 (dd, J=15.0, 6.0, 1H); 4.51 (dd, J=15.0, 6.0, 1H); 4.01 (br. s, 1H); 2.55 (br. s, 1H); 2.18 (br. s, 2H); 210-1.54 (m, 10H). IR (cm$^{-1}$, KBr): 3412 (m), 3427(m), 2909 (s), 2845 (m), 1672 (s), 1567 (m), 1524 (s), 1498 (s), 1474 (s); 1455(s).

Example 183

N(7)-cyclohexyl-5-(2-chlorophenyl)-5,6-diazatetracyclo[7.3.1.1$^{3,11}$.0$^{4,8}$]tetradeca-4(8)-6-diene-7-carboxamide The title compound was synthesized as per the procedure described for example 101 using intermediate 9 (100 mg, 0.29 mmol), DMF (2 ml), triethylamine (45 0.32 mmol), BOP reagent (136 mg, 0.32 mmol) and cyclohexylamine (37 0.32 mmol) to give the title compound (95 mg, 77%). M.P.: 218-220° C. $^1$H-NMR (δ ppm, CDCl$_3$): 7.55-7.52 (m, 1H); 7.42-7.35 (m, 3H); 6.80 (br. d, J=8.1, 1H); 4.00 (br. t, J=5.4, 1H); 3.97-3.83 (m, 1H); 2.54 (br. s, 1H); 2.17 (br. s, 2H); 1.99 (br. s, 6H); 1.92-1.52 (m, 8H); 1.55-1.05 (m, 6H). IR (cm$^{-1}$, KBr) 3409 (m), 2921(s), 2904(s), 2849(m), 1667(s), 1567(m), 1527(s), 1494(s), 1479(s).

Example 184

N(7)-piperidino-5-(2'-chlorophenyl)-5,6-diazatetracyclo[7.3.1.1$^{3,11}$.0$^{4,8}$]tetradeca-4(8)-6-diene-7-carboxamide The title compound was synthesized as per the procedure described for example 101 using intermediate 9 (100 mg, 0.29 mmol), DMF (2 ml), triethylamine (45 µl, 0.32 mmol), BOP reagent (136 mg, 0.32 mmol) and 1-aminopiperidine (35 µl, 0.32 mmol) to give the title compound (90 mg, 72%). M.P.: 251-254° C. $^1$H-NMR (δ ppm, CDCl$_3$): 7.62 (br. s, 1H); 7.54 (d, J=8.7, 1H); 7.53-7.35 (m, 3H); 3.98 (br. s, 1H); 2.84 (t, J=4.8, 4H); 2.54 (br. s, 1H), 2.17 (br. s, 2H); 1.98 (t, J=12.6, 4H); 1.93-1.50 (m, 10H); 1.44-1.34 (m, 2H). IR (cm$^{-1}$, KBr): 3314 (m), 2905 (s), 2844 (m), 2804 (m), 1686 (s), 1567 (m), 1525 (s), 1492 (s), 1480 (s).

Example 185

N7-(2-Chlorobenzyl)-5-(5-chloro-2-pyridyl)-5,6-diazatetracyclo[7.3.1.1$^{3,11}$.0$^{4,8}$]tetradeca-4(8),6-diene-7-carboxamide The title compound was synthesized by a procedure similar to that described for example 101. Intermediate 10 (100 mg, 0.29 mmol), DMF (1.0 ml), Et$_3$N (40 µl, 0.29 mmol), BOP reagent (128 mg, 0.29 mmol) and 2-chloro-benzylamine (31 mg, 0.29 mmol) furnished the title compound (64 mg, 49%). M.P.: 187-189° C. $^1$H-NMR (δ ppm, DMSO-d$_6$, 300 MHz): 8.81 (t, J=6.3, 1H), 8.60 (d, J=2.6, 1H); 8.19 (dd, J=8.6, 2.6, 1H); 7.96 (d, 8.6, 1H); 7.46-7:42 (m, 1H); 7.38-7.27 (m, 3H); 4.48 (d, J=6.0, 2H); 4.04 (s, 1H); 3.78 (m, 1H); 2.14 (br. s, 2H); 1.95-1.68 (m; 10H).

Example 186

N(7)-Benzyl-5,6-diazatetracyclo[7.3.1.1$^{3,11}$.0$^{4,8}$] tetradeca-4(8)-6-diene-7-carboxamide The title compound was synthesized as per the procedure described for example 10:1 using intermediate 11 (100 mg, 0.43 mmol), DMF (1 ml), triethylamine (0.06 ml, 0.43 mmol), BOP reagent (190 mg, 0.43 mmol) and benzylamine (0.05 ml, 0.43 mmol) to give the title compound (96 mg, 69%). M.P.: 218-219° C. $^1$H-NMR (δ ppm, DMSO-d$_6$): 12.70 (br. s, 1H); 8.44 (br. s, 1H); 7.30 (m, 5H); 4.36 (br. s, 2H); 3.71 (br. s, 1H); 2.97 (br. s, 1H); 2.10 (br. s, 2H); 1.9.1 (br. s, 4H); 1.77 (br. s, 2H); 1.65 (t, J=13.2, 10H). IR (cm$^{-1}$, KBr): 3434 (s), 2924 (s), 2854 (m), 1634 (m).

Example 187

N(7)-Piperidine-5,6-diazatetracyclo[7.3.1.1$^{3,11}$.0$^{4,8}$] tetradeca-4(8)-6-diene-7-carboxamide A solution of intermediate 11 (160 mg, 0.68 mmol) in DMF (3 ml) was treated at room temperature with EPCI (198 mg, 1.02 mmol), HOBt (93 mg, 0.68 mmol), triethylamine (0.19 ml, 1.36 mmol), DMAP (8 mg) and 1-aminopiperidine (0.081 ml, 0.68 mmol) for 16 h. Dilution of the mixture with water, extraction into ethyl acetate, drying over Na$_2$SO$_4$, evaporation and purification by flash chromatography gave the title compound (134 mg, 63%). M.P.: 295-297° C. $^1$H-NMR (δ ppm, DMSO-d$_6$): 12.61 (br. s, 1H); 8.61 (br. s, 1H); 3.65 (br. s, 1H); 3.00 (br. s, 1H); 2.10 (br. s, 2H); 1.99-1.51 (m, 1H); 1.33 (br. s, 2H). IR (cm$^{-1}$, KBr): 3314 (m), 3199(s), 3155 (m); 3085 (m), 3003 (m), 2907 (s), 2843 (s), 2805 (m),1653 (s), 1590 (m), 1543 (m), 1509 (m).

Example 188

6,7-Diazatetracyclo[7.3.1.1$^{3,11}$.0$^{4,8}$]tetradeca-4(8)-5-diene-5-yl-piperidinomethanone The title compound was synthesized as per the procedure described for example 101 using intermediate 11 (100 mg, 0.43 mmol), DMF (1 ml), triethylamine (0.06 mg, 0.43 mmol), BOP reagent (190 mg, 0.43 mmol) and piperidine (43 µl, 0.43 mmol) to give the title compound (84 mg, 66%). M.P.: 263-264° C. $^1$H-NMR (δ ppm, CDCl$_3$): 3.57 (br. s, 4H); 3.05 (br. s, 1H); 2.92 (br. s, 1H); 2.17 (br. s, 2H); 2.10-1.50 (m, 16H). IR (cm$^{-1}$, KBr): 3436 (m), 3198(s), 3155 (m); 2924 (s), 2905 (s), 2888 (s), 1607 (s), 1598 (s), 1583 (s).

Example 189a

N(7)-Piperidino-6-methyl-5,6-diazatetracyclo [7.3.1.1$^{3,11}$.0$^{4,8}$]tetradeca-4(8)-6-diene-7-carboxamide A 0.27 M solution of KOH in ethanol-water 4:3 (3.5 ml) was added to a solution of intermediate 12a (123 mg, 0.45 mmol) and refluxed for 3 h. After concentration of the mixture to approx. half of its initial volume, it was acidified with aq. 1N HCl and the precipitated solid was filtered, dried and dissolved in DMF (3 ml). The solution was treated with DMAP (5 mg), EPCI (100 mg, 0.5 mmol), HOBt (47 mg, 0.35 mmol), 1-aminopiperidine (39 mg, 0.35 mmol) and triethylamine (0.08 ml, 0.56 mmol) at room temperature for 15 h. Dilution of the mixture with water, extraction into ethyl acetate, drying over Na$_2$SO$_4$ and purification by flash chromatography gave the title compound (48 mg, 33%). M.P.: 188.9° C. $^1$H-NMR (δ ppm, DMSO-d$_6$): 6.27 (br. s, 1H); 3.88 (s, 3H); 3.06-2.92 (m, 2H); 2.87 (t, J=5.4, 4H); 2.15 (br. s, 2H); 2.10-1.91 (m, 4H); 1.90-1.70 (10H); 1.55-1.40 (m, 2H). IR (cm$^{-1}$, KBr): 3440 (br., m); 3227 (m), 2918(s), 2844 (s), 1636 (s), 1557 (m), 1532 (m).

Example 189b

N(7)-Piperidino-5-methyl-5,6-diazatetracyclo[7.3.1.1$^{3,11}$.0$^{4,8}$]tetradeca-4(8)-6-diene-7-carboxamide The title compound was synthesized as per the procedure described for example 189a using intermediate 12b (173 mg, 0.63 mmol), ethanol (2 ml), 0.27 M solution of KOH in ethanol-water 4:3 (3.5 ml), DMF (3 ml), DMAP (8 mg), EPCI (167 mg, 0.87 mmol), HOBt (78 mg, 0.58 mmol), 1-aminopiperidine (58 mg, 0.35 mmol) and triethylamine (0.13 ml, 0.93 mmol) to give the title compound in pure form (148 mg, 72%). M.P.: 218.7° C. $^1$H-NMR (δ ppm, DMSO-d$_6$): 7.56 (br. s, 1H); 3.89 (t, J=5.4, 1H); 3.74 (s, 3H); 2.97 (t, J=5.1, 1H); 2.85 (t, J=5.1, 4H); 2. 162.00-1.88 (m, 4H); 1.90-1.66 (10H); 1.47-1.36 (m, 2H).

Example 190a

N(7)-(1-Methyl-1-phenylethyl)-6-pentyl-5,6-diazatetracyclo[7.3.1.1$^{3,11}$.0$^{4,8}$]tetradeca-4,7-diene-7-carboxamide The title compound was synthesized by a procedure similar to that described for example 189a. Intermediate 13a (100 mg, 0.33 mmol), DMF (1.0 ml), Et$_3$N (52 µl, 0.36 mmol), BOP reagent (160 mg, 0.36 mmol) and α,α-dimethylbenzylamine (53 mg, 0.39 mmol) furnished the title compound (100 mg, 72%). M.P.: 66-69° C. $^1$H-NMR (δ ppm, CDCl$_3$, 300 MHz): 7.46-7.40 (m, 2H); 7.58 (t, J=7.2, 2H); 7.30-7.20 (m, 2H); 5.83 (br. s, 1H); 4.14 (t, J=7.8, 2H); 3.11 (br. t, J=5.2, 1H); 3.03 (br. t, J=5.2, 1H); 2.15 (br. s, 1H); 2.08-1.94 (m, 4H); 1.79 (s, 6H); 1.80-1.70 (m, 6H); 1.32-1.20 (m, 4H); 0.87 (t, J=7.5, 3H).

Example 190b

N(7)-(1-Methyl-1-phenylethyl)-5-pentyl-5,6-diazatetracyclo[7.3.1.1$^{3,11}$.0$^{4,8}$]tetradeca-4(8)-6-diene-7-carboxamide The title compound was synthesized by a procedure similar to that described for example 189b. Intermediate 13b (100 mg, 0.33 mmol), DMF (1.0 ml), Et$_3$N (52 µl, 0.36 mmol), BOP reagent (160 mg, 0.36 mmol) and α,α-dimethylbenzylamine (53 mg, 0.39 mmol) furnished the title compound (95 mg, 68%). M.P.: 99-102° C. $^1$H-NMR. δ ppm, CDCl$_3$, 300 MHz): 7.50-7.44 (m, 2H); 7.32 (t, J=7.2, 2H); 7.24-7.16 (m, 2H); 3.97 (t, J=7.5, 2H); 3.82 (br. s, 1H); 2.94 (br. s, 1H); 2.13 (br. s, 2H); 2.00-1.84 (m, 4H); 1.78 (s, 6H); 1.80-1.68 (m, 6H); 1.40-1.24 (m, 4H); 0.91 (t, J=7.2, 3H).

Example 191

N(7)-[(1R)-2-Hydroxy-1-phenylethyl]-5-(2,4-difluorophenyl)-5,6-diazatetracyclo[7.3.1.1$^{3,11}$.0$^{4,8}$]tetradeca-4(8),6-diene-7-carboxamide To a solution of example 154 (290 mg, 0662 mmol) in THF (3 ml) was added LiBH$_4$ (32 mg, 1.52 mmol) and the mixture was refluxed overnight. After evaporation of the solvent, the oily residue was diluted with water and acidified with 1N HCl and extracted with ethyl, acetate and the combined organic layers were washed with brine and dried over Na$_2$SO$_4$. PC (3:7 AcOEt/petroleum ether) gave the title compound (150 mg, 61%). M.P.: 161-162° C. $^1$H-NMR (δ ppm, DMSO-d$_6$, 300 MHz): 8.24 (d, J=7.5, 1H); 7.76-7.58 (m, 2H); 7.38-7.20 (m, 6H); 5.02-4.92 (m, 2H); 3.77 (br. s, 1H); 3.70-3.64 (m, 2H); 2.62 (br. s, 1H); 2.12 (br. s, 2H); 1.98-1.68 (m, 10H). IR (cm$^{-1}$, KBr): 3403 (m), 3007 (w), 2916 (s), 2848 (m), 1656 (s), 1612 (w), 1519 (s), 1483 (m), 1443 (m), 1368 (m), 1.353 (m), 1273 (m), 1225 (n) 1144 (m), 1082 (m), 966 (m), 851 (m). MS (m/z): 452.17 (M+H$^+$).

Example 192

N(7)-[(1S)-2-Hydroxy-1-phenylethyl]-5-(2,4-difluorophenyl)-5,6-diazatetracyclo[7.3.1.1$^{3,11}$.0$^{4,8}$]tetradeca-4(8),6-diene-7-carboxamide The title compound was synthesized by a procedure similar to that described for example 191. The product of example 155 (400 mg, 0.81 mmol), THF (5 ml) and LiBH$_4$ (35 mg, 1.62 mmol) furnished the title compound (130 mg, 34%). M.P.: 158-159° C. $^1$H-NMR (δ ppm, DMSO-d$_6$, 300 MHz): 8.24 (d, J=8.1, 1H); 7.71 (q, 8.4, 1H); 7.61 (t, J=8.4, 1H); 7.38-7.20 (m, 6H); 5.00-4.94 (m, 2H); 3.78 (br. s, 1H); 3.72-3.64 (m, 2H); 2.62 (br. s, 1H); 2.11 (br. s, 2H); 2.00-1.65 (m, 10H). MS (m/z): 452.17 (M+H$^+$).

Example 201

N(3)-Piperidino-1-phenyl-4,5,6,7-tetrahydro-1H-4,7-methano-indazole-3-carboxamide The title compound was synthesized by a procedure similar to that described for example 101. Intermediate 14 (100 mg, 0.39 mmol), DMF (1.0 ml), Et$_3$N (66 µl, 0.47 mmol), BOP reagent (191 mg, 0.43 mmol) and 1-aminopiperidine (42 µl, 0.39 mmol) gave the title compound (45 mg, 34%). M.P.: 144° C. $^1$H-NMR (δ ppm, CDCl$_3$, 300 MHz): 7.68 (d, J=7.8, 2H); 7.68 (br. s, 1H); 7.48 (t, J=7.8, 1H); 7.32 (t, J=7.8, 1H); 3.75 (br. s, 1H); 3.70 (br. s, 1H); 2.91 (br. s, 4H); 2.11 (br. d, J=8.1, 1H); 1.98 (br. d, J=9.3, 2H); 1.80-1.50 (m, 5H); 1.45 (br. s, 2H); 1.24 (br. d, J=8.1, 2H). IR (KBr, cm$^{-1}$): 3302 (m), 2987 (m), 2940 (s), 2856 (m), 2790 (m), 1686 (s), 1597 (m), 1537 (s), 1513 (s), 1489 (s), 1444 (m), 1339 (m), 1270 (m), 1225 (m), 1140 (m), 1127 (m), 1075 (w), 1036(w), 918 (m), 893 (m), 832 (w). MS (m/z): 337.1 ([M+H]$^+$).

Example 202

N(3)-Cyclohexyl-1-phenyl-4,5,6,7-tetrahydro-1H-4,7-methano-indazole-3-carboxamide The title compound was synthesized by a procedure similar to that described for example 101. Intermediate 14 (100 mg, 0.39 mmol), DMF (1.0 ml), Et$_3$N (66 µl, 0.48 mmol), BOP reagent (191 mg, 0.43 mmol) and cyclohexylamine (45 µl, 0.39 mmol) yielded the title compound (99 mg, 75%). M.P.: 107° C. $^1$H-NMR (δ ppm, CDCl$_3$, 300 MHz): 7.68 (d, J=8.1, 2H); 7.48 (t, J=8.1, 2H); 7.33 (t, J=7.8, 1H); 6.80 (br. d, J=8.4, 1H); 3.97-3.95 (m, 1H); 3.75 (br. s, 1H); 3.69 (br. s, 1H); 2.12 (hr. d, J=8.7, 1H); 2.11-1.90 (m, 4H); 1.79-1.65 (m, 4H); 1.48-1.15 (m, 7H). IR (KBr, cm$^{-1}$): 3327 (m), 2936 (m), 2856 (m), 1655 (s), 1595 (m), 1549 (s), 1508 (s), 1490 (s), 1462 (s), 1448 (m), 1352 (s), 1272 (m), 1249 (m), 1226 (m), 1164 (m), 1140 (m), 1121 (m). MS (m/z): 336.1 ([M+H]$^+$).

Example 203

N(3)-Benzyl-1-phenyl-4,5,6,7-tetrahydro-1H-4,7-methano-indazole-3-carboxamide

The title compound was synthesized by a procedure similar to that described for example 101. Intermediate 14 (100 mg, 0.39 mmol), DMF (1.0 ml), Et₃N (66 μl, 0.48 mmol), BOP reagent (191 mg, 0.43 mmol) and benzyl amine (45 0.39 mmol) gave the title compound (87 mg, 65%). M.P.: 115° C. ¹H-NMR (δ ppm, CDCl₃, 300 MHz): 7.66 (d, J=7.5, 2H); 7.47 (t, J=7.8, 2H); 7.40-7.26 (m, 7H); 4.64 (d, J=5.4, MO, 3.78 (br. s, 1H); 3.71 (br. s, 1H); 2.15 (br. d, J=8.4, 1H); 2.00 (br. d, J=8.7, 2H); 1.73 (br. d, J=8.4, 1H); 1.30-1.14 (m, 2H). IR (KBr, cm⁻¹): 3376 (m), 2995 (m), 2966 (m), 2948 (m), 2863 (m), 1652 (s), 1595 (s), 1552 (s), 1354 (s), 1277 (m), 1256 (m), 1235 (s), 1157 (m), 1122 (m), 1070 (m), 988 (m). MS (m/z): 344.1 ([M+H]⁺).

Example 204

N(3)-Phenylamino-1-phenyl-4,5,6,7-tetrahydro-1H-4,7-methano-indazole-3-carboxamide The title compound was synthesized by a procedure similar to that described for example 101. Intermediate 14 (100 mg, 0.39 mmol), DMF (1.0 ml), Et₃N (66 μl, 0.48 mmol), BOP reagent (191 mg, 0.43 mmol) and phenylhydrazine (38 μl, 0.39 mmol) gave the title compound (111 mg, 82%). M.P.: 189° C. ¹H-NMR (δ ppm, CDCl₃, 300 MHz): 8.59 (br. s, 1H); 7.71 (d, J=8.1, 2H); 7.50 (t, J=8.1, 2H); 7.35 (t, J=8.1, 1H); 7.24 (t, J=7.8, 2H); 6.96 (d, J=7.8, 2H); 6.90 (t, J=7.8, 1H); 3.73 (br. s, 2H); 2.14 (br. d, J=8.7, 1H); 1.90-2.10 (m, 2H); 1.73 (d, J=8.4, 1H); 1.31-1.14 (m, 2H). IR (KBr, cm⁻¹): 3413 (m), 3393 (m), 3273 (s), 2970 (m), 2955 (m), 2868 (w), 1682 (s), 1599 (m), 1541 (m), 1506 (s), 1493 (s), 1476 (s), 1458 (s), 1349 (m), 1273 (m), 1226 (m), 1157 (m), 1132 (m), 1085 (m), 1066 (m), 895 (m). MS (m/z): 345.1 ([M+H]⁺).

Example 205

N(3)-Piperidino-1-(2-chlorophenyl)-4,5,6,7-tetrahydro-1H-4,7-methano-indazole-3-carboxamide The title compound was synthesized by a procedure similar to that described for example 101. Intermediate 15 (100 mg, 0.35 mmol), DMF (1.0 ml), Et₃N (58 μl, 0.42 mmol), BOP reagent (169 mg, 0.38 mmol) and 1 aminopiperidine (38 μl, 0.35 mmol) gave the title compound (100 mg, 78%). M.P.: 232° C. ¹H-NMR (δ ppm, CDCl₃, 300 MHz): 7.60-7.47 (m, 3H); 7.42-7.35 (m, 2H); 3.76 (br. s, 1H); 3.37 (br. s, 1H); 2.80 (br. s, 4H); 2.13 (br. d, 9.3, 1H); 2.11-1.86 (m, 2H); 1.75-1.62 (m, 5H); 1.42-1.18 (m, 4H), IR (KBr, cm⁻¹): 3314 (w), 29.99 (w), 2938 (s), 2867 (w), 2781 (m), 1682 (s), 1540 (s), 1511 (s), 1484 (s), 1450 (m), 1342 (m), 1276 (w), 1257 (w), 1227 (m), 1123 (m), 1083 (m), 1035 (m), 987 (m), 893 (w). MS (m/z): 371.1 ([M+H]⁺).

Example 206

N(3)-Cyclohexyl-1-(2-chlorophenyl)-4,5,6,7-tetrahydro-1H-4,7-methano-indazole-3-carboxamide The title compound was synthesized by a procedure similar to that described for example 101. Intermediate 15 (100 mg, 035 mmol), DMF (1.0 ml), Et₃N (58 μl, 0.42 mmol), BOP reagent (169 mg, 0.38 mmol) and cyclohexyl amine (40 0.39 mmol) yielded the title compound (92 mg, 72%). M.P.: 171° C. ¹H-NMR (δ ppm, CDCl₃, 300 MHz): 7.50-7.45 (m, 2H); 7.45-7.35 (m, 2H); 6.73 (br. d, J=7.2, 1H); 3.95-3.82 (m, 1H); 3.77 (br. s, 1H); 3.37 (br. s, 1H); 2.13 (br. d, J=9.3, 1H); 2.11-1.86 (m, 4H); 1.70-1.66 (m, 4H); 1.42-1.18 (m, 7H). IR (KBr, cm⁻¹): 3407 (m), 3393 (m), 2996 (m), 2934 (s), 2850 (s), 1662 (s), 1549 (s), 1513 (s), 1506 (s), 1483 (s), 1447 (s), 1342 (s), 1223 (s), 1.125 (s), 1085 (m), 965 (m), 950 (m). MS (m/z): 370.1 ([M+H]⁺).

Example 207

N(3)-Benzyl-1-(2-chlorophenyl)-4,5,6,7-tetrahydro-1H-4,7-methano-indazole-3-carboxamide The title compound was synthesized by a procedure similar to that described for example 101. Intermediate 15 (100 mg, 0.35 mmol), DMF (1.0 ml), Et₃N (58 μl, 0.42 mmol), BOP reagent (169 mg, 0.38 mmol) and benzyl amine (37 μl, 0.34 mmol) yielded the title compound (60 mg, 46%). ¹H-NMR (δ ppm, CDCl₃, 300 MHz): 7.55-7.15 (m, 10H); 4.60 (br. s, 2H); 3.79 (br. s, 1H); 3.38 (br. s, 1H); 2.16 (hr. d, J=7.8, 1H); 1.99-1.88 (m, 2H); 1.70 (d, J=8.7, 1H); 1.31-1.20 (m, 2H). IR (Neat, cm⁻¹): 3414 (m), 2994 (m), 2968 (m), 2949 (m), 1664 (s), 1550 (s), 1513 (s), 1485 (s), 1455 (s), 1347 (m), 1275 (m), 1251 (m), 1.235 (m), 1161 (m), 1141 (m), 1121 (m). MS (m/z): 378.1 ([M+H]⁺).

Example 208

N(3)-Phenylamino-1-(2-chlorophenyl)-4,5,6,7-tetrahydro-1H-4,7-methano-indazole-3-carboxamide The title compound was synthesized by a procedure similar to that described for example 101. Intermediate 15 (100 mg, 0.35 mmol), DMF (1.0 ml), Et₃N (58 μl, 0.42 mmol), BOP reagent (169 mg, 0.38 mmol) and phenyl hydrazine (34 μl, 0.34 mmol) gave the title compound (105 mg, 80%). M.P.: 205° C. ¹H-NMR (δ ppm, CDCl₃, 300 MHz): 8.51 (s, 1H); 7.60-7.51 (m, 2H); 7.52-7.40 (m, 2H); 7.23 (t, J=7.8, 2H); 6.95 (d, J=7.8, 2H); 6.90 (t, J=7.5, 1H); 3.74 (br. s, 1H); 3.41 (br. s, 1H); 2.15 (br. d, J=8.7, 1H); 2.00-1.85 (m, 2H); 1.70 (br. d, J=8.7, 1H); 1.32-1.20 (m, 2H). IR (KBr, cm⁻¹): 3283 (s), 2993 (m), 2955 (m), 1675 (s), 1591 (m), 1603 (m), 1542 (m), 1513 (s), 1497 (s), 1439 (m), 1348 (m), 1281 (m), 1238 (m), 1137 (m), 1123 (m), 1082 (m), 1062 (m), 889 (m). MS (m/z): 379.0 ([M+H]⁺).

Example 209

N(3)-Piperidino-1-(4-chlorophenyl)-4,5,6,7-tetrahydro-1H-4,7-methano-indazole-3-carboxamide The title compound was synthesized by a procedure similar to that described for example 101. Intermediate 16 (100 mg, 0.35 mmol), DMF (1.0 ml), Et₃N (48 μl, 0.35 mmol), BOP reagent (1.52 mg, 0.35 mmol) and 1-amino piperidine (37 μl, 0.35 mmol) yielded the title compound (68 mg, 53%). MP: 78-81° C. ¹H-NMR (δ ppm, CDCl₃, 300 MHz): 7.63 (d, J=8.7, 2H); 7.44 (d, J=8.7, 2H); 3.75 (s, 1H); 3.67 (s, 1H); 2.91 (br. s, 4H); 2.11 (br. d, J=8.7, 1H); 2.00 (br. d, J=9.6, 2H); 1.80-1.65 (m, 5H): 1.45 (m, 2H); 1.20 (m, 2H). IR (KBr, cm⁻¹): 3408 (m), 2931 (m), 2871 (m), 2779 (m), 1692 (s), 1540 (m), 1506 (s), 1489 (s), 1347 (m), 1268 (m), 1227 (m), 1085 (m). MS (m/z): 371.2 ([M+H]⁺).

Example 210

1-(4-Chlorophenyl)-4,5,6,7-tetrahydro-1H-4,7-methano-indazol-3-yl piperidino methanone The title compound was synthesized by a procedure similar to that described for example 101. Intermediate 16 (0.100 mg, 0.35 mmol), DMF (1.0 ml), Et$_3$N (54 µl, 0.39 mmol), BOP reagent (160 mg, 0.36 mmol) and piperidine (38 µl, 0.38 mmol) furnished the title compound (80 mg, 65%). M.P.: 96-98° C. $^1$H-NMR (δ ppm, CDCl$_3$, 300 MHz): 7.63 (d, J=8.7, 2H); 7.41 (d, J=8.7, 2H); 3.92-3.75 (m, 4H), 3.69 (br. s, 1H), 3.57 (s, 1H), 2.13 (d, J=6.9, 1H), 1.97 (d, J=9.0, 2H), 1.80-1.60 (m, 7H), 1.24 (d, J=8.7, 2H). IR (cm$^{-1}$, KBr): 2932 (s), 2861 (m), 1613 (s), 1503 (s), 1467 (m), 1422 (m), 137.1 (m), 1352 (m), 1271 (m), 1246 (m), 1156 (w), 1132 (m), 1088 (m), 825 (m). MS (m/z): 356.0 ([M+H]$^+$).

Example 211

N(3)-Cyclohexyl-1-(4-chlorophenyl)-4,5,6,7-tetrahydro-1H-4,7-methano-indazole-3-carboxamide The title compound was synthesized by a procedure similar to that described for example 101. Intermediate 16 (100 mg, 0.35 mmol), DMF (1.0 ml), Et$_3$N (48 µl, 0.35 mmol), BOP reagent (152 mg, 0.35 mmol) and cyclohexylamine (39 µl, 0.35 mmol) to give the title compound (98 mg, 77%). M.P.: 155-158° C. $^1$H-NMR (δ ppm, CDCl$_3$, 300 MHz): 7.64 (d, J=8.7, 2H); 7.43 (d, J=8.7, 2H); 6.76 (br. d, J=8.7, 1H); 4.02-3.87 (m, 1H); 3.75 (s, 1H); 3.67 (s, 1H); 2.12 (br. d, J=8.1, 1H); 2.10-1.90 (m, 4H); 1.80-1.57 (m, 4H); 1.48-1.18 (m, 7H) IR (KBr, cm$^{-1}$): 3411 (m), 2926 (s), 2848 (m), 1666 (s), 1598 (w), 1545 (s), 1505 (s), 1486 (s), 1349 (m), 1248 (w), 1223 (m), 1159 (m), 1122 (m), 1086 (m), 829 (m), 506 (m). MS (m/z): 370.3 ([M+H]$^+$).

Example 212

N(3)-Cyclopentyl-1-(4-chlorophenyl)-4,5,6,7-tetrahydro-1H-4,7-methano-indazole-3-carboxamide The title compound was synthesized by a procedure similar to that described for example 101. Intermediate 16 (100 mg, 0.35 mmol), DMF (1.0 ml), Et$_3$N (54 µl, 0.39 mmol), BOP reagent (160 mg, 0.36 mmol) and cyclopentylamine (38 µl, 0.38 mmol) yielded the title compound (95 mg, 77%). M.P.: 176-178° C. $^1$H-NMR (δ ppm, CDCl$_3$, 300 MHz): 7.63 (d, J=8.7, 2H); 7.43 (d, J=8.7, 2H); 6.81 (d, J=7.5, 1H); 4.38 (sextet, J=7.5, 1H); 3.76 (s, 1H), 3.66 (s, 1H), 2.20-1.90 (d, J=8.7, 5H); 1.8-1.40 (m, 7H); 1.28-1.20 (m, 2H). IR (cm$^{-1}$, KBr): 3288 (m), 2964 (s), 2868 (m), 1643 (s), 1552 (s), 1505 (s), 1489 (s), 1442 (m), 1406 (m), 1364 (m), 1347 (m), 1275 (m), 1252 (m), 1243 (m), 1158 (m), 1129 (m), 1089 (m), 1008 (m), 836 (m). MS (m/z): 356.0 ([M+H]$^+$).

Example 213

N(3)-[(N-Cyclohexyl-N-methyl)amino]-1-(4-chlorophenyl)-4,5,6,7-tetrahydro-1H-4,7-ethano-indazole-3-carboxamide The title compound was synthesized by a procedure similar to that described for example 101. Intermediate 16 (300 mg, 1.039 mmol), DMF (3 ml), Et$_3$N (173 µl, 1.25 mmol), BOP reagent (459 mg, 1.039 mmol) and N-methyl-N-cyclohexylhydrazine (132 mg, 1.04 mmol) yielded the title compound (285 mg, 69%). MP: 62° C. $^1$H-NMR (δ ppm, CDCl$_3$, 300 MHz): 7.63 (d, J=8.7, 2H); 7.62 (br. s, 1H); 7.44 (d, J=9.0, 2H); 3.77 (s, 1H); 3.67 (s, 1H); 2.73 (br. s, 3H); 2.13 (br. d, J=8.7, 1H); 2.10-1.90 (m, 4H); 1.72 (br. d, J=8.7, 1H); 1.80-1.15 (m, 11H). IR (KBr, cm$^{-1}$) 3258 (m), 2930 (s), 2854 (s), 1678 (s), 1596 (m), 1544 (s), 1501 (s), 1447 (s), 1350 (s), 1274 (m), 1233 (m), 1159 (m), 1121 (m), 1090 (s), 1051 (m), 1006 (m), 915 (m), 866 (m), 831 (s). MS (m/z): 399.1 ([M+H]$^+$).

Example 214

N(3)-Phenyl-1-(4-chlorophenyl)-4,5,6,7-tetrahydro-1H-4,7-methano-indazole-3-carboxamide The title compound was synthesized by a procedure similar to that described for example 101. Intermediate 16 (100 mg, 0.35 mmol), DMF (1.0 ml), Et$_3$N (48 µl, 0.35 mmol), BOP reagent (152 mg, 0.35 mmol) and aniline (31 µl, 0.35 mmol) gave the title compound (80 mg, 64%). M.P.: 137-140° C. $^1$H-NMR (δ ppm, CDCl$_3$, 300 MHz): 8.70 (s, 1H); 7.69 (t, J=9.9, 4H); 7.48 (d, J=9.0, 2H); 7.36 (t, J=7.9, 2H); 7.12 (t, J=7.4, 1H); 3.80 (s, 1H); 3.71 (s, 1H); 2.17 (br. d, J=9.0, 1H); 2.10-1.95 (m, 2H); 1.76 (br. d, J=-9.0, 1H); 1.38-1.19 (m, 2H). IR (KBr, cm$^{-1}$): 3283 (m), 2933 (w), 2865 (w), 1663 (s), 1597 (s), 1542 (s), 1500 (s), 1433 (m), 1350 (m), 1240 (m), 1089 (m), 833 (m), 759 (m), 507 (w). MS (m/z): 364.3 ([M+H]$^+$).

Example 215

N(3)-(3-Chlorophenyl)-1-(4-chlorophenyl)-4,5,6,7-tetrahydro-1H-4,7-methano-indazole-3-carboxamide The title compound was synthesized by a procedure similar to that described for example 101. Intermediate 16 (100 mg, 0.35 mmol), DMF (1.0 ml), Et$_3$N (54 µl, 0.38 mmol), BOP reagent (162 mg, 0.37 mmol) and 3-chloroaniline (49 mg, 0.38 mmol) furnished the title compound (110 mg, 78%). M.P.: 158-161° C. $^1$H-NMR (δ ppm, CDCl$_3$, 300 MHz): 8.71 (br. s, 1H); 7.87 (t, J=1.8, 1H); 7.67 (d, J=8.7, 2H); 7.54 (br. d, J=8.1, 1H); 7.48 (d, J=8.7, 2H); 7.28 (t, J=8.1, 1H); 7.09 (br. d, J=8.1, 1H); 3.80 (br. s, 1H); 3.71 (br. s, 1H); 2.17 (br. d, J=9.0, 1H); 2.12-1.97 (m, 2H); 1.76 (d, J=8.7, 1H); 1.32-1.20 (m, 2H). IR (cm$^{-1}$, KBr): 3295 (s), 3187 (w), 3059 (w), 2987 (m), 2960 (m), 2984 (m), 2866 (m), 1677 (s), 1593 (s), 1551 (m), 1497 (s), 1484 (s), 1410 (m), 1400 (m), 1355 (m), 1308 (m), 1297 (w), 1234 (m), 1220 (m), 1157 (w), 1141 (m), 1091 (m), 1077 (w), 1048 (w), 1008 (m), 997 (m) 875 (m), 825 (m). MS (m/z): 398.2 ([M+H]$^+$).

Example 216

N(3)-(4-Chlorophenyl)-1-(4-chlorophenyl)-4,5,6,7-tetrahydro-1H-4,7-methano-indazole-3-carboxamide The title compound was synthesized by a procedure similar to that described for example 101. Intermediate 16 (100 mg, 0.35 mmol), DMF (1.0 ml), Et$_3$N (54 µl, 0.39 mmol), BOP reagent (160 mg, 0.36 mmol) and 4-chloroaniline (49 mg, 0.39 mmol) yielded the title compound (80 mg, 58%). M.P.: 182-184° C. $^1$H-NMR (δ ppm, CDCl$_3$, 300 MHz): 8.69 (s, 1H); 7.67 (d, J=8.7, 4H); 7.47 (d, J=8.7, 2H); 7.32 (d, J=8.7, 2H); 3.80 (s, 1H), 3.71 (s, 1H), 2.16 (d, J=8.7, 1H); 2.03 (d, J=7.2, 2H); 1.76 (d, J=8.7, 1H); 1.26 (d, J=7.5, 2H). IR (cm$^{-1}$, KBr): 3306 (m), 2989 (w), 2971 (w), 2945 (m), 2868 (w), 1673 (s), 1660 (m), 1594 (s), 1545 (s), 1498 (s), 1407 (s), 1397 (m), 1310 (m), 1284 (m), 1240 (m), 1089 (s), 1008 (m), 828 (s). MS (m/z): 398.0 ([M+H]$^+$).

Example 217

N(3)-(3-Bromophenyl)-1-(4-chlorophenyl)-4,5,6,7-tetrahydro-1H-4,7-methano-indazole-3-carboxamide The title compound was synthesized by a procedure similar to that described for example 101. Intermediate 16 (100 mg, 0.35 mmol), DMF (1.0 ml), Et$_3$N (54 μl, 0.39 mmol), BOP reagent (160 mg, 0.36 mmol) and 3-bromoaniline (42 μl, 0.38 mmol) furnished the title compound (90 mg, 59%). M.P.: 176-178° C. $^1$H-NMR (δ ppm, CDCl$_3$, 300 MHz): 8.69 (s, 1H); 8.00 (d, J=2.1, 1H); 7.66 (d, J=7.5, 2H); 7.61 (br. d, J=7.5, 1H); 7.47 (d, J=7.5, 2H); 7.25-7.17 (m, 2H); 3.80 (s, 1H), 3.71 (s, 1H), 2.16 (d, J=8.7, 1H); 2.03 (d, J=-7.8, 2H); 1.76 (d, J=8.7, 1H); 1.26 (d, J=7.2, 2H). IR (cm$^{-1}$, KBr) 3292 (m), 2987 (w), 2865 (w), 1675 (s), 1587 (s), 1497 (s), 1481 (s), 1409 (m), 1397 (m), 1355 (m), 1306 (m), 1233 (m), 1157 (m), 1091 (m), 874 (w), 825.

Example 218

N(3)-(2-Methoxyphenyl)-1-(4-chlorophenyl)-4,5,6,7-tetrahydro-1H-4,7-methano-indazole-3-carboxamide The title compound was synthesized by a procedure similar to that described for example 101. Intermediate 16 (100 mg, 0.35 mmol), DMF (1.0 ml), Et$_3$N (48 μl, 0.35 mmol), BOP reagent (153 mg, 0.35 mmol) and o-anisidine (39 μl, 0.35 mmol) gave the title compound (100 mg, 74%). M.P.: 149-151° C. $^1$H-NMR (δ ppm, CDCl$_3$, 300 MHz): 9.32 (br. s, 1H); 8.54 (dd, J=8.1, 2.1, 1H); 7.69 (d, J=9.0, 2H); 7.47 (d. J=9.0, 2H); 7.1.0-7.02 (m, 2H); 6.92 (dd, J=7.8, 1.5, 1H); 3.94 (s, 3H); 3.81 (br. s, 1H); 3.71 (br. s, 1H); 2.17 (d, J=7.8, 1H); 2.02 (br. d, J=8.4, 2H); 1.76 (d, J=8.7, 1H); 1.40-1.18 (m, 2H). IR (KBr, cm$^{-1}$): 3380 (m), 2873 (w), 1684 (s), 1601 (m), 1541 (s), 1499 (s), 1479 (s), 1461 (s), 1349 (m), 1247 (m), 1219 (m), 1118 (m), 1089 (m), 1044(M), 1027 (m), 838 (m). MS (m/z): 394.2 ([M+H]$^+$).

Example 219

N(3)-(4-tert-Butylphenyl)-1-(4-chlorophenyl)-4,5,6,7-tetrahydro-1H-4,7-methano-indazole-3-carboxamide The title compound was synthesized by a procedure similar to that described for example 101. Intermediate 16 (100 mg, 0.35 mmol), DMF (1.0 ml), Et$_3$N (54 μl, 0.39 mmol), BOP reagent (160 mg, 0.36 mmol) and 4-tert-butylaniline (62 0.38 mmol) yielded the title compound (100 mg, 69%). M.P.: 76-78° C. $^1$H-NMR (δ ppm, CDCl$_3$, 300 MHz): 8.65 (s, 1H); 7.67 (d, J=8.7, 2H); 7.63 (d, J=8.7, 2H); 7.47 (d, J=8.7, 2H); 7.37 (d, J=9.0, 2H); 3.81 (s, 1H), 3.70 (s, 1H), 2.16 (d, J=9.0, 1H); 2.02 (d, J=8.4, 1H); 1.75 (d, J=9.0, 1H); 1.33 (s, 9H); 1.40-1.20 (m, 2H). IR (cm$^{-1}$, KBr): 2962 (m), 2868 (m), 1685 (s), 1589 (m), 1537 (s), 1519 (s), 1492 (s), 1407 (m), 1349 (m), 1243 (m), 1219 (m), 1134 (w), 1121 (w), 1091 (s), 1047 (w), 1009 (w), 830 (s). MS (m/z): 420.1 ([M+H]$^+$).

Example 220

N(3)-Benzyl-1-(4-chlorophenyl)-4,5,6,7-tetrahydro-1H-4,7-methano-indazole-3-carboxamide The title compound was synthesized by a procedure similar to that described for example 101. Intermediate 16 (100 mg, 0.35 mmol), DMF (1.0 ml), Et$_3$N (48 μl, 0.35 mmol), BOP reagent (152 mg, 0.35 mmol) and benzylamine (37 μl, 0.35 mmol) gave the title compound (67 mg, 51%) MP: 112-115° C. $^1$H-NMR (δ ppm, CDCl$_3$, 300 MHz): 7.61 (d, J=9.0, 2H); 7.45-7.20 (m, 8H); 4.63 (br. d, J=5.7, 2H); 3.78 (s, 1H); 3.68 (s, 1H); 2.14 (br. d, J=8.5, 1H); 2.05-1.90 (m, 2H); 1.73 (br. d, J=8.5, 1H); 1.35-1.17 (m, 2H). IR (KBr, cm$^{-1}$): 3318 (m), 2995 (m), 2930 (m), 1652 (s), 1548 (s), 1501 (s), 1352 (m), 1275 (m), 1239 (m), 1120 (m), 1089 (m), 830 (m), 701(w), 508 (w). MS (m/z): 378.3 ([M+H]$^+$).

Example 221

N(3)-(2-Chloro benzyl)-1-(4-chlorophenyl)-4,5,6,7-tetrahydro-1H-4,7-methano-indazole-3-carboxamide The title compound was synthesized by a procedure similar to that described for example 101. Intermediate 16 (100 mg, 0.35 mmol), DMF (1.0 ml), Et$_3$N (48 μl, 0.35 mmol), BOP reagent (152 mg, 0.35 mmol) and 2-chlorobenzylamine (41 μl, 0.35 mmol) gave the title compound (91 mg, 64%). M.P.: 119-122° C. $^1$H-NMR (δ ppm, CDCl$_3$, 300 MHz): 7.63 (d, J=9.0, 2H); 7.43 (d, j=9.0, 2H); 7.51-7.20 (m, 5H); 4.72 (d, J=6.3, 2H); 3.76 (s, 1H); 3.67 (s, 1H); 2.12 (br d, J=8.6, 1H); 2.10-1.90 (m, 2H); 1.73 (hr. d, J=8.6, 1H); 1.35-1.19 (m, 2H). IR (KBr, cm$^{-1}$): 3319 (m), 2955 (m), 2868 (m), 1651 (s), 1595 (m), 1547 (m), 1490 (s), 1442 (m), 1352 (m), 1277 (m), 1237 (m), 1160 (m), 1123 (m), 1091 (m), 1007 (m), 993 (m), 835 (m). MS (m/z): 412.0 ([M+H]$^+$).

Example 222

N(3)-(4-Chlorobenzyl)-1-(4-chlorophenyl)-4,5,6,7-tetrahydro-1H-4,7-methano-indazole-3-carboxamide The title compound was synthesized by a procedure similar to that described for example 101. Intermediate 16 (100 mg, 0.35 mmol), DMF (1.0 ml), Et$_3$N (48 μl, 0.35 mmol), BOP reagent (152 mg, 0.35 mmol) and 4-chlorobenzylamine (42 μl, 0.35 mmol) yielded the title compound (104 mg, 73%). M.P.: 157-160° C. $^1$H-NMR (δ ppm, CDCl$_3$, 300 MHz): 7.61 (d, J=8.7, 2H); 7.42 (d, J=8.7, 2H); 7.31 (s, 4H); 7.23 (br. s, 1H); 4.59 (d, J=5.6, 2H); 3.77 (s, 1H); 3.68 (s, 1H); 2.14 (br. d, J=8.6, 1H); 2.10-1.90 (m, 2H); 1.73 (hr. d, J=8.6, 1H); 1.35-1.18 (m, 2H). IR (KBr, cm$^{-1}$): 3324 (m), 2979 (m), 2951 (m), 287.5 (m), 1649 (m), 1560 (s), 1513 (s), 1444 (m), 1406 (m), 1354 (m), 1244 (m), 1160 (m), 1144 (m), 1092 (s), 1007 (m), 980 (m), 946 (m), 835 (s), 626 (m), 509 (w). MS (m/z): 412.0 ([M+H]$^+$).

Example 223

N(3)-(2,4-Dichlorobenzyl)-1-(4-chlorophenyl)-4,5,6,7-tetrahydro-1H-4,7-methano-indazole-3-carboxamide The title compound was synthesized by a procedure similar to that described for example 101. Intermediate 16 (100 mg, 0.35 mmol), DMF (1.0 ml), Et$_3$N (48 μl, 0.35 mmol), BOP reagent (152 mg, 0.35 mmol) and 2,4-dichlorobenzylamine (46 μl, 0.35 mmol) gave the title compound (104 mg, 67%). MP: 108-111° C. $^1$H-NMR (δ ppm, CDCl$_3$, 300 MHz): 7.62 (d, J=8.7, 2H); 7.50-7.30 (m, 4H); 7.34 (br. s, 1H); 4.70 (d, J=6.3, 2H); 3.75 (s, 1H); 3.68 (s, 1H); 2.13 (br. d, J=9.0, 1H); 2.10-1.90 (m, 2H); 1.73 (br d, J=9.0, 1H); 1.40-1.18 (m, 2H). IR (KBr, cm$^{-1}$): 3294 (m), 2988 (w), 2949 (w), 1652 (s), 1554

(m), 1502 (s), 1491 (s), 1356 (m), 1.252 (m), 1092 (m), 831 (s). MS (m/z): 447.9 ([M+H]$^+$).

Example 224

N(3)-(2-Bromobenzyl)-1-(4-chlorophenyl)-4,5,6,7-tetrahydro-1H-4,7-methano-indazole-3-carboxamide The title compound was synthesized by a procedure similar to that described for example 101. Intermediate 16 (100 mg, 0.35 mmol), DMF (1.0 ml), Et$_3$N (0.10 ml, 0.69 mmol), BOP reagent (0.153 g, 0.35 mmol) and 2-bromobenzylamine hydrochloride (77 mg, 0.35 mmol) to give the title compound (105 mg, 67%). M.P.: 141-142° C. $^1$H-NMR (δ ppm, CDCl$_3$, 300 MHz): 7.60-7.50 (m, 3H); 7.50-7.22 (m, 5H); 7.14 (td, J=7.8, 1.5, 1H); 4.70 (d, J=6.3, 2H); 3.80 (s, 1H); 3.70 (s, 1H); 2.14 (br. d, J=8.7, 1H); 2.10-1.80 (m, 2H); 1.70 (br. d, J=8.7, 1H); 1.35-1.15 (m, 2H). IR (KBr, cm$^{-1}$): 3322 (m), 2954 (w), 2867 (w), 1651 (s), 1548 (m), 1503 (s), 1350 (m), 1277 (w), 1236 (w), 1091 (s), 835 (m). MS (m/z): 458.1 ([M+H]$^+$).

Example 225

N(3)-(4-Bromobenzyl)-1-(4-chlorophenyl)-4,5,6,7-tetrahydro-1H-4,7-methano-indazole-3-carboxamide The title compound was synthesized by a procedure similar to that described for example 101. Intermediate 16 (100 mg, 0.35 mmol), DMF (1.0 ml), Et$_3$N (0.096 ml, 0.69 mmol), BOP reagent (0.153 g, 0.35 mmol) and 4-bromobenzylamine hydrochloride (77 mg, 0.35 mmol) furnished the title compound (118 mg, 64%). M.P.; 181-183° C. $^1$H-NMR (δ ppm, CDCl$_3$, 300 MHz): 7.60 (d, J=6.9, 2H); 7.50-7.40 (m, 4H); 7.30-7.20 (m, 2H); 4.60 (br. d, J=5.1, 2H); 3.80 (s, 1H); 3.70 (s, 1H); 2.14 (br. d, J=9.0, 1H); 2.07-1.92 (m, 2H); 1.70 (br. d, J=9.0, 1H); 1.30-1.15 (m, 2H). IR (KBr, cm$^{-1}$): 3325 (m), 2979 (m), 2950 (m), 1648 (s), 1558 (m), 1505 (s), 1489 (s), 1353 (m), 1253 (m), 1092 (m), 835 (s). MS (m/z): 458.0 ([M+H]$^+$).

Example 226

N(3)-(4-Fluorobenzyl)-1-(4-chlorophenyl)-4,5,6,7-tetrahydro-1H-4,7-methano-indazole-3-carboxamide The title compound was synthesized by a procedure similar to that described for example 101. Intermediate 1.6 (100 mg, 0.35 mmol), DMF (1.0 ml), Et$_3$N (48 µl, 0.35 mmol), BOP reagent (152 mg, 0.35 mmol) and 4-fluorobenzylamine (39 µl, 0.35 mmol) yielded the title compound (95 mg, 69%). M.P.: 104-107° C. $^1$H-NMR (δ ppm, CDCl$_3$, 300 MHz): 7.61 (d, J=9.0, 2H); 7.42 (d, J=9.0, 2H); 7.35 (dd, J=8.6, 5.7, 2H); 7.21 (br. s, 1H); 7.02 (t, J=8.6, 2H); 4.59 (d, J=6.0, 2H); 3.77 (s, 1H); 3.68 (s, 1H); 2.13 (br. d, J=8.7, 1); 2.10-1.90 (m, 2H); 1.73 (br. d, J=9.0, 1H); 1.40-1.18 (m, 2H). IR (KBr, cm$^{-1}$): 3314 (m), 2968 (m), 2940 (m), 2872 (w), 1647 (m), 1554 (m), 1509 (s), 1357 (m), 1218 (m), 1091 (m), 832 (s), 626 (w), 564 (w). MS (m/z): 396.1 ([M+H]$^+$).

Example 227

N(3)-(4-Trifluoromethylbenzyl)-1-(4-chlorophenyl)-4,5,6,7-tetrahydro-1H-4,7-methano-indazole-3-carboxamide The title compound was synthesized by a procedure similar to that described for example 101. Intermediate 16 (100 mg, 0.35 mmol), DMF (1.0 ml), Et$_3$N (48 µl, 0.35 mmol), BOP reagent (152 mg, 0.35 mmol) and 4-trifluoromethylbenzylamine (49 µl, 0.35 mmol) to furnished title compound (104 mg, 68%). M. P.: 165-168° C. $^1$H-NMR (δ ppm, CDCl$_3$, 300 MHz): 7.67-7.57 (m, 4H); 7.48 (d, J=8.7, 2H); 7.43 (d, J=8.7, 2H); 7.30 (br. t, J=6.0, 1H); 4.68 (d, J=5.7, 2H); 3.77 (s, 1H); 3.69 (s, 1H); 2.13 (br. d, J=8.4, 1H); 2.10-1.90 (m, 2H); 1.73 (br. d, J=7.2, 1H); 1.30-1.18 (m, 2H). IR (KBr, cm$^{-1}$): 3323 (m), 2969 (m), 2953 (m), 2874 (w), 1648 (s), 1557 (m), 1504 (s), 1439 (m), 1406 (m), 1417 (m), 1325 (s), 1282 (m), 1245 (m), 1161 (s), 1122 (s), 1110 (s), 1092 (s), 1064 (s), 847 (m), 832 (m), 625 (w), 509 (w). MS (m/z): 446.0 ([M+H]$^+$).

Example 228

N(3)-Phenylamino-1-(4-chlorophenyl)-4,5,6,7-tetrahydro-1H-4,7-methano-indazole-3-carboxamide The title compound was synthesized by a procedure similar to that described for example 101. Intermediate 16 (100 mg, 0.35 mmol), DMF (1.0 ml), Et$_3$N (48 µl, 0.35 mmol), BOP reagent (152 mg, 0.35 mmol) and phenylhydrazine (34 µl, 0.35 mmol) gave the title compound (92 mg, 70%). MP: 138-141° C. $^1$H-NMR (δ ppm, CDCl$_3$, 300 MHz): 8.55 (s, 1H); 7.67 (d, J=8.5, 2H); 7.46 (d, J=8.5, 2H); 7.24 (t, J=7.5, 2H); 6.95 (d, J=8.4, 2H); 6.90 (t, J=7.5); 3.71 (br. s, 2H); 2.13 (br. d, J=8.1, 1H); 2.10-1.95 (m, 2H); 1.73 (br. d, J=8.7, 1H); 1.40-1.18 (m, 2H). IR (KBr, cm$^{-1}$): 3258 (m), 2951 (m), 1660 (s), 1603 (s), 1500 (s), 1358 (m), 1306 (m), 1277 (m), 1127 (m), 1092 (s), 892 (w), 828 (m), 749 (m), 691 (m), 510 (m). MS (m/z): 379.0 ([M+H]$^+$).

Example 229

N(3)-[(4-Chlorophenyl)-amino]-1-(4-chlorophenyl)-4,5,6,7-tetrahydro-1H-4,7-methano-indazole-3-carboxamide The title compound was synthesized by a procedure similar to that described for example 101. Intermediate 16 (100 mg, 0.35 mmol), DMF (1.0 ml), Et$_3$N (48 µl, 0.35 mmol), BOP reagent (152 mg, 0.35 mmol) and 4-chlorophenylhydrazine hydrochloride (61 mg, 0.35 mmol) to give the title compound (98 mg, 69%). M.P.: 202-205° C. $^1$H-NMR (δ ppm, CDCl$_3$, 300 MHz): 8.60 (s, 1H); 7.66 (d, J=9.0, 2H); 7.47 (d, J=9.0, 2H); 7.18 (d, J=8.6, 2H); 6.87 (d, J=8.6, 2H); 3.71 (s, 2H); 2.13 (br. d, J=8.7, 1H); 2.10-1.90 (m, 2H); 1.73 (br. d, J=9.0, 1H); 1.38-1.18 (m, 2H). IR (KBr, cm$^{-1}$): 3256 (m), 2995 (m), 2950 (m), 2870 (m), 1661 (s), 1595 (m), 1500 (s), 1357 (m), 1278 (m), 1236 (m), 1128 (m), 1092 (s), 894 (w), 826 (m), 658 (w), 610 (w), 503 (w). MS (m/z): 413.0 ([M+H]$^+$).

Example 230

N(3)-[(2,4-Dichlorophenyl)-amino]-1-(4-chlorophenyl)-4,5,6,7-tetrahydro-1H-4,7-methano-indazole-3-carboxamide The title compound was synthesized by a procedure similar to that described for example 101. Intermediate 16 (100 mg, 0.35 mmol), DMF (1.0 ml), Et$_3$N (57 µl, 0.42 mmol), BOP reagent (152 mg, 0.35 mmol) and 2,4-dichlorophenylhydrazine hydrochloride (73 mg, 0.35 mmol)/furnished the title compound (73 mg, 34%). M. P.=180-182° C. $^1$H-NMR (δ ppm, CDCl$_3$, 300 MHz): 8.54 (d, J=3.0, 1H); 7.66 (d, J=8.7, 2H); 7.47 (d, J=8.7, 2H); 7.31 (d, J=2.1, 1H); 7.11 (dd, J=8.7, 2.1, 1H); 6.96 (d, J=8.7, 1H); 6.51 (d, J=3.0, 1H); 3.71 (br. s, 2H); 2.13 (br. d, J=7.8, 1H); 2.0 (m, 2H); 1.74 (br. d, J=9.0, 1H); 1.232-1.25 (m, 2H). IR (KBr, cm$^{-1}$): 3301 (m), 2993 (m), 2873 (m), 1674 (s), 1595 (w), 1542 (m), 1499 (s), 1352 (m), 1304 (m), 1232 (m), 1021 (m), 1049 (m), 814 (m).

Example 231

N(3)-[(3,4-Dichlorophenyl)amino]-1-(4-chlorophenyl)-4,5,6,7-tetrahydro-1H-4,7-methano-indazole-3-carboxamide The title compound was synthesized by a procedure similar to that described for example 101. Intermediate 16 (200 mg, 0.69 mmol), DMF (2.0 ml), Et$_3$N (0.193 ml, 1.38 mmol), BOP reagent (306 mg, 0.69 mmol) and 3,4-dichlorophenylhydrazine hydrochloride (148 mg, 0.69 mmol) gave the title compound (222 mg, 64.5%). M.P.: 235-237° C. $^1$H-NMR (δ ppm, CDCl$_3$, 300 MHz): 8.50 (s, 1H); 7.67 (d, J=9.0, 2H); 7.48 (d, J=9.0, 2H); 7.28 (d, J=8.4, 1H); 7.05 (d, J=2.4, 1H); 6.79 (dd, J=8.4, 2.4, 1H); 6.19 (br. s, 1H); 3.70 (s, 2H); 2.14 (br. d, J=8.5, 1H); 2.10-1.90 (m, 2H); 1.7 (br. d, J=8.5, 1H); 1.30-1.18 (m, 2H). IR (KBr, cm$^{-1}$): 3250 (m), 2995 (w), 2968 (w), 2946 (w), 2869 (m), 1667 (s), 1650 (s), 1598 (m), 1500 (s), 1475 (s), 1353 (m), 1277 (m), 1092 (m), 828 (m), 610 (w). MS (m/z): 449.0 ([M+H]$^+$).

Example 232

N(3)-[(2-Fluorophenyl)amino]-1-(4-chlorophenyl)-4,5,6,7-tetrahydro-1H-4,7-methano-indazole-3-carboxamide The title compound was synthesized by a procedure similar to that described for example 101. Intermediate 16 (200 mg, 0.69 mmol), DMF (2.0 ml), Et$_3$N (0.193 ml, 1.38 mmol), BOP reagent (306 mg, 0.69 mmol) and 2-fluorophenylhydrazine hydrochloride (113 mg, 0.69 mmol) gave the title compound (240 mg, 87%). M.P.: 91° C. $^1$H-NMR (δ ppm, CDCl$_3$, 300 MHz): 8.50 (s, 1H); 7.65 (d, J=7.2, 2H); 7.46 (d, J=7.2, 2H); 6.95-7.10 (m, 3H); 6.80-6.90 (m, 1H); 6.40 (br. s, 1H); 3.70 (br. s, 2H); 2.14 (br. d, J=9.0, 1H); 2.05-1.90 (m, 2H); 1.70 (br. d, J=9.0, 1H); 1.30-1.17 (m, 2H). IR (KBr, cm$^{-1}$): 3292 (m), 2925 (m), 2870 (m), 1676 (s), 1502 (s), 1351 (m), 1276 (m), 1194 (m), 1091 (s), 831 (s). MS (m/z): 397.0 ([M+H]$^+$).

Example 233

N(3)-[(3-Fluorophenyl)amino]-1-(4-chlorophenyl)-4,5,6,7-tetrahydro-1H-4,7-methano-indazole-3-carboxamide The title compound was synthesized by a procedure similar to that described for example 101. Intermediate 16 (200 mg, 0.69 mmol), DMF (2.0 ml), Et$_3$N (0.193 ml, 1.38 mmol), BOP reagent (306 mg, 0.69 mmol) and 3-fluorophenylhydrazine hydrochloride (113 mg, 0.69 mmol) yielded the title compound (158 mg, 58%). M.P.: 199° C. $^1$H-NMR (δ ppm, CDCl$_3$, 300 MHz): 8.50 (s, 1H); 7.70 (d, J=9.0, 2H); 7.50 (d, J=9.0, 2H); 7.30-7.10 (m, 1H); 6.70-6.50 (m, 3H); 6.20 (br. s, 1H); 3.70 (s, 2H); 2.14 (br. d, J=9.0, 1H); 2.10-1.90 (m, 2H); 1.73 (br. d, J=9.0, 1H); 1.35-1.18 (m, 2H). IR (KBr, cm$^{-1}$): 3257 (m), 2952 (w), 2872 (w), 1663 (s), 1619 (m), 1597 (m), 1501 (s), 1358 (m), 1266 (m), 1092 (m), 827 (m). MS (m/z): 397.1 ([M+H]$^+$).

Example 234

N(3)-[(4-Fluorophenyl)-amino]-1-(4-chlorophenyl)-4,5,6,7-tetrahydro-1H-4,7-methano-indazole-3-carboxamide The title compound was synthesized by a procedure similar to that described for example 101. Intermediate 16 (200 mg, 0.69 mmol), DMF (2.0 ml), Et$_3$N (0.193 ml, 1.38 mmol), BOP reagent (306 mg, 0.69 mmol) and 4-fluorophenylhydrazine hydrochloride (113 mg, 0.69 mmol) furnished the title compound (179 mg, 65%). M.P.: 212° C. $^1$H-NMR (δ ppm, CDCl$_3$, 300 MHz): 8.50 (s, 1H); 7.70 (d, J=9.0, 2H); 7.50 (d, J=9.0, 2H); 7.00-6.80 (m, 4H); 3.70 (s, 2H); 2.14 (br. d, J=9.0, 1H); 2.07-1.90 (m, 2H); 1.73 (br. d, J=9.0, 1H); 1.35-1.18 (m, 2H). IR (KBr, cm$^{-1}$): 3268 (m), 2986 (w), 2950 (w), 1663 (m), 1502 (s), 1359 (m), 1214 (w), 1092 (m), 827 (m), 504 (w). MS (m/z): 397.0 ([M+H]$^+$).

Example 235

N(3)-[(2,4-Difluorophenyl)amino]-1-(4-chlorophenyl)-4,5,6,7-tetrahydro-1H-4,7-methano-indazole-3-carboxamide The title compound was synthesized by a procedure similar to that described for example 101. Intermediate 1.6 (200 mg, 0.69 mmol), DMF (2.0 ml), Et$_3$N (0.19 ml, 1.38 mmol), BOP reagent (306 mg, 0.69 mmol) and 2,4-difluorophenylhydrazine hydrochloride (113 mg, 0.69 mmol) to give the title compound (160 mg, 56%). M.P.: 1.18-120° C. $^1$H-NMR (δ ppm, CDCl$_3$, 300 MHz): 8.50 (br. s, 1H); 7.70 (d, J=8.7, 2H); 7.50 (d, J=8.7, 2H); 7.10-6.70 (m, 3H); 6.25 (br. s, 1H); 3.70 (s, 2H); 2.14 (br. d, J=8.7, 1H); 2.08-1.95 (m, 2H); 1.70 (br. d, J=8.7, 1H); 1.35-1.20 (m, 2H). IR (KBr, cm$^{-1}$): 3422 (m), 3286 (m), 2925 (m), 2871 (w), 1666 (m), 1501 (s), 1093 (m), 961 (m), 831 (m). MS (m/z): 417.1 ([M+H]$^+$).

Example 236

N(3)-(N',N'-Diphenylamino-1-(4-chlorophenyl)-4,5,6,7-tetrahydro-1H-4,7-methano-indazole-3-carboxamide The title compound was synthesized by a procedure similar to that described for example 101. Intermediate 16 (200 mg, 0.69 mmol), DMF (2.0 ml), Et$_3$N (0.19 ml, 1.38 mmol), BOP reagent (306 mg, 0.69 mmol) and N,N-diphenylhydrazine hydrochloride (113 mg, 0.69 mmol) gave the title compound (250 mg, 79.4%). M.P.: 193-195° C. $^1$H-NMR (δ ppm, CDCl$_3$, 300 MHz): 8.98 (s, 1H); 7.66 (d, J=9.0, 2H); 7.45 (d, J=9.0, 2H); 7.40-7.20 (m, 8H); 7.00 (m, 2H); 3.74 (br. s, 1H); 3.71 (br. s, 1H); 2.14 (br. d, J=8.7, 1H); 2.05-1.95 (m, 2H); 1.70 (br. d, J=8.7, 1H); 1.30-1.18 (m, 2H). IR (KBr, cm$^{-1}$): 3232 (w), 2924 (m), 1664 (m), 1590 (m), 1497 (s), 1357 (m), 1223 (m), 1092 (m), 828 (w). MS (m/z): 455.0 ([M+H]$^+$).

Example 237

N(3)-Cyclohexyl-1-(2,4-dichlorophenyl)-4,5,6,7-tetrahydro-1H-4,7-methano-indazole-3-carboxamide The title compound was synthesized by a procedure similar to that described for example 101. Intermediate 17 (100 mg, 0.31 mmol), DMF (1.0 ml), Et$_3$N (43 µl, 0.31 mmol), BOP reagent (136 mg, 0.31 mmol) and cyclohexylamine (33 µl, 0.31 mmol) gave the title compound (104 mg, 83%). M.P.:

157-160° C. ¹H-NMR (δ ppm, CDCl₃, 300 MHz): 7.55 (s, 1H); 7.46 (d, J=8.0, 1H); 7.37 (d, J=8.0, 1H); 6.70 (br. d, J=8.1, 1H); 4.05-3.85 (m, 1H); 3.75 (br. s, 1H); 3.36 (br. s, 2.13 (d, J=8.1, 1H); 2.00-1.85 (m, 4H); 1.70-1.58 (m, 4H); 1.46-1.15 (m, 7H). IR (KBr, cm⁻¹): 3398 (m), 2923 (m), 2850 (m), 1658 (s), 1543 (s), 1520 (s), 1485 (m), 1343 (m), 1249 (m), 1122 (m), 1105 (m), 836 (m).

Example 238

N(3)-Cyclohexylmethyl-1-(2,4-dichlorophenyl)-4,5,6,7-tetrahydro-1H-4,7-methano-indazole-3-carboxamide The title compound was synthesized by a procedure similar to that described for example 101. Intermediate 17 (100 mg, 0.31 mmol), DMF (1.0 ml), Et₃N (51 μl, 0.37 mmol), BOP reagent (136 mg, 0.31 mmol) and cyclohexanemethylamine (40 μl, 0.31 mmol) furnished the title compound (90 mg, 69%). M.P.: 111-113° C. ¹H-NMR (δ ppm, CDCl₃, 300 MHz): 7.56 (br. s, 1H); 7.45 (d, J=8.7, 1H); 7.39 (br. d, J=8:7, 1H); 6.88 (br. t, J=6.3, 1H); 3.77 (br. s, 1H); 3.36 (br. s, 1H); 3.32-3.18 (m, 2H); 2.13 (br. d, J=8.6, 1H); 2.00-1.50 (m, 9H); 1.25-1.11 (m, 5H); 1.00-0.80 (m, 2H). IR (KBr, cm⁻¹): 3291 (m), 2922 (s), 2948 (m), 1643 (s), 1553 (m), 1501 (s), 1486 (s), 1445 (m), 1351 (m), 1274 (m), 1241 (m), 1107 (m), 1074 (m), 869 (m), 831 (m), 800 (m), 623 (m). MS (m/z): 418.1 ([M+H]⁺).

Example 239

N(3)-(N,N-Dicyclohexylamino)-1-(2,4-dichlorophenyl)-4,5,6,7-tetrahydro-1H-4,7-methano-indazole-3-carboxamide The title compound was synthesized by a procedure similar to that described for example 101. Intermediate 17 (100 mg, 0.31 mmol), DMF (1.0 ml), Et₃N (51 μl, 0.37 mmol), BOP reagent (136 mg, 0.31 mmol) and N,N-dicyclohexylhydrazine (121 mg, 0.31 mmol) gave the title compound (70 mg, 45%). 127-130° C. ¹H-NMR (δ ppm, CDCl₃, 300 MHz): 7.56 (d, J=2.1, 1H); 7.48 (d, J=8.7, 1H); 7.35 (dd, J=8.7, 2.1, 1H); 7.33 (br. s, 1H); 3.78 (s, 1H); 3.37 (s, 1H); 2.84 (br. s, 2H); 2.12 (br. d, J=8.4, 1H); 1.97-1.80 (m, 6H); 1.80-1.58 (m, 6H); 1.40-1.00 (m, 13H). IR (KBr, cm⁻¹): 3328 (m); 2932 (s), 2854 (s), 1693 (s), 1537 (m), 1501 (m), 1482 (m), 1345 (m), 1229 (m), 1102 (m), 1079 (m), 867 (m), 837 (m). MS (m/z): 501.50 ([M+H]⁺).

Example 240

N(3)-(4H-1,2,4-triazol-4-yl)-1-(2,4-dichlorophenyl)-4,5,6,7-tetrahydro-1H-4,7-methano-indazole-3-carboxamide The title compound was synthesized by a procedure similar to that described for example 101. Intermediate 17 (100 mg, 0.31 mmol), DMF (1.0 ml), Et₃N (42 μl, 0.31 mmol), BOP reagent (136 mg, 0.31 mmol) and 4-amino-1,2,4-triazole (26 mg, 0.31 mmol) gave the title compound (38 mg, 32%). M.P.: 231-233° C. ¹H-NMR (δ ppm, DMSO-d₆, 300 MHz): 11.95 (s, 1H); 8.72 (s, 2H); 8.0 (d, J=2.1, 1H); 7.71 (d, J=8.4, 1H); 7.67 (dd, J=8.4, 2.1, 1H); 3.58 (s, 1H); 3.41 (s, 1H); 2.05 (br. d, J=8.7, 1H); 1.98-1.90 (m, 2H); 1.71 (d, J=8.7, 1H); 1.24-1.08 (m, 2H). IR (KBr, cm⁻¹): 3125 (w), 3090 (m), 2997 (m), 2876 (m), 1699 (s), 1506 (s), 1350 (m), 1129 (m), 1065 (s), 923 (w), 826 (w). MS (m/z): 389.3 ([M+H]⁺).

Example 241

N(3)-(1,3,3-Trimethyl bicyclo[2.2.1]hept-2-yl)-1-(2,4-dichlorophenyl)-4,5,6,7-tetrahydro-1H-4,7-methano-indazole-3-carboxamide The title compound was synthesized by a procedure similar to that described for example 101. Intermediate 17 (100 mg, 0.31 mmol), DMF (1.0 ml), Et₃N (51 μl, 0.37 mmol), BOP reagent (136 mg, 0.31 mmol) and (1S)-2endo-amino-1,3,3-trimethylbicyclo[2.2.1]heptane [prepared as described by Suchocki et. al. in *J. Med. Chem.* 1991, 34, 1003-1010 (46 mg, 0.34 mmol)] gave the title compound (76 mg, 54%). M.P.: 156-159° C. ¹H-NMR (δ ppm, CDCl₃, 300 MHz): 7.56 (d, J=2.1, 1H); 7.47 J=8.4, 1H); 7.38 (dd, J=8.4, 2.1, 1H); 6.91 (br. d, J=8.4, 1H); 3.76 (br. s, 2H); 3.38 (br. s, 1H); 2.12 (br. d, J=7.5, 1H); 2.00-1.84 (m, 2H); 1.80-1.58 (m, 4H); 1.02 (m, 12H); 0.85 (s, 3H). IR (KBr, cm⁻¹): 3420 (m), 2954 (s), 2869 (m), 1677 (s), 1538 (s), 1483 (s), 1386 (m), 1229 (m), 1161 (m), 1113 (m), 1078 (s), 823 (w), 798 (w). MS (m/z): 458.10 ([M+H]⁺).

Example 242

N(3)-(Adamantan-1yl)-1-(2,4-dichlorophenyl)-4,5,6,7-tetrahydro-1H-4,7-methano-indazole-3-carboxamide The title compound was synthesized by a procedure similar to that described for example 101. Intermediate 17 (100 mg, 0.31 mmol), DMF (1.0 ml), Et₃N (0.51 μl, 0.37 mmol), BOP reagent (136 mg, 0.31 mmol) and 1-adamantylamine (46 mg, 0.31 mmol) furnished the title compound (108 mg, 76%). M.P.: 201-20° C. ¹H-NMR (δ ppm, CDCl₃, 300 MHz): 7.55 (d, J=1.8, 1H); 7.45 (d, J=8.4, 2H); 7.37 (dd, J=8.4, 1.8, 1H); 6.60 (br. s, 1H); 3.75 (br. s, 1H); 3.35 (br. s, 1H); 2.13 (br. s, 10H); 2.02-1.80 (m, 2H); 1.70 (br. s, 7H); 1.40-1.13 (m, 2H). IR (cm⁻¹, KBr): 3400 (s), 2907 (s), 2851 (m), 1667 (s), 1542 (s), 1516 (s), 1483 (s), 1452 (m), 1359 (m), 1289 (w), 1230 (m), 1105 (m), 862 (w), 832 (m). MS (m/z): 456.3 ([M+H]⁺).

Example 243

N(3)-Phenyl-1-(2,4-dichlorophenyl)-4,5,6,7-tetrahydro-1H-4,7-methano-indazole-3-carboxamide The title compound was synthesized by a procedure similar to that described for example 101. Intermediate 17 (100 mg, 0.31 mmol), DMF (1.0 ml), Et₃N (42 μl, 0.30 mmol), BOP reagent (12.1 mg, 0.31 mmol) and aniline (28 0.31 mmol) gave the title compound (90 mg, 71%). M.P.: 66-68° C. ¹H-NMR (δ ppm, CDCl₃, 300 MHz): 8.63 (br. s, 1H); 7.68 (d, J=8.1, 2H); 7.59 (d, J=2.1, 1H); 7.49 (d, J=8.4, 1H); 7.41 (dd, J=8.4, 2.1, 1H); 7.34 (t, J=8.1, 2H); 7.11 (t, J=7.5, 1H); 3.81 (br. s, 1H); 3.39 (br. s, 1H); 2.16 (br. d, J=9.0, 1H); 2.05-1.86 (m, 2H); 1.73 (d, J=8.7, 1H); 1.35-1.15 (m, 2H). IR (KBr, cm⁻¹): 3382 (m), 2948 (m), 2869 (m), 1681 (s), 1596 (s), 1542 (s), 1500 (s), 1434 (s), 1380 (m), 1347 (m), 1321 (m), 1282 (m), 1237 (m), 1218 (m), 1159 (m), 1096 (m), 1077 (m), 810 (m). MS (m/z): 398.1 ([M+H]⁺).

Example 244

N(3)-(2,4-Difluorophenyl)-1-(2,4-dichlorophenyl)-4,5,6,7-tetrahydro-1H-4,7-methano-indazole-3-carboxamide The title compound was synthesized by a procedure similar to that described for example 101. Intermediate 17 (100 mg, 0.31 mmol), DMF (1.0 ml), Et$_3$N (57 μl, 0.37 mmol), BOP reagent (136 mg, 0.31 mmol) and 2,4-difluoroaniline (31 μl, 0.31 mmol) yielded the title compound (62 mg, 46%). M.P.: 152-155° C. $^1$H-NMR (δ ppm, CDCl$_3$, 300 MHz): 8.79 (br. s, 1H); 8.50-8.40 (m, 1H); 7.59 (d, J=2.1, 1H); 7.48 (d, i=8.4, 1H); 7.41 (dd, J=8.4, 2.1, 1H); 6.95-6.82 (m, 2H); 3.79 (br. s, 1H); 3.40 (br. s, 1H); 2.17 (br. d, J=8.7, 1H); 2.10-1.90 (m, 2H); 1.73 (d, J=8.7, 1H); 1.35-1.15 (m, 2H). IR (KBr, cm$^{-1}$): 3389 (s), 2993 (m), 2874 (m), 1685 (s), 1543 (s), 1505 (s), 1428 (m), 1345 (m), 1123 (m), 1102 (m), 1085 (m), 961 (w), 852 (w), 619 (w). MS (m): 434.0 ([M+H]$^+$).

Example 245

N(3)-(2-Fluorobenzyl)-1-(2,4-dichlorophenyl)-4,5,6,7-tetrahydro-1H-4,7-methano-indazole-3-carboxamide The title compound was synthesized by a procedure similar to that described for example 101. Intermediate 17 (100 mg, 0.31 mmol), DMF (1.0 ml), Et$_3$N (51 μl, 0.37 mmol), BOP reagent (136 mg, 0.31 mmol) and 2-fluorobenzylamine (35 μl, 0.31 mmol) gave the title compound (55 mg, 41%). M.P.: 54° C. (fuses). $^1$H-NMR (δ ppm, CDCl$_3$, 300 MHz): 7.55 (br. s, 1H); 7.50-7.30 (m, 3H); 7.28-7.20 (m, 2H); 7.15-7.00 (m, 2H); 4.65 (br. d, J=5.1, 2H); 3.77 (br. s, 1H); 3.37 (br. s, 1H); 2.12 (br. d, J=7.5, 1H); 1.99-1.84 (m, 2H); 1.69 (br. d, J=8.4, 1H); 1.28-1.15 (m, 2H). IR (KBr, cm$^{-1}$): 3419 (m), 2950 (m), 2874 (m), 1668 (s), 1548 (s), 1487 (s), 1455 (s), 1346 (m), 1275 (m), 1229 (s), 1107 (s), 832 (n). MS (m/z): 430.10 ([M+H]$^+$).

Example 246

N(3)-(4-Fluorobenzyl)-1-(2,4-dichlorophenyl)-4,5,6,7-tetrahydro-1H-4,7-methano-indazole-3-carboxamide The title compound was synthesized by a procedure similar to that described for example 101. Intermediate 17 (100 mg, 0.31 mmol), DMF (1.0 ml), Et$_3$N (43 μl, 0.31 mmol), BOP reagent (136 mg, 0.31 mmol) and 4-fluorobenzylamine (35 μl, 0.31 mmol) gave the title compound (90 mg, 68%), M.P.: 106-108° C. $^1$H-NMR (δ ppm, CDCl$_3$, 300 MHz): 7.55 (d, J=2.1, 1H); 7.41 (d, J=8.4, 1H); 7.39-7.25 (m, 3H); 7.15 (br. t, J=6.6, 1H); 7.00 (t, J=8.7, 2H); 4.54 (dd, J=17.0, 6.6, 1H); 4.59 (dd, J=17.0, 6.6, 1H); 3.77 (br. s, 1H); 3.36 (br. s, 1H); 2.12 (br. d, J=9.0, 1H); 2.10-1.82 (m, 2H), 1.70 (br. d, J=9.0, 1H); 1.32-1.10 (m, 2H). IR (KBr, cm$^{-1}$): 3277 (m), 2951 (m), 2979 (m), 2871 (m), 1648 (s), 1551(m), 1510 (s), 1350 (m), 1273 (m), 1223 (s), 1108 (m), 1076 (w), 833 (m). MS (m/z): 432.1 ([M+H]$^+$).

Example 247

N(3)-(2,4-Difluorobenzyl)-1-(2,4-dichlorophenyl)-4,5,6 7-tetrahydro-1H-4,7-methano-indazole-3-carboxamide The title compound was synthesized by a procedure similar to that described for example 101. Intermediate 17 (100 mg, 0.31 mmol), DMF (1.0 ml), Et$_3$N (51 μl, 0.37 mmol), BOP reagent (136 mg, 0.31 mmol) and 2,4-difluorobenzylamine (36 μl, 0.31 mmol) gave the title compound (93 mg, 67%). M.P.: 73-76° C. $^1$H-NMR (δ ppm, CDCl$_3$, 300 MHz): 7.55 (d, J=1.8, 1H); 7.40 (m, 3H); 7.20 (br. s, 1H); 6.90-6.75 (m, 2H); 4.50-4.70 (m, 2H); 3.77 (br. s, 1H); 3.36 (br. s, 1H); 2.12 (br. d, J=8.7, 1H); 2.02-1.86 (m, 2H); 1.69 (d, J=8.7, 1H); 1.14 (br. d, J=9.0, 2H). IR (KBr, cm$^{-1}$): 3421 (w), 3283 (m), 2996 (m), 2926 (w), 1648 (s), 1552(m), 1505 (s), 1487 (s), 1455 (s), 1280 (m), 1138 (m), 1117 (m), 1098 (m), 832 (m), 964 (w), 851 (w), 332 (w). MS (m/z): 448.10 ([M+H]$^+$).

Example 248

N(3)-(2,6-Difluorobenzyl)-1-(2,4-dichlorophenyl)-4,5,6,7-tetrahydro-1H-4,7-methano-indazole-3-carboxamide The title compound was synthesized by a procedure similar to that described for example 101. Intermediate 17 (100 mg, 0.31 mmol), DMF (1.0 ml), Et$_3$N (0.51 μl, 0.37 mmol), BOP reagent (136 mg, 0.31 mmol) and 2,6-difluorobenzylamine (36 mg, 0.31 mmol) furnished the title compound (74 mg, 53%). M.P.: 130-133° C. $^1$H-NMR (δ ppm, CDCl$_3$, 300 MHz): 7.50-7.33 (m, 2H); 7.29-7.06 (m, 2H); 6.94-6.82 (m, 2H); 4.78-4.61 (m, 2H); 3.78 (br. s, 1H); 3.35 (br. s, 1H); 2.10 (br. d, J=8.7, 1H); 2.04-1.81 (m, 2H); 1.68 (d, J=8.7, 1H); 1.38-1.10 (m, 2H). IR (cm$^{-1}$, KBr): 3305 (m), 2988 (w), 2971 (w), 2945 (w), 2868 (w), 1672 (s), 1660 (s), 1593 (s), 1545 (s), 1498 (s), 1406 (m), 1397 (m), 1355 (m), 1310 (w), 1240 (m), 1218 (w), 1120 (w), 1189 (s), 1048 (w), 1008 (w), 829 (s). MS (m/z): 448.1 ([M+H]$^+$).

Example 249

N(3)-(2-Chlorobenzyl)-1-(2,4-dichlorophenyl)-4,5,6,7-tetrahydro-1H-4,7-methano-indazole-3-carboxamide The title compound was synthesized by a procedure similar to that described for example 101. Intermediate 17 (100 mg, 0.31 mmol), DMF (1.0 ml), Et$_3$N (43 μl, 0.31 mmol), BOP reagent (136 mg, 0.31 mmol) and 2-chlorobenzylamine (37 μl, 0.31 mmol) gave the title compound (102 mg, 74%). M.P.: 117-120° C. $^1$H-NMR (δ ppm, CDCl$_3$, 300 MHz): 7.55 (d, J=2.4, 1H); 7.50-7.30 (m, 4H); 730-7.16 (m, 3H); 4.67 (dd, J=17, 6.3, 1H); 4.72 (dd, J=17.0, 6.3, 1H); 3.77 (br. s, 1H); 3.36 (br. s, 1H); 2.12 (br. d, J=8.6, 1H); 2.00-1.86 (m, 2H); 1.68 (br. d, J=8.6, 1H); 1.31-1.13 (m, 2171). IR (KBr, cm$^{-1}$): 3309 (m), 2998 (m), 2968 (m), 2951 (m), 2925 (m), 2869 (m), 1640 (s), 1564 (s), 1504 (s), 1487 (s), 1442 (m), 1346 (m), 1281 (m), 1241 (m), 1110 (m), 1056 (m), 870 (m), 832 (m). MS (m/z): 448.1 ([M+H]$^+$).

Example 250

N(3)-(4-Chlorobenzyl)-1-(2,4-dichlorophenyl)-4,5,6,7-tetrahydro-1H-4,7-methano-indazole-3-carboxamide The title compound was synthesized by a procedure similar to that described for example 101. Intermediate 17 (100 mg, 0.31 mmol), DMF (1.0 ml), Et$_3$N (43 μl, 0.31 mmol), BOP reagent (136 mg, 0.31 mmol) and 4-chlorobenzylamine (37 μl, 0.31 mmol) gave the title compound (108 mg, 78%). M.P.: 139-142° C. $^1$H-NMR (δ ppm, CDCl$_3$, 300 MHz): 7.56 (d, J=2.2, 1H); 7.42 (d, 8.4, 1H); 7.36 (dd, J=8.4, 2.2, 1H); 7.29

(s, 4H); 7.16 (br. t, J=5.1, 1H); 4.65-4.47 (m, 2H); 3.77 (br. s, 1H); 3.36 (br. s, 1H); 2.12 (br. d, J=8.6, IR); 2.0-1.85 (m, 2H); 1.70 (br. d, J=8.6, 1H); 1.32-1.15 (m, 2H). IR (KBr, cm$^{-1}$): 3290 (m), 2934 (m), 2869 (m), 1652 (s), 1553 (s), 1489 (s), 1436 (m), 1351 (m), 1276 (m), 1249 (m), 1142 (m), 1076 (m), 851 (m), 799 (m), 707 (m), 654 (m), 623 (m). MS (m/z): 448.2

Example 251

N(3)-(2,4-Dichlorobenzyl)-1-(2,4-dichlorophenyl)-4,5,6,7-tetrahydro-1H-4,7-methano-indazole-3-carboxamide The title compound was synthesized by a procedure similar to that described for example 101. Intermediate 17 (100 mg, 0.31 mmol), DMF (1.0 ml), Et$_3$N (43 µl, 0.31 mmol), BOP reagent (136 mg, 0.31 mmol) and 2,4-dichlorobenzylamine (41 µl, 0.31 mmol) gave the title compound (118 mg, 79%). M.P.: 57-59° C. $^1$H-NMR (δ ppm, CDCl$_3$, 300 MHz): 7.56 (s, 1H); 7.45-7.37 (m, 4H); 7.27-7.20 (m, 3H); 4.60 (br. d, J=4.8, 2H); 3.76 (s, 1H); 3.37 (s, 1H); 2.12 (br. d, J=8.4, 1H); 2.05-1.86 (m, 2H); 1.71-1.65 (br. d, J=8.4, 1H); 1.26-1.13 (m, 2H). IR (KBr, cm$^{-1}$): 3337 (m), 2948 (m), 2870 (m), 1737 (m), 1666 (s), 1545 (s), 1483 (s), 1381 (m), 1347 (m), 1236 (s), 1104 (s), 1078 (m), 1046 (m), 865 (m), 832 (s). MS (m/z): 482.3 ([M+H]$^+$).

Example 252

N(3)-[S-(1-phenylethyl)]-1-(2,4-dichlorophenyl)-4,5,6,7-tetrahydro-1H-4,7-methano-indazole-3-carboxamide The title compound was synthesized by a procedure similar to that described for example 101. Intermediate 17 (100 mg, 0.31 mmol), DMF (1.0 ml), Et$_3$N (51 µl, 0.37 mmol), BOP reagent (136 mg, 0.31 mmol) and (S)-(−)-1-phenylethylamine (39 0.31 mmol) gave the title compound (74 mg, 66%). M.P.: 91-94° C. $^1$H-NMR (δ ppm, CDCl$_3$, 300 MHz): 7.56 (d, J=2.1, 1H); 7.47-7.20 (m, 7H); 7.08 (d, J=7.5, 1H); 5.38-5.22 (m, 1H); 3.75 (br. s, 1H); 3.35 (br. s, 1H); 2.11 (br. t, J=8.7, 1H); 2.00-1.80 (m, 2H); 1.69 (br. s, 1H); 1.58 (d, J=6.9, 3H); 1.40-1.08 (m, 1H). MS (m/z): 426.10 ([M+H]$^+$).

Example 253

N(3)-[R-(1-phenylethyl)]-1-(2,4-dichlorophenyl)-4,5,6,7-tetrahydro-1H-4,7-methano-indazole-3-carboxamide The title compound was synthesized by a procedure similar to that described for example 101. Intermediate 17 (100 mg, 0.31 mmol), DMF (1.0 ml), Et$_3$N (51 µl, 0.37 mmol), BOP reagent (136 mg, 0.31 mmol) and R-(+)-1-phenethylamine (33 µl, 0.31 mmol) gave the title compound (66 mg, 50%). M.P.: 89-92° C. $^1$H-NMR (δ ppm, CDCl$_3$, 300 MHz): 7.55 (d, J=2.1, 1H); 7.50-7.20 (m, 7H); 7.08 (d, J=7.8, 1H); 5.30 (m, 1H); 3.75 (br. s, 1H); 3.35 (br. s, 1H); 2.10 (t, J=9.0, 1H); 2.00-1.80 (m, 2H); 169 (br. s, 1H); 1.58 (d, J=6.9, 3H); 1.40-1.10 (m, 2H). IR (KBr, cm$^{-1}$): 3411 (m), 3247 (m), 2972 (m), 2952 (m), 2870 (m), 1638 (s), 1545 (m), 1502 (s), 1483 (s), 1448 (m), 1378 (m), 1359 (m), 1239 (m), 1262 (m), 1138 (m), 1101 (m), 1076 (m), 815 (w), 699 (m). MS (m/z): 426.0 ([M+H]$^+$).

Example 254

N(3)-(2-phenylethyl)-1-(2,4-dichlorophenyl)-4,5,6,7-tetrahydro-1H-4,7-methano-indazole-3-carboxamide The title compound was synthesized by a procedure similar to that described for example 101. Intermediate 17 (100 mg, 0.31 mmol), DMF (1.0 ml), Et$_3$N (43 µl, 0.31 mmol), BOP reagent (136 mg, 0.31 mmol) and phenethylamine (38 µl, 0.31 mmol) gave the title compound (70 mg, 53%) as waxy solid. $^1$H-NMR (δ ppm, CDCl$_3$, 300 MHz): 7.55 (d, J=1.8, 1H); 7.43 (d, J=8.4, 1H); 7.36 (dd, J=8.4, 1.8, 1H); 7.35-7.19 (m, 5H); 6.91 (br. s, 1H); 3.75 (br. s, 1H); 3.70-3.60 (m, 2H); 3.36 (br. s, 1H); 2.90 (t, J=7.2, 2H); 2.12 (br. d, J=8.6, 1H); 2.01-1.84 (m, 2H); 1.69 (br. d, J=8.6, 1H); 1.31-1.13 (m, 2H).

Example 255

N(3)-[2-(4-fluorophenyl)ethyl]-1-(2,4-dichlorophenyl)-4,5,6,7-tetrahydro-1H-4,7-methano-indazole-3-carboxamide The title compound was synthesized by a procedure similar to that described for example 101. Intermediate 17 (100 mg, 0.31 mmol), DMF (1.0 ml), Et$_3$N (43 µl, 0.31 mmol), BOP reagent (136 mg, 0.31 mmol) and 4-fluorophenethylamine (40 µl, 0.31 mmol) yielded the title compound (100 mg, 73%) as a glassy paste. $^1$H-NMR (δ ppm, CDCl$_3$, 300 MHz): 7.56 (d, J=2.1, 1H); 7.41 (d, J=8.4, 1H); 7.37 (d, J=8.4, 2.1, 1H); 7.19 (dd, J=8.4, 5.4, 2H); 6.98 (t, J=8.7, 2H); 6.90 (br. t, J=4.6, 1H); 3.75 (br. s, 1H); 3.71-3.57 (m, 2H); 3.36 (br. s, 1H); 2.90 (t, J=7.5, 2H); 2.12 (br. d, J=8.7, 1H); 2.02-1.86 (m, 2H); 1.69 (br. d, J=8.7, 1H); 1.31-1.13 (m, 2H).

Example 256

N(3)-Phenylamino-1-(2,4-dichlorophenyl)-4,5,6,7-tetrahydro-1H-4,7-methano-indazole-3-carboxamide The title compound was synthesized by a procedure similar to that described for example 101. Intermediate 17 (100 mg, 0.31 mmol), DMF (1.0 ml), Et$_3$N (51 µl, 0.37 mmol), BOP reagent (136 mg, 0.31 mmol) and phenylhydrazine hydrochloride (30 µl, 0.31 mmol) gave the title compound (84 mg, 66%). M.P.: 182-185° C. $^1$H-NMR (δ ppm, CDCl$_3$, 300 MHz): 8.48 (br. s, 1H); 7.58 (d, J=1.8, 1H); 7.48 (d, J=8.5, 1H); 7.40 (dd, J=8.5, 1.8, 1H); 7.26-7.20 (m, 3H); 7.00-6.82 (m, 3H); 3.73 (br. s, 1H); 3.40 (br. s, 1H); 2.13 (br. d, J=8.1, 1H); 1.97-1.90 (m, 2H); 1.71 (br. d, J=9.0, 1H); 1.30-1.15 (m, 2H). IR (KBr, cm$^{-1}$): 3251 (s), 2996 (m), 2947 (m), 2870 (m), 1663 (s), 1604 (m), 1542 (m), 1498 (s), 1483 (s), 1352 (m), 1279 (m), 1230 (m), 1231 (m), 1111 (m), 1083 (m), 1060 (m), 937 (m), 899 (m), 889 (m), 867 (m). MS (m/z): 413.0 ([M+H]$^+$).

Example 257

N(3)-[(2-Chlorophenyl)amino]-1-(2,4-dichlorophenyl)-4,5,6,7-tetrahydro-1H-4,7-methano-indazole-3-carboxamide The title compound was synthesized by a procedure similar to that described for example 101. Intermediate 17 (100 mg, 0.31 mmol), DMF (1.0 ml), Et$_3$N (107 µl, 0.77 mmol), BOP reagent (136 mg, 0.31 mmol) and 2-chlorophenylhydrazine hydrochloride (55 mg, 0.31 mmol) gave the title compound (78 mg, 57%). M.P.: 180-183° C. $^1$H-NMR (δ ppm, CDCl$_3$, 300 MHz): 8.49 (br. s, 1H); 7.59 (d, J=2.4, 1H); 7.48 (d, J=8.4, 1H); 7.41 (dd, J=8.4, 2.4, 1H); 7.29 (d, J=8.0, 1H); 7.14 (t, J=7.8, 1H); 7.03 (d, J=8.1, 1H); 6.83 (t, J=8.0, 1H); 6.55 (br. s, 1H); 3.73 (br. s, 1H); 3.40 (br. s, 1H); 2.13 (br. d, J=9.0, 1H); 2.01-1.87 (m, 2H); 1.70 (br. d, J=9.0, 1H); 1.30-1.16 (m, 2H). IR (KBr, cm$^{-1}$): 3255 (br., m), 2959 (w), 2874 (w), 1667 (s), 1508 (s), 1346 (m), 1279 (m), 1110 (m), 1079 (m), 1066 (m), 862 (w). MS (m/z): 448.9 ([M+H]$^+$).

Example 258

N(3)-[N-(2-Chlorophenyl)-N-methylamino]-1-(2,4-dichlorophenyl)-4,5,6,7-tetrahydro-1H-4,7-methano-indazole-3-carboxamide The title compound was synthesized by a procedure similar to that described for example 101. Intermediate 17 (100 mg, 0.31 mmol), DMF (1.0 ml), Et$_3$N (0.51 µl, 0.37 mmol), BOP reagent (136 mg, 0.31 mmol) and N-(2-chlorophenyl)-N-methylhydrazine hydrochloride (59 mg, 0.31 mmol) furnished the title compound (104 mg, 70%). M.P.: 121-124° C. $^1$H-NMR (δ ppm, CDCl$_3$, 300 MHz): 8.82 (br. s, 1H); 7.56 (d, J=2.1, 2H); 7.45 (d, J=8.4, 1H); 7.42 (dd, J=8.1, 1.5, 1H); 7.38 (dd, j=8.4, 2.1, 1H); 7.31 (dd, J=8.1, 1.5, 1H); 7.24 (td, J=8.1, 1.5, 1H); 6.99 (td, J=8.1, 1.5 1H); 3.70 (br. s, 1H); 3.37 (br. s, 4H); 2.09 (br. d, J=8.4, 1H); 2.00-1.82 (m, 2H); 1.67 (br. d, J=8.7, 1H); 1.30-1.10 (m, 2H). IR (cm$^{-1}$, KBr): 3404 (s), 3253 (m), 2951 (w), 2868 (w), 1654 (s), 1587 (w), 1545 (w), 1500 (s), 1484 (s), 1475 (s), 1443 (m), 1348 (w), 1276 (m), 1236 (m), 1122 (m), 1107 (m), 1052 (m), 832 (s). MS (m/z): 461.0 ([M+H]$^+$).

Example 259

N(3)-[(4-Chlorophenyl)amino]-1-(2,4-dichlorophenyl)-4,5,6,7-tetrahydro-1H-4,7-methano-indazole-3-carboxamide The title compound was synthesized by a procedure similar to that described for example 101. Intermediate 17 (200 mg, 0.62 mmol), DMF (2.0 ml), Et$_3$N (189 µl, 1.36 mmol), BOP reagent (273 mg, 0.62 mmol) and 4-chlorophenylhydrazine hydrochloride (110 mg, 0.62 mmol) gave the title compound (195 mg, 70%). M.P.: 141-144° C. $^1$H-NMR (δ ppm, CDCl$_3$, 300 MHz): 8.47 (s. 1H); 7.59 (d, J=1.8, 1H); 7.48 (d, J=8.3, 1H); 7.40 (dd, J=8.3, 1.8, 1H); 7.18 (d, J=8.7, 2H); 6.87 (d, J=8.7, 2H); 6.17 (br. s, 1H); 3.72 (s, 1H); 3.40 (s, 1H); 2.15 (br. d, J=8.7, 1H); 1.99-1.88 (m, 2H); 1.70 (br. d, J=8.7, 1H); 1.26-1.19 (m, 2H). IR (KBr, cm$^{-1}$): 3271 (s), 2991 (m), 1667 (m), 1596 (m), 1505 (m), 1491 (m), 1348 (m), 1276 (m), 1230 (m), 1080 (m), 1065 (m), 889 (m), 824 (s). MS (m/z): 447.0 ([M+H]$^+$).

Example 260

N(3)-[(2,4-Dichlorophenyl)amino]-1-(2,4-dichlorophenyl)-4,5,6,7-tetrahydro-1H-4,7-methano-indazole-3-carboxamide The title compound was synthesized by a procedure similar to that described for example 101. Intermediate 17 (200 mg, 0.62 mmol), DMF (2.0 ml), Et$_3$N (189 µl, 1.36 mmol), BOP reagent (273 mg, 0.62 mmol) and 2,4-dichlorophenylhydrazine hydrochloride (132 mg, 0.62 mmol) to give the title compound (205 mg, 69%). M.P.: 187-190° C. $^1$H-NMR (δ ppm, CDCl$_3$, 300 MHz): 8.47 (d, J=3.0, 1H); 7.59 (d, J=2.1, 1H); 7.47 (d, J=8.6, 1H); 7.40 (dd, J=8.6, 2.1, 1H); 7.30 (d, J=2.4, 1H); 7.11 (dd, J=8.7, 1H); 6.95 (d, J=9.0, 1H); 6.49 (d, J=3.0, 1H); 3.71 (s, 1H); 3.39 (s, 1H); 2.12 (br. d, J=9.3, 1H); 1.97-1.90 (m, 2H); 1.70 (br. d, J=9.3, 1H); 1.25-1.15 (m, 2H). IR (KBr, cm$^{-1}$): 3348 (m), 3191 (m), 2984 (m), 2968 (m), 2873 (w), 1661 (s), 1588 (m), 1557 (m), 1495 (s), 1343 (m), 1279 (m), 1108 (m), 1078 (m), 1068 (m), 861 (m).

Example 261

N(3)-[(2,4-dichlorophenyl)-N-methylamino]-1-(2,4-dichlorophenyl)-4,5,6,7-tetrahydro-1H-4,7-methano-indazole-3-carboxamide The title compound was synthesized by a procedure similar to that described for example 101. Intermediate 17 (100 mg, 0.31 mmol), DMF (1.0 ml), Et$_3$N (0.51 µl, 0.37 mmol), BOP reagent (136 mg, 0.31 mmol) and N-(2,4-dichlorophenyl)-N-methylhydrazine (59 mg, 0.31 mmol) furnished the title compound (97 mg, 63%). M.P.: 135-138° C. $^1$H-NMR (δ ppm, CDCl$_3$, 300 MHz): 8.81 (br. s, 1H); 7.57 (d, J=1.8, 1H); 7.42 (d, J=1H); 7.40 (dd, J=8.3, 1.8, 1H); 7.35 (d, J=8.3, 1H); 7.31 (d, J=2.4, 1H); 7.21 (dd, 8.3, 2.4, 1H); 3.69 (br. s, 1H); 3.35 (br. s, 4H); 2.09 (br. d, J=9.0, 1H); 2.00-1.80 (m, 2H); 1.67 (br. d, J=9.0, 1H); 1.35-1.20 (m, 2H). IR (cm$^{-1}$, KBr): 3348 (s), 3081 (w), 2963 (m), 2871 (w), 1683 (s), 1586 (w), 1565 (w), 1533 (m), 1505 (s), 1482 (s), 1470 (s), 1438 (m), 1345 (m), 1122 (m), 1105 (m), 1085 (m), 1464 (s), 1049 (m), 814 (m). MS (m/z): 495.0 ([M+H]$^+$).

Example 262

N(3)-[(3,4-Dichlorophenyl)amino]-1-(2,4-dichlorophenyl)-4,5,6,7-tetrahydro-1H-4,7-methano-indazole-3-carboxamide The title compound was synthesized by a procedure similar to that described for example 101. Intermediate 17 (200 mg, 0.619 mmol), DMF (2.0 ml), Et$_3$N (189 µl, 1.361 mmol), BOP reagent (273 mg, 0.619 mmol) and 3,4-dichlorophenylhydrazine hydrochloride (132 mg, 0.619 mmol) furnished the title compound (205 mg, 69%). 176-179° C. $^1$H-NMR (δ ppm, CDCl$_3$, 300 MHz): 8.48 (s, 1H); 7.59 (d, J=2.1, 1H); 7.48 (d, J=8.4, 1H); 7.40 (dd, J=8.4, 2.1, 1H); 7.26 (d, J=8.7, 1H); 7.03 (d, J=2.7, 1H); 6.77 (dd, J=2.7, 1H); 6.22 (br. s, 1H); 3.72 (br. s, 1H); 3.40 (br. s, 1H); 2.13 (br. d, J=9.0, 1H); 2.03-1.88 (m, 2H); 1.70 (br d, J=9.0, 1H); 1.30-1.16 (m, 2H). IR (KBr, cm$^{-1}$): 3314 (m), 2951 (m), 2870 (m), 1678 (s), 1602 (m), 1511 (s), 1475 (s), 1384 (m), 133.9 (m), 1253 (m), 1225 (m), 1126 (m), 1062 (s), 863 (m), 819 (s). MS (m/z): 481.0 ([M+H]$^+$).

Example 263

N(3)-[(2-Bromophenyl)amino]-1-(2,4-dichlorophenyl)-4,5,6,7-tetrahydro-1H-4,7-methano-indazole-3-carboxamide The title compound was synthesized by a procedure similar to that described for example 101. Intermediate 17 (100 mg, 0.31 mmol), DMF (1.0 ml), Et$_3$N (103 µl, 0.74 mmol), BOP reagent (136 mg, 0.31 mmol) and 2-bromophenylhydrazine hydrochloride (69 mg, 0.31 mmol) yielded the title compound (115 mg, 76%). M.P.: 159° C. $^1$H-NMR (δ ppm, CDCl$_3$, 300 MHz): 8.50 (d, J=3.3, 1H); 7.59 (d, J=2.4, 1H); 7.50-7.39 (m, 3H); 7.20 (t, J=7.7, 1H); 7.01 (t, J=6.9, 1H); 6.77 (t, J=7.5, 1H); 6.52 (d, J=3.3, 1H); 3.73 (s, 1H); 3.40 (s, 1H); 2.14 (br. d, J=8.7, 1H); 2.02-1.91 (m, 2H); 1.70 (br d, J=8.7, 1H); 1.30-1.19 (m, 2H). IR (KBr, cm$^{-1}$): 3256 (m), 2925 (m), 2859 (m), 1666 (s), 1505 (s), 1344 (m), 1278 (m), 1232 (m), 1110 (m), 1079 (m), 1064 (m), 742 (m). MS (m/z): 491:0 ([M+H]$^+$).

Example 264

N(3)-[(2-Fluorophenyl)amino]-1-(2,4-dichlorophenyl)-4,5,6,7-tetrahydro-1H-4,7-methano-indazole-3-carboxamide The title compound was synthesized by a procedure similar to that described for example 101. Intermediate 17 (200 mg, 0.62 mmol), DMF (2.0 ml), Et$_3$N (0.2.0 ml, 1.49 mmol), BOP reagent (273 mg, 0.62 mmol) and 2-fluorophenylhydrazine hydrochloride (100 mg, 0.62 mmol) gave the title compound (96 mg, 72%). $^1$H-NMR (δ ppm, CDCl$_3$, 300 MHz): 8.51 (br. s, 1H); 7.59 (d, J=2.1, 1H); 7.48 (d, J=8.6, 1H); 7.40 (dd, J=8.6, 2.1, 1H); 7.10-6.95 (m, 3H); 6.90-6.80 (m, 1H); 3.73 (br. s, 1H); 3.40 (br. s, 1H); 2.14 (br. d, J=9.0, 1H); 2.02-1.85 (m, 2H); 1.70 (d, J=9.0, 1H); 1.30-1.15 (m, 2H). IR (KBr, cm$^{-1}$): 3256 (br. s), 2989 (m), 2959 (m), 2873 (w), 1666 (s), 1618 (m), 1508 (s), 1456 (m), 1345 (m), 1279 (m), 1243(m), 1194 (m), 1099 (s), 1063 (m), 863 (m).

Example 265

N(3)-[(2,4-Difluorophenyl)amino]-1-(2,4-dichlorophenyl)-4,5,6,7-tetrahydro-1H-4,7-methano-indazole-3-carboxamide The title compound was synthesized by a procedure similar to that described for example 101. Intermediate 17 (150 mg, 0.46 mmol), DMF (2.0 ml), Et$_3$N (154 μl, 1.11 mmol), BOP reagent (205 mg, 0.46 mmol) and 2,4-difluorophenylhydrazine hydrochloride (83 mg, 0.46 mmol) furnished the title compound (143 mg, 69%). M.P.: 157-160° C. $^1$H-NMR (δ ppm, CDCl$_3$, 300 MHz): 8.50 (br. s, 1H); 7.59 (d, J=1.8, 1H); 7.47 (d, J=8.4, 1H); 7.39 (dd, J=8.4, 1.8, 1H); 7.00 (dt, J=9.0, 5.4, 1H); 6.82 (td, J=8.4, 2.7, 1H); 6.72 (br. t, J=8.1, 1H); 3.72 (br. s, 1H); 3.40 (br. s 1H); 2.13 (br. d, J=8.4, 1H); 2.05-1.85 (m, 2H); 1.70 (d, J=8.4, 1H); 1.30-1.15 (m, 2H). IR (KBr, cm$^{-1}$): 3358 (m), 3198 (m), 3061 (m), 2989 (m), 2874 (m), 1664 (s), 1565 (s), 1520 (s), 1468 (m), 1382 (m), 1320 (m), 1281 (m), 1262 (m), 1207 (m), 1123 (m), 1108 (m), 1077 (m), 959 (m), 798 (m). MS (m/z): 449.0 ([M+H]$^+$).

Example 266

N(3)-[(3-Fluorophenyl)amino]-1-(2,4-dichlorophenyl)-4,5,6,7-tetrahydro-1H-4,7-methano-indazole-3-carboxamide The title compound was synthesized by a procedure similar to that described for example 101. Intermediate 17 (100 mg, 0.31 mmol), DMF (1.0 ml), Et$_3$N (103 μl, 0.74 mmol), BOP reagent (136 mg, 0.31 mmol) and 3-fluorophenylhydrazine hydrochloride (50 mg, 0.31 mmol) yielded the title compound (98 mg, 74%). M.P.: 190° C. $^1$H-NMR (δ ppm, CDCl$_3$, 300 MHz): 8.46 (s, 1H); 7.59 (d, J=2.4, 1H); 7.49 (d, J=8.4, 1H); 7.40 (dd, J=8.7, 2.4, 1H); 7.21-7.13 (m, 1H); 6.77-6.47 (m, 3H); 6.20 (br. s, 1H); 3.73 (s, 1H); 3.40 (s, 1H); 2.14 (br. d, J=8.6, 1H); 2.02-1.88 (m, 2H); 1.70 (br. d, J=8.6, 1H); 1.31-1.16 (m, 2H). IR (KBr, cm$^{-1}$): 3411 (s), 3277 (s), 2986 (m), 2940 (m), 2870 (m), 1670 (s), 1615 (s), 1544 (s), 1504 (s), 1469 (s), 1444 (s), 1475 (s), 1341(m), 1273 (n1), 1237 (m), 1105 (m), 1081 (m), 835 (n). MS (m/z): 431.1 ([M+H]$^+$).

Example 267

N(3)-[(3-chloropyridin-2-yl)amino]-1-(2,4-dichlorophenyl)-4,5,6,7-tetrahydro-1H-4,7-methano-indazole-3-carboxamide The title compound was synthesized by a procedure similar to that described for example 101. Intermediate 17 (100 mg, 0.30 mmol), DMF (1.0 ml), Et$_3$N (51 μl, 0.32 mmol), BOP reagent (129 mg, 0.32 mmol) and 3-chloro-2-hydrazinopyridine (44 mg, 0.31 mmol.) to give the title compound (50 mg, 36%). M.P.: 95° C. (fuses). $^1$H-NMR (δ ppm, CDCl$_3$, 300 MHz): 9.40 (br. s, 1H); 8.10 (br. d, J=4.8, 1H); 7.60 (br. d, J=7.8, 2H); 7.58-7.50 (m, 1H); 7.39 (br. d, J=8.1, 2H); 6.78 (dt, J=7.5, 2.4, 1H); 3.72 (br. s, 1H); 3.41 (br. s, 1H); 2.15 (t, J=8.7, 1H), 2.00-1.85 (m, 2H); 1.69 (br. d, J=8.7, 1H); 1.20-1.10 (m, 2H). IR (cm$^{-1}$, KBr): 3368 (br. m), 2954 (m), 2870 (m), 1677 (s), 1591 (s), 1537 (m), 1498 (s), 1470 (s), 1406 (m), 1252 (m), 1227 (m), 1125 (s), 1080 (m), 1033 (m), 866 (w), 832 (m). MS (m/z): 448.0 ([M+H]$^+$).

Example 268

N(5)-piperidino-3-(2',4'-dichlorophenyl)-3,4-diazatricyclo[5.2.1.0$^{2,6}$]deca-2(6),4-diene-5-carboxamide The title compound was synthesized as per the procedure described for example 101 using intermediate 17 (100 mg, 0.31 mmol), DMF (1 ml), triethylamine (0.04 ml, 0.31 mmol), BOP reagent (136 mg, 0:31 mmol) and 1-aminopiperidine (0.033 ml, 0.31 mmol) to give the title compound (62 mg, 50%). $^1$H-NMR (δ ppm, CDCl$_3$): 7.56 (d, J=2.1, 1H); 7.45 (d, J=8.4, 1H); 7.37 (dd, J=8.4, 2.1, 1H); 3.76 (br. s, 1H); 3.36 (br. s, 1H); 2.91 (br. s, 4H); 2.12 (br. d, J=10.2, 1H); 2.04-1.82 (m, 2H); 1.81-1.56 (m, 5H); 1.50-1.38 (m, 2H); 1.34-1.10 (m, 2H).

Example 269

N(5)-benzyl-3-(2',4'-dichlorophenyl)-3,4-diazatricyclo[5.2.1.0$^{2,6}$]deca-2(6),4-diene-5-carboxamide The title compound was synthesized as per the procedure described for example 101 using intermediate 17 (100 mg, 0.31 mmol), DMF (1 ml), triethylamine (0.04 ml, 0.31 mmol), BOP reagent (136 mg, 0.31 mmol) and benzylamine (0.033 ml, 0.31 mmol) to give the title compound (94 mg, 74%). $^1$H-NMR (δ ppm, CDCl$_3$): 7.55 (d, J=2.1, 1H); 7.42 (d, J=8.4, 1H); 7.37-7.23 (m, 6H); 7.15 (br. s, 1H); 4.63 (dd, J=11.0, 5.0, 1H); 4.57 (dd, J=11.0, 5.0, 1H); 3.78 (br. s, 1H); 3.36 (br. s, 1H); 2.13 (br. d, J=8.4, 1H); 2.04-1.82 (m, 2H); 1.70 (br. d, J=8.4, 1H); 1.35-1.11 (m, 2H).

Example 270

N(3)-Piperidino-1-(2-bromophenyl)-4,5,6,7-tetrahydro-1H-4,7-methano-indazole-3-carboxamide The title compound was synthesized by a procedure similar to that described for example 101. Intermediate 18 (100 mg, 0.30 mmol), DMF (1.0 ml), Et$_3$N (50 μl, 0.36 mmol), BOP reagent (146 mg, 0.33 mmol) and 1-aminopiperidine (32 μl, 0.30 mmol) gave the title compound (52 mg, 42%). M.P.: 236° C. $^1$H-NMR (δ ppm, CDCl$_3$, 300 MHz): 7.73 (d, J=8.4, 1H); 7.58 (br. s, 1H); 7.39-7.46 (m, 2H); 7.36-7.30 (m, 1H); 3.77 (br. s, 1H); 3.35 (br. s, 1H); 2.85 (br. s, 4H); 2.15 (br. d, J=7.8, 1H); 2.00-1.71 (m, 6H); 1.44-1.16 (m, 5H). IR (KBr, cm$^{-1}$): 3308 (m), 3000 (m), 2940 (s), 2864 (m), 2793 (m), 1685 (s), 1540 (s), 1511 (s), 1484 (s), 1449 (m), 1340 (w), 1229 (m), 1133 (m), 1123 (m), 1036 (m), 986 (m), 904 (m), 832 (w). MS (m/z): 415.1 ([M+H]$^+$).

Example 271

N(3)-Cyclohexyl-1-(2-bromophenyl)-4,5,6,7-tetrahydro-1H-4,7-methano-indazole-3-carboxamide The title compound was synthesized by a procedure similar to that described for example 101. Intermediate 18 (100 mg, 0.30 mmol), DMF (1.0 ml), Et$_3$N (50 µl, 0.36 mmol), BOP reagent (146 mg, 0.33 mmol) and cyclohexylamine (39 µl, 0.34 mmol) gave the title compound (100 mg, 80%). M.P.: 178° C. $^1$H-NMR (δ ppm, CDCl$_3$, 300 MHz): 7.26: (d, J=8.1, 1H); 7.51-7.40 (m, 2H); 7.33 (br. t, J=8.1, 1H); 6.73 (br. d, J=8.4, 1H); 3.85-4.05 (m, 1H); 3.77 (br. s, 1H); 3.35 (br. s, 1H); 2.15 (br. d, J=7.2, 1H); 2.00-1.85 (m, 4H); 1.80-1.65 (m, 4H); 1.50-1.14 (m, 7H). IR (KBr, cm$^{-1}$): 3413 (m), 2938 (s), 2854 (m), 1662 (s), 1541 (s), 1512 (s), 1480 (s), 1450 (s), 1341 (m), 1299 (m), 1222 (m), 1159 (m), 1125 (m). MS (m/z): 414.0 ([M+H]$^+$).

Example 272

N(3)-Benzyl-1-(2-bromophenyl)-4,5,6,7-tetrahydro-1H-4,7-methano-indazole-3-carboxamide The title compound was synthesized by a procedure similar to that described for example 101. Intermediate 18 (100 mg, 0.30 mmol), DMF (1.0 ml), Et$_3$N (50 µl, 0.36 mmol), BOP reagent (146 mg, 0.33 mmol) and benzylamine (32 µl, 0.30 mmol) gave the title compound (60 mg, 47%). M.P.: 110° C. $^1$H-NMR (δ ppm, CDCl$_3$, 300 MHz): 7.70 (d, J=8.4, 1H); 7.45-7.16 (m, 9H); 4.61 (m, 2H); 3.79 (br. s, 1H); 3.56 (br. s, 1H); 2.16 (br. d, J=8.7, 1H); 2.05-1.80 (m, 2H); 1.70 (br. d, J=8.7, 1H); 1.35-1.15 (m, 2H). IR (KBr, cm$^{-1}$): 3419 (w), 3020 (s), 240.1 (w), 1661 (w), 1549 (w), 1516 (w), 1484 (w), 1427 (w), 1343 (w), 1216 (s). MS (m/z): 422.0 ([M+H]$^+$).

Example 273

N(3)-Phenylamino-1-(2-bromophenyl)-4,5,6,7-tetrahydro-1H-4,7-methano-indazole-3-carboxamide The title compound was synthesized by a procedure similar to that described for example 101. Intermediate 18 (100 mg, 0.30 mmol), DMF (1.0 ml), Et$_3$N (50 µl, 0.36 mmol), BOP reagent (146 mg, 0.33 mmol) and phenylhydrazine (30 µl, 0.30 mmol) gave the title compound (101 mg, 80%). M.P.: 219° C. $^1$H-NMR (δ ppm, CDCl$_3$, 300 MHz): 8.51 (br. s, 1H); 7.50 (d, J=7.8, 1H); 7.60-7.41 (m, 2H); 7.36 (br. t, J=8.4, 1H); 7.34 (t, J=7.8, 2H); 6.95 (d, J=7.8, 2H); 6.89 (t, J=7.5, 1H); 3.73 (br. s, 1H); 3.39 (br. s, 1H); 2.16 (br. d, J=7.2, 1H); 2.00-1.85 (m, 2H); 7.70 (d, J=8.7, 1H); 1.28-1.20 (m, 2H). IR (KBr, cm$^{-1}$) δ 3283 (m), 2992 (m), 2959 (m), 2863 (w), 1675 (s), 1603 (m), 1542 (m), 1511 (s), 1497 (m), 1438 (m), 1348 (m), 1281 (m), 1240 (m), 1136 (m), 1123 (m), 1084 (m), 1029 (m), 888 (m). MS (m/z): 423.0 ([M+H]$^+$).

Example 274

N(3)-Piperidino-1-(4-bromophenyl)-4,5,6,7-tetrahydro-1H-4,7-methano-indazole-3-carboxamide The title compound was synthesized by a procedure similar to that described for example 101. Intermediate 19 (100 mg, 0.30 mmol), DMF (1.0 ml), Et$_3$N (50 µl, 0.36 mmol), BOP reagent (146 mg, 033 mmol) and 1-aminopiperidine (33 0.30 mmol) furnished the title compound (124 mg, 99%). M.P.: 173° C. $^1$H-NMR (δ ppm, CDCl$_3$, 300 MHz): 7.60 (br. s, 4H); 3.70 (br. s, 1H); 3.65 (br. s, 1H); 2.90 (br. s, 4H); 2.20 (br. d, J=7.14, 1H); 2.00 (br. d, J=8.6, 2H); 1.90-1.60 (m, 6H); 1.30-1.20 (m, 3H). IR (KBr, cm$^{-1}$): 3408 (w), 3308 (w), 2929 (s), 2859 (m), 2780 (m), 1692 (s), 1591 (m), 1541 (s), 1503 (s), 1489 (s), 1440 (m), 1401 (m), 1348 (s), 1268 (m), 1226 (s), 1154 (m), 1122 (s), 1064 (m), 1006 (m), 827 (s). MS (m/z): 415.1 ([M+H]$^+$).

Example 275

N(3)-Cyclohexyl-1-(4-bromophenyl)-4,5,6,7-tetrahydro-1H-4,7-methano-indazole-3-carboxamide The title compound was synthesized by a procedure similar to that described for example 101. Intermediate 19 (100 mg, 0.30 mmol), DMF (1.0 ml), Et$_3$N (50 µl, 0.36 mmol), BOP reagent (146 mg, 0.33 mmol) and cyclohexylamine (34 µl, 0.30 mmol) gave the title compound (91 mg, 73%). M.P.: 164° C. $^1$H-NMR (δ ppm, CDCl$_3$, 300 MHz): 7.58 (s, 4H); 6.75 (br. d, J=8.1, 1H); 3.93 (m, 1H); 3.75 (br. s, 1H); 3.67 (br. s, 1H); 2.12 (br. d, J=8.4, 1H); 2.10-1.90 (m, 4H); 1.80-1.70 (m, 3H); 1.60-1.20 (m, 8H). IR (KBr, cm$^{-1}$): 3410 (m), 2922 (m), 2848 (m), 1667 (s), 1591 (w), 1546 (s), 1504 (s), 1486 (s), 1450 (m), 1349 (m), 1224 (m), 1160 (m), 1122 (m), 1065 (m), 1006 (m), 827 (m). MS (m/z): 414.1 ([M+H]$^+$).

Example 276

N(3)-Benzyl-1-(4-bromophenyl)-4,5,6,7-tetrahydro-1H-4,7-methano-indazole-3-carboxamide The title compound was synthesized by a procedure similar to that described for example 101. Intermediate 19 (100 mg, 0.30 mmol), DMF (1.0 ml), Et$_3$N (50 µl, 0.36 mmol), BOP reagent (146 mg, 0.33 mmol) and benzyl amine (33 µl, 0.30 mmol) yielded the title compound (107 mg, 85%). M.P.: 89° C. $^1$H-NMR (δ ppm, CDCl$_3$, 300 MHz): 7.56 (br. s, 4H); 7.40-7.22 (m, 6H); 4.64 (d, J=5.4, 2H); 3.80 (br. s. 1H); 3.68 (br. s, 1H); 2.14 (br. d, J=8.1, 1H); 2.00 (br. d, J=5.7, 2H); 1.74 (d, J=8.4, 1H); 1.26-1.20 (m, 2H). IR (KBr, cm$^{-1}$): 3321 (m), 2937 (m), 2868 (m), 1649 (s), 1590 (m), 1551 (s), 1499 (s), 1455 (m), 1347 (s), 1275 (m), 1241 (m), 1121 (m), 1070 (m), 1005 (m), 975 (m), 825 (m). MS (m/z): 422.1 ([M+H]$^+$).

Example 277

N(3)-Phenylamino-1(4-bromophenyl)-4,5,6,7-tetrahydro-1H-4,7-methano-indazole-3-carboxamide The title compound was synthesized by a procedure similar to that described for example 101. Intermediate 19 (100 mg, 0.30 mmol), DMF (1.0 ml), Et$_3$N (50 µl, 0.36 mmol), BOP reagent (146 mg, 0.33 mmol) and phenylhydrazine (29 µl, 0.30 mmol) furnished the title compound (90 mg, 71%). M.P.: 138° C. $^1$H-NMR (δ ppm, CDCl$_3$, 300 MHz): 8.54 (br. s, 1H); 7.61 (s, 4H); 7.24 (t, J=7.8, 2H); 6.95 (d, J=8.4, 2H); 6.90 (t, J=7.2, 1H); 3.72 (br. 2H); 2.13 (br. d, J=8.0, 1H); 1.99 (br. d, J=7.8, 2H); 1.73 (br. d, J=8.0, 1H); 1.40-1.15 (m, 2H). IR (KBr, cm$^{-1}$): 3262 (m), 2948 (m), 2869 (m), 1666 (s), 1603 (s), 1591 (s), 1545 (m), 1497 (s), 1401 (m), 1357 (m), 1279 (m), 1252 (m), 1227 (m), 1124 (m), 1083 (m), 1070 (m), 1005 (m), 894 (m). MS (m/z): 422.9 ([M+H]$^+$).

Example 278

N(3)-[(2-Fluorophenyl)amino]-1-(4-bromophenyl)-4,5,6,7-tetrahydro-1H-4,7-methano-indazole-3-carboxamide The title compound was synthesized by a procedure similar to that described for example 101. Intermediate 19 (100 mg, 0.30 mmol), DMF (1.0 ml), Et$_3$N (63 µl, 0.45 mmol), BOP reagent (146 mg, 0.33 mmol) and 2-fluorophenylhydrazine hydrochloride (48 mg, 0.30 mmol) furnished the title compound (50 mg, 38%). M.P.: 123° C. $^1$H-NMR (δ ppm, CDCl$_3$, 300 MHz): 8.57 (br. s, 1H); 7.61 (s, 4H); 7.10-6.70 (m, 3N); 7.00-6.80 (m, 1H); 3.71 (s, 2H); 2.17 (br. d, J=8.4, 1H); 2.10-1.90 (m, 2H); 1.73 (d, J=8.7, 1H); 1.35-1.15 (m, 2H). MS (m/z): 441.1 ([M+H]$^+$).

Example 279

N(3)-Cyclohexyl-1-(4-fluorophenyl)-4,5,6,7-tetrahydro-1H-4,7-methano-indazole-3-carboxamide The title compound was synthesized by a procedure similar to that described for example 101. Intermediate 20 (100 mg, 0.37 mmol), DMF (1.0 ml), Et$_3$N (61 µl, 0.44 mmol), BOP reagent (178 mg, 0.40 mmol) and cyclohexylamine (42 µl, 0.37 mmol) gave the title compound (72 mg, 56%). M.P.: 127° C. $^1$H-NMR (δ ppm, CDCl$_3$, 300 MHz): 7.64-7.62 (m, 2H); 7.17 (t, J=8.4, 2H); 6.75 (br. d, J=7.7, 1H); 4.05-3.80 (m, 1H); 3.75 (br. s, 1H); 3.64 (br. s, 1H); 2.20-1.90 (br. s, 5H); 1.74-1.66 (m, 5H); 1.44-1.10 (m, 6H). IR (KBr, cm$^{-1}$): 3352 (m), 3310 (w), 2934 (m), 2834 (m), 1656 (s), 1642 (s), 1517 (s), 1499 (s), 1451 (m), 1350 (m), 1276 (w), 1252 (w), 1223 (s), 1163 (m), 1123 (m), 842 (m). MS (m/z): 354.1 ([M+H]$^+$).

Example 280

N(3)-Benzyl-1-(4-fluorophenyl)-4,5,6,7-tetrahydro-1H-4,7-methano-indazole-3-carboxamide The title compound was synthesized by a procedure similar to that described for example 101. Intermediate 20 (100 mg, 0.37 mmol), DMF (1.0 ml), Et$_3$N (61 µl, 0.44 mmol), BOP reagent (178 mg, 0.40 mmol) and benzylamine (39 µl, 0.36 mmol) gave the title compound (43 mg, 33%). M.P.: 104° C. $^1$H-NMR (δ ppm, CDCl$_3$, 300 MHz): 7.62 (br. s, 2H); 7.38-7.00 (m, 8H); 4.63 (br. d, J=5.1, 2H); 3.78 (br. s, 1H); 3.66 (br. s, 1H); 2.12 (br. d, J=8.4, 1H); 1.90-2.10 (m, 2H); 1.73 (d, J=8.4, 1H); 1.40-1.10 (m, 2H). IR (KBr, cm$^{-1}$): 3411 (m), 3009 (w), 286.9 (w), 1670 (s), 1543 (s), 1500 (s), 1492 (s), 1454 (m), 1416 (m), 1349 (s), 1276 (m), 1226 (s), 1212 (s), 1164 (m), 1124 (m), 954 (w); 835 (s). MS (m/z): 362.1 ([M+H]$^+$).

Example 281

N5-(Adamantan-2-yl)-3-(4-fluorophenyl)-3,4-diazatricyclo[5.2.1.0$^{2,6}$]deca-2(6),4-diene-5-carboxamide The title compound was synthesized by a procedure similar to that described for example 101. Intermediate 20 (100 mg, 0.36 mmol), DMF (1.0 ml), Et$_3$N (124 µl, 0.88 mmol), BOP reagent (170 mg, 0.38 mmol) and 2-adamantylamine hydrochloride (103 mg, 0.55 mmol) furnished the title compound (120 mg, 80%). M.P.: 196-198° C. $^1$H-NMR (δ ppm, CDCl$_3$, 300 MHz): 7.69-7.63 (m, 2H); 7.17 (t, J=8.1, 2H); 4.23 (d, J=8.4, 1H); 3.75 (br. s, 1H); 3.65 (br. s, 1H); 2.14-1.87 (m, 14H); 1.78-1.54 (m, 4H); 1.26-1.21 (m, 2H). IR (cm$^{-1}$, KBr): 3414 (s), 2979 (w), 2901 (s), 2851 (s), 1663 (s), 1542 (s), 1517 (s), 1488 (s), 1454 (m), 1445 (m), 1347 (w), 1255 (w), 1224 (m), 1213 (s), 1159 (m), 1126 (m), 1091 (m), 953 (w), 833 (m). MS (m/z): 406.2 ([M+H]$^+$).

Example 282

N5-(1-Methyl-1-phenylethyl)-3-(4-fluorophenyl)-3,4-diazatricyclo[5.2.1.0$^{2,6}$]deca-2(6),4-diene-5-carboxamide The title compound was synthesized by a procedure similar to that described for example 101. Intermediate 20 (100 mg, 0.36 mmol), DMF (1.0 ml), Et$_3$N (41 µl, 0.40 mmol), BOP reagent (170 mg, 0.38 mmol) and α,α-dimethylbenzylamine (75 mg, 0.55 mmol) furnished the title compound (77 mg, 54%). M.P.: 119-122° C. $^1$H-NMR (δ ppm, CDCl$_3$, 300 MHz): 7.68-7.62 (m, 2H); 7.51-7.46 (m, 2H); 7.37-7.30 (m, 2H); 7.27-7.13 (m, 3H); 3.70 (br. s, 1H); 3.63 (br. s, 1H); 2.08 (d, J=9.0, 1H), 1.95 (d, J=7.8, 2H); 1.84 (s, 6H); 1.68 (d, J=8.4, 1H), 1.23 (d, J=12.0, 2H). IR (cm$^{-1}$, KBr): 3358 (m), 2972 (m), 2927 (m), 2870 (m), 1664 (s), 1605 (w), 1542 (m), 1515 (s), 1489 (m), 1383 (w), 1357 (m), 1276 (m) 1219 (m), 1136 (m), 1117 (m), 1093 (m), 1031 (w), 1088 (w), 949 (w), 858 (w), 839 (m). MS (m/z): 390.0 (M+H$^+$).

Example 283

N5-(Adamantan-1-yl)-3-(4-fluorophenyl)-3,4-diazatricyclo[5.2.1.0$^{2,6}$]deca-2(6),4-diene-5-carboxamide The title compound was synthesized by a procedure similar to that described for example 101. Intermediate 20 (100 mg, 0.36 mmol), DMF (1.0 ml), Et$_3$N (41 µl, 0.40 mmol), BOP reagent (170 g, 0.38 mmol) and 1-adamantylamine (83 mg, 0.54 mmol) furnished the title compound (127 mg, 85%). M.P.: 189-191° C. $^1$H-NMR (δ ppm, CDCl$_3$, 300 MHz): 7.66-7.60 (m, 2H); 7.19-7.12 (m, 2H); 6.66 (br. s, 1H); 3.74 (br. s, 1H); 3.63 (br. s, 1H); 2.15-2.10 (m, 9H); 1.97 (d, J=8.7, 2H); 1.75-1.68 (m, 8H); 1.30-1.20 (m, 2H). IR (cm$^{-1}$, KBr): 3361 (m), 2986 (m), 2909 (s), 2849 (m), 1658 (s), 1517 (s), 1550 (s), 1493 (s), 1445 (m), 1412 (m), 1308 (w), 1289 (w), 1278 (w), 1256 (s), 1219 (s), 868 (m). MS (m/z): 406.1 ([M++H]$^+$).

Example 284

N(3)-Phenylamino-1-(4-fluorophenyl)-4,5,6,7-tetrahydro-1H-4,7-methano-indazole-3-carboxamide The title compound was synthesized by a procedure similar to that described for example 101. Intermediate 20 (100 mg, 0.37 mmol), DMF (1.0 ml), Et$_3$N (61 µl, 0.44 mmol), BOP reagent (178 mg, 0.40 mmol) and phenylhydrazine (36 µl, 0.37 mmol) gave the title compound (72 mg, 54%). M.P.: 163° C. $^1$H-NMR (δ ppm, CDCl$_3$, 300 MHz): 8.55 (s, 1H); 7.69 (dd, J=9.3, 5.2, 2H); 7.27-7.16 (m, 4H); 6.95 (d, J=7.5, 2H); 6.90 (t, J=7.2, 1H); 3.73 (br. s, 1H); 3.69 (br. s, 1H); 2.06-1.99 (m, 2H); 1.73 (d, J=8.7, 1H); 1.25 (br. d, J=7.2, 2H). IR (KBr, cm$^{-1}$): 3376 (m), 2991 (m), 2952

(m), 2871 (m), 1674 (s), 1604 (s), 1517 (s), 1497 (s), 1441 (m), 1350 (m), 1279 (m), 1223 (s), 1154 (m), 1127(m), 1093 (m), 1083 (m), 1066 (m), 1041 (w), 889 (m), 841 (m). MS (m/z): 363.1 ([M+H]$^+$).

Example 285

N(3)-Phenylamino-1-(2,4-difluorophenyl)-4,5,6,7-tetrahydro-1H-4,7-methano-indazole-3-carboxamide The title compound was synthesized by a procedure similar to that described for example 101. Intermediate 21 (100 mg, 0.36 mmol), DMF (1.0 ml), Et$_3$N (44 µl, 0.32 mmol), BOP reagent (125 mg, 0.28 mmol) and phenylhydrazine (34 µl, 0.34 mmol) gave the title compound (87 mg, 44%). M.P.: 161° C. $^1$H-NMR (δ ppm, CDCl$_3$, 300 MHz): 8.50 (br. s, 1H); 7.70 (m, 1H); 7.24 (t, J=7.8, 2H); 7.09-6.99 (m, 2H); 6.99-6.86 (m, 3H); 3.72 (br. s, 1H); 3.48 (br. s, 1H); 2.09 (br. d, J=8.4, 1H), 1.97 (br. d, J=9.3, 2H); 1.69 (br. d, J=8.7, 1H); 1.27 (br. d, J=9.3, 2H). IR (cm$^{-1}$, KBr): 3274 (s), 2991 (m), 2957 (m), 1672 (s), 1605 (s), 1525 (s), 1497 (s), 1441 (m), 1352 (m), 1273 (s), 1230 (m), 1146 (m), 1126 (m), 1085 (m), 966 (m), 889 (m), 851 (m). MS (m/z): 381.0 ([M+H]$^+$).

Example 286

N(3)-[(2-Chlorophenyl)amino]-1-(2,4-difluorophenyl)-4,5,6,7-tetrahydro-1H-4,7-methano-indazole-3-carboxamide The title compound was synthesized by a procedure similar to that described for example 101. Intermediate 21 (100 mg, 0.34 mmol), DMF (1.0 ml), Et$_3$N (114 µl, 0.83 mmol), BOP reagent (152 mg, 0.34 mmol) and 2-chlorophenylhydrazine hydrochloride (61 mg, 0.34 mmol) gave the title compound (108 mg, 76% M. M.P.: 126-129° C. $^1$H-NMR (δ ppm, CDCl$_3$, 300 MHz): 8.55 (br. s, 1H); 7.75-7.65 (m, 1H); 7.29 (d, J=7.2, 1H); 7.14 (t, J=8.1, 1H); 7.04 (br. t, J=8.1, 3H); 6.83 (t, J=6.9, 1H); 3.71 (br. s, 1H); 3.49 (br. s, 1H); 2.09 (d, J=9.0, 1H); 1.97 (d, J=9.0, 2H); 1.70 (d, J=9.0, 1H); 1.26 (br. d, J=8.4, 2H). IR (KBr, cm$^{-1}$): 3247 (br. m), 2956 (m), 2873 (m), 1670 (s), 1595 (m), 1524 (s), 1494 (s), 1439 (m), 1349 (m), 1270 (s), 1254 (m), 1141(m), 1048 (m), 1034 (m), 964 (m), 887 (w), 848 (m), 750 (s). MS (m/z): 415.10 ([M+H]$^+$).

Example 287

N(3)-[(2-bromophenyl)amino]-1-(2,4-difluorophenyl)-4,5,6,7-tetrahydro-1H-4,7-methano-indazole-3-carboxamide The title compound was synthesized by a procedure similar to that described tier example 101. Intermediate 21 (100 mg, 0.34 mmol), DMF (1.0 ml), Et$_3$N (114 µl, 0.83 mmol), BOP reagent (152 mg, 0.34 mmol) and 2-bromophenylhydrazine hydrochloride (76 mg, 0.34 mmol) gave the title compound (125 mg, 79%). M.P.: 134-137° C. $^1$H-NMR (δ ppm, CDCl$_3$, 300 MHz): 8.57 (br. s, 1H); 7.74-7.65 (m, 1H); 7.46 (d, J=7.8, 1H); 7.19 (t, J=7.8, 1H); 7.10-6.90 (m, 3H); 6.77 (t, J=8.1, 1H); 3.72 (br. s, 1H); 3.49 (br. s, 1H); 2.12 (br. d, J=8.7, 1H); 1.97 (br. d, J=9.0, 2H); 1.70 (br. d, J=8.7, 1H); 1.27 (br. d, J=9.0, 2H). IR (KBr, cm$^{-1}$): 3327 (s), 3295 (m), 2969 (m), 2869 (m), 1656 (m), 1609 (m), 1594 (m),1524 (s), 1481 (s), 1449 (m), 1353 (m), 1271 (s), 1.229 (m), 1093 (m), 1071 (m), 1046 (m), 1021 (m), 846 (s).

Example 288

N(3)-[(2-Fluorophenyl)amino]-1-(2,4-difluorophenyl)-4,5,6,7-tetrahydro-1H-4,7-methano-indazole-3-carboxamide The title compound was synthesized by a procedure similar to that described for example 101. Intermediate 21 (100 mg, 0.34 mmol), DMF (1.0 ml), Et$_3$N (114 µl, 0.83 mmol), BOP reagent (152 mg, 0.34 mmol) and 2-fluorophenylhydrazine hydrochloride (55 mg, 0.34 mmol) gave the title compound (94 mg, 69%). M.P.: 172-175° C. $^1$H-NMR (δ ppm, CDCl$_3$, 300 MHz): 8.54 (br. s, 1H); 7.71 (dt, J=8.4, 2.4, 1H); 7.10-6.96 (m, 5H); 6.90-6.80 (m, 1H); 3.72 (br. s, 1H); 3.49 (br. s, 1H); 2.11 (br. d, J=7.2, 1H); 1.97 (d, J=9.3, 2H); 1.71 (d, J=9.0, 1H); 1.30-1.25 (m, 2H). IR (KBr, cm$^{-1}$): 3339 (s), 2989 (m), 2871 (m), 1685 (s), 1614 (m), 1.523 (s), 1498 (s), 1439 (s), 1271 (m), 1233 (m), 1192 (m), 1143(m), 1061 (m), 1027 (m), 966 (m), 862 (m). MS (m/z): 399.10 ([M+H]$^+$).

Example 289

N(3)-Piperidino-1-(2,4-difluorophenyl)-4,5,6,7-tetrahydro-1H-4,7-methano-indazole-3-carboxamide The title compound was synthesized by a procedure similar to that described for example 101. Intermediate 21 (100 mg, 0.34 mmol), DMF (1.0 ml), Et$_3$N (58 µl, 0.42 mmol), BOP reagent (166 mg, 0.38 mmol) and 1-aminopiperidine (37 µl, 0.34 mmol) gave the title compound (42 mg, 33%). M.P.: 143° C. $^1$H-NMR (δ ppm, CDCl$_3$, 300 MHz): 7.72-7.61 (m, 1H); 7.58 (br. s, 1H); 7.02 (t, J=8.4, 2H); 3.75 (br. s, 1H); 3.44 (br. s, 1H), 2.8.8 (br. s, 4H); 2.09 (br. d, J=8.7, 1H); 2.10-1.90 (m, 2H); 1.78-1.65 (m, 5H); 1.50-1.34 (m, 2H); 1.34-1.08 (m, 2H). IR (KBr, cm$^{-1}$): 3263 (m), 2994 (m), 2942 (m), 2872 (m), 2853 (m), 1658 (s), 1611 (m), 1521 (s), 1444 (m); 1353 (m), 1269 (s), 1233 (m), 1143 (m), 1121 (m), 1089 (m), 965 (m), 907 (m). MS (m/z): 373.2 ([M+H]$^+$).

Example 290

N(3)-Cyclohexyl-1-(2,4-difluorophenyl)-4,5,6,7-tetrahydro-1H-4,7-methano-indazole-3-carboxamide The title compound was synthesized by a procedure similar to that described for example 101. Intermediate 21 (100 mg, 0.34 mmol), DMF (1.0 ml), Et$_3$N (57 µl, 0.42 mmol), BOP reagent (166 mg, 0.38 mmol) and cyclohexylamine (39 µl, 0.34 mmol) gave the title compound (41 mg, 32%). M.P.: 119° C. $^1$H-NMR (δ ppm, CDCl$_3$, 300 MHz): 7.70-7.60 (m, 1H); 7.01 (t, J=7.8, 2H); 6.72 (br. d, J=8.1, 1H); 4.03-3.85 (m, 1H); 3.75 (br. s, 1H), 3.44 (br. s, 1H); 2.10-1.95 (m, 5H); 1.80-1.42 (m, 5H); 1.40-1.15 (m, 6H). IR (KBr, cm$^{-1}$): 3294 (m), 2995 (m), 2933 (s), 2853 (m), 1641 (s), 1610 (m), 1548 (s), 1520 (s), 1499 (s), 1451 (m), 1352 (m), 1269 (m), 1251 (m), 1239 (m), 1160 (m), 1142 (m), 1122 (m), 1090 (m), 964 (m), 851 (m). MS (m/z): 372.1 ([M+H]$^+$).

Example 291

N(3)-(Cyclohexylmethyl)-1-(2,4-difluorophenyl)-4,5,6,7-tetrahydro-1H-4,7-methano-indazole-3-carboxamide The title compound was synthesized by a procedure similar to that described for example 101. Intermediate 21 (100 mg, 0.34 mmol), DMF (1.0 ml), Et$_3$N (57 µl, 0.41 mmol), BOP reagent (152 mg, 0.34 mmol) and 2-cyclohexylmethyl amine (44 µl, 0.34 mmol) gave the title compound (87 mg, 65%). M.P.: 94-97° C. $^1$H-NMR (δ ppm, CDCl$_3$, 300 MHz): 7.67 (m, 1H); 7.01 (t, J=8.1, 2H); 6.91 (br. s, 1H); 3.75 (br. s, 1H); 3.44 (br. s, 1H); 3.26 (t, J=6.6, 2H); 2.08 (br. d, J=8.7, 1H); 2.05-1.85 (m, 2H); 1.83-1.50 (m, 6H); 1.26-1.18 (m, 6H); 1.05-0.85 (m, 2H). IR (KBr, cm$^{-1}$): 3379 (m), 2926 (s), 2848 (m), 1655 (s), 1556 (m), 1519 (s), 1499 (m), 1450 (m), 1271 (m), 1241 (m), 1.142 (m), 1088 (m), 962 (w), 852 (w). MS (m/2): 386.20 ([M+H]$^+$).

Example 292

N(3)-[S-(1-Phenylethyl]-1-(2,4-difluorophenyl)-4,5,6,7-tetrahydro-1H-4,7-methano-indazole-3-carboxamide The title compound was synthesized by a procedure similar to that described for example 101. Intermediate 21 (100 mg, 0.34 mmol), DMF (1.0 ml), Et$_3$N (57 µl, 0.41 mmol), BOP reagent (152 mg, 0.34 mmol) and S-(–)-1-phenethylamine (44 µl, 0.34 mmol) gave the title compound (85 mg, 63%). M.P.: 54-57° C. $^1$H-NMR (δ ppm, CDCl$_3$, 300 MHz): 7.66 (dt, J=9.0, 5.7, 1H); 7.40-7.20 (m, 5H); 7.11 (br. d, J=7.5, 1H); 7.00 (t, J=8.7, 2H); 5.35-5.28 (m, 1H); 3.74 (br. s, 1H); 3.44 (br. s, 1H); 2.07 (br. t, J=8.6, 1H); 1.94 (br. s, 2H); 1.70-1.55 (m, 4H); 1.33-1.25 (m, 2H). IR (KBr, cm$^{-1}$): 3412 (m), 3310 (w), 2971 (m), 2872 (m), 1664 (s), 161.1 (m), 1523 (s), 1493 (s), 1447 (s), 1359 (m), 1271 (s), 1232 (m), 1180 (m), 1144 (s), 1121 (m), 1091 (m), 965 (an), 850 (n). MS (m/z): 394.0 ([M+H]$^+$).

Example 293

N(3)-(R-1-phenylethyl)-1-(2,4-difluorophenyl)-4,5,6,7-tetrahydro-1H-4,7-methano-indazole-3-carboxamide The title compound was synthesized by a procedure similar to that described for example 101. Intermediate 21 (100 mg, 0.34 mmol), DMF (1.0 ml), Et$_3$N (54 µl, 0.38 mmol), BOP reagent (152 mg, 0.36 mmol) and R-1-phenylethylamine (44 µl, 0.37 mmol) furnished the title compound (75 mg, 56%). M.P.: 40-45° C. $^1$H-NMR (δ ppm, CDCl$_3$, 300 MHz): 7.72-7.60 (m, 1H); 7.46-7.19 (m, 5H); 7.15-6.90 (m, 3H); 5.31 (br. s, 1H); 3.74 (br. s, 1H); 3.43 (br. s, 1H); 2.07 (br. s, 1H); 1.95 (br. s, 2H); 1.72-1.51 (m, 4H); 1.44-1.17 (m, 2H). IR (cm$^{-1}$, KBr): 3412 (s), 3062 (m), 3029 (m), 2970 (s), 29230 (s), 2872 (m), 1663 (s), 1610 (s), 1523 (s), 1493 (s), 1447 (s), 1358 (m), 1326 (m), 1270 (s), 1252 (s), 1232 (s), 1210 (m), 1160 (s), 1143 (s), 1121 (s), 1191 (s), 965 (m) 850 (m), 831(m). MS (m/z): 394.2 ([M+H]$^+$); 290.2 (100).

Example 294

N(3)-(1-Methyl-1-phenylethyl)-1-(2,4-difluorophenyl)-4,5,6,7-tetrahydro-1H-4,7-methano-indazole-3-carboxamide The title compound was synthesized by a procedure similar to that described for example 101. Intermediate 21 (100 mg, 0.34 mmol), DMF (1.0 ml), Et$_3$N (54 µl, 0.38 mmol), BOP reagent (152 mg, 0.36 mmol) and α,α-dimethylbenzylamine (56 mg, 0.41 mmol) furnished the title compound (80 mg, 58%). M.P.: 105° C. $^1$H-NMR (δ ppm, CDCl$_3$, 300 MHz): 7.69 (dt, J=9.6, 6.0, 1H); 7.49 (d, J=7.8, 2H); 7.34 (t, J=7.8, 2H); 7.28-7.18 (m, 2H); 7.06-6.96 (m, 2H); 3.70 (br. s, 1H); 3.43 (br. s, 1H); 2.06 (br. d, J=8.7, 1H); 2.00-1.86 (m, 2H); 1.66 (br. d, J=8.4, 1H); 1.35-1.17 (m, 2H). IR (cm$^{-1}$, KBr): 3334 (s), 2965 (s), 2929 (s), 2873 (m), 1656 (s), 1609 (s), 1522 (s), 1495 (s), 1449 (s), 1385 (m), 1362 (m), 1326 (w), 1308 (m), 1271 (s), 1252 (m), 1237 (s), 1194 (m), 1156 (w), 1143 (m), 1121 (m), 1106 (m), 1091 (m), 965 (m) 848 (m), 831(m). MS (m/z): 408.1 (40, [M+H]$^+$); 290.3 (100).

Example 295

N5-[1-(2-Chlorophenyl)-1-methylethyl]-3-(2,4-difluorophenyl)-3,4-diazatricyclo[5.2.1.0$^{2,6}$]deca-2(6),4-diene-5-carboxamide The title compound was synthesized by a procedure similar to that described for example 101. Intermediate 21 (100 mg, 0.34 mmol), DMF (1.0 ml), Et$_3$N (54 µl, 0.37 mmol), BOP reagent (152 mg, 0.37 mmol) and 2-(2-chlorophenyl)-prop-2-ylamine (87 mg, 0.51 mmol) furnished the title compound (87 mg, 57%). M.P.: 176-179° C. $^1$H-NMR (δ ppm, CDCl$_3$, 300 MHz): 7.75-7.60 (m, 1H); 7.58 (d, J=7.8, 1H); 7.41-7.12 (m, 4H); 7.06-6.95 (m, 2H); 3.64 (s, 1H); 3.42 (s, 1H); 2.04 (d, J=8.4, 1H); 1.95-1.85 (m, 8H), 1.62 (d, J=9.3, 1H), 1.23 (d, J=9.0, 2H). IR (cm$^{-1}$, KBr): 3413 (m), 2975 (m), 2871 (m), 1675 (s), 1613 (w), 1522 (s), 1491 (m), 1447 (m), 1383 (w), 1362 (w), 1270 (s), 1244 (m), 1144 (m), 1091 (w), 1037 (w), 965 (w), 853 (w), 755 (w). MS (m/z): 442.1 ([M+H]$^+$).

Example 296

N(3)-(1,3,3-Trimethylbicyclo[2.2.1]hept-2-yl)-1-(2,4-difluorophenyl)-4,5,6,7-tetrahydro-1H-4,7-methano-indazole-3-carboxamide The title compound was synthesized by a procedure similar to that described for example 101. Intermediate 21 (120 mg, 0.41 mmol), DMF (1.0 ml), Et$_3$N (137 µl, 0.99 mmol), BOP reagent (182 mg, 0.41 mmol) and 1S,2 endo-1,3,3-trimethyl-bicyclo[2.2.1]hept-2-ylamine hydrochloride (77 mg, 0.41 mmol) furnished the title compound (86 mg. 49%). M.P.: 114-117° C. $^1$H-NMR (δ ppm, DMSO-d$_6$, 300 MHz): 7.86-7.76 (m, 1H), 7.60 (br. t, J=9.3, 1H); 7.29 (br. t, J=8.1, 1H); 7.00 (d, J=9.6, 1H); 3.63 (d, J=9.3, 1H); 3.52, (br. s, 1H); 3.46 (br. s, 1H); 2.05-1.85 (m, 3H); 1.75-1.55 (m, 4H); 1.50-1.35 (m, 2H); 1.25-0.95 (m, 10H); 0.77 (d, J=5.1, 3H). IR (cm$^-$, KBr): 3390 (m), 2952 (s), 2873 (m), 1658 (s), 1607 (m), 1520 (s), 1496 (s), 1451 (m), 1475 (m), 1368 (w), 1329 (m), 1252 (m), 1232 (m), 1158 (m), 1148 (m), 964 (m), 822 (w). MS (m/z): 426.3 ([M+H]$^+$).

Example 297

N5-(2-Chlorobenzyl)-3-(2,4-difluorophenyl)-3,4-diazatricyclo[5.2.1.0$^{2,6}$]deca-2(6),4-diene-5-carboxamide The title compound was synthesized by a procedure similar to that described for example 101. Intermediate 21 (100 mg, 0.34 mmol), DMF (1.0 ml), Et$_3$N (57 µl, 0.41 mmol), BOP reagent (167 mg, 0.37 mmol) and 2-chlorobenzylamine (41 µl, 0.34 mmol) furnished the title compound (100 mg, 68%). M.P.: 102-105° C. $^1$H-NMR (δ ppm, DMSO-d$_6$, 300 MHz): 8.67-8.73 (m, 1H), 7.89-7.77 (m, 1H); 7.66-7.57 (m, 1H); 7.44 (d, J=7.2, 1H); 7.34-7.30 (m, 4H); 4.49 (br. s, 2H); 3.55 (br. s, 1H); 3.47 (br. s, 1H); 2.00-1.92 (m, 3H); 1.66 (d, J=8.7, 1H); 1.17-1.05 (m, 2H). IR (cm$^{-1}$, KBr): 3337 (m), 2965 (m), 2868 (w), 1657 (m), 1645 (s), 1623 (m), 1526 (s), 1271 (m), 1243 (w), 1234 (w), 1160 (m), 846 (m), 738 (w).

Example 298

N5-(4-Chlorobenzyl)-3-(2,4-difluorophenyl)-3,4-diazatricyclo[5.2.1.0$^{2,6}$]deca-2(6),4-diene-5-carboxamide The title compound was synthesized by a procedure similar to that described for example 101. Intermediate 21 (100 mg, 0.34 mmol), DMF (1.0 ml), Et$_3$N (50 µl, 0.37 mmol), BOP reagent (159 mg, 0.36 mmol) and 4-chloro-benzylamine (63 µl, 0.51 mmol) furnished the title compound (96 mg, 67%). M.P.: 121-125° C. $^1$H-NMR (δ ppm, CDCl$_3$, 300 MHz): 7.67-7.57 (m, 1H); 7.30-7.25 (m, 4H); 7.20-7.15 (m, 1H); 7.05-6.95 (m, 2H); 4.57 (d, J=4.8, 2H); 3.76 (br. s, 1H); 3.45 (br. s, 1H), 2.09 (d, J=9.0, 1H); 2.00-1.93 (m, 2H); 1.69 (d, J=9.0, 1H); 1.28-1.24 (m, 2H). IR (cm$^{-1}$, KBr): 3310 (m), 2964 (m), 2939 (m), 2874 (m), 1644 (s), 1607 (m), 1557 (s), 1520 (s), 1491 (m), 1454 (m), 1407 (m), 1358 (m), 13.26 (w), 1272 (m), 1254 (m), 1232 (M), 1160 (m), 1142 (m), 1088 (m), 1013 (m), 962 (m), 853 (m). MS (m/z): 412.25 (100%), 414.2 ([M+H]$^+$).

Example 299

N5-(1-Ethyl-1-phenylpropyl)-3-(2,4-difluorophenyl)-3,4-diazatricyclo[5.2.1.0$^{2,6}$]deca-2(6),4-diene-5-carboxamide The title compound was synthesized by a procedure similar to that described for example 101. Intermediate 21 (100 mg, 0.34 mmol), DMF (1.0 ml), Et$_3$N (54 µl, 0.37 mmol), BOP reagent (1.52 mg, 0.34 mmol) and α,α-diethylbenzylamine (72 mg, 0.44 mmol) furnished the title compound (85 mg, 86%). M.P.: 45-48° C. $^1$H-NMR (δ ppm, CDCl$_3$, 300 MHz): 7.76-7.66 (m, 1H), 7.42-7.10 (m, 6H); 7.07-6.96 (m, 2H); 3.70 (br. s, 1H); 3.45 (br. s, 1H); 2.23 (q, J=7.2, 4H); 2.06 (d, J=9.0, 1H); 1.93 (d, J=8.4, 2H); 1.66 (d, J=8.7, 1H); 1.26 (d, J=5.4, 2H); 0.78 (t, J=7.2, 6H). IR (cm$^{-1}$, KBr): 3407 (m), 3059 (m), 2968 (s), 2975 (s), 2935 (s), 1.681 (s), 1610 (m), 1583 (s), 1524 (s), 1491 (m), 1447 (m), 1377 (w), 1327 (w), 1270 (m), 1234 (m), 1144 (m), 1091 (m), 965 (m), 850 (m), 756 (m), 698 (m). MS (m/z): 436.0 [M+H]$^+$.

Example 300

N5-[(1S)-1-Phenylpropyl]-3-(2,4-difluorophenyl)-3,4-diazatricyclo[5.2.1.0$^{2,6}$]deca-2(6),4-diene-5-carboxamide The title compound was synthesized by a procedure similar to that described for example 101. Intermediate 21 (100 mg, 0.34 mmol), DMF (1.0 ml), Et$_3$N (54 µl, 0.37 mmol), BOP reagent (152 mg, 0.34 mmol) and (s)-(α)-ethylbenzyl amine (51 mg, 0.37 mmol) furnished the title compound (70 mg, 50%). M.P.: 100-103° C. $^1$H-NMR (δ ppm, CDCl$_3$, 300 MHz): 7.71-7.62 (m, 1H), 7.39-7.25 (m, 5H); 7.23-6.96 (m, 3H); 5.05 (quintet, J=7.8, 1H); 3:72 (br. s, 1H); 3.43 (br. s, 1H); 2.10-1.85 (m, 5H); 1.66 (d, J=9.0, 1H); 1.27-1.19 (m, 2H); 1.00-0.92 (m, 3H). IR (cm$^{-1}$, KBr): 3282 (m), 2968 (m), 2874 (m), 1641 (s), 1614 (m), 1522 (s), 1494 (s), 1454 (m), 1359 (m), 1269 (m), 1231 (m) 1159 (m), 1140 (m), 1120 (m), 1094 (m), 963 (m), 847 (m), 701 (m). MS (m/z): 290 (100%), 408.2 (M+H$^+$).

Example 301

Methyl(2S)-2-[5-(2,4-difluorophenyl)-4,5-diazatricyclo[5.2.1.0$^{2,6}$]deca-2(6),3-dien-3-ylcarboxamido]-2-phenylethanoate The title compound was synthesized by a procedure similar to that described for example 101. Intermediate 21 (510 mg, 1.76 mmol), DMF (4.0 ml), Et$_3$N (580 µl, 4.20 mmol), BOP reagent (777 mg, 1.76 mmol) and (S)-(+)-2-phenylglycine methyl ester hydrochloride (354 mg, 1.76 mmol) furnished the title compound (420 mg, 55%). M.P.: 72-75° C. $^1$H-NMR (δ ppm, CDCl$_3$, 300 MHz): 8.47 (d, J=7.5, 1H), 7.86-7.81 (m, 1H); 7.61 (t, J=8.4, 1H); 7.45-7.29 (m, 6H); 5.65 (d, J=6.9, 1H); 3.66 (s, 3H); 3.52 (br. s, 1H); 3.47 (br. s, 1H); 1.94 (br. s, 3H); 1.67 (br. s, 1H); 1.25-1.05 (m, 2H); IR (cm$^{-1}$, KBr): 3412 (m), 2953 (m), 2872 (m), 1745 (s), 1674 (s), 1610 (m), 1524 (s), 1488 (s), 1452 (m), 1358 (m), 1328 (w), 1295 (w) 1270 (s), 1211 (m), 1160 (m), 1144 (m), 1121 (m), 1092 (m), 965 (m), 850 (w), 698 (m). MS (m/z): 438.2 (M+H$^+$.

Example 302

N5-[(1S)-2-Hydroxy-1-phenylethyl]-3-(2,4-difluorophenyl)-3,4-diazatricyclo[5.2.1.0$^{2,6}$]deca-2(6),4-diene-5-carboxamide The title compound was synthesized by a procedure similar to that described for example 191. To a solution of Example 301 (290 mg, 0662 mmol) in THF (3 ml) was added LiBH$_4$ (32 mg, 1.52 mmol) and the mixture was refluxed overnight. After evaporation of the solvent, the oily residue was diluted with water and acidified with 1N HCl and extracted with ethyl acetate and the combined organic layers were washed with brine and dried over Na$_2$SO$_4$. FC (3:7 AcOEt/petroleum ether) gave the title compound (170 mg, 63%). M.P.: 91° C. $^1$H-NMR (δ ppm, CDCl$_3$, 300 MHz): 7.71-7.61 (m, 1H); 7.46-7.29 (m, 6H); 7.00 (t, J=8.4, 2H); 5.23 (br. q, J=5.1, 1H), 3.98 (br. s, 2H); 3.73 (br. s, 1H); 3.44 (br. s, 1H); 2.92 (br. s, 1H); 2.14-1.93 (m, 3H); 1.69 (d, J=8.7, 1H); 1.32-1.24 (m, 2H). MS (m/z): 410.1 (M+H$^+$).

Example 303

N(3)-(tert-Butyl)-1-(2,4-difluorophenyl)-4,5,6,7-tetrahydro-1H-4,7-methano-indazole-3-carboxamide

[N5-(tert-butyl)-3-(2,4-difluorophenyl)-3,4-diazatricyclo[5.2.1.0$^{2,6}$]deca-2(6),4-diene-5-carboxamide]

The title compound was synthesized by a procedure similar to that described for example 101. Intermediate 21 (100 mg, 0.34 mmol), DMF (1.0 ml), Et$_3$N (57 µl, 0.40 mmol), BOP reagent (165 mg, 0.37 mmol) and 2-amino-2-methylpropane (36 µl, 0.34 mmol) furnished the title compound (31 mg, 26%). M.P.: 109-111° C. $^1$H-NMR (δ ppm, CDCl$_3$, 300 MHz): 7.71-7.62 (m, 1H), 7.04-6.97 (m, 2H); 6.74 (br. s, 1H); 3.75 (br. s, 1H); 3.43 (br. s, 1H); 2.10-2.04 (m, 1H); 2.01-1.90 (m, 2H); 1.67 (d, J=8.4, 1H); 1.46 (s, 9H); 1.33-1.19 (m, 2H). IR (cm$^{-1}$, KBr): 3323 (m), 2968 (m), 1652 (s), 1609 (s), 1547 (s), 1522 (s), 1495 (w), 1448 (m), 1391 (w), 1360 (m), 1272 (m) 1258 (w), 1145 (w), 1109 (m), 965 (m), 849 (m). MS (m/z): 346.0 (M+H$^+$).

Example 304 & Example 305

(4R,7S) and (4S,7R)N(3)-(tert-Butyl)-1-(2,4-difluorophenyl)-4,5,6,7-tetrahydro-1H-4,7-methano-indazole-3-carboxamide Preparation I: The title compound was synthesized by a procedure similar to that described for example 101. Intermediate 21a (late eluting enantiomer, 100 mg, 0.34 mmol), DMF (1.0 ml), Et$_3$N (57 µl, 0.41 mmol), BOP reagent (167 mg, 0.37 mmol) and 2-amino-2-methylpropane (36 0.34 mmol) furnished the title compound (91 mg, 76%). HPLC: R$_t$ (CHIRALCEL OD-H column, dimensions: 250×4.6 mm, particle size: 5µ, eluent: 0.2% isopropanol in n-hexane, flow rate: 1 ml/min.)=26.59 min.; e.e=92.3%. M.P.: 89-92° C. $^1$H-NMR (δ ppm, CDCl$_3$, 300 MHz): 7.72-7.60 (m, 1H), 7.04-6.96 (m, 2H); 6.74 (br. s, 1H); 3.75 (br. s, 1H); 3.43 (br. s, 1H); 2.07 (d, J=8.1, 1H); 2.01-1.90 (m, 2H); 1.67 (d, J=8.7, 1H); 1.46 (s, 9H); 1.33-1.19 (m, 2H).

Preparation II: The title compound was synthesized by a procedure similar to that described for example 101. Intermediate 21b (fast eluting enantiomer, 70 mg, 0.24 mmol), DMF (1.0 ml), Et$_3$N (38 µl, 0.28 mmol), BOP reagent (118 mg, 0.26 mmol) and 2-amino-2-methylpropane (25 pd, 0.24 mmol) furnished the title compound (63 mg, 75%). HPLC: R$_t$ (CHIRALCEL OD-H column, dimensions: 250×4.6 mm, particle size: 5µ, eluent: 0.2% isopropanol in n-hexane, flow rate: 1 ml/min.)=24.73 min.; e.e.: 90%. M.P.: 89-90° C. Example 305 was cryptochiral at 25° C. in chloroform (C=0.5). $^1$H-NMR (δ ppm, CDCl$_3$, 300 MHz): 7.72-7.62 (m, 1H), 7.00 (t, J=10.8, 2H); 6.74 (br. s, 1H); 3.75 (br. s, 1H); 3.43 (br. s, 1H); 2.07 (d, J=8.4, 1H); 2.01-1.89 (m, 2H); 1.67 (d, J=8.1, 1H); 1.46 (s, 9H); 1.33-1.19 (m, 2H).

Example 306

N5-n-Pentyl-3-(2,4-difluorophenyl)-3,4-diazatricyclo[5.2.1.0$^{2,6}$]deca-2(6),4-diene-5-carboxamide The title compound was synthesized by a procedure similar to that described for example 101. Intermediate 21 (100 mg, 0.34 mmol), DMF (1.0 ml), Et$_3$N (54 µl, 0.37 mmol), BOP reagent (152 mg 0.34 mmol) and n-pentylamine (32 mg, 0.37 mmol) furnished the title compound (50 mg, 40%). M.P.: 75-78° C. $^1$H-NMR (δ ppm, CDCl$_3$, 300 MHz): 7.70-7.61 (m, 1H), 7.01 (t, J=8.4, 2H), 6.83 (br. s, 1H); 3.75 (br. s, 1H); 3.43-3.36 (m, 3H); 2.08 (d, J=8.7, 1H), 2.02-1.89 (m, 2H), 1.68 (d, J=8.7, 1H), 1.62-1.56 (m, 2H); 1.38-1.24 (m, 6H); 0.94 (t, J=7.2, 3H). IR (cm$^{-1}$, KBr): 3338 (m), 2960 (m), 2932 (m), 2872 (m), 2857 (m), 1648 (s), 1607 (w), 1552 (s), 1453 (s), 151.9 (m), 1356 (m), 1251 (m), 1235 (m) 1159 (m), 1142 (m), 1112 (w), 1144 (m), 1087 (m), 1013 (m),853 (m), 624 (m). MS (m/z): 360.1 (M+H$^+$).

Example 307

N5-(2,4-Dichlorobenzyl)-3-(2,4-difluorophenyl)-3,4-diazatricyclo[5.2.1.0$^{2,6}$]deca-2(6),4-diene-5-carboxamide The title compound was synthesized by a procedure similar to that described for example 101. Intermediate 21 (100 mg, 0.34 mmol), DMF (1.0 ml), Et$_3$N (54 µl, 0.37 mmol), BOP reagent (152 mg, 0.34 mmol) and 2,4-dichlorobenzylamine (66 mg, 0.34 mmol) furnished the title compound (110 mg, 71%). M.P.: 105-108° C. $^1$H-NMR (δ ppm, CDCl$_3$, 300 MHz): 7.69-7.60 (m, 1H), 7.44 (d, J=7.8, 1H); 7.39 (d, J=1.8, 2H); 7.29-7.19 (m, 2H); 7.00 (t, J=8.1, 2H), 4.65 (d, J=6.3, 2H); 3.74 (br. s, 1H); 3.45 (br. s, 1H); 2.08 (d, J=8.4, 1H); 1.98-1.93 (m, 2H); 1.68 (d, J=8.4, 1H); 1.56 (d, J=8.4, 2H). IR (cm$^1$, KBr): 3394 (m), 2973 (m), 2933 (m), 2871 (m), 1660 (s), 1607 (w), 1551 (w), 1587 (m), 1519 (s), 1493 (m), 1350 (m), 1326 (w), 1270 (m) 1231 (m), 1162 (m), 1142 (m), 1125 (m), 1091 (m), 1050 (m), 985 (w), 961 (m), 856 (m), 824 (m). MS (m/z): 448.1 (M+H$^+$).

Example 308

N5-(1-phenylcyclopropyl)-3-(2,4-difluorophenyl)-3,4-diazatricyclo[5.2.1.0$^{2,6}$]deca-2(6),4-diene-5-carboxamide The title compound was synthesized by a procedure similar to that described for example 101. Intermediate 21 (100 mg, 0.34 mmol), DMF (1.0 ml), Et$_3$N (54 µl, 0.37 mmol), BOP reagent (152 mg, 0.34 mmol) and α,α-cyclopropylbenzylamine (59 mg, 0.44 mmol) furnished the title compound (55 mg, 40%). M.P.: 90° C. $^1$H-NMR (δ ppm, CDCl$_3$, 300 MHz): 7.72-7.61 (m, 1H), 7.51 (br. s, 1H); 7.35-7.14 (m, 5H); 7.06-6.96 (m, 2H); 3.73 (br. s, 1H); 3.44 (br. s, 1H); 2.06 (d, J=8.7, 1H); 2.00-1.92 (m, 2H); 1.67 (d, J=8.7, 1H); 1.43-1.23 (m, 6H). IR (cm$^{-1}$, KBr): 3407 (w), 3296 (m), 3088 (w), 3056 (w), 2953 (m), 1660 (s), 1607 (m), 1522 (s), 1491 (m), 1453 (m), 1355 (m), 1322 (w), 1270 (m), 1230 (m), 1158 (m), 1142 (m), 1089 (m), 965 (m), 851 (w). MS (m/z): 406.1 [M+H]$^+$.

Example 309

N5-(2-Adamantyl)-3-(2,4-difluorophenyl)-3,4-diazatricyclo[5.2.1.0$^{2,6}$]deca-2(6),4-diene-5-carboxamide The title compound was synthesized by a procedure similar to that described for example 101. Intermediate 21 (100 mg, 0.34 mmol), DMF (1.0 ml), Et$_3$N (54 µl, 0.37 mmol), BOP reagent (152 mg, 0.34 mmol) and 2-adamantanamine hydrochloride (71 mg, 0.37 mmol) furnished the title compound (123 mg, 84%). M.P.: 159-161° C. $^1$H-NMR (δ ppm, CDCl$_3$, 300 MHz): 7.74-7.64 (m, 1H), 7.21 (d, J=7.8, 1H), 7.05-6.95 (m, 2H); 4.23 (d, J=8.4, 1H); 3.73 (br. s, 1H); 3.44 (br. s, 1H); 2.10-1.79 (m, 13H); 1.77-1.55 (m, 7H). IR (cm$^{-1}$, KBr): 3414 (m), 2909 (s), 2855 (m), 1659 (s), 1614 (w), 1603 (w), 1545 (s), 1530 (s), 1494 (m), 1470 (w), 1448 (w), 1346 (w) 1290 (s), 1272 (m), 1226 (m), 1154 (m), 1122 (m), 967 (m), 869 (m). MS (m/z): 424.3 (M+H$^+$).

Example 310

N5-(2-Methyl-2-adamantyl)-3-(2,4-difluorophenyl)-3,4-diazatricyclo[5.2.1.0$^{2,6}$]deca-2(6),4-diene-5-carboxamide The title compound was synthesized by a procedure similar to that described for example 101. Intermediate 21 (100 mg, 0.34 mmol), DMF (1.0 ml), Et$_3$N (54 µl, 0.37 mmol), BOP reagent (152 mg, 0.34 mmol) and 2-methyl-2-adamantylamine (73 mg, 0.44 mmol) furnished the title compound (110 mg, 73%). M.P.: 60° C. $^1$H-NMR, □ppm, CDCl$_3$, 300 MHz): 7.71-7.63 (m, 1H), 7.02-6.95 (m, 2H); 6.82 (br. s, 1H); 3.74 (br. s, 1H); 3.44 (br. s, 1H); 2.30 (br. s, 2H); 2.04-1.79 (m, 9H); 1.73-1.62 (m, 10H); 1.25 (s, 3H). IR (cm$^{-1}$, KBr): 3406 (m), 2920 (s), 2861 (s), 1672 (s), 1610 (m), 1543 (s), 1524 (s), 1493 (s), 1446 (s), 1377 (w), 1368 (w), 1353 (m), 1270 (s), 1256 (m), 1227 (m), 1161 (m), 1144 (m), 1105 (m), 965 (m), 849 (m), 815 (w), 578 (m). MS (m/z): 438.1.

Example 311

N7-(3-Hydroxyadamantan-1-yl)-5-(2,4-difluorophenyl)-5,6-diazatetracyclo[7.3.1.1$^{3,11}$.0$^{4,8}$]tetradeca-4(8),6-diene-7-carboxamide The title compound was synthesized by a procedure similar to that described for example 101. Intermediate 21 (200 mg, 0.68 mmol), DMF (2.0 ml), Et$_3$N (110 μl, 0.82 mmol), BOP reagent (335 mg, 0.75 mmol) and 3-amino-1-adamantanol (115 mg, 0.68 mmol) furnished the title compound (185 mg, 55%). M.P.: 180-182° C. $^1$H-NMR (δ ppm, CDCl$_3$, 300 MHz): 7.70-7.61 (m, 1H); 7.04-6.96 (m, 2H); 6.69 (br. s, 1H); 3.72 (br. s, 1H); 3.43 (br. s, 1H); 2.30 (br. s, 2H); 2.13 (br. s, 2H); 2.10-1.94 (m, 7H); 1.73-1.51 (m, 8H); 1.33-1.19 (m, 2H). IR (cm$^{-1}$, KBr): 3418 (s), 3369 (s), 2913 (s), 2885 (s), 1651 (s), 1610 (m), 1548 (s), 1519 (s), 1495 (s), 1455 (m), 1421 (w), 1359 (m), 1341 (w), 1314 (m), 1270 (s), 1233 (s), 1145 (m), 1115 (m), 1102 (m), 1049 (w), 1032 (w), 965 (m), 846 (m). MS (m/z): 440.1 ([M+H]$^+$).

Example 312

4-[5-(2,4-Difluorophenyl)-4,5-diazatricyclo[5.1.1.0$^{2,6}$]deca-2(6),3-dien-3-ylcarboxamido]morpholine The title compound was synthesized by a procedure similar to that described for example 101. Intermediate 21 (100 mg, 0.34 mmol), DMF (1.0 ml), Et$_3$N (53 μl, 0.37 mmol), BOP reagent (159 mg, 0.36 mmol) and 4-morpholinamine (115 mg, 0.68 mmol) furnished the title compound (100 mg, 78%). M.P.: 106-110° C. $^1$H-NMR (δ ppm, CDCl$_3$, 300 MHz): 7.70-7.61 (m, 2H); 7.06-6.98 (m, 2H); 3.85 (t, J=4.5, 4H); 3.74 (br. s, 1H); 3.44 (br. s, 1H); 2.96 (t, J=4.5, 4H); 2.08 (d, J=8.7, 113); 1.97-1.94 (m, 2H); 1.69 (d, J=9.0, 1H); 1.27-1.23 (m, 2H). IR (cm$^{-1}$, KBr): 3435 (m), 3262 (m), 3085 (w), 2954 (m), 2925 (m), 2870 (m), 1670 (s), 1614 (m), 1523 (s), 1498 (m), 1450 (m), 1387 (w), 1357 (m), 1326 (w), 1269 (s), 1232 (s), 1145 (m), 1108 (m), 1093 (m), 1002 (m), 966 (m), 847 (m). MS (m/z): 375.2 ([M+H]$^+$).

Example 313

N(3)-(tert-Pentyl)-1-(2,4-difluorophenyl)-4,5,6,7-tetrahydro-1H-4,7-methano-indazole-3-carboxamide The title compound was synthesized by a procedure similar to that described for example 101. Intermediate 21 (100 mg, 0.34 mmol), DMF (1.0 ml), Et$_3$N (53 μl, 0.37 mmol), BOP reagent (159 mg, 0.36 mmol) and tert-amyl amine (60 0.52 mmol) furnished the title compound (109 mg, 88%). M.P.: 78-80° C. $^1$H-NMR (δ ppm, CDCl$_3$, 300 MHz): 7.71-7.61 (m, 1H); 7.04-7.02 (m, 2H); 6.66 (br. s, 1H); 3.74 (br. s, 1H); 3.43 (br. s, 1H), 2.07 (d, J=8.4, 1H); 1.98-1.78 (m, 4H); 1.67 (d, J=9.0, 1H); 1.41 (s, 6H); 1.26-1.20 (m, 2H); 0.91 (t, J=7.2, 3H). MS (m/z): 360.2 ([M+H]$^+$).

Example 314

N(3)-Cyclopropanmethyl-1-(2,4-difluorophenyl)-4,5,6,7-tetrahydro-1H-4,7-methano-indazole-3-carboxamide The title compound was synthesized by a procedure similar to that described for example 101. Intermediate 21 (100 mg, 0.34 mmol), DMF (1.0 ml), Et$_3$N (116 μl, 0.83 mmol), BOP reagent (159 mg, 0.36 mmol) and amino methyl cyclopropane hydrochloride (55 mg, 0.51 mmol) furnished the title compound (101 mg, 85%). M.P.: 113-115° C. $^1$H-NMR (δ ppm, CDCl$_3$, 300 MHz): 7.72-7.62 (m, 1H); 7.06-6.92 (m, 3H); 3.75 (br. s, 1H); 3.44 (br. s, 1H), 3.28 (t, J=5.7, 2H); 2.08 (d, 7.8, 1H); 1.96 (br. s, 2H); 1.68 (d, J=9.3, 1H); 1.26 (br. s, 2H); 1.06-1.02 (m, 1H); 0.52 (d, J=7.5, 2H); 0.26 (d, J=4.2, 2H). MS (m/z): 344.1 ([M+H]$^+$).

Example 315

N(3)-Cyclobutyl-1-(2,4-difluorophenyl)-4,5,6,7-tetrahydro-1H-4,7-methano-indazole-3-carboxamide The title compound was synthesized by a procedure similar to that described for example 101. Intermediate 21 (100 mg, 0.34 mmol), DMF (1.0 ml), Et$_3$N (116 μl, 0.83 mmol), BOP reagent (160 mg, 0.36 mmol) and cyclobutyl amine hydrochloride (115 mg, 0.68 mmol) furnished the title compound (92 mg, 77%). M.P.: 123-125° C. $^1$H-NMR (δ ppm, CDCl$_3$, 300 MHz): 7.70-7.62 (m, 1H); 7.06-6.96 (m, 3H); 4.56 (quintet, J=7.5, 1H); 3.74 (br. s, 1H); 3.43 (br. s, 1H), 2.46-2.36 (m, 2H); 2.07 (d, J=7.8, 1H), 2.04-1.95 (m, 5H); 1.78-1.60 (m, 2H); 1.25 (br. s, 2H). MS (m/z): 344.2 ([M+H]$^+$).

Example 316

N(3)-(Tetrahydro-2H-4-pyranmethyl)-1-(2,4-difluorophenyl)-4,5,6,7-tetrahydro-1H-4,7-methano-indazole-3-carboxamide The title compound was synthesized by a procedure similar to that described for example 101. Intermediate 21 (100 mg, 0.34 mmol), DMF (1.0 ml), Et$_3$N (54 μl, 0.37 mmol), BOP reagent (160 mg, 0.36 mmol) and tetrahydro-2H-4-pyranylmethylamine (60 mg, 0.51 mmol) furnished the title compound (103 mg, 77%). M.P.: 107-109° C. $^1$H-NMR (δ ppm, CDCl$_3$, 300 MHz): 7.70-7.60 (m, 1H); 7.05-6.96 (m, 3H); 4.10-3.94 (m, 2H); 3.75 (br. s, 1H); 3.46-3.2.9 (m, 5H), 2.12-2.02 (m, 1H); 2.00-1.62 (m, 5H); 1.44-1.20 (m, 5H). MS (m/z): 386.0 ([M+H]$^+$).

Example 317

N(3)-Cyclopropyl-1-(2,4-difluorophenyl)-4,5,6,7-tetrahydro-1H-4,7-methano-indazole-3-carboxamide The title compound was synthesized by a procedure similar to that described for example 101. Intermediate 21 (100 mg, 0.34 mmol), DMF (1.0 ml), Et$_3$N (54 μl, 0.37 mmol), BOP reagent (160 mg, 0.36 mmol) and cyclopropylamine (36 μl, 0.51 mmol) furnished the title compound (103 mg, 86%). M.P.: 59-61° C. $^1$H-NMR (δ ppm, CDCl$_3$, 300 MHz): 7.70-7.62 (m, 1H); 7.00 (t, J=9.9, 2H); 6.90 (br. s, 3.75 (br. s, 1H); 3.43 (br. s, 1H), 2.88-2.84 (m, 1H); 2.07 (d, J=8.7, 1H); 2.02-1.90 (m, 2H); 1.68 (d, J=8.7, 1H); 1.32-1.15 (m, 2H); 0.82 (d, J=5.1, 2H); 0.62 (br. s, 2H). MS (m/z): 328.0 ([M+H]$^+$).

Example 318

N(3)-(4-methylpiperazino)-1-(2,4-difluorophenyl)-4,5,6,7-tetrahydro-1H-4,7-methano-indazole-3-carboxamide The title compound was synthesized by a procedure similar to that described for example 101. Intermediate 21 (100 mg, 0.34 mmol), DMF (1.0 ml), Et₃N (51 µl, 0.37 mmol), BOP reagent (165 mg, 0.37 mmol) and N-amino-N-methyl piperazine (61 µl, 0.51 mmol) furnished the title compound (97 mg, 72%). M.P.: 154-156° C. $^1$H-NMR (δ ppm, CDCl₃, 300 MHz): 7.70-7.62 (m, 1H); 7.58 (br. s, 1H); 7.08-6.96 (m, 2H); 3.74 (br. s, 1H); 3.44 (br. s, 1H); 3.03 (br. s, 4H); 2.76 (br. s, 4H); 2.41 (s, 3H); 2.08 (d, J=9.3, 1H); 2.00-1.94 (m, 2H); 1.68 (d, J=8.1, 1H); 1.30-1.24 (m, 2H).

Example 319

Methyl (2R)-2-[5-(2,4-difluorophenyl)-4,5-diazatricyclo[5.2.1.0$^{2,6}$]deca-2(6),3-diene-3-ylcarboxamido]-2-phenylethanoate The title compound was synthesized by a procedure similar to that described for example 101. Intermediate 21 (300 mg, 1.03 mmol), DMF (3.0 ml), Et₃N (343 µl, 2.48 mmol), BOP reagent (502 mg, 1.13 mmol) and R-(−)-2-phenylglycinmethylester hydrochloride (208 mg, 1.03 mmol) furnished the title compound (334 mg, 74%). M.P.: 61-63° C. $^1$H-NMR (δ ppm, CDCl₃, 300 MHz): 7.78-7.64 (m, 2H); 7.45 (d, J=7.8, 2H); 7.40-7.31 (m, 3H); 7.04-6.95 (m, 2H); 5.76 (dd, J=2.1, 7.2, 1H); 3.76 (2s, 3H); 3.71 (br. S, 1H); 3.44 (br. S, 1H); 2.11-2.01 (m, 1H); 1.99-1.90 (m, 2H); 1.66 (d, J=8.7, 1H); 1.30-1.21 (m, 2H). IR (cm$^{-1}$, KBr): 3411 (m), 3065 (w), 2953 (m), 2872 (w), 1744 (s), 1672 (s), 1610 (m), 1541 (s), 1523 (s), 1489 (s), 1454 (m), 1358 (m), 1328 (w), 1295 (w), 1271 (s), 1213 (m), 1160 (m), 1145 (m), 1122 (m), 1093 (w), 966 (m), 851 (m). MS (m/z): 480.24 ([M+H]⁺).

Example 320

N(3)-[(1R)-2-Hydroxy-1-phenylethyl]-1-(2,4-difluorophenyl)-4,5,6,7-tetrahydro-1H-4,7-methano-indazole-3-carboxamide The title compound was synthesized by a procedure similar to that described for example 191. Example 319 (235 mg, 0.54 mmol), TI-IF (4 ml) and LiBH₄ (24 mg, 1.09 mmol) furnished the title compound (153 mg, 69%). M.P.: 68-70° C. $^1$H-NMR (δ ppm, CDCl₃, 300 MHz): 8.25 (d, J=9.0, 1H); 7.87-7.82 (m, 1H); 7.63-7.58 (m, 1H); 7.36-7.22 (m, 6H); 5.05-4.94 (m, 2H), 3.73-3.67 (m, 2H); 3.50 (br. s, 1H); 3.45 (br. s, 1H); 2.05-1.84 (m, 3H); 1.70-1.62 (m, 1H); 1.24-1.20 (m, 2H). MS (m/z): 452.17 (M+H⁺).

Example 321

N(3)-(tert-Butyl)-1-(4-chlorophenyl)-4,5,6,7-tetrahydro-1H-4,7-methano-indazole-3-carboxamide The title compound was synthesized by a procedure similar to that described for example 101. Intermediate 16 (100 mg, 0.34 mmol), DMF (1.0 ml), Et₃N (52 µl, 0.38 mmol), BOP reagent (157 mg, 0.35 mmol) and 2-amino-2-methylpropane (53 0.51 mmol) furnished the title compound (56 mg, 47%). M.P.: 170-173° C. $^1$H-NMR (δ ppm, CDCl₃, 300 MHz): 7.62 (d, J=8.7, 2H); 7.43 (d, J=8.7, 2H); 6.78 (br. s, 1H); 3.75 (br. s, 1H); 3.65 (br. s, 1H); 2.08-1.99 (m, 1H); 2.02-1.94 (m, 2H); 1.70 (d, J=8.4, 1H); 1.47 (s, 9H); 1.28-0.99 (m, 2H).

Example 322

N(3)-(Tetrahydro-2-furanylmethyl)-1-(2,4-difluorophenyl)-4,5,6,7-tetrahydro-1H-4,7-methano-indazole-3-carboxamide The title compound was synthesized by a procedure similar to that described for example 101. Intermediate 21 (100 mg, 0.34 mmol), DMF (1.0 ml), Et₃N (54 µl, 0.37 mmol), BOP reagent (160 mg, 0.36 mmol) and tetrahydro-2-furanylmethylamine (54 µl, 0.51 mmol) furnished the title compound (82 mg, 64%). M.P.: 91-93° C. $^1$H-NMR (δ ppm, CDCl₃, 300 MHz): 7.74-7.62 (m, 1H); 7.15 (br. s, 1H); 7.08-6.94 (m, 2H); 4.12-4.00 (m, 1H); 3.94-3.86 (m, 1H); 3.80-3.68 (m, 3H); 3.50-3.30 (m, 2H), 2.10-1.85 (m, 6H); 1.72-1.58 (m, 1H); 1.25 (br. s, 3H). MS (m/z): 374.2 ([M+H]⁺).

Example 323

N(3)-(tert-Butyl)-1-(4-fluorophenyl)-4,5,6,7-tetrahydro-1H-4,7-methano-indazole-3-carboxamide The title compound was synthesized by a procedure similar to that described for example 101. Intermediate 20 (100 mg, 0.36 mmol), DMF (1.0 ml), Et₃N (54 µl, 0.40 mmol), BOP reagent (170 g, 0.38 mmol) and t-butylamine (57 µl, 0.55 mmol) furnished the title compound (102 mg, 85%). M.P.: 131-133° C. $^1$H-NMR (δ ppm, CDCl₃, 300 MHz): 7.66-7.60 (m, 2H); 7.20-7.12 (m, 2H); 6.78 (br. s, 1H); 3.76 (br. s, 1H); 3.63 (br. s, 1H); 2.15-2.10 (m, 1H); 2.00-1.92 (m, 2H); 1.74-1.68 (m, 1H); 1.47 (s, 9H); 1.30-1.16 (m, 2H). MS (m/z): 328.15 ([M+H]⁺), Example 324

N(3)-(tert-Butyl)-1-(4-bromophenyl)-4,5,6,7-tetrahydro-1H-4,7-methano-indazole-3-carboxamide The title compound was synthesized by a procedure similar to that described for example 101. Intermediate 19 (100 mg, 0.30 mmol), DMF (1.0 ml), Et₃N (45 µl, 0.33 mmol), BOP reagent (139 mg, 0.31 mmol) and 2-amino-2-methylpropane (47 µl, 0.45 mmol) furnished the title compound (87 mg, 75%). M.P.: 157-159° C. $^1$H-NMR (δ ppm, CDCl₃, 300 MHz): 7.57 (s, 4H); 6.78 (br. s, 1H); 3.75 (br. s, 1H); 3.65 (br. s, 1H); 2.18-2.07 (m, 1H); 2.02-1.92 (m, 2H); 1.70 (d, J=9.0, 1H); 1.47 (s, 9H); 1.28-0.99 (m, 2H).

Example 325

N(3)-(tert-Butyl)-1-(3,4-dichlorophenyl)-4,5,6,7-tetrahydro-1H-4,7-methano-indazole-3-carboxamide The title compound was synthesized by a procedure similar to that described for example 101. Intermediate 29 (100 mg, 0.31 mmol), DMF (1.0 ml), Et₃N (47 µl, 0.34 mmol), BOP reagent (143 mg, 0.32 mmol) and 2-amino-2-methylpropane (48 µl, 0.46 mmol) furnished the title compound (77 mg, 66%). 205-207° C. $^1$H-NMR (δ ppm, CDCl₃, 300 MHz): 7.83 (s, 1H); 7.52 (s, 2H); 6.77 (br. s. 1H); 3.75 (br. s, 1H); 3.67 (br. s, 1H); 2.11 (d, J=8.7, 1H); 1.99 (d, 6.3, 2H); 1.71 (d, H=8.7, 1H); 1.48 (s, 9H); 1.28-1.16 (m, 2H).

Example 326

Methyl (2S)-2-[5-(2,4-difluorophenyl)-4,5-diazatricyclo[5.2.1.0$^{2,6}$]deca-2(6),3-dien-3-ylcarboxamido]-2-(4-fluorophenyl)ethanoate The title compound was synthesized by a procedure similar to that described for example 101. Intermediate 21 (400 mg, 1.37 mmol), DMF (4.0 ml), Et₃N (450 µl, 3.31 mmol), BOP reagent (670 mg, 1.51 mmol) and (S)-(−)-2-(4-fluorophenyl) glycine methyl ester hydrochloride (302 mg, 1.37 mmol) furnished the title compound (543 mg, 86%). M.P.: 51-52° C.

¹H-NMR (δ ppm, CDCl₃, 300 MHz): 7.78-7.68 (m, 2H): 7.44-7.41 (m, 2H); 7.06-6.95 (m, 4H); 5.63 (d, J=6.9, 1H); 3.77, 3.76 (2s, 3H); 3.70 (brs, 1H); 3.44 (br. s, 1H); 2.10-2.02 (m, 1H); 2.00-1.90 (m, 2H); 1.67 (d, J=7.8, 1H); 1.30-1.19 (m, 2H).

Example 327

N(3)-(tert-Butyl)-1-(2,4-dichlorophenyl)-4,5,6,7-tetrahydro-1H-4,7-methano-indazole-3-carboxamide The title compound was synthesized by a procedure similar to that described for example 101. Intermediate 17 (100 mg, 0.30 mmol), DMF (1.0 ml), Et₃N (48 µl, 0.34 mmol), BOP reagent (144 mg, 0.32 mmol) and 2-amino-2-methylpropane (48 µl, 0.46 mmol) furnished the title compound (90 mg, 77%). 129-131° C. ¹H-NMR (δ ppm, CDCl₃, 300 MHz): 7.55 (d, J=2.4, 1H); 7.45 (d, J=8.4, 1H); 7.37 (dd, J=8.4, 2.1, 1H); 6.71 (br. s, 1H); 3.76 (br. s, 1H); 3.34 (br. s, 1H); 2.11 (d, J=9.0, 1H); 2.02-1.82 (m, 2H); 1.68 (d, J=8.7, 1H); 1.45 (s, 9H); 1.33-1.12 (m, 2H).

Example 328

N(3)-(4-Hydroxyphenyl)-1-(2,4-difluorophenyl)-4,5,6,7-tetrahydro-1H-4,7-methano-indazole-3-carboxamide The title compound was synthesized by a procedure similar to that described for example 101. Intermediate 21 (100 mg, 0.34 mmol), DMF (1.0 ml), Et₃N (51 µl, 0.37 mmol), BOP reagent (160 mg, 0.36 mmol) and 4-amino-phenol (56 mg, 0.51 mmol) furnished the title compound (112 mg, 85%). M.P.: 189-191° C. ¹H-NMR (δ ppm, CDCl₃, 300 MHz): 8.56 (br. s, 1H); 7.75-7.64 (m, 1H); 7.52 (d, J=9.3, 2H); 7.08-6.99 (m, 2H); 6.82 (d, J=8.7, 2H); 5.30 (br. s, 1H); 3.79 (br. s, 1H); 3.47 (br. s, 1H); 2.11 (d, J=8.7, 1H); 2.00-1.94 (m, 2H); 1.71 (d, J=8.7, 1H); 1.32-1.22 (m, 2H).

Example 329

N(3)-tert-Butyl)-1-(2-ethoxy,4-fluorophenyl)-4,5,6,7-tetrahydro-1H-4,7-methano-indazole-3-carboxamide The title compound was synthesized by a procedure similar to that described for example 101. Intermediate 30 (100 mg, 0.31 mmol), DMF (1.0 ml), Et₃N (50 µl, 0.34 mmol), BOP reagent (146 mg, 0.33 mmol) and 2-amino-2-methylpropane (40 µl, 0.37 mmol) furnished the title compound (96 mg, 82%). M.P.: 117-120° C. ¹H-NMR (δ ppm, CDCl₃, 300 MHz): 7.54-7.44 (m, 1H), 6.82-6.69 (m, 3H); 4.12-4.00 (m, 2H); 3.73 (br. s, 1H); 3.31 (br. s, 1H); 2.06 (d, J=8.1, 1H); 1.98-1.82 (m, 2H); 1.65 (d, J=8.4, 1H); 1.45 (s, 9H); 1.38 (t, J=6.9, 3H); 1.28-1.20 (m, 2H).

Example 330

N(3)-(2-furylmethyl)-1-(2,4-difluorophenyl)-4,5,6,7-tetrahydro-1H-4,7-methano-indazole-3-carboxamide The title compound was synthesized by a procedure similar to that described for example 101. Intermediate 21 (100 mg, 0.34 mmol), DMF (1.0 ml), Et₃N (57 µl, 0.41 mmol), BOP reagent (167 mg, 0.37 mmol) and furfurylamine (38 µl, 0.41 mmol) furnished the title compound (98 mg, 77%). M.P.: 99-100° C. ¹H-NMR (δ ppm, CDCl₃, 300 MHz): 7.71-7.61 (m, 1H); 7.36 (br. s, 1H); 7.19-7.11 (m, 1H); 7.00 (t, J=8.4, 2H); 6.30 (d, J=7.5, 2H); 4.60 (d, J=5.1, 2H); 3.76 (br. s, 1H); 3.44 (br. s, 1H); 2.08 (d, J=7.5, 1H); 2.02-1.90 (m, 2H), 1.68 (d, J=8.1, 1H); 1.32-1.22 (m, 2H).

Example 331

N(3)-(2-thiophenemethyl)-1-(2,4-difluorophenyl)-4,5,6,7-tetrahydro-1H-4,7-methano-indazole-3-carboxamide The title compound was synthesized by a procedure similar to that described for example 101. Intermediate 21 (100 mg, 0.34 mmol), DMF (1.0 ml), Et₃N (57 µl, 0.37 mmol), BOP reagent (167 mg, 0.37 mmol) and 2-thiophene methylamine (42 µl, 0.41 mmol) furnished the title compound (106 mg, 80%). M.P.: 103-105° C. ¹H-NMR (δ ppm, CDCl₃, 300 MHz): 7.70-7.58 (m, 1H); 7.24-7.12 (m, 2H); 7.05-6.94 (m, 4H); 4.78 (d, J=4.5, 2H); 3.77 (br. s, 1H); 3.44 (br. s, 1H); 2.08 (d, J=6.3, 1H); 2.02-1.89 (m, 2H); 1.69 (d, J=9.0, 1H); 1.34-1.20 (m, 2H).

Example 332

N(3)-[(1S)-2-Hydroxy-1)-(4-fluorophenyl)ethyl]-1-(2,4-difluorophenyl)-4,5,6,7-tetrahydro-1H-4,7-methano-indazole-3-carboxamide The title compound was synthesized by a procedure similar to that described for example 191. Example 326 (400 mg, 0.87 mmol), THF (6 ml) and LiBH4 (38 mg, 1.75 mmol) furnished the title compound (288 mg, 76%). M.P.: 116-119° C. ¹H-NMR (δ ppm, CDCl₃, 300 MHz): 7.65 (q, J=8.4, 1H); 7.49-7.41 (m, 1H); 7.40-7.32 (m, 2H); 7.08-6.96 (m, 4H); 5.24-5.18 (m, 1H); 3.96 (d, J=5.1, 2H); 3.72 (br. s, 1H); 3.44 (br. s, 1H); 2.12-2.02 (m, 2H); 1.99-1.92 (m, 2H); 1.68 (d, J=8.7, 1H); 1.28-1.20 (m, 2H).

Example 333

Methyl-(2S)-2-[5-(2,4-difluorophenyl)-4,5-diazatricyclo[5.2.1.0²,⁶]deca-2(6),3-dien-3-ylcarboxamido]-4-methylpentanoate The title compound was synthesized by a procedure similar to that described for example 101. Intermediate 21 (100 mg, 0.34 mmol), DMF (1.0 ml), Et₃N (104 µl, 0.74 mmol), BOP reagent (159 mg, 0.37 mmol) and L-leucine methyl ester hydrochloride (75 mg, 0.50 mmol) furnished the title compound (87 mg, 60%) as a waxy solid. ¹H-NMR (δ ppm, CDCl₃, 300 MHz): 7.78-7.65 (m, 1H); 7.21-7.10 (m, 1H); 7.12-6.95 (m, 2H); 4.90-4.75 (m, 1H); 3.75 (s, 4H); 3.45 (br. s, 1H); 2.12-2.02 (m, 1H); 2.00-1.90 (m, 2H); 1.80-1.60 (m, 6H); 1.34-1.18 (m, 2H), 1.02-0.90 (m, 4H).

Example 334

N(3)-(Adamantan-1yl)-1-(2,4-difluorophenyl)-4,5,6,7-tetrahydro-1H-4,7-methano-indazole-3-carboxamide The title compound was synthesized by a procedure similar to that described for example 101. Intermediate 21 (100 mg, 0.34 mmol), DMF (1.0 ml), Et₃N (50 µl, 0.37 mmol), BOP reagent (159 mg, 0.36 mmol) and 1-adamantyl amine (78 mg, 0.51 mmol) furnished the title compound (88 mg, 60%). M.P.: 146-148° C. ¹H-NMR (δ ppm, CDCl₃, 300 MHz): 7.72-7.60

(m, 1H); 7.04-6.94 (m, 2H); 6.61 (br. s, 1H); 3.73 (br. s. 1H); 3.42 (br. s, 1H); 2.20-2.03 (m, 10H); 1.98-1.92 (m, 2H); 1.80-1.52 (m, 4H); 1.44-1.19 (m, 5H).

Example 335a

N(3)-(tert-butyl)-1-(4-fluorobenzyl)-4,5,6,7-tetrahydro-1H-4,7-methano-indazole-3-carboxamide The title compound was synthesized by a procedure similar to that described for example 101. Intermediate 32a (100 mg, 0.34 mmol), DMF (1.0 ml), Et$_3$N (55 µl, 0.39 mmol), BOP reagent (162 mg, 0.36 mmol) and 2-amino-2-methylpropane (44 µl, 0.41 mmol) furnished the title compound (85 mg, 71%) as an oil. $^1$H-NMR (δ ppm, CDCl$_3$, 300 MHz): 7.24-7.14 (m, 2H); 7.04 (t, J=8.4, 2H); 6.67 (br. s, 1H); 5.18 (s, 2H); 3.64 (br. s, 1H); 3.03 (br. s, 1H); 1.98-1.65 (m, 3H), 1.55 (d, J=8.7, 1H); 1.45 (s, 9H); 1.18-1.08 (m, 1H); 0.86-0.74 (m, 1H).

Example 335b

N(3)-(tert-butyl)-2-(4-fluorobenzyl)-4,5,6,7-tetrahydro-1H-4,7-methano-indazole-3-carboxamide The title compound was synthesized by a procedure similar to that described for example 101. Intermediate 32b (50 mg, 0.17 mmol), DMF (1.0 ml), Et$_3$N (30 µl, 0.19 mmol), BOP reagent (80 mg, 0.18 mmol) and 2-amino-2-methylpropane (20 µl, 0.19 mmol) furnished the title compound (40 mg, 67%). M.P.: 130-134° C. $^1$H-NMR (δ ppm, CDCl$_3$, 300 MHz): 7.30-7.20 (m, 2H); 6.94 (t, J=8.7, 2H); 5.80 (d, J=14.7, 1H); 5.72 (br. s, 1H); 5.43 (d, J=14.4, 1H); 3.40 (br. s, 1H); 3.29 (br. s, 1H), 1.98-1.88 (m, 3H); 1.68 (d, J=8.4, 1H); 1.42 (s, 9H); 1.21 (d, J=9.6, 2H).

Example 336a

N(3)-(tert-butyl)-1-(4-methylbenzyl)-4,5,6,7-tetrahydro-1H-4,7-methano-indazole-3-carboxamide The title compound was synthesized by a procedure similar to that described for example 101. Intermediate 31a (100 mg, 0.35 mmol), DMF (1.0 ml), Et$_3$N (55 µl, 0.39 mmol), BOP reagent (164 mg, 0.37 mmol) and 2-amino-2-methylpropane (56 µl, 0.53 mmol) furnished the title compound (71 mg, 65%). $^1$H-NMR (δ ppm, CDCl$_3$, 300 MHz): 7.16 (d, J=8.1, 2H); 7.10 (d, J=8.1, 2H); 6.69 (br. s, 1H); 5.17 (s, 2H); 3.63 (br. s, 1H); 2.99 (br. s, 1H); 2.34 (s, 3H), 1.94-1.78 (m, 2H); 1.72-1.64 (m, 1H); 1.53 (d, J=8.7, 1H); 1.45 (s, 9H); 1.18-1.08 (m, 1H); 0.90-0.78 (m, 1H).

Example 336b

N(3)-(tert-butyl)-2(4-methylbenzyl)-4,5,6,7-tetrahydro-1H-4,7-methano-indazole-3-carboxamide The title compound was synthesized by a procedure similar to that described for example 101. Intermediate 32b (68 mg, 0.24 mmol), DMF (1.0 ml), Et$_3$N (38 µl, 0.26 mmol), BOP reagent (111 mg, 0.25 mmol) and 2-amino-2-methylpropane (38 µl, 0.41 mmol) furnished the title compound (44 mg, 54%). M.P.: 142-1.44° C. $^1$H-NMR (δ ppm, CDCl$_3$, 300 MHz): 7.18 (d, J=7.8, 2H); 7.07 (d, J=7.8, 2H); 5.80 (d, J=14.7, 1H); 5.71 (br. s, 1H); 5.41 (d, J=14.7, 1H); 3.39 (br. s, 1H); 3.28 (br. s, 1H); 2.28 (s, 3H); 1.98-1.89 (m, 3H); 1.70-1.62 (m, 1H); 1.42 (s, 9H), 1.20 (d, J=9.0, 2H).

Example 401

N(3)-Phenyl-1-(2,4-dichlorophenyl)-7,8,8-trimethyl-4,5,6,7-tetrahydro-1H-4,7-methano-indazole-3-carboxamide The title compound was synthesized by a procedure similar to that described for example 101. Intermediate 22 (100 mg, 0.27 mmol), DMF (1.0 ml), Et$_3$N (43 µl, 0.30 mmol), BOP reagent (127 mg, 0.29 mmol) and aniline (28 µl, 0.30 mmol) furnished the title compound (85 mg, 71%). M.P.: 112-115° C. $^1$H-NMR (δ ppm, CDCl$_3$, 300 MHz): 8.64 (br. s, 1H); 7.67 (d, J=7.8, 2H); 7.59 (br. s, 1H); 7.47-7.25 (m, 4H); 7.09 (t, J=7.5, 1H); 3.29 (d, J=3.6, 1H); 2.22-2.08 (m, 1H); 1.83 (br. t, J=9.3, 1H); 1.43-1.20 (m, 2H); 0.93 (s, 6H); 0.85 (s, 3H). IR (cm$^{-1}$, KBr): 3274 (s), 3251 (s), 2955 (m), 2928 (s), 2869 (m), 1663 (s), 1517 (s), 1546 (s), 1533 (m), 1596 (s), 1502 (s), 1474 (m), 1436 (s), 1388 (m), 1345 (m), 1323 (s), 1252 (m), 1220 (m), 1229 (m), 1129 (m), 1117 (m), 1102 (m), 1077 (m), 1062 (s), 1014 (m), 1001 (m). MS (m/z): 440.3 ([M+H]$^+$).

Example 402

N(3)-[2-Fluorophenyl)amino]-1-(2,4-Dichlorophenyl)-7,8,8-trimethyl-4,5,6,7-tetrahydro-1H-4,7-methano-indazole-3-carboxamide The title compound was synthesized by a procedure similar to that described for example 101. Intermediate 22 (100 mg, 0.27 mmol), DMF (1.0 ml), Et$_3$N (43 µl, 0.30 mmol), BOP reagent (127 mg, 0.29 mmol) and 2-fluorophenyl hydrazine (49 mg, 0.30 mmol) to give the title compound (85 mg, 83%). M.P.: 72-80° C. $^1$H-NMR (δ ppm, CDCl$_3$, 300 MHz): 8.54 (br. s, 1H); 7.60 (br. s, 1H); 7.42 (d, J=8.4, 1H); 7.38 (d, J=8.7, 1H); 7.14-6.95 (m, 3H); 6.87-6.78 (m, 1H); 3.21 (d, J=3.3, 1H); 2.20-2.06 (m, 1H); 1.82 (br. t, J=9.0, 1H); 1.41-1.18 (m, 2H); 0.93 (s, 3H); 0.91 (s, 3H); 0.82 (s, 3H): IR (cm$^{-1}$, KBr): 3413 (m), 2912 (s), 2845 (m), 1667 (s), 1535 (s), 1497 (s), 1478 (s), 1352 (m), 1233 (m), 1219 (m), 1162 (m), 1103 (m), 1088 (m), 996 (m), 866 (w). MS (m/z): 473.10 ([M+H]$^+$).

Example 403

N(3)-[(2,4-fluorophenyl)amino]-1-(2,4-Dichlorophenyl)-7,8,8-trimethyl-4,5,6,7-tetrahydro-1H-4,7-methano-indazole-3-carboxamide The title compound was synthesized by a procedure similar to that described for example 101. Intermediate 22 (100 mg, 0.27 mmol), DMF (1.0 ml), Et$_3$N (43 µl, 0.31 mmol), BOP reagent (127 mg, 0.29 mmol) and 3,5-difluorophenylhydrazine hydrochloride (55 mg, 0.31 mmol) gave the title compound (90 mg, 67%). M.P.: 145-148° C. $^1$H-NMR (δ ppm, CDCl$_3$, 300 MHz): 8.78 (br. s, 1H); 7.60 (d, J=1.8, 1H); 7.45-7.35 (m, 2H); 7.10-6.98 (m, 1H); 6.86-6.70 (m, 2H); 3.22 (d, J=3.6, 1H); 2.20-2.05 (m, 1H); 1.88-1.80 (m, 1H); 1.40-1.20 (m, 2H); 0.93, 0.88, 0.82 (3s, 9H). IR (cm$^{-1}$, KBr): 3339 (m), 3269 (m), 2979 (m), 2961 (m), 1678 (s), 1508 (s), 1472 (m), 1211 (m), 1132 (m), 1102 (m), 959 (m), 844 (m). MS (m/z): 491.10 ([M+H]$^+$).

Example 404

N(3)-[(3-chloropyridin-2-yl)amino]-1-(2,4-Dichlorophenyl)-7,8,8-trimethyl-4,5,6,7-tetrahydro-1H-4,7-methano-indazole-3-carboxamide The title compound was synthesized by a procedure similar to that described for example 101. Intermediate 22 (100 mg, 0.27 mmol), DMF (1.0 ml), Et₃N (43 µl, 0.31 mmol), BOP reagent (127 mg, 0.29 mmol) and 3-chloro-2-hydrazinopyridine (45 mg, 0.31 mmol) to give the title compound (75 mg, 56%). M.P.: 142-145° C. $^1$H-NMR (3 ppm, DMSO-d₆, 300 MHz): 9.88 (br. s, 1H); 8.42 (br. s, 1H); 8.00 (d, J=9.6, 2H); 7.30-7.55 (m, 3H); 6.75 (br. s, 1H); 3.05 (br. s, 1H); 2.09 (br. s, 1H); 1.80 (br. s, 1H); 1.40-1.05 (m, 2H); 0.88, 0.86, 0.80 (3s, 9H). IR (cm⁻¹, KBr): 3339 (m), 3269 (m), 2961 (m), 2979 (m), 1678 (s), 1508 (s), 1472 (m), 1437 (m), 1312 (m), 1211 (m), 1132 (m), 1102 (m), 959 (m), 844 (m). MS (m/z): 490.00 ([M+H]⁺).

Example 405

N(3)-(Adamantan-1-yl)-1-(2,4-difluorophenyl)-7,8,8-trimethyl-4,5,6,7-tetrahydro-1H-4,7-methano-indazole-3-carboxamide The title compound was synthesized by a procedure similar to that described for example 101. Intermediate 23 (120 mg, 0.36 mmol), DMF (1.0 ml), Et₃N (60 µl, 0.43 mmol), BOP reagent (159 mg, 0.36 mmol) and 1-adamantylamine (54 mg, 0.36 mmol) furnished the title compound (120 mg, 71%). M.P.: 162-165° C. $^1$H-NMR (δ ppm, CDCl₃, 300 MHz): 7.50-7.40 (m, 1H); 7.03-6.93 (m, 2H); 6.59 (s, 1H); 3.21 (d, J=3.6, 1H); 2.13-2.07 (m, 9H); 1.84-1.63 (m, 7H); 1.37-1.24 (m, 3H); 0.97 (s, 3H); 0.90 (s, 3H); 0.77 (s, 3H). IR (cm⁻¹, KBr): 3299 (m), 2958 (m), 2910 (s), 1652 (s), 1614 (m), 1605 (m), 1548 (s), 1524 (s), 1499 (s), 1454 (m), 1358 (m), 1324 (w), 1269 (m), 1224 (s), 1202 (m), 1143 (m), 1121 (w), 1017 (w), 981 (w), 945 (w), 847 (m). MS (m/z): 466.2 ([M+H]⁺).

Example 406

N(3)-(1,3,3-Trimethylbicyclo[2.2.1]hept-2-yl)-1-(2,4-difluorophenyl)-7,8,8-trimethyl-4,5,6,7-tetrahydro-1H-4,7-methano-indazole-3-carboxamide The title compound was synthesized by a procedure similar to that described for example 101. Intermediate 23 (120 mg, 0.36 mmol), DMF (1.0 ml), Et₃N (120 µl, 0.86 mmol), BOP reagent (159 mg, 0.36 mmol) and 1S,2endo-1,3,3-trimethylbicyclo[2.2.1]hept-2-*mine hydrochloride (68 mg, 0.36 mmol) furnished the title compound (95 mg, 57%). M.P.: 1.71-173° C. $^1$H-NMR (δ ppm, CDCl₃, 300 MHz): 7.56-7.45 (m, 1H), 7.05-6.90 (m, 2H); 6.89 (d, J=9.0, 1H); 3.76 (d, J=9.0, 1H); 3.22 (t, J=3.9, 1H); 2.19-2.06 (m, 1H); 1.86-1.62 (m, 4H); 1.54-0.74 (m, 24H). IR (cm⁻¹, KBr): 3419 (m), 2954 (s), 2871 (s), 1672 (s), 1612 (m), 1542 (s), 1521 (s), 1493 (s), 1388 (m), 1328 (w), 1318 (w), 1220 (m), 1176 (w), 1117 (s), 1087 (m), 1018 (m), 962(m), 859 (m), 791(w). MS (m/z): 468.3 ([M+H]⁺).

Example 407

N(3)-(1-Methyl-1-phenylethyl))-1-(2,4-difluorophenyl)-7,8,8-trimethyl-4,5,6,7-tetrahydro-1H-4,7-methano-indazole-3-carboxamide The title compound was synthesized by a procedure similar to that described for example 101. Intermediate 23 (120 mg, 0.36 mmol), DMF (1.0 ml), Et₃N (60 µl, 0.43 mmol), BOP reagent (159 mg, 0.36 mmol) and 2-phenylprop-2-ylamine (48 mg, 0.36 mmol) furnished the title compound (107 mg, 66%). M.P.: 114-117° C. $^1$H-NMR (δ ppm, CDCl₃, 300 MHz): 7.82-7.73 (m, 1H); 7.66-7.54 (m, 2H); 7.39 (d, J=7.8, 2H); 7.35-7.26 (m, 3H); 7.22-7.15 (m, 1H); 2.95 (hr. d, J=2.7, 1H); 2.12-2.05 (m, 1H); 1.85-1.74 (m, 1H); 1.65 (d, J=9.6, 2H); 1.30-0.95 (m, 1H); 0.90 (s, 3H); 0.85 (s, 3H); 0.71 (s, 3H). IR (cm⁻¹, KBr): 3390 (m), 2973 (m), 2931 (m), 2871 (m), 1605 (w), 1583 (w), 1542 (s), 1526(s), 1494 (s), 1446 (m), 1392 (w), 1378 (w), 1360 (w), 1319 (w), 1268 (m), 1108 (m), 928 (m), 870 (m), 766 (m). MS (m/z): 450.0 ([M+]⁺).

Example 408

N(3)-tert-Butyl-1-(2,4-difluorophenyl)-7,8,8-trimethyl-4,5,6,7-tetrahydro-1H-methano-indazole-3-carboxamide The title compound was synthesized by a procedure similar to that described for example 101. Intermediate 23 (100 mg, 0.30 mmol), DMF (1.0 ml), Et₃N (46 µl, 0.33 mmol), BOP reagent (139 mg, 0.31 mmol) and tert-Butylamine (32 mg, 0.45 mmol) furnished the title compound (90 mg, 77%). M.P.: 150-154° C. $^1$H-NMR (δ ppm, CDCl₃, 300 MHz): 7.53-7.43 (m, 1H); 7.03-6.95 (m, 2H); 6.71 (br. s, 1H); 3.22 (d, J=3.9, 1H); 2.13-2.06 (m, 1H); 1.84-1.76 (m, 1H); 1.45 (s, 9H); 1.32-1.24 (m, 2H); 0.97, 0.90, 0.78 (3s, 9H). IR (cm⁻¹, KBr): 3402 (s), 3070 (w), 2966 (s), 2873 (m), 1671 (s), 1613 (m), 1549 (m), 1500 (s), 1472 (w), 1448 (m), 1390 (m), 1.364 (m), 1322 (m), 1268 (s), 1219 (m), 1139 (s), 1116 (m), 1090 (m), 1018 (m), 961 (m), 861 (m), 846 (m). MS (m/z): 388.2 ([M+H]⁺).

Example 409

Methyl (2R)-2-[1-(2,4-difluorophenyl)-7,8,8-trimethyl-4,5,6,7-tetrahydro-1H-4,7-methano-indazole-3-carboxamido]-2-phenylethanoate The title compound was synthesized by a procedure similar to that described for example 101. Intermediate 23 (300 mg, 0.90 mmol), DMF (4.0 ml), Et₃N (284 µl, 0.33 mmol), BOP reagent (418 mg, 0.94 mmol) and (R)-(–)-2-phenylglycine methylester hydrochloride (272 mg, 1.35 mmol) furnished the title compound (290 mg, 67%). M.P.: 107-109° C. $^1$H-NMR (δ ppm, DMSO-d₆, 300 MHz): 8.42-8.36 (m, 1H); 7.78-7.72 (m, 1H); 7.63-7.56 (m, 1H); 7.44-7.28 (m, 6H); 5.64 (d, J=7.5, 1H); 3.65, 3.64 (2s, 3H); 3.03 (br. s, 1H); 2.12-2.02 (m, 1H); 1.84-1.76 (m, 1H); 1.26-1.20 (m, 1H); 1.12-1.00 (m, 1H); 0.91, 0.88 (2s, 6H); 0.74, 0.70 (2s, 3H). MS (m/z): 480.24 ([M+H]⁺).

Example 410

N(3)-[(1R)-Hydroxy-1-phenylethyl]-1-(2,4-difluorophenyl)-7,8,8-trimethyl)-4,5,6,7-tetrahydro-1H-4,7-methano-indazole-3-carboxamide The title compound was synthesized by a procedure similar to that described for example 192. Example 409 (170 mg, 0.34 mmol), THF (3 ml) and LiBH₄ (15 mg, 0.68 mmol) furnished the title compound (120 mg, 75%). M.P.: 68-70° C. $^1$H-NMR (δ ppm, CDCl₃, 300 MHz): 7.52-7.42 (m, 1H); 7.40-7.30 (m, 6H); 7.04-6.94 (m, 2H); 5.26-5.16 (m, 1H), 4.04-3.94 (m, 2H); 3.20 (d, J=3.6, 1H); 3.02 (br. s, 1H);

2.13-2.06 (m, 1H); 1.84-1.76 (m, 1H); 1.34-1.20 (m, 2H); 0.98, 0.91 (2s, 6H); 0.79, 0.76 (2s, 3H). MS (m/z): 452.17 (M+H$^+$).

Example 411

(4S,7R)—N(3)-tert-Butyl-1-(2,4-difluorophenyl)-7,8,8-trimethyl-4,5,6,7-tetrahydro-1H-methano-indazole-3-carboxamide The title compound was synthesized by a procedure similar to that described for example 101. Intermediate 23 (100 mg, 0.30 mmol), DMF (1.0 ml), Et$_3$N (45 μl, 0.33 mmol), BOP reagent (139 mg, 0.31 mmol) and 2-amino-2-methylpropane (47 μl, 0.45 mmol) furnished the title compound (65 mg, 56%). M.P.: 173-175° C. $^1$H-NMR (δ ppm, CDCl$_3$, 300 MHz): 7.54-7.44 (m, 1H); 7.04-6.94 (m, 2H); 6.73 (br. s, 1H); 3.22 (d, J=3.6, 1H); 2.13-2.06 (m, 1H); 1.85-1.76 (m, 1H); 1.45 (s, 9H); 1.33-1.24 (m, 2H); 0.97, 0.90, 0.78 (3s, 9H).

Example 501

N(12)-Benzyl-10-(2,4-dichlorophenyl)-10,11-diazatetracyclo[6.5.2.0$^{2,7}$.0$^{9,13}$]pentadeca-2,4,6,9(13),11-pentaene-12-carboxamide The title compound was synthesized by a procedure similar to that described for example 101. Intermediate 24 (90 mg, 0.23 mmol), DMF (1.0 ml), Et$_3$N (36 μl, 0.26 mmol), BOP reagent (103 mg, 0.23 mmol) and benzylamine (25 μl, 0.23 mmol) yielded the title compound (40 mg, 33%). M.P.; 164-166° C. $^1$H-NMR (δ ppm, CDCl$_3$, 300 MHz): 7.60 (s, 1H); 7.40-7.22 (m, 8H); 7.20-7.00 (m, 4 H); 5.06 (s, 1H); 4.60 (d, J=6.3, 2H); 4.28 (s, 1H); 2.00-1.70 (m, 4H). MS (an/z): 474.0 ([M+H]$^+$).

Example 502

N(12)-Piperidino-10-(2,4-dichlorophenyl)-10,11-diazatetracyclo[6.5.2.0$^{2,7}$.0$^{9,13}$]pentadeca-2,4,6,9(13),11-pentaene-12-carboxamide The title compound was synthesized by a procedure similar to that described for example 101. Intermediate 24 (90 mg, 0.23 mmol), DMF (1.0 ml), Et$_3$N (36 μl, 0.26 mmol), BOP reagent (105 mg, 0.24 mmol) and 1-aminopiperidine (26 μl, 0.23 mmol) yielded the title compound (40 mg, 37%). M.P.: 164-166° C. $^1$H-NMR (δ ppm, CDCl$_3$, 300 MHz): 7.61 (s, 1H); 7.44-7.32 (m, 3H); 7.16-7.05 (m, 4 H); 5.02 (s, 1H); 4.27 (s, 1H); 2.83 (br. s, 4H); 2.20-1.70 (m, 8H); 1.41 (br. s, 2H). IR (cm$^{-1}$, KBr): 2934 (s), 2854 (m), 1648 (s), 1551 (m), 1509 (s), 1488 (s), 1441 (s), 1381 (m), 1355 (m), 1342 (m), 1146 (m), 1097 (m), 1070 (m), 898 (m), 818 (w). MS (m/z): 467.0 ([M+H]$^+$).

Example 503

N(12)-Piperidino-10-(2,4-dichlorophenyl)-10,11-diazatetracyclo[6.5.2.0$^{2,7}$.0$^{9,13}$]pentadeca-2,4,6,9(13),11-pentaene-12-carboxamide hydrochloride A solution of example 502 (250 mg, 0.53 mmol) in ether (5 ml) was treated with ether saturated with HCl (10 ml) and maintained at RT for 1 hour and the precipitated solid was concentrated to yield the title compound (200 mg, 74%). M.P.: 100-110° C. $^1$H-NMR (δ ppm, CDCl$_3$, 300 MHz): 7.61 (s, 1H); 7.58 (br. s, 1H); 7.41 (s, 2H); 7.33 (d, J=7.5, 1H); 7.15-7.00 (m, 3H); 5.03 (br. s, 1H); 4.27 (br. s, 1H); 2.86 (br. s, 4H); 1.80-1.70 (m, 8H); 1.43 (br. s, 2H).

Example 504

N(12)-[(N'-Cyclohexyl-N'-methyl)amino]-10-(2,4-dichlorophenyl)-10,11-diazatetracyclo[6.5.2.0$^{2,7}$.0$^{9,13}$]pentadeca-2,4,6,9(13),11-pentaene-12-carboxamide The title compound was synthesized by a procedure similar to that described for example 101. Intermediate 24 (100 mg, 0.26 mmol), DMF (1.0 ml), Et$_3$N (40 μl, 0.29 mmol), BOP reagent (121 mg, 0.27 mmol) and N-cyclohexyl-N-methyl hydrazine (37 mg, 0.29 mmol) to give the title compound (70 mg, 55%). M.P.: 127-132° C. $^1$H-NMR (δ ppm, CDCl$_3$, 300 MHz): 7.62 (s, 1H); 7.52 (br. s, 1H); 7.42-7.20 (m, 3H); 7.20-7.00 (m, 3H); 5.05 (s, 1H); 4.28 (s, 1H); 2.69 (s, 3H); 2.82-2.55 (m, 1H); 1.96 (br. s, 2H); 1.88-1.70 (m, 6H); 1.40-1.00 (m, 6H). IR (cm$^{-1}$, KBr): 3422 (s), 2930 (s), 2854 (s), 1667 (s), 1508 (s), 1474 (s), 1381 (m), 1354 (m), 1280 (m), 1248 (w), 1134 (m), 1118 (m), 1083 (m), 1012 (m), 815 (m). MS (m/z): 495.1 ([M+H]$^+$).

Example 505

N(12)-[N'-(2,4-Dichlorophenyl)-N'-methyl]amino)-10-(2,4-dichlorophenyl)-10,11-diazatetracyclo[6.5.2.0$^{2,7}$.0$^{9,13}$]pentadeca-2,4,6,9(13),11-pentaene-12-carboxamide The title compound was synthesized by a procedure similar to that described for example 101. Intermediate 24 (100 mg, 0.26 mmol), DMF (1.0 ml), Et$_3$N (40 μl, 0.29 mmol), BOP reagent (120 mg, 0.27 mmol) and N-(2,4-dichlorophenyl)-N-methylhydrazine (88 mg, 0.46 mmol) to give the title compound (80 mg, 55%). M.P.: 220-223° C. $^1$H-NMR (δ ppm, CDCl$_3$, 300 MHz): 8.82 (s, 1H); 7.61 (d, J=1.2, 1H); 7.42-7.24 (m, 6 H); 7.15-7.05 (m, 3H); 4.94 (s, 1H); 4.28 (s, 1H); 3.33 (s, 3H); 1.79-1.69 (m, 4H). IR (cm$^{-1}$, KBr): 3376 (s), 3005 (w), 2964 (m), 2867 (m), 1682 (s), 1546 (m), 1500 s), 1471 (s), 1352 (m), 1271 (m), 1241 (m), 1116 (m), 1100 (m), 81.1 (m), 759 (m). MS (m/z) 556.9 ([M+H]$^+$).

Example 506

N(12)-(Adamantan-1yl)-10-(2,4-dichlorophenyl)-10,11-diazatetracyclo[6.5.2.0$^{2,7}$.0$^{9,13}$]pentadeca-2,4,6,9(13),11-pentaene-12-carboxamide The title compound was synthesized by a procedure similar to that described for example 101. Intermediate 24 (100 mg, 0.26 mmol), DMF (1 ml), Et$_3$N (40 μl, 0.28 mmol), BOP reagent (121 mg, 0.27 mmol) and 1-adamantylamine (43 mg, 0.28 mmol) furnished the title compound (80 mg, 59%). M.P.: 120-124° C. $^1$H-NMR (δ ppm, CDCl$_3$, 300 MHz): 7.60 (s, 1H); 7.46-7.31 (m, 3H); 7.20-6.99 (m, 3H); 6.59 (br. s 3H); 5.04 (br. s, 1H); 4.26 (br. s, 1H); 2.12 (br. s, 9H); 1.90-1.54 (m, 10H). IR (cm$^{-1}$, KBr): 3396 (m), 2906 (s), 2849 (s), 1670 (s), 1548 (s), 1537 (s), 1508 (s), 1483 (s), 1457 (m), 1356 (m),

Example 507

N12-(1,3,3-Trimethylbicyclo[2.2.1]hept-2-yl)-10-(2,4-dichlorophenyl)-10,11-diazatetracyclo[6.5.2.0$^{2,7}$.0$^{9,13}$]pentadeca-2(7),3,5,9(13),11-pentaene-12-carboxamide The title compound was synthesized by a procedure similar to that described for example 101. Intermediate 24 (100 mg, 0.26 mmol), DMF (1.0 ml), Et$_3$N (40 µl, 0.28 mmol), BOP reagent (120 mg, 0.27 mmol) and 1S,2endo-amino-1,3,3-trimethyl-bicyclo[2.2.1]heptane (43 mg, 0.28 mmol) furnished the title compound (95 mg, 70%). M.P.: 82-85° C. $^1$H-NMR (δ ppm, CDCl$_3$, 300 MHz): 7.60 (br. s, 1H), 7.43-7.07 (m, 6H); 6.92 (d, J=7.8, 1H); 5.04 (br. s, 1H); 4.29 (br. s, 1H); 3.77 (br. s, 1H); 1.92-1.58 (m, 8H); 1.42-0.76 (m, 12H).

Example 508

N12-(1-Methyl-1-phenylethyl)-10-(2,4,dichlorophenyl)-10,11-diazatetracyclo[6.5.2.0$^{2,7}$.0$^{9,13}$]pentadeca-2,4,6,9(13),11-pentaene-12-carboxamide The title compound was synthesized by a procedure similar to that described for example 101. Intermediate 24 (100 mg, 0.26 mmol), DMF (1.0 ml), Et$_3$N (41 µl, 0.28 mmol), BOP reagent (120 mg, 0.27 mmol) and α,α-dimethylbenzylamine (56 mg, 0.41 mmol) furnished the title compound (70 mg, 53%), M.P.: 190° C. $^1$H-NMR (δ ppm, CDCl$_3$, 300 MHz): 7.61 (br. s, 1H); 7.45-7.05 (m, 12H); 4.98 (br. s, 1H); 4.26 (br. s. 1H); 1.80 (s, 3H); 1.77 (s, 3H); 1.75-1.58 (m, 4H).

Example 509

N12-(1-Methyl-1-phenylethyl)-10-(2,4-difluorophenyl)-10,11-diazatetracyclo[6.5.2.0$^{2,7}$.0$^{9,13}$]pentadeca-2,4,6,9(13),11-pentaene-12-carboxamide The title compound was synthesized by a procedure similar to that described for example 101. Intermediate 25 (100 mg, 0.28 mmol), DMF (1.0 ml), Et$_3$N (44 µl, 0.31 mmol), BOP reagent (131 mg, 0.29 mmol) and α,α-dimethylbenzylamine (58 mg, 0.42 mmol) furnished the title compound (78 mg, 58%). M.P.: 175-178° C. $^1$H-NMR (δ ppm, CDCl$_3$, 300 MHz): 7.64-7.54 (m, 1H); 7.43 (d, J=7.5, 2H); 7.35-7.02 (m, 10H); 4.98 (br. s, 1H); 4.35 (br. s, 1H); 1.81, 1.77 (2s, 6H); 1.80-1.68 (m, 4H). IR (cm$^{-1}$, KBr): 3403 (s), 3077 (m), 2961 (m), 2973 (m), 1665 (s), 1609 (m), 1526 (s), 1493 (s), 1471 (m), 1446 (m), 1383 (w), 1.361 (w), 1328 (w), 1269 (m), 1256 (m), 1160 (m), 1146 (m), 1095 (m), 846 (m), 758 (m), 699 (m). MS (m/z); 470.2 ([M+H]$^+$).

Example 601

N(12)-Benzyl-16-(4-chlorophenyl)-10-(2,4-dichlorophenyl)-15,17-dioxo-10,11,16-triazapentacyclo[6.5.5.0$^{2,7}$. 0$^{9,13}$. 0$^{14,18}$]octadeca-2,4,6,9(13),11-pentaene-12-carboxamide The title compound was synthesized by a procedure similar to that described for example 101. Intermediate 26 (100 mg, 0.29 mmol), DMF (1.0 ml), Et$_3$N (49 µl, 0.35 mmol), BOP reagent (130 mg, 0.29 mmol) and α,α-dimethylbenzylamine (47 mg, 0.35 mmol) furnished the title compound (90 mg, 67%). M.P.: 84-87° C. $^1$H-NMR (δ ppm, CDCl$_3$, 300 MHz): 7.92-7.79 (m, 2H), 7.71-7.61 (m, 1H); 7.41-7.15 (m, 8H); 6.98-6.90 (m, 2H); 4.43 (br. s, 1H); 4.36 (s, 1H); 2.88 (d, J=7.8, 1H); 2.70 (d, J=7.5, 1H); 1.66, 1.64 (2s, 6H); IR (cm$^{-1}$, KBr): 3404 (m), 2974 (w), 2933 (w), 2867 (w), 1679 (s), 1608 (w), 1522 (s), 1507 (m), 1447 (m), 1382 (w), 1362 (w), 1347 (w), 1270 (m), 1257 (m), 1209 (m), 1133 (m), 1029 (w), 1006 (w), 965 (m), 847 (m), 786 (w), 761(m). MS (m/z): 456.2 [M+H]$^+$); 338.1 (100).

Example 602

N(12)-Piperidino-16-(4-chlorophenyl)-10-(2,4-dichlorophenyl)-15,17-dioxo-10,11,16-triazapentacyclo[6.5.5.0$^{2,7}$. 0$^{9,13}$. 0$^{14,18}$]octadeca-2,4,6,9(13),11-pentaene-12-carboxamide The title compound was synthesized by a procedure similar to that described for example 101. Intermediate 26 (100 mg, 0.18 mmol), DMF (1.0 ml), Et$_3$N (30 µl, 0.20 mmol), BOP reagent (85 mg, 0.19 mmol) and 1-aminopiperidine (22 µl, 0.20 mmol) afforded the title compound (35 mg, 31%). M.P.: 150° C. $^1$H-NMR (δ ppm, CDCl$_3$, 300 MHz): 7.66 (s, 1H); 7.60 (br. s, 1H); 7.46-7.40 (m, 3H); 7.26-7.17 (m, 5H); 6.44 (d, J=8.4, 2H); 5.58 (d, J=3.3, 1H); 4.81 (d, J=1H); 3.58 (dd, J=8.4, 3.3, 1H); 3.46 (dd, J=8.1, 3.3, 1H); 2.89-1.20 (m, 10H). IR (cm$^{-1}$, KBr): MS (m/z): 646.2 ([M+H]$^+$).

Example 701

N12-Benzyl-10-(2,4-difluorophenyl)-10,11-diazatetracyclo[6.5.1.0$^{2,7}$.0$^{9,13}$]tetradeca-2,4,6,9(13),11-pentaene-12-carboxamide The title compound was synthesized by a procedure similar to that described for example 101. Intermediate 27 (100 mg, 0.29 mmol), DMF (1.0 ml), Et$_3$N (49 µl, 0.35 mmol), BOP reagent (130 mg, 0.29 mmol) and benzyl amine (32 µl, 0.29 mmol) furnished the title compound (90 mg, 71%). M.P.: 65-67° C. $^1$H-NMR (δ ppm, CDCl$_3$, 300 MHz): 8.70 (br. s, 1H); 7.85-7.75 (m, 1H); 7.65 (t, J=9.0, 1H); 7.23-7.30 (m, 8H); 6.95 (br. d, J=2.9, 2H); 4.39-4.47 (m, 4H); 2.8.9 (d, J=7.5, 1H); 2.73 (d, J=7.5, 1H). IR (cm$^{-1}$, KBr): 3404 (m), 3063 (w), 2974 (w), 2933 (w), 2867 (w), 1679 (s), 1608 (w), 1522 (s), 1507 (s), 1447 (m), 1382 (w), 1362 (w), 1347 (w), 1270 (m), 1257 (m), 1209 (m), 1133 (m), 965 (m), 847 (w), 761 (m). MS (m/z): 428.2 [M+H]$^+$.

Example 702

N(12)-tert-Butyl-10-(2,4-difluorophenyl)-10,11-diazatetracyclo[6.5.1.0$^{2,7}$.0$^{9,13}$]tetradeca-2,4,6,9(13), 11-pentaene-12-carboxamide The title compound was synthesized by a procedure similar to that described for example 101. Intermediate 27 (100 mg, 0.29 mmol), DMF (1.0 ml), Et$_3$N (49 µl, 0.35 mmol), BOP reagent (143 mg, 0.32 mmol) and 2-amino-2-methylpropane (31 µl, 0.29 mmol) furnished the title compound (91 mg, 78%). M.P.: 59° C. $^1$H-NMR (δ ppm, CDCl$_3$, 300 MHz): 7.72-7.62 (m, 1H); 7.41 (d, J=5.7, 1H); 7.32-7.26 (m, 1H); 7.07-6.92 (m, 4H); 6.65 (br. s, 1H); 4.62 (br. s, 1H); 4.29 (br. s, 1H); 2.96 (d, J=7.5, 1H); 2.82 (d, J=7.5, 1H); 1.43 (s, 9H).

Example 801

N5-(tert-Butyl)-3-(2,4-difluorophenyl)-3,4-diazatricyclo[5.2.2.0$^{2,6}$]undeca-2(6),4-diene-5-carboxamide The title compound was synthesized by a procedure similar to that described for example 101. Intermediate 28 (100 mg, 0.32 mmol), DMF (1.0 ml), Et$_3$N (54 μl, 0.35 mmol), BOP reagent (159 mg, 0.36 mmol) and 2-amino-2-methylpropane (34 0.32 mmol) furnished the title compound (96 mg, 81%). M.P.: 105-108° C. $^1$H-NMR (δ ppm, CDCl$_3$, 300 MHz): 7.62-7.54 (m, 1H): 7.08-6.99 (m, 2H); 6.82 (br. s, 1H); 3.83 (br. s, 1H); 3.11 (br. s, 1H); 1.75 (d, J=6.6, 4H); 1.52-1.26 (m, 4H); 1.47 (s, 9H).

Example 802

N(5)-(tert-Pentyl)-3-(2,4-difluorophenyl)-3,4-diazatricyclo[5.2.2.0$^{2,6}$]undeca-2(6),4-diene-5-carboxamide The title compound was synthesized by a procedure similar to that described for example 101. Intermediate 28 (100 mg, 0.32 mmol), DMF (1.0 ml), Et$_3$N (54 μl, 0.39 mmol), BOP reagent (159 mg, 0.36 mmol) and tert-amyl amine (38 μl, 0.32 mmol) furnished the title compound (81 mg, 66%). M.P.: 102-105° C. $^1$H-NMR (δ ppm, CDCl$_3$, 300 MHz): 7.66-7.54 (m, 1H); 7.10-6.96 (m, 2H); 6.74 (br. s, 1H); 3.82 (br. s, 1H); 3.13 (br. s, 1H); 1.89-1.70 (m, 6H); 1.42 (s, 6H); 1.48-1.43 (m, 2H); 1.30-1.20 (m, 2H); 0.92 (t, J=7.2, 3H). MS (m/z): 374.1 ([M+H]$^+$).

Protocols

I. In vitro Protocol for Rat CB1 Receptor Binding Using Brain Membrane

In this assay, [$^3$H]SR141716A (5-(4-chlorophenyl)-1-(2,4-dichlorophenyl)-4-methyl-N-(1-piperidyl)pyrazole-3-carboxamide) was used to bind the CB1 receptor present in a rat brain membrane preparation which can be displaced by unlabeled ligands having affinity to the CB1 receptor.

The assay was performed according to the modified method of Thomas et al., 1998 (JET 285: 285-292). The total reaction mixture (250 ml) contained Tris-BSA buffer (50 mM Tris, pH 7.4 with 1.5% BSA) or unlabeled SR141716A. (1 mM) or test samples (1 mM), [$^3$H] SR141716A (2 nM) and 100 mg of rat brain membrane. The non-specific binding was defined by 1 mM of SR141716A. The assay mixture was incubated at 37° C. for 1 hour. The reaction was then stopped by rapid filtration under vacuum using Whatman GF/B-96 micro filter plate. A scintillation cocktail was added and radioactive counts were measured using a Topcount beta scintillation counter.

The standard and test sample dilutions were made in an assay buffer containing either ethanol or DMSO at a final concentration of 1%.

The percent (%) displacement by a test ligand was calculated by comparing the specific bound values. The results of the assay are shown in Table II below.

II. Protocol for In vitro Assay Using hCB1-CHO Membranes

In this assay, [$^3$H]-CP-55,940 ((−)-3-[2-hydroxyl-4-(1,1-dimethylheptyl)-phenyl]-4-[3-hydroxypropyl]cyclohexan-1-ol) was used as the radioligand to bind human CB1 receptors expressed on the membranes from CHO cells (the hCB1-CHO cell line was generated in-house) which can be displaced by unlabeled ligands having affinity to the CB1 receptor.

The assay was performed according to the modified method of Ross et al., 1999 (Br. J. Pharmacol. 128, 735-743). The reaction was set up in a total volume of 200 μl in PEI (Poly(ethyleneimine)) (0.2%) precoated Millipore GFB (Glass Fibre-B) filter plates. 1 mM stocks of test compounds were prepared in DMSO and tested at a final concentration of 300 nM. The non-specific binding was determined by 0.5 μM CP-55, 940. The total reaction mixture contained Tris-BSA buffer (50 mM Tris, 5 mM MgCl$_2$, 1 mM EDTA, pH 7.4 with 0.1% BSA), unlabelled CP-55, 940 (0.5 μM) or test samples, [$^3$H]-CP-55, 940 (0.75 nM) and 50 μg of human CB1 receptor preparation. The assay mixture (with or without the test compound) was incubated at 37° C. for 1 hour. The reaction was stopped by rapid filtration under vacuum and the radioactivity on the filters was measured by liquid scintillation counting. The results of the assay are shown in Table II below.

III. In vitro Protocol for Rat CB2 Receptor Binding Using Spleen Membrane

In this assay, [$^3$H]CP55,940 was used to bind the CB2 receptor present in a rat spleen membrane preparation which can be displaced by unlabeled ligands having affinity to the CB2 receptor.

The assay was performed according to the modified method of Rinaldi-Carmona et al., 1998 (WET 284: 644-650). The total reaction mixture (250 ml) contained Tris-BSA buffer (50 mM Tris, pH 7.4 with 1.5% BSA) or unlabeled SR144528 (N-[(1S)-endo-1,3,3-trimethyl bicyclo[2.2.1]heptan-2-yl]-5-(4-chloro-3-methylphenyl)-1-(4-methyl-benzyl)-pyrazole-3-carboxamide]) (1 mM) or test samples (300 nM), [$^3$H]CP55,940 (1 nM) and 100 mg of rat brain membrane. The non-specific binding was defined by 1 mM of SR 144528. The assay mixture was incubated at 37° C. for 1 hour. The reaction was then stopped by rapid filtration under vacuum using a Whatman GF/B-96 micro filter plate. A scintillation cocktail was added and radioactive counts were measured using a Topcount beta scintillation counter.

The standard and test sample dilutions were made in an assay buffer containing either ethanol or DMSO at a final concentration of 1%.

The percent (%) displacement by a test ligand was calculated by comparing the specific bound values. The results of the assay are shown in. Table II below.

IV. Protocol for In vitro Assay Using hCB2-CHO Membranes:

In this assay, [$^3$H]-CP-55,940 was used as the radioligand to bind human CB2 receptor expressed on the membranes from CHOcells (hCB2-CHO cell line was generated in-house) which can be displaced by unlabeled ligands having affinity to the CB2 receptor.

The assay was performed according to the modified method of Ross et al., 1999 (Br. J. Pharmacol. 128, 735-743). The reaction was set up in a total volume of 200 μl in PEI (0.2%) precoated Millipore GFB filter plates. 1 mM stocks of test compounds were prepared in DMSO and tested at a final concentration of 300 nM. The non-specific binding was determined by 0.5 μM CP-55, 940. The total reaction mixture contained. Tris-BSA buffer (50 mM Tris, 5 mM MgCl$_2$, 1 mM EDTA, pH 7.4 with 0.1% BSA), unlabelled CP-55, 940 (0.5 μM) or test samples, [$^3$H]-CP-55, 940 (0.75 nM) and 25-50 μg of human CB2 receptor preparation. The assay mixture (with or without the test compound) was incubated at 30° C. for 1 hour. The reaction was stopped by rapid filtration under vacuum and the radioactivity on the filters was measured by liquid scintillation counting.

The percent (%) displacement by a test ligand was calculated by comparing the specific bound values. The results of the assay are shown in Table II below.

V. Neuropathic Hyperalgesia Model—Partial Sciatic Nerve Ligation (Seltzer's Model)

This protocol was performed with the compound of Example 294 at 0.01, 0.1, 0.3, and 1 mg/kg (I.P.), and gabapentin at 100 mg/kg (I.P.) to evaluate the ability of the compound of Example 294 in reducing neuropathic hyperalgesia. The Seltzer method is also generally described in Seltzer et al., Pain 1990, 43:205-18.

1. Rats were anesthetised using ketamine/xylazine (40/5 mg/kg/ml, i.p.). After induction of anaesthesia, the left thigh was shaved and cleaned.
2. The left sciatic nerve was exposed at mid thigh level through a small incision.
3. The nerve was cleared from adhering muscle tissue.
4. One half of the nerve thickness was tightly ligated just after the bifurcation of common sciatic nerve using 7.0 silk sutures.
5. The wound was closed with muscle and skin sutures and povidone was applied.
6. The animals were allowed to recover for 12 to 15 days post ligation.
7. Mechanical hyperalgesia was examined in the model of rat neuropathic pain, using the paw pressure technique (Ugo Basile Analgesymeter, Cat. No. 37215, Comerio, Italy).
8. Paw withdrawal thresholds were recorded for both the ipsilateral and the contralateral hind paws before (predose) and 0.5 and 1 hour after drug or vehicle administration (postdose).
9. The cut-off was set at 150 g pressure and the endpoint was taken as paw withdrawal or vocalization.

Data Analysis:

The threshold withdrawal latency (naïve, predose & postdose) values are represented as mean±SEM. See Walker K M, Urban L A, Medhurst S J, Patel S, Panesar M, Fox A J and Mcintyre P., "The VR1 antagonist capsazepine reverses mechanical hyperalgesia in models of inflammatory and neuropathic pain", *J. Pharmacol. Expt. Ther.* 304: 56-62, 2003. The percent reversal of neuropathic mechanical hyperalgesia was calculated from withdrawal threshold latency values according to the following formula:

$$\% \text{ Reversal} = \frac{\text{Ipsilateral postdose} - \text{Ipsilateral predose}}{\text{Contralateral predose} - \text{Ipsilateral predose}} \times 100\%$$

Data statistical analyses were performed on the percent reversal values by one-way ANOVA followed by post hoc Tukey's test using GraphPad Prism software.

The results are shown in FIG. 1. 1 mg/kg of the compound of Example 294 significantly reversed neuropathic hyperalgesia in this model.

VI. Chronic Constriction Injury (CCI) to Sciatic Nerve Model (CCI Model)

This protocol was performed with the compound of Example 294 at 0.1 mg/kg (p.o), and gabapentin at 100 mg/kg (i.p.) to evaluate the ability of the compound of Example 294 in reducing neuropathic hyperalgesia. This method is also generally described in Miletic G and Miletic V, "Long-term changes in sciatic-evoked A-fiber dorsal horn field potentials accompany loose ligation of the sciatic nerve in rats," *Pain* 84:353-359, 2000.

1. Rats were anesthetised using ketamine/xylazine (40/5 mg/kg, i.p.). After induction of anaesthesia, the left thigh was shaved and cleaned.
2. The left sciatic nerve was exposed at mid thigh level through small incision.
3. The nerve was cleared from adhering muscle tissue.
4. Four loose ligatures of Ethicon 4-0 chromic gut (Johnson & Johnson) at 1 mm space were placed around the nerve after the bifurcation of common sciatic nerve.
5. The wound was closed with muscle and skin sutures & povidone was applied.
6. The animals were used for experiment after 7 days of ligation.
7. Mechanical hyperalgesia was examined in the model of rat neuropathic pain, using the paw pressure technique (Ugo Basile Analgesymeter, Cat. No. 37215, Comerio, Italy).
8. Paw withdrawal thresholds were recorded for both the ipsilateral and the contralateral hind paws before (predose) and 0.5 and 1 hour after drug or vehicle administration (postdose).
9. The cut-off was set at 150 g pressure and the endpoint was taken as paw withdrawal or vocalization.

Figure 2:
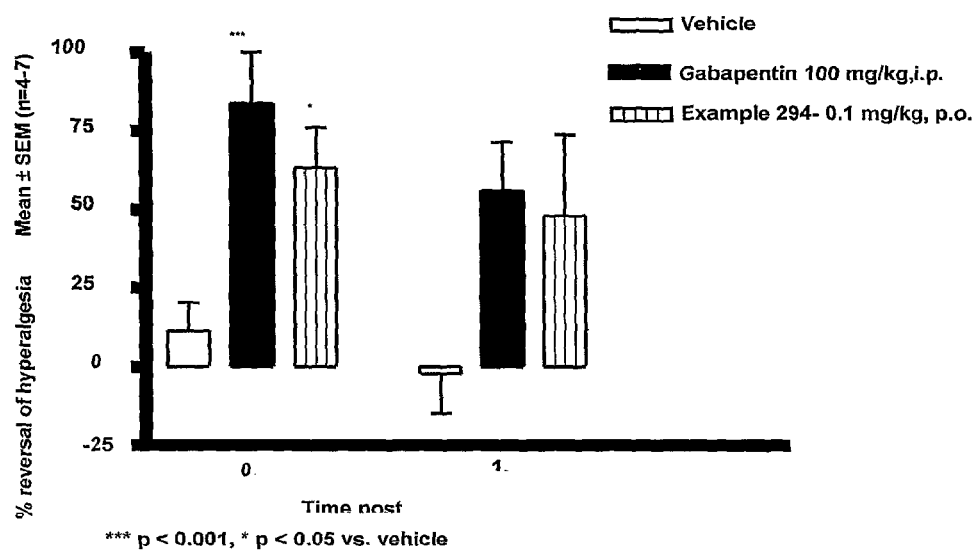
FIG. 2 is a bar graph of the mean percent reversal of neuropathic hyperalgesia (±SEM) as measured by the chronic constriction injury to sciatic nerve model (protocol VI) 0.5 and 1 hour after dosing with vehicle, 100 mg/kg gabapentin, or 0.1 mg/kg of the compound of Example 294.

Data analysis was performed as described in protocol V. The results are shown in FIG. 2.

VII. Tail-Flick Analgesia Testing in Mice

Tail flick latency (basal) was measured in naive mice at 55° C. treated with vehicle, WIN 55212-2 (a CB1 receptor agonist) (3 mg/kg i.p.), or Example 294 (0.3, 1, or 3 mg/kg i.p.) using a water bath (Julabo, Germany). See Murielle R., Barth F., Congy C., Martinez S., Oustric D., Perio A., Poncelet M., Maruani J., Arnone M., Finance O., Soubrie P., and Le'Fur G., "SR147778 (5-(4-Bromophenyl)-1-(2,4-dichlorophenyl)-4-ethyl-N-(1-piperidinyl)-1H-pyrazole-3-carboxamide), a New Potent and Selective Antagonist of the CB1 Cannabinoid Receptor:Biochemical and Pharmacological Characterization," *J. Pharmacol. Exp. Ther.*, 310: 905-914, 2004. The mice were given intraperitoneal (i.p.) injection of vehicle, standard or test drug. Analgesia was assessed by measuring tail flick latency (reaction) at 1, 3, 6, 12, and 18 hours post dosing. The cut-off latency was set at 10 Seconds and the endpoint was taken as tail flick response of the tail.

Data Analysis

The tail flick latency (basal & reaction) values were represented as mean± SEM. Maximum analgesia (% MPE) was calculated according to the following formula:

$$\% \text{ Maximum Possible analgesic effect} = \frac{(\text{Reaction latency} - \text{Basal latency})}{(\text{Cut-off latency} - \text{Basal latency})} \times 100$$

Figure 3:
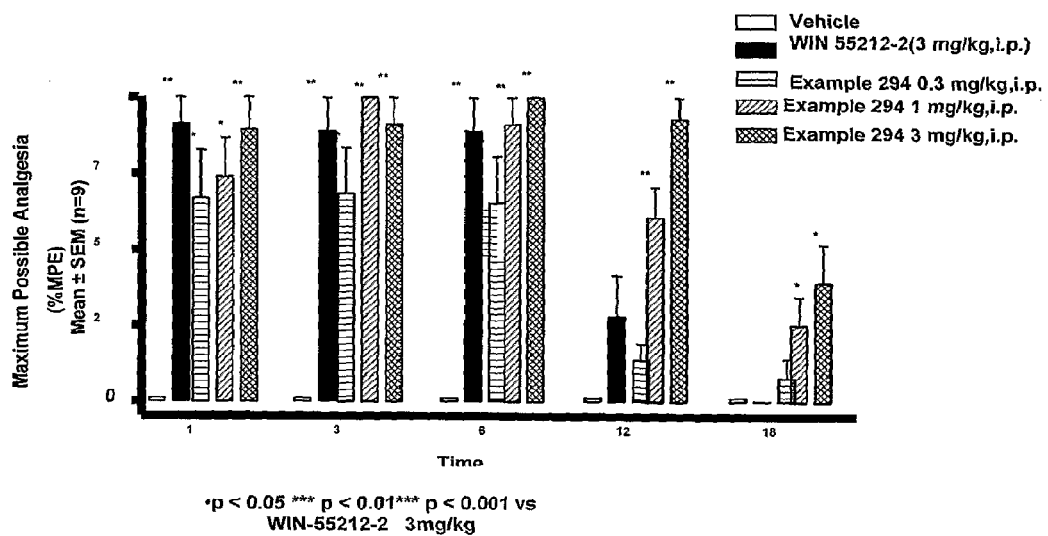
FIG. 3 is a bar graph of the mean percent of maximum possible analgesia (MPE) (±SEM) as measured by the tail-flick method (protocol VII) 1, 3, 6, 12, and 18 hours after dosing with vehicle, 3 mg/kg (i.p.) WIN 55212-2, or 0.3, 1, or 3 mg/kg (i.p.) of the compound of Example 294.

Data analyses were performed on the percent MPE values by one-way ANOVA followed by post hoc Tukey's test. The results are shown in FIG. 3.

VIII. Protocol for GTPγS Binding, Assay (CB1 Functional Assay in Rat Cerebellar Membrane)

In this GTPγS binding assay, total, basal and nonspecific binding were determined. See Griffin G., Atkinson P. J., Showalter V. M., Martin. B. R. and Abood M. E., "Evaluation of cannabinoid receptor agonists and antagonists using the Guanosine-5'-O-(3-($^{35}$S)thio)-triphosphate binding assay in rat cerebellar membranes," *J Pharmacol Exp Ther* 285: 553-560, 1998. Three wells for total binding, three wells for basal binding, and three wells for nonspecific binding at 0.2 nM concentration of radioligand were used. Basal binding was defined by 50 μM GDP (Guanosine diphosphate) and nonspecific binding was defined by 10 μM unlabeled GTPγS. 10 μg rat cerebellum membrane, 50 μM of GDP, WIN-55212-2 or test compound (1 μM or 300 nM), 10 μM unlabeled GTPγS, and 0.2 nM of [$^{35}$S]GTPγS were added into a 96 well plate and the final volume of the reaction mixture was made with GTPγS buffer (50 mM Tris, 3 mM anhydrous MgCl$_2$, 0.2 mM EGTA and 100 mM NaCl pH 7.4) to 200 μl. The plates were incubated at 30° C. for 1 hour. Then the reaction was stopped by filtration using a Whatman GF/B-96 microfilter plate. Three washings were given using Tris-HCl. The radioactivity bound to the brain membrane was retained on the filter disks to which scintillation fluid was added (Microscint PS). Then plates were read for radioactive counts using a Beta Liquid Scintillation Counter (Packard Instruments, IL, USA).

The rat cerebellar brain membrane was prepared as follow:
1. Sacrifice the rat and take out the whole brain and separate cerebellum as fast as possible and keep it on ice.
2. Take the weight of the cerebellum and homogenize in 30 ml of homogenizing buffer (50 mM Tris-HCL containing 1 mM EDTA and 5% sucrose, pH 7.5) using homogenizer in cold condition.
3. Centrifuge the homogenized cerebellum at 18000 rpm (38000 g) for 15 min at 4° C.
4. Resuspend the pellet in 5 ml 50 mM Tris-HCL containing 1 mM EDTA and keep it on ice for 30 min.
5. Pass the membrane through insulin syringe to ensure uniform suspension.
6. Centrifuge the membrane at 18000 rpm at 4° C. for 20 mM.
7. Reconstitute the pellet in 3 ml of GTPγS buffer and estimate the protein by BCA assay and store the membrane in aliquots of 1000 μg of protein.

CB1 Agonist and Antagonist Activity Screening Assay

The test compounds were screened at a final concentration of 1 μM or 300 nM in the absence and presence of 1 μM of WIN 55,212-2 in the same manner as described in the GTPγS binding assay.

An agonist will stimulate the GTPγS binding over the basal.

An antagonist will inhibit the WIN-55212-2 (CB1 agonist) and induce stimulation of GTPγS binding without significantly altering the basal binding.

An inverse agonist will decrease the basal. GTPγS binding and/or produce more than 100% inhibition of the agonist (WIN-55212-2) induced stimulation.

A partial agonist normally produces only partial stimulation over basal and also partially inhibits agonist (WIN-55212-2) induced stimulation of GTPγS binding.

Data Analysis:

The percent stimulation of GTPγS binding by each test compound at 1 μM or 300 nM concentration in the absence and presence of 1 μM WIN 55,212-2 was calculated by comparing it with basal specific bound (Basal binding—Non Specific binding) values.

The results are shown in Table III below.

IX. Assay for Determining Agonist and Antagonist Activity to CB1 and CB2 Receptors 1. Antagonism of CB1/CB2 Receptors Expressed in CHO Cells.

h-CB1/CHO or h-CB2/CHO cells were grown in HAM's F12 DMEM medium (Sigma) with 10% FBS (Hyclone), 1% penicillin-streptomycin solution and 400 μg/ml of G418 (Sigma). 5000 cells were seeded per well in a 96 well plate and incubated for 24 hours at 37° C. in 5% $CO_2$. On the day of assay, cells were washed with warm Krebs buffer containing 0.1% fatty acid free (FAF) BSA (Sigma) and re-suspended in the same buffer containing 1 mM IBMX. Test antagonist or reference compound (AM 251 (1-(2,4-dichlorophenyl)-5-(4-iodophenyl)-4-methyl-N-(1-piperidyl)pyrazole-3-carboxamide) for CB1 and SR 144528 for CB2) diluted in FAFBSA+IBMX+Krebs buffer was added to the cells and incubated for 10 minutes at room temperature. CP 55,940 (30 nM final concentration for CB1 testing and 10 nM of the same for CB2 testing) was added to cells followed by forskolin (10 μM final concentration) and incubated for 30 minutes at room temperature. At the end of incubation, cells were lysed using lysis reagent from the cAMP estimation kit and cAMP was quantitated by the chemiluminescence method described in the manufacturer's instructions (DiscoveRX). $EC_{50}$ values were calculated from dose response curves by nonlinear regression analysis using PRISM software.

2. Agonism of CB1/CB2 Receptors Expressed in CHO Cells h-CB1/CHO or h-CB2/CHO cells were grown in HAM's F12 DMEM medium (Sigma) with 10% FBS (Hyclone), 1% penicillin-streptomycin solution and 400 μg/ml of G418 (Sigma). 5000 cells were seeded per well in a 96 well plate and incubated for 24 hours at 37° C. in 5% $CO_2$. On the day of assay, cells were washed with warm Krebs Buffer containing 0.1% fatty acid free (FAF) BSA (Sigma) and re-suspended in the same buffer containing 1 mM IBMX. Test compound or CP 55,940 as a reference compound (30 nM: final concentration for CB1 testing and 10 nM of the same for CB2 testing) diluted in FFB+IBMX+Krebs buffer was added to the cells followed by forskolin addition (10 uM final concentration) and incubated for 30 minutes at room temperature. At the end of incubation, cells were lysed using lysis reagent from the cAMP estimation kit and cAMP was quantitated by chemiluminescence method described in the manufacturer's instructions (DiscoveRX). $EC_{50}$ values were calculated from dose response curves by nonlinear regression analysis using PRISM software. The results are shown in Table IV below.

TABLE II

| Example No. | % Displacement | | | |
|---|---|---|---|---|
| | Protocol I | Protocol II | Protocol III | Protocol IV |
| 101 | 28.8 | 5.75 | — | 0 |
| 102 | 27.3 | 18.56 | — | 0.74 |
| 103 | 22.2 | 0 | — | 6.99 |
| 104 | — | 5.41 | — | 20.24 |
| 105 | — | 15.03 | — | 22.35 |
| 106 | 78.6 | 15.07 | — | 75.06 |
| 107 | 97.4 | 82.49@1 | — | — |
| 108 | 82.5 | 23.19 | — | 37.15 |
| 109 | — | 8.36 | — | 63.05 |
| 110 | — | 37.69 | — | 60.7 |
| 111 | 110.6 | 32.19 | — | — |
| 112 | 59.9 | 25.76 | — | — |
| 113 | 55.9 | 27.70 | — | 17.02 |
| 114 | — | 25.27 | — | 31.67 |
| 115 | — | 39.62 | — | — |
| 116 | 24.9 | 1.85 | — | — |
| 117 | — | 80.08 | 59.8 | — |
| 118 | — | 45.43 | — | 61.23 |
| 119 | — | 89.21 | 85.2 | — |
| 120 | 30.4 | 15.43 | — | 9.18 |
| 121 | 65.4 | 3.01 | — | 29.8 |
| 122* | 66.4 | 80.08 | — | — |
| 123 | 89.0 | — | — | 47.63 |
| 124 | 80.1 | 66.41 | — | — |
| 125 | 52.7 | 22.07 | — | 5.04 |
| 126 | 118.0 | — | — | — |
| 127 | 85.3 | — | — | — |
| 128 | 83 | 37.28 | — | — |
| 129 | 65.2 | 19.78 | — | 62.85 |
| 130 | 60.6 | 12.32 | — | — |
| 131 | 85.2 | 22.78 | — | 10.84 |
| 132 | 64.5 | 16.09 | — | 3.94 |
| 133 | 59.7 | 65.9@1 | — | — |
| 134 | 89.6 | 63.68 | — | — |
| 135 | 20.5 | 10.05 | — | 6.48 |
| 136 | 31.3 | 1.01 | — | 15.44 |
| 137 | 76.7 | 50.75 | — | — |
| 138 | — | 79.4 | — | 67.99 |
| 139 | 62.4 | — | — | — |
| 140 | 50.4 | 57.85 | — | 15.79 |
| 141 | 17 | — | — | — |

TABLE II-continued

| Example No. | % Displacement | | | |
|---|---|---|---|---|
| | Protocol I | Protocol II | Protocol III | Protocol IV |
| 142 | 25 | — | — | 9.86 |
| 143 | 102.2 | 81.7 | — | — |
| 144 | — | 40.13 | — | 69.24 |
| 145 | — | 54.01 | — | 75.88 |
| 146 | — | 60.51 | — | 68.16 |
| 147 | — | 39.9 | — | 37.14 |
| 148 | — | 75.56 | — | 79.21 |
| 149 | — | 82.67 | — | — |
| 150 | — | 78.72 | — | — |
| 151 | — | 92.43 | — | 69.16 |
| 152 | — | 84.24 | — | 60.26 |
| 153 | — | 96.92 | — | 99.46 |
| 154 | — | 96.1 | — | 70.19 |
| 155 | — | 96.65 | — | 72.38 |
| 156 | — | 86.37 | — | 89.29 |
| 157 | — | 84.84 | — | 88.5 |
| 158 | — | 70.12 | — | 95.4 |
| 158a | — | — | — | 94.62 |
| 159 | — | 81.31 | — | 97.65 |
| 160 | 10.0 | 7.32 | — | 20.75 |
| 161 | 27.9 | 22.54 | — | 39.35 |
| 162 | 38.9 | 9.52 | — | 33.8 |
| 163 | — | 17.3 | — | 14.46 |
| 164 | 8.2 | 19.15 | — | 13.15 |
| 165 | 14.2 | 6.64 | — | 45.27 |
| 166 | — | 8.7@1 | — | 18.16 |
| 167 | 61.3 | 44.72 | — | 24.59 |
| 168 | 37 | 11.47 | — | — |
| 169 | 19 | 29.65 | — | — |
| 170 | 40.0 | 29.49 | — | 27.16 |
| 171 | 0 | 19.37 | — | 0.56 |
| 172 | 59.2 | — | — | 25.11 |
| 173 | 67.1 | — | — | — |
| 174 | 76.4 | 21.69 | — | 22.53 |
| 175 | 66 | 25.7 | — | 18.48 |
| 176 | 65.6 | 39.34 | — | 30.48 |
| 177 | 75.6 | — | — | 15.26 |
| 178 | 47 | — | — | 6.04 |
| 179 | 48 | 30.88 | — | 18.21 |
| 180 | 40.6 | 28.65 | — | 13.19 |
| 181 | 16.4 | — | — | — |
| 182 | 39.9 | 19.35 | — | 12.78 |
| 183 | 45.9 | 17.24 | — | 18.23 |
| 184 | 41 | 3.24 | — | 8.76 |
| 185 | — | 51.98 | — | 60.66 |
| 186 | 17.2 | 16.13 | — | 59.06 |
| 187 | 6.0 | 15.66 | — | 0.7 |
| 188 | 19.5 | 12.5 | — | 36.01 |
| 189a | 7 | 21.2 | — | 0.81 |
| 189b | 3 | 24.03 | — | 2.56 |
| 190a | — | — | — | 0 |
| 190b | — | 100 | — | 96.07 |
| 191 | — | 78.71 | — | 62.18 |
| 192 | — | — | — | 19.12 |
| 201 | 9.0 | 24.91 | — | 19.79 |
| 202 | 28.2 | 16.53 | — | 70.13 |
| 203 | −10.4 | 56.51 | — | — |
| 204 | −10.3 | 23.84 | — | 10.53 |
| 205 | −12.7 | 22.27 | — | 15.93 |
| 206 | 27.4 | 15.15 | — | 71.87 |
| 207 | −1.2 | 9.39 | — | — |
| 208 | −1.2 | — | — | 0 |
| 209 | 23.5 | 30.35 | — | 50.52 |
| 210 | 12.6 | 11.58 | — | 17.69 |
| 211 | 27.6 | 19.47 | — | 80.4 |
| 212 | 68.4 | 72.25 | — | — |
| 213 | 48.5 | 17.57 | — | 71.8 |
| 214 | 10.1 | 9.01 | — | 41.3 |
| 215 | — | 1.38 | — | — |
| 216 | 32.2 | 34.03 | — | 20.74 |
| 217 | 20.5 | 38.55 | — | 10.74 |
| 218 | 29.9 | 44.41 | — | — |
| 219 | 33.7 | 59.57 | — | — |
| 220 | 29.5 | 17.92 | — | 25.29 |
| 221 | 68.6 | 0 | — | 75.66 |
| 222 | 39.4 | — | — | 15.72 |
| 223 | 52.1 | 21.5 | — | 59.5 |
| 224 | 81.6 | 42.62 | — | — |
| 225 | 31.1 | 46.8 | — | — |
| 226 | 38.4 | 72.08 | — | — |
| 227 | 25.3 | 3.51 | — | — |
| 228 | 16.1 | 0 | — | 9.4 |
| 229 | 47.1 | 0.01 | — | 24.6 |
| 230 | 87.2 | 72.54@ 1 μm | — | — |
| 231 | 31.9 | 30.79 | — | — |
| 232 | 49.7 | 1.15 | — | 13.76 |
| 233 | 73.2 | 10.79 | — | 46.22 |
| 234 | 36.3 | 3.33 | — | 10.64 |
| 235 | 46.8 | 80.94 | — | — |
| 236 | 75.5 | 55.25 | — | — |
| 237 | 65.6 | 80.77 | — | — |
| 238 | 73.9 | 24.52 | — | — |
| 239 | 23.5 | 8.09 | — | 77.12 |
| 240 | 1.5 | 0 | — | 7.98 |
| 241 | 92.5 | 87.5 | — | — |
| 242 | — | 84.89 | — | — |
| 243 | 23.5 | 1.74 | — | — |
| 244 | — | 1.7 | — | 88.35 |
| 245 | — | 30.82 | — | 84.79 |
| 246 | 46.0 | — | — | 30.44 |
| 247 | — | 22.75 | — | 79.12 |
| 248 | — | 40.11 | — | — |
| 249 | 47.7 | — | — | — |
| 250 | 27.1 | 6.46 | — | 27.93 |
| 251 | 42.3 | 20.93 | — | 60.18 |
| 252 | 99.8 | 74.52 | — | — |
| 253 | 63.0 | 43.16 | — | — |
| 254 | 9.1 | — | — | — |
| 255 | 23.9 | — | — | — |
| 256 | 63.3 | 7.71 | — | — |
| 257 | 73.5 | 30.69 | — | 83.94 |
| 258 | — | 61.78 | — | — |
| 259 | 18.3 | 2.72 | — | 33.33 |
| 260 | 84.4 | 30.22 | — | 80.22 |
| 261 | — | 34.15 | — | — |
| 262 | −1.6 | 21.54 | — | 32.58 |
| 263 | 69.1 | 26.73 | — | 79.04 |
| 264 | 85.6 | 60.85@ 1 μm | — | — |
| 265 | 31.6 | 25.85 | — | 70.16 |
| 266 | 34.5 | 23.00 | — | 61.98 |
| 267 | 90.0 | 60.43 | — | — |
| 268 | 41.0 | 74.52 | — | — |
| 269 | 47.7 | 57.25 | — | — |
| 270 | −14.6 | 18.04 | — | 8.62 |
| 271 | 11.7 | 17.7 | — | 45.96 |
| 272 | −4.5 | 13.99 | — | 18.37 |
| 273 | −5.9 | 8.94 | — | 26.25 |
| 274 | 25.7 | 7.83 | — | 35.42 |
| 275 | 38.8 | 7.02 | — | 72.28 |
| 276 | 25.3 | 3.97 | — | 14.11 |
| 277 | −12.8 | 5.41 | — | 22.13 |
| 278 | — | 26.86 | — | — |
| 279 | 62.0 | 44.84 | — | — |
| 280 | 33.0 | 40.37 | — | — |
| 281 | — | — | — | 97.11 |
| 282 | — | — | — | 92.31 |
| 283 | — | 58.84 | — | 94.79 |
| 284 | 13.7 | 25.15 | — | 0.9 |
| 285 | 61.9 | 53.9@1 μm | — | — |
| 286 | — | 32.35 | — | — |
| 287 | — | 36.8 | — | — |
| 288 | — | 1.05 | — | 60.78 |
| 289 | 71.3 | 40.2 | — | — |
| 290 | 80.3 | 70.03 | — | — |
| 291 | — | 64.44 | — | — |
| 292 | — | 69.79 | — | — |
| 293 | — | 51.88 | — | — |
| 294 | 110.7 | 78.08 | — | — |
| 295 | — | 93 | — | 100 |
| 296 | — | 94.62 | — | 95.88 |
| 297 | — | 71.92 | — | 70.29 |
| 298 | — | 28.07 | — | 11.25 |

TABLE II-continued

| Example No. | % Displacement | | | |
|---|---|---|---|---|
| | Protocol I | Protocol II | Protocol III | Protocol IV |
| 299 | — | 86.48 | — | 77.61 |
| 300 | — | 54.93 | — | 90.14 |
| 301 | — | 82.54 | — | 82.09 |
| 302 | — | 2.43 | — | 71.77 |
| 303 | — | 9.41 | — | 89.67 |
| 304 | — | — | — | — |
| 305 | — | — | — | — |
| 306 | — | 3.56 | — | 62.9 |
| 307 | — | 26.11 | — | 70.32 |
| 308 | — | 91.26 | — | 86.58 |
| 309 | — | 92.57 | — | 98.49 |
| 310 | — | 96.75 | — | 94.25 |
| 311 | — | 69.58 | — | 94.38 |
| 312 | — | 10.97 | — | 4.47 |
| 313 | — | 65.99 | — | 98.17 |
| 314 | — | 23.25 | — | 64.87 |
| 315 | — | 36.78 | — | 64.23 |
| 316 | — | 13.83 | — | 66.65 |
| 317 | — | — | — | 16.92 |
| 318 | — | — | — | 30.99 |
| 319 | — | 88.02 | — | 86.68 |
| 320 | — | 39.42 | — | 67.77 |
| 321 | — | 11.78 | — | 92.91 |
| 322 | — | 16.74 | — | 43.44 |
| 323 | — | 4.25 | — | 82.49 |
| 324 | — | 7.23 | — | 88.53 |
| 325 | — | 50.42 | — | 99.64 |
| 326 | — | 73.99 | — | 99.18 |
| 327 | — | 70.23 | — | 99.99 |
| 328 | — | 2.00 | — | 64.39 |
| 329 | — | 11.58 | — | 88.50 |
| 330 | — | — | — | 64.88 |
| 331 | — | — | — | 75.26 |
| 332 | — | — | — | 70.06 |
| 333 | — | — | — | 100.00 |
| 334 | — | — | — | 100.00 |
| 335a | — | — | — | 96.49 |
| 335b | — | — | — | 8.70 |
| 336b | — | — | — | 26.46 |
| 401 | — | 12.04 | — | — |
| 402 | — | 16.52 | — | 2.66 |
| 403 | — | 26.52 | — | 13.35 |
| 404 | — | 24.34 | — | 23.79 |
| 405 | — | 63.21 | — | 87.87 |
| 406 | — | 72.49 | — | 94.3 |
| 407 | — | 87.28 | — | 88.44 |
| 408 | — | 24.93 | — | 61.92 |
| 409 | — | 85.98 | — | 65.34 |
| 410 | — | — | — | 15.5 |
| 411 | — | — | — | 49.68 |
| 501 | 82.5 | 70.15 | — | — |
| 502 | 81.3 | 52.76 | — | — |
| 503 | 81.2 | 56.25 | — | — |
| 504 | 79.7 | 62.9 | — | — |
| 505 | 90.6 | 77.51 | — | — |
| 506 | — | 0 | — | 52.4 |
| 507 | — | 76.33 | — | 91.7 |
| 508 | — | 95.97 | — | 67.67 |
| 509 | — | 93.35 | — | 67.18 |
| 601 | 2.8 | — | — | 0.99 |
| 602 | 4.1 | — | — | 16.4 |
| 701 | — | 46.7 | — | 28.34 |
| 702 | — | — | — | 33.00 |
| 802 | — | 81.33 | — | 100.00 |

TABLE III

| PROTOCOL-VIII | | |
|---|---|---|
| Example No. | Per Se % Stimulation | % Inhibition of WIN-55212-2 induced stimulation |
| 106 | −10.0% | 65.3% |
| 107 | 4.0% | 71.5% |
| 111 | 6.1% | 101.1% |
| 121 | 16.0% | 81.3% |
| 122 | 1.2% | 59.3% |
| 123 | 13.5% | 99.1% |
| 126 | −7.9% | 104.1% |
| 127 | 18.0% | 100.2% |
| 131 | −1.7% | 86.0% |
| 132 | 7.2% | 89.2% |
| 137 | 13.0% | 76.0% |
| 139 | −8.5% | 109.1% |
| 140 | 24.9% | 71.9% |
| 143 | 43.1% | 45.0% |
| 170 | 17.5% | 80.3% |
| 172 | −18.3% | 115.3% |
| 173 | 1.3% | 99.5% |
| 174 | −20.8% | 75.5% |
| 177 | 9.7% | 109.1% |
| 178 | −0.7% | 88.0% |
| 179 | 7.8% | 89.7% |
| 180 | 10.0% | 87.9% |
| 183 | 13.0% | 72.5% |
| 184 | 9.5% | 75.9% |
| 212 | −13.8% | 97.4% |
| 221 | −16.7% | 95.7% |
| 224 | 5.0% | 78.1% |
| 230 | 42.4% | 99.4% |
| 233 | −16.3% | 79.5% |
| 236 | 8.0% | 83.0% |
| 237 | 7.1% | 74.7% |
| 238 | 0.4% | 59.1% |
| 246 | 0.7% | 98.9% |
| 256 | −21.5% | 69.7% |
| 257 | −5.1% | 48.3% |
| 260 | 38.0% | 78.8% |
| 264 | −0.1% | 94.5% |
| 268 | 29.1% | 55.3% |
| 269 | 6.0% | 91.4% |
| 290 | 3.8% | 35.3% |
| 501 | 53.7% | 40.1% |
| 502 | 1.8% | 91.1% |
| 503 | 1.5% | 92.0% |
| 505 | 15.6% | 94.4% |
| Above examples were tested at 1 uM | | |
| 117 | 4.4% | 55.7% |
| 119 | 46.0% | 38.9% |
| 134 | −6.0% | 58.1% |
| 162 | −29.2% | 72.0% |
| 241 | 54.7% | 32.9% |
| 242 | 33.4% | 22.9% |
| 252 | 48.2 | 58.8 |
| 253 | −9.3% | 79.9% |
| 267 | 12.3% | 43.6% |
| 294 | 102.8% | 9.8% |
| Above examples were tested at 300 nM | | |

TABLE IV

FUNCTIONAL ASSAY DATA

| Example No. | hCB1 Agonism | hCB1 Antagonism | hCB2 Agonism | hCB2 Antagonism |
|---|---|---|---|---|
| 106 | | NT | 0% | 50.90% |
| 109 | | NT | 61.64% at 10 uM | NT |
| 117 | 18.87 nM-IC$_{50}$ | 14.91% | | NT |
| 119 | 38.33 nM-IC$_{50}$ | 18.42% at 10 uM | | NT |
| 122* | NT | 40.66% at 10 uM | | NT |
| 134 | 75.61% at 10 uM | 17.53% at 10 uM | | NT |
| 140 | 48.88% at 10 uM | 19.31% at 10 uM | | NT |
| 149 | 79.86% at 10 uM | 15.98% at 10 uM | | NT |
| 150 | 61.1% at 10 uM | 42.93% at 10 uM | | NT |
| 186 | 29.4% at 10 uM | 0% at 10 uM | 8.51 nM IC$_{50}$ | 21% at 10 uM |
| 202 | 0% at 10 uM | 0% at 10 uM | 16.79 | 0 |
| 206 | NT | NT | 10.52 nM IC$_{50}$ | 15.96% at 10 uM |
| 211 | 16.87 at 10 uM | 0% at 10 uM | 40.65 nM IC$_{50}$ | 20.33% at 10 uM |
| 212 | NT | 39.13% at 10 uM | | NT |
| 213 | 0% at 10 uM | 0% at 10 uM | 12.67 nM IC$_{50}$ | 22.05% at 10 uM |
| 219 | NT | 33.4% at 10 uM | | NT |
| 221 | 0% at 10 uM | 0% at 10 uM | 36.43 nM IC$_{50}$ | 30.07% at 10 uM |
| 223 | NT | 0% at 10 uM | 1.49 nM IC$_{50}$ | 24.37% at 10 uM |
| 226 | NT | 71.03% at 10 uM | | NT |
| 235 | NT | 59.85% at 10 uM | | NT |
| 238 | | NT | 55.05% at 10 uM | 24.54% at 10 uM |
| 239 | | NT | 42.52 nM IC$_{50}$ | 64.1% at 10 uM |
| 244 | 0% at 10 uM | 61.52% at 10 uM | 5.66 nM IC$_{50}$ | 25.33% at 10 uM |
| 245 | 0% at 10 uM | 70.67% at 10 uM | 50.42 nM IC$_{50}$ | 32.91% at 10 uM |
| 247 | 0% at 10 uM | 75.31% at 10 uM | 5.44 nM IC$_{50}$ | 29.24% at 10 uM |
| 251 | 37% at 10 uM | 0% at 10 uM | 40.24 nM IC$_{50}$ | 40.78% at 10 uM |
| 257 | 0 | 0 | 3.7 nM IC$_{50}$ | 37.53% at 10 uM |
| 260 | 0 | 0 | 4.1 nM IC50 | 34.83% at 10 uM |
| 263 | 16.19% at 10 uM | 72.13% at 1 uM | 2.5 nM IC$_{50}$ | 27.08% at 10 uM |
| 265 | | NT | 23.11 nM IC$_{50}$ | 27.24% at 10 uM |
| 266 | 12.14% at 10 uM | 0 | 14 nM IC$_{50}$ | 27.71% at 10 uM |
| 268 | | 50.9% at 1 uM | | |
| 275 | 16.42% at 10 uM | 0% at 10 uM | 4.49 nM IC$_{50}$ | 19.14% at 10 uM |
| 288 | 0% at 10 uM | 55.26% at 10 uM | 4.76 nM IC$_{50}$ | 17.13% at 10 uM |
| 302 | 19% at 10 uM | NT | 9.75 nM IC$_{50}$ | 0% at 10 uM |
| 303 | 857 nM IC$_{50}$ | 0% at 10 uM | 0.61 nM IC$_{50}$ | 17.6% at 10 uM |
| 304 | 55% at 10 uM | 0% at 10 uM | 0.93 nM IC$_{50}$ | 51.60% at 10 uM |
| 305 | 20% at 10 uM | 0% at 10 uM | 2.16 nM IC$_{50}$ | 37.45% at 10 uM |
| 306 | | | 11.95 nM IC$_{50}$ | 14.36% at 10 uM |
| 307 | | | 0.81 nM IC50 | 21.64% at 10 uM |
| 314 | 3.41% at 10 uM | 0% at 10 uM | 8.52 nM IC$_{50}$ | 22.88% at 10 uM |
| 315 | 12.59% at 10 uM | 1% at 10 uM | 0.16-1.76 nM IC$_{50}$ | 16.09% at 10 uM |
| 316 | 18.53% at 10 uM | 2% at 10 uM | 1.2-4.27 nM IC$_{50}$ | 37.63% at 10 uM |
| 320 | 29.08% at 10 uM | 0% at 10 uM | 0.76-1.25 nM IC$_{50}$ | 22.48% at 10 uM |
| 323 | 0% at 10 uM | 0% at 10 uM | 14.12 nM IC$_{50}$ | 18.03% at 10 uM |
| 408 | | NT | 16.05 nM IC$_{50}$ | NT |
| 506 | | NT | 0% at 10 uM | 80.15% at 10 uM |

NT = Not tested.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as claimed in the appending claims.

All publications, patents, and patent applications cited in this application are herein incorporated by reference to the same extent as if each individual publication, patent, or patent application was specifically and individually indicated to be incorporated herein by reference.

We claim:

1. A method of treating pain associated with diabetic neuropathy in a subject in need thereof comprising administering to the subject a therapeutically effective amount of a compound of formula (IA):

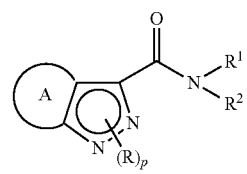

(1A)

or an analog thereof, pharmaceutically acceptable salt thereof, pharmaceutically acceptable ester thereof, tautomer thereof, stereoisomer thereof, enantiomer thereof, or diastereomer thereof, wherein each occurrence of R is independently substituted or unsubstituted alkyl, substituted or unsubstituted aryl or substituted or unsubstituted heteroaryl;

$R^1$ is hydrogen;

$R^2$ is substituted or unsubstituted alkyl, substituted or unsubstituted cycloalkyl, substituted or unsubstituted cycloalkylalkyl, substituted or unsubstituted aryl, substituted or unsubstituted arylalkyl, substituted or unsubstituted heterocyclic group, substituted or unsubstituted heteroaryl group, substituted or unsubstituted heteroarylalkyl, or $NR^3R^4$;

or $R^1$ and $R^2$ may be joined together to form an optionally substituted piperidinyl $R^3$ is hydrogen, substituted or unsubstituted alkyl, substituted or unsubstituted aryl or substituted or unsubstituted cycloalkyl and $R^4$ is substituted or unsubstituted aryl, substituted or unsubstituted heteroaryl or substituted or unsubstituted cycloalkyl;

or $R^3$ and $R^4$ may be joined together to form an optionally substituted 3 to 7 membered saturated or unsaturated cyclic ring, which may optionally include at least two heteroatoms selected from O, $NR^3$ or S;

p is 1; and

A is (a)
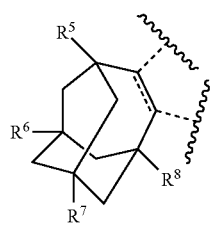

(b)
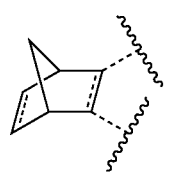

(c)
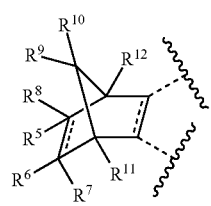

(d)
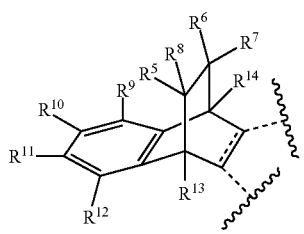

(e)
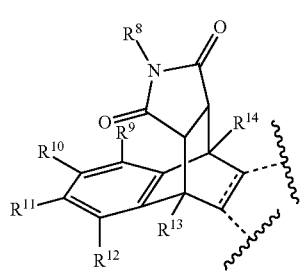

(f)
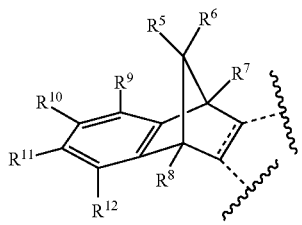

(g)
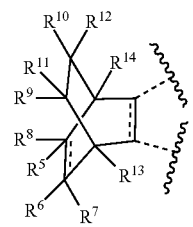

wherein
each of the dotted lines in A independently represents an optional bond, and
each occurrence of $R^5$, $R^6$, $R^7$, $R^8$, $R^9$, $R^{10}$, $R^{11}$, $R^{12}$, $R^{13}$, and $R^{14}$ is the same or different and selected from hydrogen, substituted or unsubstituted alkyl or substituted or unsubstituted aryl;

with the proviso that the compound does not have the formula:

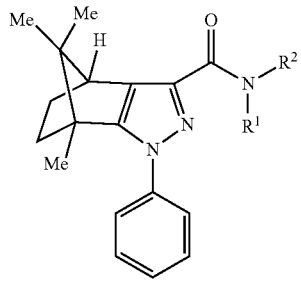

wherein $R^1$ and $R^2$ are as defined above.

2. The method according to claim 1, wherein the compound of Formula (1A) is

1(a)
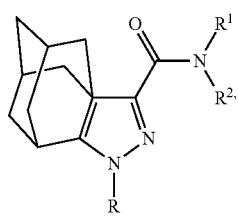

1(b)
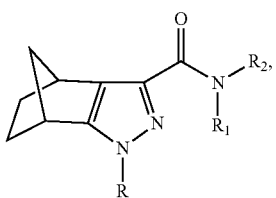

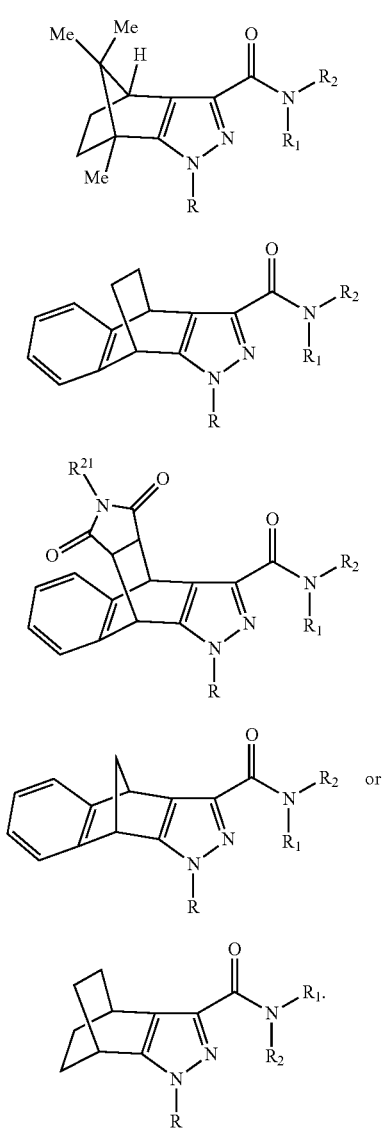

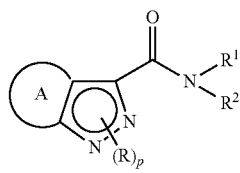

or an analog thereof, pharmaceutically acceptable salt thereof, pharmaceutically acceptable ester thereof, tautomer thereof, stereoisomer thereof, enantiomer thereof, or diastereomer thereof, wherein each occurrence of R is independently substituted or unsubstituted alkyl, substituted or unsubstituted aryl or substituted or unsubstituted heteroaryl;

$R^1$ is hydrogen;

$R^2$ is substituted or unsubstituted alkyl, substituted or unsubstituted cycloalkyl, substituted or unsubstituted cycloalkylalkyl, substituted or unsubstituted aryl, substituted or unsubstituted arylalkyl, substituted or unsubstituted heterocyclic group, substituted or unsubstituted heteroaryl group, substituted or unsubstituted heteroarylalkyl, or $NR^3R^4$;

or $R^1$ and $R^2$ may be joined together to form an optionally substituted piperidinyl $R^3$ is hydrogen, substituted or unsubstituted alkyl, substituted or unsubstituted aryl or substituted or unsubstituted cycloalkyl and $R^4$ is substituted or unsubstituted aryl, substituted or unsubstituted heteroaryl or substituted or unsubstituted cycloalkyl;

or $R^3$ and $R^4$ may be joined together to form an optionally substituted 3 to 7 membered saturated or unsaturated cyclic ring, which may optionally include at least two heteroatoms selected from O, $NR^3$ or S;

p is 1; and

A is

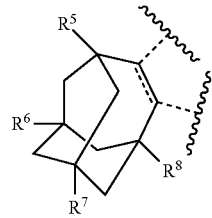

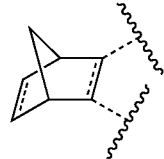

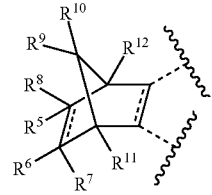

3. The method according to claim 1, wherein the compound of formula (IA) is (4S,7R) N(3)-(tert-Butyl)-1-(2,4-difluorophenyl)-4,5,6,7-tetrahydro-1H-4,7-methano-indazole-3-carboxamide, or a pharmaceutically acceptable salt thereof.

4. The method according to claim 1, which comprises administering to the subject a pharmaceutical composition comprising a therapeutically effective amount of the compound (4S,7R) N(3)-(tert-Butyl)-1-(2,4-difluorophenyl)-4,5,6,7-tetrahydro-1H-4,7-methano-indazole-3-carboxamide, or a pharmaceutically acceptable salt thereof.

5. The method according to claim 1, wherein the subject is human.

6. The method according to claim 3, wherein the subject is human.

7. The method according to claim 4, wherein the subject is human.

8. A method of treating Alzheimer's disease in a subject in need thereof comprising administering to the subject a therapeutically effective amount of a compound of formula (IA):

-continued (d)
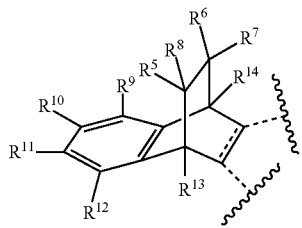

(e)
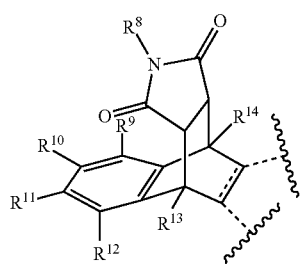

(f)
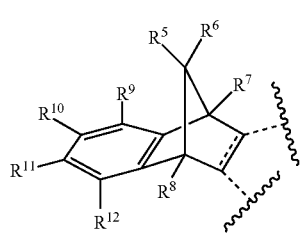

(g)
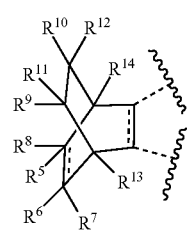

wherein
  each of the dotted lines in A independently represents an optional bond, and
  each occurrence of $R^5$, $R^6$, $R^7$, $R^8$, $R^9$, $R^{10}$, $R^{11}$, $R^{12}$, $R^{13}$, and $R^{14}$ is the same or different and selected from hydrogen, substituted or unsubstituted alkyl or substituted or unsubstituted aryl;
with the proviso that the compound does not have the formula:

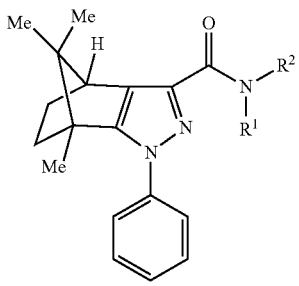

wherein $R^1$ and $R^2$ are as defined above.

9. The method according to claim 8, wherein the compound of Formula (1A) is

1(a)
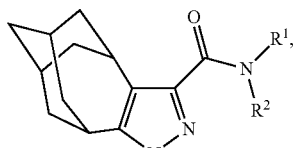

1(b)
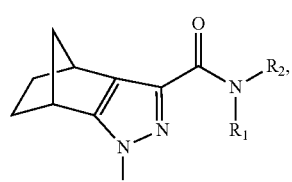

1(c)
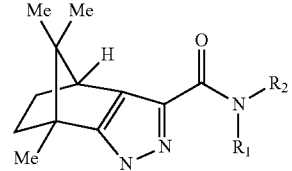

1(d)
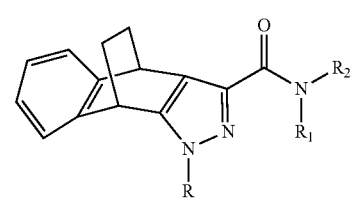

1(e)
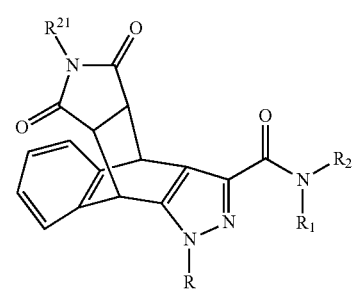

1(f)
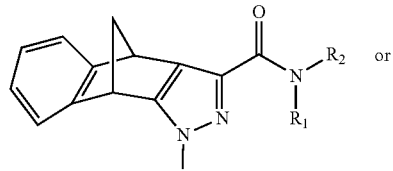

or

1(g)
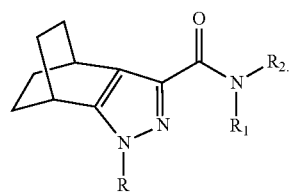

10. The method according to claim 8, wherein the compound of formula (IA) is (4S,7R) N(3)-(tert-Butyl)-1-(2,4-difluorophenyl)-4,5,6,7-tetrahydro-H-4,7-methano-indazole-3-carboxamide, or a pharmaceutically acceptable salt thereof.

11. The method according to claim 8, which comprises administering to the subject a pharmaceutical composition comprising a therapeutically effective amount of the compound (4S,7R) N(3)-(tert-Butyl)-1-(2,4-difluorophenyl)-4,5,6,7-tetrahydro-1H-4,7-methano-indazole-3-carboxamide, or a pharmaceutically acceptable salt thereof.

12. The method according to claim 8, wherein the subject is human.

13. The method according to claim 10, wherein the subject is human.

14. The method according to claim 11, wherein the subject is human.

15. A method of treating psoriasis in a subject in need thereof comprising administering to the subject a therapeutically effective amount of a compound of formula (IA):

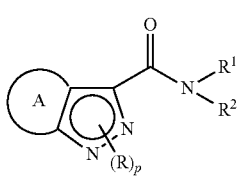

(1A)

or an analog thereof, pharmaceutically acceptable salt thereof, pharmaceutically acceptable ester thereof, tautomer thereof, stereoisomer thereof, enantiomer thereof, or diastereomer thereof, wherein each occurrence of R is independently substituted or unsubstituted alkyl, substituted or unsubstituted aryl or substituted or unsubstituted heteroaryl;

$R^1$ is hydrogen;

$R^2$ is substituted or unsubstituted alkyl, substituted or unsubstituted cycloalkyl, substituted or unsubstituted cycloalkylalkyl, substituted or unsubstituted aryl, substituted or unsubstituted arylalkyl, substituted or unsubstituted heterocyclic group, substituted or unsubstituted heteroaryl group, substituted or unsubstituted heteroarylalkyl, or $NR^3R^4$;

or $R^1$ and $R^2$ may be joined together to form an optionally substituted piperidinyl $R^3$ is hydrogen, substituted or unsubstituted alkyl, substituted or unsubstituted aryl or substituted or unsubstituted cycloalkyl and $R^4$ is substituted or unsubstituted aryl, substituted or unsubstituted heteroaryl or substituted or unsubstituted cycloalkyl;

or $R^3$ and $R^4$ may be joined together to form an optionally substituted 3 to 7 membered saturated or unsaturated cyclic ring, which may optionally include at least two heteroatoms selected from O, $NR^3$ or S;

p is 1; and

A is

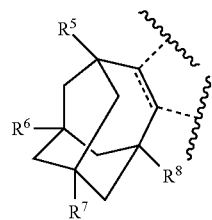 (a)

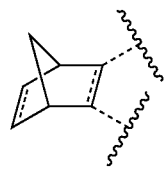 (b)

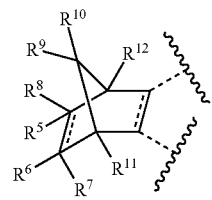 (c)

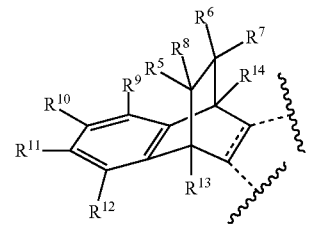 (d)

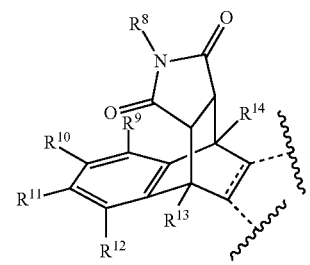 (e)

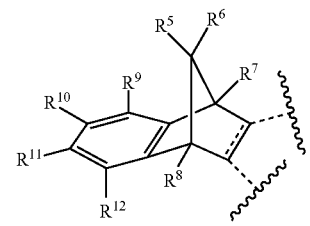 (f)

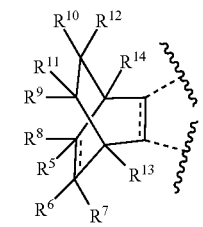 (g)

wherein
  each of the dotted lines in A independently represents an optional bond, and
  each occurrence of $R^5$, $R^6$, $R^7$, $R^8$, $R^9$, $R^{10}$, $R^{11}$, $R^{12}$, $R^{13}$, and $R^{14}$ is the same or different and selected from hydrogen, substituted or unsubstituted alkyl or substituted or unsubstituted aryl;
with the proviso that the compound does not have the formula:

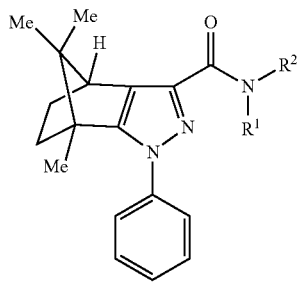

wherein $R^1$ and $R^2$ are as defined above.

16. The method according to claim 15, wherein the compound of Formula (1A) is

1(a)
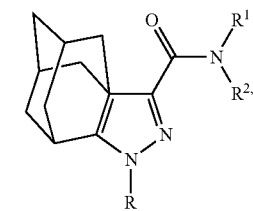

1(b)
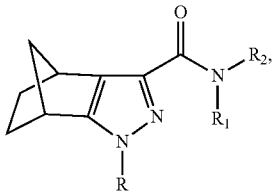

1(c)
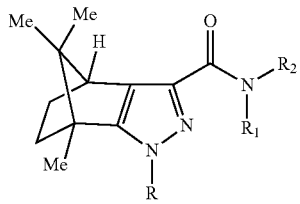

1(d)
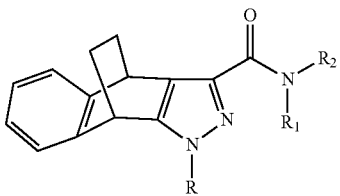

1(e)
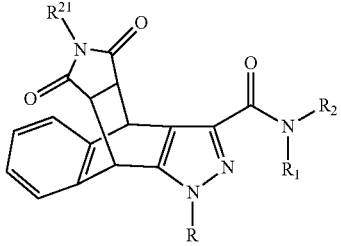

1(f)
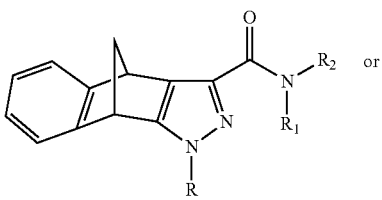

or

1(g)
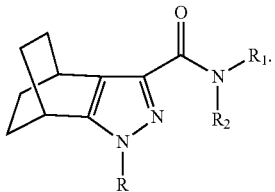

17. The method according to claim 15, wherein the compound of formula (IA) is (4S,7R) N(3)-(tert-Butyl)-1-(2,4-difluorophenyl)-4,5,6,7-tetrahydro-1H-4,7-methano-indazole-3-carboxamide, or a pharmaceutically acceptable salt thereof.

18. The method according to claim 15, which comprises administering to the subject a pharmaceutical composition comprising a therapeutically effective amount of the compound (4S,7R) N(3)-(tert-Butyl)-1-(2,4-difluorophenyl)-4,5,6,7-tetrahydro-1H-4,7-methano-indazole-3-carboxamide, or a pharmaceutically acceptable salt thereof.

19. The method according to claim 15, wherein the subject is human

20. The method according to claim 17, wherein the subject is human.

21. The method according to claim 18, wherein the subject is human.

* * * * *